(12) United States Patent
Chen et al.

(10) Patent No.: US 10,617,736 B2
(45) Date of Patent: Apr. 14, 2020

(54) METHOD FOR MODULATING INSULIN-INDEPENDENT GLUCOSE TRANSPORT USING TENEURIN C-TERMINAL ASSOCIATED PEPTIDE (TCAP)

(71) Applicants: Yani Chen, Aurora (CA); David Lovejoy, Stouffville (CA)

(72) Inventors: Yani Chen, Aurora (CA); David Lovejoy, Stouffville (CA)

( * ) Notice: Subject to any disclaimer, the term of this patent is extended or adjusted under 35 U.S.C. 154(b) by 401 days.

(21) Appl. No.: 15/326,735

(22) PCT Filed: Jul. 21, 2015

(86) PCT No.: PCT/CA2015/000437
§ 371 (c)(1),
(2) Date: Jan. 17, 2017

(87) PCT Pub. No.: WO2016/008034
PCT Pub. Date: Jan. 21, 2016

(65) Prior Publication Data
US 2018/0333455 A1    Nov. 22, 2018

Related U.S. Application Data

(60) Provisional application No. 62/026,346, filed on Jul. 18, 2014.

(51) Int. Cl.
*A61K 38/00* (2006.01)
*A61K 38/16* (2006.01)
*A61K 38/17* (2006.01)
*C07K 14/705* (2006.01)

(52) U.S. Cl.
CPC .......... *A61K 38/16* (2013.01); *A61K 38/1709* (2013.01); *C07K 14/705* (2013.01)

(58) Field of Classification Search
None
See application file for complete search history.

(56) References Cited

U.S. PATENT DOCUMENTS 8,088,889 B2 *   1/2012   Lovejoy ................. A61K 38/17
530/324

OTHER PUBLICATIONS

International Search Report dated Nov. 9, 2015 (Application No. PCT/CA2015/000437).
Chen et al., "Teneurin C-terminal associated peptides (TCAP): modulators of corticotripin-releasing factor (CRF) physiology and behavior". Front. Neurosci., Sep. 17, 2013 (Sep. 17, 2013), vol. SN 1662-453X (Electronic) 1662-4548 (Print) (online) [retrieved on Jul. 9, 2019 (Jul. 9, 2019). Retrieved from the Internet: <http://press.endocrine.org/doi/abs/10.1210/endo-meetings.2015.DGM.11.SAT-632>.
Chen et al., "Insulin-independent transport of glucose into the prolonged reduction of plasma glucose by teneurin C-terminal associated peptide (TCAP) -1: A potential new approach to the treatment of type II diabetes". Endocrine Society's 97th Annual Meeting and Expo, Mar. 5-8, 2015—San Diego, Mar. 7, 2015 (Mar. 7, 2015), (abstract) [online] [retrieved on Nov. 9, 2015 (Nov. 9, 2015)]. Retrieved from the Internet: <http://press.endocrine.org/doi/abs/10.1210/endo-meetings.2015.DGM.11.Sat-632>.

* cited by examiner

*Primary Examiner* — Jeanette M Lieb
(74) *Attorney, Agent, or Firm* — The Dobrusin Law Firm, P.C.

(57) ABSTRACT

This invention relates to a method of increasing energy available to skeletal muscle cells comprising administering to the cells an effective amount of Tenurin C-terminal Associated Peptide (TCAP). The invention provides the use of TCAP to enhance muscle performance or recovery after injury as well as to prevent and/or treat a number of conditions including insulin resistance, type II diabetes, hypoxia and glycogen storage diseases.

21 Claims, 19 Drawing Sheets

Specification includes a Sequence Listing.

Anti-Hexokinase     Anti-TOM20 + Anti-Hexokinase

SEQUENCE LISTING

<160> NUMBER OF SEQ ID NOS: 141

<210> SEQ ID NO 1
<211> LENGTH: 1490
<212> TYPE: DNA
<213> ORGANISM: Artificial Sequence
<220> FEATURE:
<223> OTHER INFORMATION: Rainbow Trout Ten M3 carboxy termini'

<400> SEQUENCE: 1

```
tccatctcgg gggtgcaaca ggaagtgacc cggcaagcca aggctttcct gtccttcgag      60
aggatgccgg agatccagct gagccgccgg cgctccaacc gggagaaacc ctggctgtgg     120
ttcgccaccg ccaagtctct gatcggtaag ggtgtcatgt tggcggtgac gcagggccgt    180
gtggtcacca acgctctgaa catcgccaac gaggactgca tcaaggtcgc cgccgtcctc     240
aacaatgcgt tctacctgga ggacctgcac ttcacggtgg agggacgcga cacgcactac     300
ttcatcaaga ccagcctccc ggagagcgac ctggagcgc tgaggctgac aagcgggagg     360
aagtcgctgg agaacggaag tcaacgtgac tgtgtcccag tccaccaccg tggtgaacgg     420
cagaaccggc gcttcgccga cgtggagctg cagtacggcg ctctagcgct ccacgtgcgc     480
tatggcatga ctctggacga ggagaaggcg cgtgtgctgg agcaggccag gcagaaggcg     540
ttgtcgagtg cctggtccag ggagcaacaa cgggtgaggg aggggagga gggggtgagg    600
ctgtggacgg aggggagaa gaggcagctg ctgagcggga ggaaggttct gggctacgac     660
gggtactacg tcctctccat agagcagtac cccgagctag cagactccgc taacaacatc     720
cagttcctca ggcagagcga aatagggaag aggtaacaga cagaatcctc ggcactggcc     780
gccaaagaga ctaccccctc caaatcctgc ccccaacct ccctcgcctc ccccttttc      840
tctaaaaagg gggagggtcc aggctagtgc tgtgtttagc gccgactagc tgaaacaaac     900
agtaaaatgt agaatatctt aaactgaact atacctaata ctaccactgt ggggcctgaa     960
aatcaaacaa aacggctcca actgacgcaa atgtttgtcc catgtgctat acagcgttga    1020
atggactgtg gactctcttg aaagagaga aaaaaagtc aaaactctcg gtttgtgaaa      1080
ggagaaaaaa acgttttttt tttttttaaa tagacttcct gaatttgctt tcggaaaaaa     1140
tattttaaaa agaaagaaga aatgtgttta catacgcata acactacaac acgtctggac    1200
taatagaaga aaagccttct ggtttcttac acaggacaac gtctataatc tgattctaca    1260
tcctgacgac tgacctttga ttgacctttg cgtactgaaa aaggtagtgt tgttgttcgc    1320
agtaggacca tgggtctcca atggtggtaa ctagacagtt aaaaccactt gttgaaacca    1380
cttgcttgtt cttctgcttt tcttttccaaa agggacaaaa cagctcccac caagtgactt    1440
ctttaccaat actagatcaa agtgggacgt tttgggctcg tgccgaattc               1490
```

<210> SEQ ID NO 2
<211> LENGTH: 756
<212> TYPE: DNA
<213> ORGANISM: Artificial Sequence
<220> FEATURE:
<223> OTHER INFORMATION: Rainbow Trout Ten M3 coding sequence of carboxy
      termini of Ten M3

<400> SEQUENCE: 2

```
tccatctcgg gggtgcaaca ggaagtgacc cggcaagcca aggctttcct gtccttcgag      60
aggatgccgg agatccagct gagccgccgg cgctccaacc gggagaaacc ctggctgtgg     120
ttcgccaccg ccaagtctct gatcggtaag ggtgtcatgt tggcggtgac gcagggccgt    180
```

```
gtggtcacca acgctctgaa catcgccaac gaggactgca tcaaggtcgc cgccgtcctc    240
aacaatgcgt tctacctgga ggacctgcac ttcacggtgg agggacgcga cacgcactac    300
ttcatcaaga ccagcctccc ggagagcgac ctggagcgc tgaggctgac aagcgggagg     360
aagtcgctgg agaacggaag tcaacgtgac tgtgtcccag tccaccaccg tggtgaacgg    420
cagaaccggc gcttcgccga cgtggagctg cagtacggcg ctctagcgct ccacgtgcgc    480
tatggcatga ctctggacga ggagaaggcg cgtgtgctgg agcaggccag gcagaaggcg    540
ttgtcgagtg cctggtccag ggagcaacaa cgggtgaggg aggggggagga gggggtgagg   600 ctgtggacgg aggggggagaa gaggcagctg ctgagcggga ggaaggttct gggctacgac   660
gggtactacg tcctctccat agagcagtac cccgagctag cagactccgc taacaacatc    720
cagttcctca ggcagagcga aatagggaag aggtaa                              756
```

<210> SEQ ID NO 3
<211> LENGTH: 251
<212> TYPE: PRT
<213> ORGANISM: Artificial Sequence
<220> FEATURE:
<223> OTHER INFORMATION: Rainbow Trout Ten M3 carboxy termini of Ten M3

<400> SEQUENCE: 3

```
Ser Ile Ser Gly Val Gln Gln Glu Val Thr Arg Gln Ala Lys Ala Phe
1               5                   10                  15

Leu Ser Phe Glu Arg Met Pro Glu Ile Gln Leu Ser Arg Arg Arg Ser
            20                  25                  30

Asn Arg Glu Lys Pro Trp Leu Trp Phe Ala Thr Ala Lys Ser Leu Ile
        35                  40                  45

Gly Lys Gly Val Met Leu Ala Val Thr Gln Gly Arg Val Val Thr Asn
    50                  55                  60

Ala Leu Asn Ile Ala Asn Glu Asp Cys Ile Lys Val Ala Ala Val Leu
65                  70                  75                  80

Asn Asn Ala Phe Tyr Leu Glu Asp Leu His Phe Thr Val Glu Gly Arg
                85                  90                  95

Asp Thr His Tyr Phe Ile Lys Thr Ser Leu Pro Glu Ser Asp Leu Gly
            100                 105                 110

Ala Leu Arg Leu Thr Ser Gly Arg Lys Ser Leu Glu Asn Gly Val Asn
        115                 120                 125

Val Thr Val Ser Gln Ser Thr Val Val Asn Gly Arg Thr Arg Arg
    130                 135                 140

Phe Ala Asp Val Glu Leu Gln Tyr Gly Ala Leu Ala Leu His Val Arg
145                 150                 155                 160

Tyr Gly Met Thr Leu Asp Glu Glu Lys Ala Arg Val Leu Glu Gln Ala
                165                 170                 175

Arg Gln Lys Ala Leu Ser Ser Ala Trp Ser Arg Glu Gln Gln Arg Val
            180                 185                 190

Arg Glu Gly Glu Glu Gly Val Arg Leu Trp Thr Glu Gly Glu Lys Arg
        195                 200                 205

Gln Leu Leu Ser Gly Arg Lys Val Leu Gly Tyr Asp Gly Tyr Tyr Val
    210                 215                 220

Leu Ser Ile Glu Gln Tyr Pro Glu Leu Ala Asp Ser Ala Asn Asn Ile
225                 230                 235                 240

Gln Phe Leu Arg Gln Ser Glu Ile Gly Lys Arg
                245                 250
```

```
<210> SEQ ID NO 4
<211> LENGTH: 252
<212> TYPE: PRT
<213> ORGANISM: Artificial Sequence
<220> FEATURE:
<223> OTHER INFORMATION: Mouse Ten M1

<400> SEQUENCE: 4

Met Ile Leu Gly Ile Gln Cys Glu Leu Gln Lys Gln Leu Arg Asn Phe
1               5                   10                  15

Ile Ser Leu Asp Gln Leu Pro Met Thr Pro Gln Tyr Asn Glu Gly Arg
            20                  25                  30

Cys Leu Glu Gly Gly Lys Gln Pro Arg Phe Ala Ala Val Pro Ser Val
        35                  40                  45

Phe Gly Lys Gly Ile Lys Phe Ala Ile Lys Glu Gly Ile Val Thr Ala
    50                  55                  60

Asp Ile Ile Gly Val Ala Asn Glu Asp Ser Arg Arg Leu Ala Ala Ile
65                  70                  75                  80

Leu Asn Asn Ala His Tyr Leu Glu Asn Leu His Phe Thr Ile Glu Gly
                85                  90                  95

Arg Asp Thr His Tyr Phe Ile Lys Leu Gly Ser Leu Glu Glu Asp Leu
            100                 105                 110

Val Leu Ile Gly Asn Thr Gly Gly Arg Arg Ile Leu Glu Asn Gly Val
        115                 120                 125

Asn Val Thr Val Ser Gln Met Thr Ser Val Leu Asn Gly Arg Thr Arg
    130                 135                 140

Arg Phe Ala Asp Ile Gln Leu Gln His Gly Ala Leu Cys Phe Asn Ile
145                 150                 155                 160

Arg Tyr Gly Thr Thr Val Glu Glu Lys Asn His Val Leu Glu Met
                165                 170                 175

Ala Arg Gln Arg Ala Val Ala Gln Ala Trp Thr Gln Glu Gln Arg Arg
            180                 185                 190

Leu Gln Glu Gly Glu Gly Thr Arg Val Trp Thr Glu Gly Glu Lys
        195                 200                 205

Gln Gln Leu Leu Gly Thr Gly Arg Val Gln Gly Tyr Asp Gly Tyr Phe
    210                 215                 220

Val Leu Ser Val Glu Gln Tyr Leu Glu Leu Ser Asp Ser Ala Asn Asn
225                 230                 235                 240

Ile His Phe Met Arg Gln Ser Glu Ile Gly Arg Arg
                245                 250

<210> SEQ ID NO 5
<211> LENGTH: 253
<212> TYPE: PRT
<213> ORGANISM: Artificial Sequence
<220> FEATURE:
<223> OTHER INFORMATION: Mouse Ten M2

<400> SEQUENCE: 5

Leu Ile Thr Gly Val Gln Thr Thr Glu Arg His Asn Gln Ala Phe
1               5                   10                  15

Leu Ala Leu Glu Gly Gln Val Ile Thr Lys Lys Leu His Ala Ser Ile
            20                  25                  30

Arg Glu Lys Ala Gly His Trp Phe Ala Thr Thr Pro Ile Ile Gly
            35                  40                  45

Lys Gly Ile Met Phe Ala Ile Lys Glu Gly Arg Val Thr Thr Gly Val
    50                  55                  60
```

```
Ser Ser Ile Ala Ser Glu Asp Ser Arg Lys Val Ala Ser Val Leu Asn
 65                  70                  75                  80

Asn Ala Tyr Tyr Leu Asp Lys Met His Tyr Ser Ile Glu Gly Lys Asp
                 85                  90                  95

Thr His Tyr Phe Val Lys Ile Gly Ala Ala Asp Gly Asp Leu Val Thr
            100                 105                 110

Leu Gly Thr Thr Ile Gly Arg Lys Val Leu Glu Ser Gly Val Asn Val
        115                 120                 125

Thr Val Ser Gln Pro Thr Leu Val Asn Gly Arg Thr Arg Arg Phe
130                 135                 140

Thr Asn Ile Glu Phe Gln Tyr Ser Thr Leu Leu Ser Ile Arg Tyr
145                 150                 155                 160

Gly Leu Thr Pro Asp Thr Leu Asp Glu Glu Lys Ala Arg Val Leu Asp
                165                 170                 175

Gln Ala Gly Gln Arg Ala Leu Gly Thr Ala Trp Ala Lys Glu Gln Gln
            180                 185                 190

Lys Ala Arg Asp Gly Arg Glu Gly Ser Arg Leu Trp Thr Glu Gly Glu
        195                 200                 205

Lys Gln Gln Leu Leu Ser Thr Gly Arg Val Gln Gly Tyr Glu Gly Tyr
    210                 215                 220

Tyr Val Leu Pro Val Glu Gln Tyr Pro Glu Leu Ala Asp Ser Ser Ser
225                 230                 235                 240

Asn Ile Gln Phe Leu Arg Gln Asn Glu Met Gly Lys Arg
                245                 250
```

<210> SEQ ID NO 6
<211> LENGTH: 251
<212> TYPE: PRT
<213> ORGANISM: Artificial Sequence
<220> FEATURE:
<223> OTHER INFORMATION: Mouse Ten M3

<400> SEQUENCE: 6

```
Pro Ile Phe Gly Val Gln Gln Val Ala Arg Gln Ala Lys Ala Phe
 1               5                  10                  15

Leu Ser Leu Gly Lys Met Ala Glu Val Gln Val Ser Arg Arg Lys Ala
                 20                  25                  30

Gly Ala Glu Gln Ser Trp Leu Trp Phe Ala Thr Val Lys Ser Leu Ile
            35                  40                  45

Gly Lys Gly Val Met Leu Ala Val Ser Gln Gly Arg Val Gln Thr Asn
        50                  55                  60

Val Leu Asn Ile Ala Asn Glu Asp Cys Ile Lys Val Ala Ala Val Leu
 65                  70                  75                  80

Asn Asn Ala Phe Tyr Leu Glu Asn Leu His Phe Thr Ile Glu Gly Lys
                 85                  90                  95

Asp Thr His Tyr Phe Ile Lys Thr Thr Thr Pro Glu Ser Asp Leu Gly
            100                 105                 110

Thr Leu Arg Leu Thr Ser Gly Arg Lys Ala Leu Glu Asn Gly Ile Asn
        115                 120                 125

Val Thr Val Ser Gln Ser Thr Thr Val Val Asn Gly Arg Thr Arg Arg
130                 135                 140

Phe Ala Asp Val Glu Met Gln Phe Gly Ala Leu Ala Leu His Val Arg
145                 150                 155                 160

Tyr Gly Met Thr Leu Asp Glu Glu Lys Ala Arg Ile Leu Glu Gln Ala
                165                 170                 175
```

```
Arg Gln Arg Ala Leu Ala Arg Ala Trp Ala Arg Glu Gln Gln Arg Val
            180                 185                 190

Arg Asp Gly Glu Glu Gly Ala Arg Leu Trp Thr Glu Gly Glu Lys Arg
        195                 200                 205

Gln Leu Leu Ser Ala Gly Lys Val Gln Gly Tyr Asp Gly Tyr Tyr Val
    210                 215                 220

Leu Ser Val Glu Gln Tyr Pro Glu Leu Ala Asp Ser Ala Asn Asn Ile
225                 230                 235                 240

Gln Phe Leu Arg Gln Ser Glu Ile Gly Lys Arg
                245                 250
```

<210> SEQ ID NO 7
<211> LENGTH: 243
<212> TYPE: PRT
<213> ORGANISM: Artificial Sequence
<220> FEATURE:
<223> OTHER INFORMATION: Mouse Ten M4

<400> SEQUENCE: 7

```
Ser Ile Leu Gly Val Gln Cys Glu Val Gln Lys Gln Leu Lys Ala Phe
1               5                   10                  15

Val Thr Leu Glu Arg Phe Asp Gln Leu Tyr Gly Ser Thr Ile Thr Ser
            20                  25                  30

Cys Gln Gln Ala Pro Glu Thr Lys Lys Phe Ala Ser Ser Gly Ser Ile
        35                  40                  45

Phe Gly Lys Gly Val Lys Phe Ala Leu Lys Asp Gly Arg Val Thr Thr
    50                  55                  60

Asp Ile Ile Ser Val Ala Asn Glu Asp Gly Arg Ile Ala Ala Ile
65                  70                  75                  80

Leu Asn Asn Ala His Tyr Leu Glu Asn Leu His Phe Thr Ile Asp Gly
                85                  90                  95

Val Asp Thr His Tyr Phe Val Lys Pro Gly Pro Ser Glu Gly Asp Leu
            100                 105                 110

Ala Ile Leu Gly Leu Ser Gly Gly Arg Arg Thr Leu Glu Asn Gly Val
        115                 120                 125

Asn Val Thr Val Ser Gln Ile Asn Thr Met Leu Ile Gln Leu Gln Tyr
    130                 135                 140

Arg Ala Leu Cys Leu Asn Thr Arg Tyr Gly Thr Thr Val Asp Glu Glu
145                 150                 155                 160

Lys Val Arg Val Leu Glu Leu Ala Arg Gln Arg Ala Val Arg Gln Ala
                165                 170                 175

Trp Ala Arg Glu Gln Gln Arg Leu Arg Glu Gly Glu Gly Leu Arg
            180                 185                 190

Ala Trp Thr Asp Gly Glu Lys Gln Gln Val Leu Asn Thr Gly Arg Val
        195                 200                 205

Gln Gly Tyr Asp Gly Phe Phe Val Thr Ser Val Glu Gln Tyr Pro Glu
    210                 215                 220

Leu Ser Asp Ser Ala Asn Asn Ile His Phe Met Arg Gln Ser Glu Met
225                 230                 235                 240

Gly Arg Arg
```

<210> SEQ ID NO 8
<211> LENGTH: 252
<212> TYPE: PRT
<213> ORGANISM: Artificial Sequence
<220> FEATURE:
<223> OTHER INFORMATION: Human Ten M1

<400> SEQUENCE: 8

```
Thr Ile Leu Gly Ile Gln Cys Glu Leu Gln Lys Gln Leu Arg Asn Phe
1               5                   10                  15

Ile Ser Leu Asp Gln Leu Pro Met Thr Pro Arg Tyr Asn Asp Gly Arg
            20                  25                  30

Cys Leu Glu Gly Gly Lys Gln Pro Arg Phe Ala Ala Val Pro Ser Val
        35                  40                  45

Phe Gly Lys Gly Ile Lys Phe Ala Ile Lys Asp Gly Ile Val Thr Ala
    50                  55                  60

Asp Ile Ile Gly Val Ala Asn Glu Asp Ser Arg Arg Leu Ala Ala Ile
65                  70                  75                  80

Leu Asn Asn Ala His Tyr Leu Glu Asn Leu His Phe Thr Ile Glu Gly
                85                  90                  95

Arg Asp Thr His Tyr Phe Ile Lys Leu Gly Ser Leu Glu Glu Asp Leu
            100                 105                 110

Val Leu Ile Gly Asn Thr Gly Gly Arg Arg Ile Leu Glu Asn Gly Val
        115                 120                 125

Asn Val Thr Val Ser Gln Met Thr Ser Val Leu Asn Gly Arg Thr Arg
130                 135                 140

Arg Phe Ala Asp Ile Gln Leu Gln His Gly Ala Leu Cys Phe Asn Ile
145                 150                 155                 160

Arg Tyr Gly Thr Thr Val Glu Glu Glu Lys Asn His Val Leu Glu Ile
                165                 170                 175

Ala Arg Gln Arg Ala Val Ala Gly Ala Trp Thr Lys Glu Gln Arg Arg
            180                 185                 190

Leu Gln Glu Gly Glu Glu Gly Ile Arg Ala Trp Thr Glu Gly Glu Lys
        195                 200                 205

Gln Gln Leu Leu Ser Thr Gly Arg Val Gln Gly Tyr Asp Gly Tyr Phe
    210                 215                 220

Val Leu Ser Val Glu Gln Tyr Leu Glu Leu Ser Asp Ser Ala Asn Asn
225                 230                 235                 240

Ile His Phe Met Arg Gln Ser Glu Ile Gly Arg Arg
                245                 250
```

<210> SEQ ID NO 9
<211> LENGTH: 253
<212> TYPE: PRT
<213> ORGANISM: Artificial Sequence
<220> FEATURE:
<223> OTHER INFORMATION: Human Ten M2

<400> SEQUENCE: 9

```
Leu Ile Thr Gly Val Gln Gln Thr Thr Glu Arg His Asn Gln Ala Phe
1               5                   10                  15

Met Ala Leu Glu Gly Gln Val Ile Thr Lys Lys Leu His Ala Ser Ile
            20                  25                  30

Arg Glu Lys Ala Gly His Trp Phe Ala Thr Thr Pro Ile Ile Gly
        35                  40                  45

Lys Gly Ile Met Phe Ala Ile Lys Glu Gly Arg Val Thr Thr Gly Val
    50                  55                  60

Ser Ser Ile Ala Ser Glu Asp Ser Arg Lys Val Ala Ser Val Leu Asn
65                  70                  75                  80

Asn Ala Tyr Tyr Leu Asp Lys Met His Tyr Ser Ile Glu Gly Lys Asp
                85                  90                  95
```

```
Thr His Tyr Phe Val Lys Ile Gly Ser Ala Asp Gly Asp Leu Val Thr
                100                 105                 110

Leu Gly Thr Thr Ile Gly Arg Lys Val Leu Glu Ser Gly Val Asn Val
            115                 120                 125

Thr Val Ser Gln Pro Thr Leu Leu Val Asn Gly Arg Thr Arg Arg Phe
        130                 135                 140

Thr Asn Ile Glu Phe Gln Tyr Ser Thr Leu Leu Ser Ile Arg Tyr
145                 150                 155                 160

Gly Leu Thr Pro Asp Thr Leu Asp Glu Glu Lys Ala Arg Val Leu Asp
                165                 170                 175

Gln Ala Arg Gln Arg Ala Leu Gly Thr Ala Trp Ala Lys Glu Gln Gln
            180                 185                 190

Lys Ala Arg Asp Gly Arg Glu Gly Ser Arg Leu Trp Thr Glu Gly Glu
        195                 200                 205

Lys Gln Gln Leu Leu Ser Thr Gly Arg Val Gln Gly Tyr Glu Gly Tyr
210                 215                 220

Tyr Val Leu Pro Val Glu Gln Tyr Pro Glu Leu Ala Asp Ser Ser Ser
225                 230                 235                 240

Asn Ile Gln Phe Leu Arg Gln Asn Glu Met Gly Lys Arg
                245                 250

<210> SEQ ID NO 10
<211> LENGTH: 251
<212> TYPE: PRT
<213> ORGANISM: Artificial Sequence
<220> FEATURE:
<223> OTHER INFORMATION: Human Ten M3

<400> SEQUENCE: 10

Pro Ile Phe Gly Val Gln Gln Gln Val Ala Arg Gln Ala Lys Ala Phe
1               5                   10                  15

Leu Ser Leu Gly Lys Met Ala Glu Val Gln Val Ser Arg Arg Arg Ala
            20                  25                  30

Gly Gly Ala Gln Ser Trp Leu Trp Phe Ala Thr Val Lys Ser Leu Ile
        35                  40                  45

Gly Lys Gly Val Met Leu Ala Val Ser Gln Gly Arg Val Gln Thr Asn
    50                  55                  60

Val Leu Asn Ile Ala Asn Glu Asp Cys Ile Lys Val Ala Ala Val Leu
65                  70                  75                  80

Asn Asn Ala Phe Tyr Leu Glu Asn Leu His Phe Thr Ile Glu Gly Lys
                85                  90                  95

Asp Thr His Tyr Phe Ile Lys Thr Thr Thr Pro Glu Ser Asp Leu Gly
                100                 105                 110

Thr Leu Arg Leu Thr Ser Gly Arg Lys Ala Leu Glu Asn Gly Ile Asn
            115                 120                 125

Val Thr Val Ser Gln Ser Thr Thr Val Val Asn Gly Arg Thr Arg Arg
        130                 135                 140

Phe Ala Asp Val Glu Met Gln Phe Gly Ala Leu Ala Leu His Val Arg
145                 150                 155                 160

Tyr Gly Met Thr Leu Asp Glu Glu Lys Ala Arg Ile Leu Glu Gln Ala
                165                 170                 175

Arg Gln Arg Ala Leu Ala Arg Ala Trp Ala Arg Glu Gln Gln Arg Val
            180                 185                 190

Arg Asp Gly Glu Glu Gly Ala Arg Leu Trp Thr Glu Gly Glu Lys Arg
        195                 200                 205
```

```
Gln Leu Leu Ser Ala Gly Lys Val Gln Gly Tyr Asp Gly Tyr Tyr Val
            210                 215                 220

Leu Ser Val Glu Gln Tyr Pro Glu Leu Ala Asp Ser Ala Asn Asn Ile
225                 230                 235                 240

Gln Phe Leu Arg Gln Ser Glu Ile Gly Arg Arg
            245                 250
```

<210> SEQ ID NO 11
<211> LENGTH: 252
<212> TYPE: PRT
<213> ORGANISM: Artificial Sequence
<220> FEATURE:
<223> OTHER INFORMATION: Human Ten M4

<400> SEQUENCE: 11

```
Ser Ile Leu Gly Val Gln Cys Glu Val Gln Lys Gln Leu Lys Ala Phe
1               5                   10                  15

Val Thr Leu Glu Arg Phe Asp Gln Leu Tyr Gly Ser Thr Ile Thr Ser
            20                  25                  30

Cys Leu Gln Ala Pro Lys Thr Lys Lys Phe Ala Ser Ser Gly Ser Val
        35                  40                  45

Phe Gly Lys Gly Val Lys Phe Ala Leu Lys Asp Gly Arg Val Thr Thr
50                  55                  60

Asp Ile Ile Ser Val Ala Asn Glu Asp Gly Arg Arg Val Ala Ala Ile
65                  70                  75                  80

Leu Asn His Ala His Tyr Leu Glu Asn Leu His Phe Thr Ile Asp Gly
                85                  90                  95

Val Asp Thr His Tyr Phe Val Lys Pro Gly Pro Ser Glu Gly Asp Leu
            100                 105                 110

Ala Ile Leu Gly Leu Ser Gly Gly Arg Arg Thr Leu Glu Asn Gly Val
        115                 120                 125

Asn Val Thr Val Ser Gln Ile Asn Thr Val Leu Ser Gly Arg Thr Arg
130                 135                 140

Arg Tyr Thr Asp Ile Gln Leu Gln Tyr Gly Ala Leu Cys Leu Asn Thr
145                 150                 155                 160

Arg Tyr Gly Thr Thr Leu Asp Glu Glu Lys Ala Arg Val Leu Glu Leu
                165                 170                 175

Ala Arg Gln Arg Ala Val Arg Gln Ala Trp Ala Arg Glu Gln Gln Arg
            180                 185                 190

Leu Arg Glu Gly Glu Glu Gly Leu Arg Ala Trp Thr Glu Gly Glu Lys
        195                 200                 205

Gln Gln Val Leu Ser Thr Gly Arg Val Gln Gly Tyr Asp Gly Phe Phe
210                 215                 220

Val Ile Ser Val Glu Gln Tyr Pro Glu Leu Ser Asp Ser Ala Asn Asn
225                 230                 235                 240

Ile His Phe Met Arg Gln Ser Glu Met Gly Arg Arg
                245                 250
```

<210> SEQ ID NO 12
<211> LENGTH: 252
<212> TYPE: PRT
<213> ORGANISM: Artificial Sequence
<220> FEATURE:
<223> OTHER INFORMATION: Zebrafish Ten M3

<400> SEQUENCE: 12

```
Ser Ile Ser Gly Val Gln Gln Glu Val Met Arg Gln Ala Lys Ala Phe
1               5                   10                  15
```

```
Leu Ser Phe Glu Arg Met Pro Glu Ile Gln Leu Ser Arg Arg Ser
             20                  25                  30

Ser Arg Glu Lys Pro Trp Leu Trp Phe Ala Thr Val Lys Ser Leu Ile
         35                  40                  45

Gly Lys Gly Val Met Leu Ala Ile Thr Ser Lys Gly Gln Val Ala Thr
 50                  55                  60

Asn Ala Leu Asn Ile Ala Asn Glu Asp Cys Ile Lys Val Val Thr Val
 65                  70                  75                  80

Leu Asn Asn Ala Phe Tyr Leu Glu Asp Leu His Phe Thr Val Glu Gly
             85                  90                  95

Arg Asp Thr His Tyr Phe Ile Lys Thr Ser Leu Pro Glu Ser Asp Leu
            100                 105                 110

Gly Ala Leu Arg Leu Thr Ser Gly Arg Lys Ser Leu Glu Asn Gly Val
            115                 120                 125

Asn Val Thr Val Ser Gln Ser Thr Thr Val Val Asn Gly Arg Thr Arg
130                 135                 140

Arg Phe Ala Asp Val Glu Leu Gln Tyr Gly Ala Leu Ala Leu His Val
145                 150                 155                 160

Arg Tyr Gly Met Thr Leu Asp Glu Glu Lys Ala Arg Val Leu Glu Gln
            165                 170                 175

Ala Arg Gln Arg Ala Leu Ser Ser Ala Trp Ala Arg Glu Gln Gln Arg
            180                 185                 190

Val Arg Asp Gly Glu Glu Gly Val Arg Leu Trp Thr Glu Gly Glu Lys
            195                 200                 205

Arg Gln Leu Leu Ser Ser Gly Lys Val Leu Gly Tyr Asp Gly Tyr Tyr
            210                 215                 220

Val Leu Ser Val Glu Gln Tyr Pro Glu Leu Ala Asp Ser Ala Asn Asn
225                 230                 235                 240

Val Gln Phe Leu Arg Gln Ser Glu Ile Gly Lys Arg
            245                 250

<210> SEQ ID NO 13
<211> LENGTH: 40
<212> TYPE: PRT
<213> ORGANISM: Artificial Sequence
<220> FEATURE:
<223> OTHER INFORMATION: Rainbow Trout TCAP3 (40a.a.)

<400> SEQUENCE: 13

Gln Leu Leu Ser Gly Arg Lys Val Leu Gly Tyr Asp Gly Tyr Tyr Val
 1               5                  10                  15

Leu Ser Ile Glu Gln Tyr Pro Glu Leu Ala Asp Ser Ala Asn Asn Ile
             20                  25                  30

Gln Phe Leu Arg Gln Ser Glu Ile
         35                  40

<210> SEQ ID NO 14
<211> LENGTH: 41
<212> TYPE: PRT
<213> ORGANISM: Artificial Sequence
<220> FEATURE:
<223> OTHER INFORMATION: Rainbow Trout TCAP 3 (41a.a.)

<400> SEQUENCE: 14

Arg Gln Leu Leu Ser Gly Arg Lys Val Leu Gly Tyr Asp Gly Tyr Tyr
 1               5                  10                  15

Val Leu Ser Ile Glu Gln Tyr Pro Glu Leu Ala Asp Ser Ala Asn Asn
```

20                  25                  30

Ile Gln Phe Leu Arg Gln Ser Glu Ile
         35                  40

<210> SEQ ID NO 15
<211> LENGTH: 43
<212> TYPE: PRT
<213> ORGANISM: Artificial Sequence
<220> FEATURE:
<223> OTHER INFORMATION: Rainbow Trout preTCAP3 (43 a.a.)

<400> SEQUENCE: 15

Gln Leu Leu Ser Gly Arg Lys Val Leu Gly Tyr Asp Gly Tyr Tyr Val
1               5                   10                  15

Leu Ser Ile Glu Gln Tyr Pro Glu Leu Ala Asp Ser Ala Asn Asn Ile
            20                  25                  30

Gln Phe Leu Arg Gln Ser Glu Ile Gly Lys Arg
         35                  40

<210> SEQ ID NO 16
<211> LENGTH: 44
<212> TYPE: PRT
<213> ORGANISM: Artificial Sequence
<220> FEATURE:
<223> OTHER INFORMATION: Rainbow Trout preTCAP3 (44 a.a.)

<400> SEQUENCE: 16

Arg Gln Leu Leu Ser Gly Arg Lys Val Leu Gly Tyr Asp Gly Tyr Tyr
1               5                   10                  15

Val Leu Ser Ile Glu Gln Tyr Pro Glu Leu Ala Asp Ser Ala Asn Asn
            20                  25                  30

Ile Gln Phe Leu Arg Gln Ser Glu Ile Gly Lys Arg
         35                  40

<210> SEQ ID NO 17
<211> LENGTH: 120
<212> TYPE: DNA
<213> ORGANISM: Artificial Sequence
<220> FEATURE:
<223> OTHER INFORMATION: Rainbow Trout TCAP3 (120 n.a.)

<400> SEQUENCE: 17
cagctgctga gcggaggaa ggttctgggc tacgacgggt actacgtcct ctccatagag     60
cagtaccccg agctagcaga ctccgctaac aacatccagt tcctcaggca gagcgaaata    120

<210> SEQ ID NO 18
<211> LENGTH: 123
<212> TYPE: DNA
<213> ORGANISM: Artificial Sequence
<220> FEATURE:
<223> OTHER INFORMATION: Rainbow Trout TCAP3 (123 n.a.)

<400> SEQUENCE: 18
aggcagctgc tgagcgggag gaaggttctg ggctacgacg gtactacgt cctctccata     60 gagcagtacc ccgagctagc agactccgct aacaacatcc agttcctcag gcagagcgaa    120
ata                                                                  123

<210> SEQ ID NO 19
<211> LENGTH: 129
<212> TYPE: DNA
<213> ORGANISM: Artificial Sequence
<220> FEATURE:

-continued

<223> OTHER INFORMATION: Rainbow Trout preTCAP3 (129 n.a.)

<400> SEQUENCE: 19

```
cagctgctga gcgggaggaa ggttctgggc tacgacgggt actacgtcct ctccatagag    60
cagtaccccg agctagcaga ctccgctaac aacatccagt tcctcaggca gagcgaaata   120
gggaagagg                                                           129
```

<210> SEQ ID NO 20
<211> LENGTH: 132
<212> TYPE: DNA
<213> ORGANISM: Artificial Sequence
<220> FEATURE:
<223> OTHER INFORMATION: Rainbow Trout preTCAP3 (132 n.a.)

<400> SEQUENCE: 20

```
aggcagctgc tgagcgggag gaaggttctg gctacgacg gtactacgt cctctccata    60
gagcagtacc ccgagctagc agactccgct aacaacatcc agttcctcag gcagagcgaa   120
atagggaaga gg                                                       132
```

<210> SEQ ID NO 21
<211> LENGTH: 40
<212> TYPE: PRT
<213> ORGANISM: Artificial Sequence
<220> FEATURE:
<223> OTHER INFORMATION: Zebrafish TCAP3 (40 a.a.)

<400> SEQUENCE: 21

```
Gln Leu Leu Ser Ser Gly Lys Val Leu Gly Tyr Asp Gly Tyr Tyr Val
1               5                   10                  15
Leu Ser Val Glu Gln Tyr Pro Glu Leu Ala Asp Ser Ala Asn Asn Val
            20                  25                  30
Gln Phe Leu Arg Gln Ser Glu Ile
        35                  40
```

<210> SEQ ID NO 22
<211> LENGTH: 41
<212> TYPE: PRT
<213> ORGANISM: Artificial Sequence
<220> FEATURE:
<223> OTHER INFORMATION: Zebrafish TCAP3 (41 a.a.)

<400> SEQUENCE: 22

```
Arg Gln Leu Leu Ser Ser Gly Lys Val Leu Gly Tyr Asp Gly Tyr Tyr
1               5                   10                  15
Val Leu Ser Val Glu Gln Tyr Pro Glu Leu Ala Asp Ser Ala Asn Asn
            20                  25                  30
Val Gln Phe Leu Arg Gln Ser Glu Ile
        35                  40
```

<210> SEQ ID NO 23
<211> LENGTH: 43
<212> TYPE: PRT
<213> ORGANISM: Artificial Sequence
<220> FEATURE:
<223> OTHER INFORMATION: Zebrafish preTCAP3 (43 a.a.)

<400> SEQUENCE: 23

```
Gln Leu Leu Ser Ser Gly Lys Val Leu Gly Tyr Asp Gly Tyr Tyr Val
1               5                   10                  15
Leu Ser Val Glu Gln Tyr Pro Glu Leu Ala Asp Ser Ala Asn Asn Val
            20                  25                  30
```

-continued

<210> SEQ ID NO 24
<211> LENGTH: 44
<212> TYPE: PRT
<213> ORGANISM: Artificial Sequence
<220> FEATURE:
<223> OTHER INFORMATION: Zebrafish preTCAP3 (44 a.a.)

<400> SEQUENCE: 24

Arg Gln Leu Leu Ser Ser Gly Lys Val Leu Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Val Gln Phe Leu Arg Gln Ser Glu Ile Gly Lys Arg
        35                  40

<210> SEQ ID NO 25
<211> LENGTH: 120
<212> TYPE: DNA
<213> ORGANISM: Artificial Sequence
<220> FEATURE:
<223> OTHER INFORMATION: Zebrafish TCAP3 (120 n.a.)

<400> SEQUENCE: 25
cagttgctca gctctgggaa ggtgctgggt tacgatggtt actatgtact atcagtggag      60
caataccctg aactggccga cagtgccaac aatgtccagt tcttgaggca gagtgagata    120

<210> SEQ ID NO 26
<211> LENGTH: 123
<212> TYPE: DNA
<213> ORGANISM: Artificial Sequence
<220> FEATURE:
<223> OTHER INFORMATION: Zebrafish TCAP3 (123 n.a.)

<400> SEQUENCE: 26
aggcagttgc tcagctctgg gaaggtgctg ggttacgatg gttactatgt actatcagtg      60
gagcaatacc ctgaactggc cgacagtgcc aacaatgtcc agttcttgag gcagagtgag    120
ata                                                                  123

<210> SEQ ID NO 27
<211> LENGTH: 129
<212> TYPE: DNA
<213> ORGANISM: Artificial Sequence
<220> FEATURE:
<223> OTHER INFORMATION: Zebrafish TCAP3 (129 n.a.)

<400> SEQUENCE: 27
cagttgctca gctctgggaa ggtgctgggt tacgatggtt actatgtact atcagtggag      60
caataccctg aactggccga cagtgccaac aatgtccagt tcttgaggca gagtgagata    120
gggaagagg                                                            129

<210> SEQ ID NO 28
<211> LENGTH: 132
<212> TYPE: DNA
<213> ORGANISM: Artificial Sequence
<220> FEATURE:
<223> OTHER INFORMATION: Zebrafish preTCAP3 (132 n.a.)

<400> SEQUENCE: 28

```
aggcagttgc tcagctctgg gaaggtgctg ggttacgatg gttactatgt actatcagtg    60
gagcaatacc ctgaactggc cgacagtgcc aacaatgtcc agttcttgag cagagtgag   120 atagggaaga gg                                                      132
```

<210> SEQ ID NO 29
<211> LENGTH: 40
<212> TYPE: PRT
<213> ORGANISM: Artificial Sequence
<220> FEATURE:
<223> OTHER INFORMATION: Zebrafish TCAP4 (40 a.a.)

<400> SEQUENCE: 29

```
Gln Leu Leu Ser Ser Gly Arg Val Gln Gly Tyr Glu Gly Phe Tyr Ile
1               5                   10                  15

Val Ser Val Asp Gln Phe Pro Glu Leu Thr Asp Asn Ile Asn Asn Val
            20                  25                  30

His Phe Trp Arg Gln Thr Glu Met
        35                  40
```

<210> SEQ ID NO 30
<211> LENGTH: 41
<212> TYPE: PRT
<213> ORGANISM: Artificial Sequence
<220> FEATURE:
<223> OTHER INFORMATION: Zebrafish TCAP4 (41 a.a.)

<400> SEQUENCE: 30

```
Gln Gln Leu Leu Ser Ser Gly Arg Val Gln Gly Tyr Glu Gly Phe Tyr
1               5                   10                  15

Ile Val Ser Val Asp Gln Phe Pro Glu Leu Thr Asp Asn Ile Asn Asn
            20                  25                  30

Val His Phe Trp Arg Gln Thr Glu Met
        35                  40
```

<210> SEQ ID NO 31
<211> LENGTH: 43
<212> TYPE: PRT
<213> ORGANISM: Artificial Sequence
<220> FEATURE:
<223> OTHER INFORMATION: Zebrafish preTCAP4 (43 a.a.)

<400> SEQUENCE: 31

```
Gln Leu Leu Ser Ser Gly Arg Val Gln Gly Tyr Glu Gly Phe Tyr Ile
1               5                   10                  15

Val Ser Val Asp Gln Phe Pro Glu Leu Thr Asp Asn Ile Asn Asn Val
            20                  25                  30

His Phe Trp Arg Gln Thr Glu Met Gly Arg Arg
        35                  40
```

<210> SEQ ID NO 32
<211> LENGTH: 44
<212> TYPE: PRT
<213> ORGANISM: Artificial Sequence
<220> FEATURE:
<223> OTHER INFORMATION: Zebrafish preTCAP4 (44 a.a.)

<400> SEQUENCE: 32

```
Gln Gln Leu Leu Ser Ser Gly Arg Val Gln Gly Tyr Glu Gly Phe Tyr
1               5                   10                  15

Ile Val Ser Val Asp Gln Phe Pro Glu Leu Thr Asp Asn Ile Asn Asn
            20                  25                  30
```

Val His Phe Trp Arg Gln Thr Glu Met Gly Arg Arg
            35                      40

<210> SEQ ID NO 33
<211> LENGTH: 120
<212> TYPE: DNA
<213> ORGANISM: Artificial Sequence
<220> FEATURE:
<223> OTHER INFORMATION: Zebrafish TCAP4 (120 n.a.)

<400> SEQUENCE: 33
cagctcctaa gctctggacg tgtacagggc tacgaaggct tctacatagt atcagtcgac    60
cagttcccag agttgactga acacataaat aacgtccatt tctggcgaca gactgagatg   120

<210> SEQ ID NO 34
<211> LENGTH: 123
<212> TYPE: DNA
<213> ORGANISM: Artificial Sequence
<220> FEATURE:
<223> OTHER INFORMATION: Zebrafish TCAP4 (123 n.a.)

<400> SEQUENCE: 34
cagcagctcc taagctctgg acgtgtacag ggctacgaag gcttctacat agtatcagtc    60
gaccagttcc cagagttgac tgacaacata ataacgtcc atttctggcg acagactgag   120
atg                                                                 123

<210> SEQ ID NO 35
<211> LENGTH: 129
<212> TYPE: DNA
<213> ORGANISM: Artificial Sequence
<220> FEATURE:
<223> OTHER INFORMATION: Zebrafish preTCAP4 (129 n.a.)

<400> SEQUENCE: 35
cagctcctaa gctctggacg tgtacagggc tacgaaggct tctacatagt atcagtcgac    60
cagttcccag agttgactga acacataaat aacgtccatt tctggcgaca gactgagatg   120
ggacgcagg                                                           129

<210> SEQ ID NO 36
<211> LENGTH: 132
<212> TYPE: DNA
<213> ORGANISM: Artificial Sequence
<220> FEATURE:
<223> OTHER INFORMATION: Zebrafish preTCAP4 (132 n.a.)

<400> SEQUENCE: 36
cagcagctcc taagctctgg acgtgtacag ggcttctacat agtatcagtc    60 gaccagttcc cagagttgac tgacaacata ataacgtcc atttctggcg acagactgag   120
atgggacgca gg                                                       132

<210> SEQ ID NO 37
<211> LENGTH: 40
<212> TYPE: PRT
<213> ORGANISM: Artificial Sequence
<220> FEATURE:
<223> OTHER INFORMATION: Mouse TCAP1 (40 a.a.)

<400> SEQUENCE: 37

Gln Leu Leu Gly Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile

His Phe Met Arg Gln Ser Glu Ile
        35              40

<210> SEQ ID NO 38
<211> LENGTH: 41
<212> TYPE: PRT
<213> ORGANISM: Artificial Sequence
<220> FEATURE:
<223> OTHER INFORMATION: Mouse TCAP1 (41 a.a.)

<400> SEQUENCE: 38

Gln Gln Leu Leu Gly Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35              40

<210> SEQ ID NO 39
<211> LENGTH: 43
<212> TYPE: PRT
<213> ORGANISM: Artificial Sequence
<220> FEATURE:
<223> OTHER INFORMATION: Mouse preTCAP1 (43 a.a.)

<400> SEQUENCE: 39

Gln Leu Leu Gly Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile Gly Arg Arg
        35              40

<210> SEQ ID NO 40
<211> LENGTH: 44
<212> TYPE: PRT
<213> ORGANISM: Artificial Sequence
<220> FEATURE:
<223> OTHER INFORMATION: Mouse preTCAP1 (44 a.a.)

<400> SEQUENCE: 40

Gln Gln Leu Leu Gly Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile Gly Arg Arg
        35              40

<210> SEQ ID NO 41
<211> LENGTH: 120
<212> TYPE: DNA
<213> ORGANISM: Artificial Sequence
<220> FEATURE:
<223> OTHER INFORMATION: Mouse TCAP1 (120 n.a.)

<400> SEQUENCE: 41
cagcttttgg gcaccgggag ggtgcagggg tatgatgggt attttgtctt gtctgttgag      60
cagtatttag aactttcaga cagtgccaac aatattcact tcatgagaca gagtgaaata     120

<210> SEQ ID NO 42
<211> LENGTH: 123

<212> TYPE: DNA
<213> ORGANISM: Artificial Sequence
<220> FEATURE:
<223> OTHER INFORMATION: Mouse TCAP1 (123 n.a.)

<400> SEQUENCE: 42
cagcagcttt tgggcaccgg gagggtgcag gggtatgatg ggtattttgt cttgtctgtt      60
gagcagtatt tagaactttc agacagtgcc aacaatattc acttcatgag acagagtgaa      120
ata                                                                    123

<210> SEQ ID NO 43
<211> LENGTH: 129
<212> TYPE: DNA
<213> ORGANISM: Artificial Sequence
<220> FEATURE:
<223> OTHER INFORMATION: Mouse preTCAP1 (129 n.a.)

<400> SEQUENCE: 43
cagcttttgg gcaccgggag ggtgcagggg tatgatgggt attttgtctt gtctgttgag      60
cagtatttag aactttcaga cagtgccaac aatattcact tcatgagaca gagtgaaata      120
ggcaggagg                                                              129

<210> SEQ ID NO 44
<211> LENGTH: 132
<212> TYPE: DNA
<213> ORGANISM: Artificial Sequence
<220> FEATURE:
<223> OTHER INFORMATION: Mouse preTCAP1 (132 n.a.)

<400> SEQUENCE: 44
cagcagcttt tgggcaccgg gagggtgcag gggtatgatg ggtattttgt cttgtctgtt      60
gagcagtatt tagaactttc agacagtgcc aacaatattc acttcatgag acagagtgaa      120
ataggcagga gg                                                          132

<210> SEQ ID NO 45
<211> LENGTH: 40
<212> TYPE: PRT
<213> ORGANISM: Artificial Sequence
<220> FEATURE:
<223> OTHER INFORMATION: Mouse TCAP2 (40 a.a.)

<400> SEQUENCE: 45

Gln Leu Leu Ser Thr Gly Arg Val Gln Gly Tyr Glu Gly Tyr Tyr Val
1               5                   10                  15

Leu Pro Val Glu Gln Tyr Pro Glu Leu Ala Asp Ser Ser Ser Asn Ile
            20                  25                  30

Gln Phe Leu Arg Gln Asn Glu Ile
        35                  40

<210> SEQ ID NO 46
<211> LENGTH: 41
<212> TYPE: PRT
<213> ORGANISM: Artificial Sequence
<220> FEATURE:
<223> OTHER INFORMATION: Mouse TCAP2 (41 a.a.)

<400> SEQUENCE: 46

Gln Gln Leu Leu Ser Thr Gly Arg Val Gln Gly Tyr Glu Gly Tyr Tyr
1               5                   10                  15

Val Leu Pro Val Glu Gln Tyr Pro Glu Leu Ala Asp Ser Ser Ser Asn
            20                  25                  30

Ile Gln Phe Leu Arg Gln Asn Glu Met
        35                  40

<210> SEQ ID NO 47
<211> LENGTH: 43
<212> TYPE: PRT
<213> ORGANISM: Artificial Sequence
<220> FEATURE:
<223> OTHER INFORMATION: Mouse preTCAP2 (43 a.a)

<400> SEQUENCE: 47

Gln Leu Leu Ser Thr Gly Arg Val Gln Gly Tyr Glu Gly Tyr Tyr Val
1               5                   10                  15

Leu Pro Val Glu Gln Tyr Pro Glu Leu Ala Asp Ser Ser Asn Ile
            20                  25                  30

Gln Phe Leu Arg Gln Asn Glu Met Gly Lys Arg
        35                  40

<210> SEQ ID NO 48
<211> LENGTH: 44
<212> TYPE: PRT
<213> ORGANISM: Artificial Sequence
<220> FEATURE:
<223> OTHER INFORMATION: Mouse preTCAP2 (44 a.a.)

<400> SEQUENCE: 48

Gln Gln Leu Leu Ser Thr Gly Arg Val Gln Gly Tyr Glu Gly Tyr Tyr
1               5                   10                  15

Val Leu Pro Val Glu Gln Tyr Pro Glu Leu Ala Asp Ser Ser Ser Asn
            20                  25                  30

Ile Gln Phe Leu Arg Gln Asn Glu Met Gly Lys Arg
        35                  40

<210> SEQ ID NO 49
<211> LENGTH: 120
<212> TYPE: DNA
<213> ORGANISM: Artificial Sequence
<220> FEATURE:
<223> OTHER INFORMATION: Mouse TCAP2 (120 n.a.)

<400> SEQUENCE: 49
caactcctga gcacgggacg ggtacaaggt tatgagggct attacgtact tccggtggaa    60
cagtacccgg agctggcaga cagtagcagc aacatccagt tcttaagaca gaatgagagg   120

<210> SEQ ID NO 50
<211> LENGTH: 123
<212> TYPE: DNA
<213> ORGANISM: Artificial Sequence
<220> FEATURE:
<223> OTHER INFORMATION: Mouse TCAP 2 (123 n.a.)

<400> SEQUENCE: 50
cagcaactcc tgagcacggg acgggtacaa ggttatgagg gctattacgt acttccggtg    60
gaacagtacc cggagctggc agacagtagc agcaacatcc agttcttaag acagaatgag   120
atg                                                                 123

<210> SEQ ID NO 51
<211> LENGTH: 129
<212> TYPE: DNA
<213> ORGANISM: Artificial Sequence
<220> FEATURE:
<223> OTHER INFORMATION: Mouse preTCAP2 (129 n.a.)

-continued

<400> SEQUENCE: 51
caactcctga gcacgggacg ggtacaaggt tatgagggct attacgtact tccggtggaa    60
cagtacccgg agctggcaga cagtagcagc aacatccagt tcttaagaca gaatgagatg   120
ggaaagagg                                                          129

<210> SEQ ID NO 52
<211> LENGTH: 132
<212> TYPE: DNA
<213> ORGANISM: Artificial Sequence
<220> FEATURE:
<223> OTHER INFORMATION: Mouse preTCAP2 (132 n.a.)

<400> SEQUENCE: 52
cagcaactcc tgagcacggg acgggtacaa ggttatgagg gctattacgt acttccggtg    60
gaacagtacc cggagctggc agacagtagc agcaacatcc agttcttaag acagaatgag   120
atgggaaaga gg                                                      132

<210> SEQ ID NO 53
<211> LENGTH: 40
<212> TYPE: PRT
<213> ORGANISM: Artificial Sequence
<220> FEATURE:
<223> OTHER INFORMATION: Mouse TCAP3 (40 a.a.)

<400> SEQUENCE: 53

Gln Leu Leu Ser Ala Gly Lys Val Gln Gly Tyr Asp Gly Tyr Tyr Val
1               5                   10                  15

Leu Ser Val Glu Gln Tyr Pro Glu Leu Ala Asp Ser Ala Asn Asn Ile
            20                  25                  30

Gln Phe Leu Arg Gln Ser Glu Ile
        35                  40

<210> SEQ ID NO 54
<211> LENGTH: 41
<212> TYPE: PRT
<213> ORGANISM: Artificial Sequence
<220> FEATURE:
<223> OTHER INFORMATION: Mouse TCAP3 (41 a..a)

<400> SEQUENCE: 54

Arg Gln Leu Leu Ser Ala Gly Lys Val Gln Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Ile Gln Phe Leu Arg Gln Ser Glu Ile
        35                  40

<210> SEQ ID NO 55
<211> LENGTH: 43
<212> TYPE: PRT
<213> ORGANISM: Artificial Sequence
<220> FEATURE:
<223> OTHER INFORMATION: Mouse preTCAP3 (43 a.a.)

<400> SEQUENCE: 55

Gln Leu Leu Ser Ala Gly Lys Val Gln Gly Tyr Asp Gly Tyr Tyr Val
1               5                   10                  15

Leu Ser Val Glu Gln Tyr Pro Glu Leu Ala Asp Ser Ala Asn Asn Ile
            20                  25                  30

```
Gln Phe Leu Arg Gln Ser Glu Ile Gly Lys Arg
        35                  40
```

<210> SEQ ID NO 56
<211> LENGTH: 44
<212> TYPE: PRT
<213> ORGANISM: Artificial Sequence
<220> FEATURE:
<223> OTHER INFORMATION: Mouse preTCAP3 (44 a.a.)

<400> SEQUENCE: 56

```
Arg Gln Leu Leu Ser Ala Gly Lys Val Gln Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Ile Gln Phe Leu Arg Gln Ser Glu Ile Gly Lys Arg
        35                  40
```

<210> SEQ ID NO 57
<211> LENGTH: 120
<212> TYPE: DNA
<213> ORGANISM: Artificial Sequence
<220> FEATURE:
<223> OTHER INFORMATION: Mouse TCAP3 (120 n.a.)

<400> SEQUENCE: 57

```
cagctgctga gcgctggcaa ggtgcagggc tacgatgggt actacgtact gtcggtggag    60
cagtaccccg agctggctga cagtgccaac aacatccagt tcttgcgaca aagtgagatc   120
```

<210> SEQ ID NO 58
<211> LENGTH: 123
<212> TYPE: DNA
<213> ORGANISM: Artificial Sequence
<220> FEATURE:
<223> OTHER INFORMATION: Mouse TCAP3 (123 n.a.)

<400> SEQUENCE: 58

```
cggcagctgc tgagcgctgg caaggtgcag ggctacgatg gtactacgt actgtcggtg     60 gagcagtacc ccgagctggc tgacagtgcc aacaacatcc agttcttgcg acaaagtgag   120
atc                                                                 123
```

<210> SEQ ID NO 59
<211> LENGTH: 129
<212> TYPE: DNA
<213> ORGANISM: Artificial Sequence
<220> FEATURE:
<223> OTHER INFORMATION: Mouse preTCAP3 (129 n.a.)

<400> SEQUENCE: 59

```
cagctgctga gcgctggcaa ggtgcagggc tacgatgggt actacgtact gtcggtggag    60
cagtaccccg agctggctga cagtgccaac aacatccagt tcttgcgaca aagtgagatc   120
ggcaagagg                                                           129
```

<210> SEQ ID NO 60
<211> LENGTH: 132
<212> TYPE: DNA
<213> ORGANISM: Artificial Sequence
<220> FEATURE:
<223> OTHER INFORMATION: Mouse preTCAP3 (132 n.a.)

<400> SEQUENCE: 60

```
cggcagctgc tgagcgctgg caaggtgcag ggctacgatg gtactacgt actgtcggtg     60
```
gagcagtacc ccgagctggc tgacagtgcc aacaacatcc agttcttgcg acaaagtgag    120
atcggcaaga gg    132

<210> SEQ ID NO 61
<211> LENGTH: 40
<212> TYPE: PRT
<213> ORGANISM: Artificial Sequence
<220> FEATURE:
<223> OTHER INFORMATION: Mouse TCAP4 (40 a.a.)

<400> SEQUENCE: 61

Gln Val Leu Asn Thr Gly Arg Val Gln Gly Tyr Asp Gly Phe Phe Val
1               5                   10                  15

Thr Ser Val Glu Gln Tyr Pro Glu Leu Ser Asp Ser Ala Asn Asn Ile
            20                  25                  30

His Phe Met Arg Gln Ser Glu Met
        35                  40

<210> SEQ ID NO 62
<211> LENGTH: 41
<212> TYPE: PRT
<213> ORGANISM: Artificial Sequence
<220> FEATURE:
<223> OTHER INFORMATION: Mouse TCAP4 (41 a.a.)

<400> SEQUENCE: 62

Gln Gln Val Leu Asn Thr Gly Arg Val Gln Gly Tyr Asp Gly Phe Phe
1               5                   10                  15

Val Thr Ser Val Glu Gln Tyr Pro Glu Leu Ser Asp Ser Ala Asn Asn
            20                  25                  30

Ile His Phe Met Arg Gln Ser Glu Met
        35                  40

<210> SEQ ID NO 63
<211> LENGTH: 43
<212> TYPE: PRT
<213> ORGANISM: Artificial Sequence
<220> FEATURE:
<223> OTHER INFORMATION: Mouse preTCAP4 (43 a.a.)

<400> SEQUENCE: 63

Gln Val Leu Asn Thr Gly Arg Val Gln Gly Tyr Asp Gly Phe Phe Val
1               5                   10                  15

Thr Ser Val Glu Gln Tyr Pro Glu Leu Ser Asp Ser Ala Asn Asn Ile
            20                  25                  30

His Phe Met Arg Gln Ser Glu Met Gly Arg Arg
        35                  40

<210> SEQ ID NO 64
<211> LENGTH: 44
<212> TYPE: PRT
<213> ORGANISM: Artificial Sequence
<220> FEATURE:
<223> OTHER INFORMATION: Mouse preTCAP4 (44 a.a.)

<400> SEQUENCE: 64

Gln Gln Val Leu Asn Thr Gly Arg Val Gln Gly Tyr Asp Gly Phe Phe
1               5                   10                  15

Val Thr Ser Val Glu Gln Tyr Pro Glu Leu Ser Asp Ser Ala Asn Asn
            20                  25                  30

Ile His Phe Met Arg Gln Ser Glu Met Gly Arg Arg

<210> SEQ ID NO 65
<211> LENGTH: 120
<212> TYPE: DNA
<213> ORGANISM: Artificial Sequence
<220> FEATURE:
<223> OTHER INFORMATION: Mouse TCAP4 (120 n.a.)

<400> SEQUENCE: 65
caggtgctga acacggggcg ggtgcaaggc tacgacggct tctttgtgac ctcggtcgag    60
cagtacccag aactgtcaga cagcgccaac aatatccact tcatgagaca gagcgagatg   120

<210> SEQ ID NO 66
<211> LENGTH: 123
<212> TYPE: DNA
<213> ORGANISM: Artificial Sequence
<220> FEATURE:
<223> OTHER INFORMATION: Mouse TCAP4 (123 n.a.)

<400> SEQUENCE: 66
cagcaggtgc tgaacacggg gcgggtgcaa ggctacgacg gcttctttgt gacctcggtc    60
gagcagtacc cagaactgtc agacagcgcc aacaatatcc acttcatgag acagagcgag   120
atg                                                                 123

<210> SEQ ID NO 67
<211> LENGTH: 129
<212> TYPE: DNA
<213> ORGANISM: Artificial Sequence
<220> FEATURE:
<223> OTHER INFORMATION: Mouse preTCAP4 (129 n.a.)

<400> SEQUENCE: 67
caggtgctga acacggggcg ggtgcaaggc tacgacggct tctttgtgac ctcggtcgag    60
cagtacccag aactgtcaga cagcgccaac aatatccact tcatgagaca gagcgagatg   120
ggccgaagg                                                           129

<210> SEQ ID NO 68
<211> LENGTH: 132
<212> TYPE: DNA
<213> ORGANISM: Artificial Sequence
<220> FEATURE:
<223> OTHER INFORMATION: Mouse preTCAP4 (132 n.a.)

<400> SEQUENCE: 68
cagcaggtgc tgaacacggg gcgggtgcaa ggctacgacg gcttctttgt gacctcggtc    60
gagcagtacc cagaactgtc agacagcgcc aacaatatcc acttcatgag acagagcgag   120
atgggccgaa gg                                                       132

<210> SEQ ID NO 69
<211> LENGTH: 40
<212> TYPE: PRT
<213> ORGANISM: Artificial Sequence
<220> FEATURE:
<223> OTHER INFORMATION: Human TCAP1 (40 a.a.)

<400> SEQUENCE: 69

Gln Leu Leu Ser Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile
        35                  40

<210> SEQ ID NO 70
<211> LENGTH: 41
<212> TYPE: PRT
<213> ORGANISM: Artificial Sequence
<220> FEATURE:
<223> OTHER INFORMATION: Human TCAP1 (41 a.a.)

<400> SEQUENCE: 70

Gln Gln Leu Leu Ser Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35                  40

<210> SEQ ID NO 71
<211> LENGTH: 43
<212> TYPE: PRT
<213> ORGANISM: Artificial Sequence
<220> FEATURE:
<223> OTHER INFORMATION: Human preTCAP1 (43 a.a.)

<400> SEQUENCE: 71

Gln Leu Leu Ser Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile Gly Arg Arg
        35                  40

<210> SEQ ID NO 72
<211> LENGTH: 44
<212> TYPE: PRT
<213> ORGANISM: Artificial Sequence
<220> FEATURE:
<223> OTHER INFORMATION: Human preTCAP1 (44 a.a.)

<400> SEQUENCE: 72

Gln Gln Leu Leu Ser Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile Gly Arg Arg
        35                  40

<210> SEQ ID NO 73
<211> LENGTH: 120
<212> TYPE: DNA
<213> ORGANISM: Artificial Sequence
<220> FEATURE:
<223> OTHER INFORMATION: Human TCAP1 (120 n.a.)

<400> SEQUENCE: 73
cagcttttga gcactgggcg ggtacaaggt tacgatgggt attttgtttt gtctgttgag      60
cagtatttag aacttctga cagtgccaat aatattcact ttatgagaca gagcgaaata     120

<210> SEQ ID NO 74
<211> LENGTH: 123
<212> TYPE: DNA

<213> ORGANISM: Artificial Sequence
<220> FEATURE:
<223> OTHER INFORMATION: Human TCAP1 (123 n.a.)

<400> SEQUENCE: 74

```
cagcagcttt tgagcactgg gcgggtacaa ggttacgatg ggtattttgt tttgtctgtt    60
gagcagtatt tagaactttc tgacagtgcc aataatattc actttatgag acagagcgaa   120
ata                                                                 123
```

<210> SEQ ID NO 75
<211> LENGTH: 129
<212> TYPE: DNA
<213> ORGANISM: Artificial Sequence
<220> FEATURE:
<223> OTHER INFORMATION: Human preTCAP1 (129 n.a.)

<400> SEQUENCE: 75

```
cagcttttga gcactgggcg ggtacaaggt tacgatgggt attttgtttt gtctgttgag    60
cagtatttag aactttctga cagtgccaat aatattcact ttatgagaca gagcgaaata   120
ggcaggagg                                                           129
```

<210> SEQ ID NO 76
<211> LENGTH: 132
<212> TYPE: DNA
<213> ORGANISM: Artificial Sequence
<220> FEATURE:
<223> OTHER INFORMATION: Human preTCAP1 (132 n.a.)

<400> SEQUENCE: 76

```
cagcagcttt tgagcactgg gcgggtacaa ggttacgatg ggtattttgt tttgtctgtt    60
gagcagtatt tagaactttc tgacagtgcc aataatattc actttatgag acagagcgaa   120
ataggcagga gg                                                       132
```

<210> SEQ ID NO 77
<211> LENGTH: 40
<212> TYPE: PRT
<213> ORGANISM: Artificial Sequence
<220> FEATURE:
<223> OTHER INFORMATION: Human TCAP2 (40 a.a.)

<400> SEQUENCE: 77

```
Gln Leu Leu Ser Thr Gly Arg Val Gln Gly Tyr Glu Gly Tyr Tyr Val
1               5                   10                  15
Leu Pro Val Glu Gln Tyr Pro Glu Leu Ala Asp Ser Ser Ser Asn Ile
            20                  25                  30
Gln Phe Leu Arg Gln Asn Glu Met
        35                  40
```

<210> SEQ ID NO 78
<211> LENGTH: 41
<212> TYPE: PRT
<213> ORGANISM: Artificial Sequence
<220> FEATURE:
<223> OTHER INFORMATION: Human preTCAP2 (41 a.a.)

<400> SEQUENCE: 78

```
Gln Gln Leu Leu Ser Thr Gly Arg Val Gln Gly Tyr Glu Gly Tyr Tyr
1               5                   10                  15
Val Leu Pro Val Glu Gln Tyr Pro Glu Leu Ala Asp Ser Ser Ser Asn
            20                  25                  30
```

Ile Gln Phe Leu Arg Gln Asn Glu Met
         35                  40

<210> SEQ ID NO 79
<211> LENGTH: 43
<212> TYPE: PRT
<213> ORGANISM: Artificial Sequence
<220> FEATURE:
<223> OTHER INFORMATION: Human preTCAP2 (43 a.a.)

<400> SEQUENCE: 79

Gln Leu Leu Ser Thr Gly Arg Val Gln Gly Tyr Glu Gly Tyr Tyr Val
1               5                   10                  15

Leu Pro Val Glu Gln Tyr Pro Glu Leu Ala Asp Ser Ser Ser Asn Ile
            20                  25                  30

Gln Phe Leu Arg Gln Asn Glu Met Gly Lys Arg
         35                  40

<210> SEQ ID NO 80
<211> LENGTH: 44
<212> TYPE: PRT
<213> ORGANISM: Artificial Sequence
<220> FEATURE:
<223> OTHER INFORMATION: Human preTCAP2 (44 a.a.)

<400> SEQUENCE: 80

Gln Gln Leu Leu Ser Thr Gly Arg Val Gln Gly Tyr Glu Gly Tyr Tyr
1               5                   10                  15

Val Leu Pro Val Glu Gln Tyr Pro Glu Leu Ala Asp Ser Ser Ser Asn
            20                  25                  30

Ile Gln Phe Leu Arg Gln Asn Glu Met Gly Lys Arg
         35                  40

<210> SEQ ID NO 81
<211> LENGTH: 120
<212> TYPE: DNA
<213> ORGANISM: Artificial Sequence
<220> FEATURE:
<223> OTHER INFORMATION: Human TCAP2 (120 n.a.)

<400> SEQUENCE: 81
cagcttctga gcaccgggcg cgtgcaaggg tacgagggat attacgtgct tcccgtggag    60
caatacccag agcttgcaga cagtagcagc aacatccagt ttttaagaca gaatgagatg   120

<210> SEQ ID NO 82
<211> LENGTH: 123
<212> TYPE: DNA
<213> ORGANISM: Artificial Sequence
<220> FEATURE:
<223> OTHER INFORMATION: Human TCAP2 (123 n.a.)

<400> SEQUENCE: 82
cagcagcttc tgagcaccgg gcgcgtgcaa gggtacgagg gatattacgt gcttcccgtg    60
gagcaatacc cagagcttgc agacagtagc agcaacatcc agttttttaag acagaatgag  120 atg                                                                 123

<210> SEQ ID NO 83
<211> LENGTH: 129
<212> TYPE: DNA
<213> ORGANISM: Artificial Sequence
<220> FEATURE:
<223> OTHER INFORMATION: Human preTCAP2 (129 n.a.)

```
<400> SEQUENCE: 83
cagcttctga gcaccgggcg cgtgcaaggg tacgagggat attacgtgct tcccgtggag    60
caatacccag agcttgcaga cagtagcagc aacatccagt ttttaagaca gaatgagatg   120
ggaaagagg                                                          129

<210> SEQ ID NO 84
<211> LENGTH: 132
<212> TYPE: DNA
<213> ORGANISM: Artificial Sequence
<220> FEATURE:
<223> OTHER INFORMATION: Human preTCAP2 (132 n.a.)

<400> SEQUENCE: 84
cagcagcttc tgagcaccgg gcgcgtgcaa gggtacgagg gatattacgt gcttcccgtg    60
gagcaatacc cagagcttgc agacagtagc agcaacatcc agttttttaag acagaatgag  120 atgggaaaga gg                                                      132

<210> SEQ ID NO 85
<211> LENGTH: 40
<212> TYPE: PRT
<213> ORGANISM: Artificial Sequence
<220> FEATURE:
<223> OTHER INFORMATION: Human TCAP3 (40 a.a.)

<400> SEQUENCE: 85

Gln Leu Leu Ser Ala Gly Lys Val Gln Gly Tyr Asp Gly Tyr Tyr Val
1               5                   10                  15

Leu Ser Val Glu Gln Tyr Pro Glu Leu Ala Asp Ser Ala Asn Asn Ile
            20                  25                  30

Gln Phe Leu Arg Gln Ser Glu Ile
        35                  40

<210> SEQ ID NO 86
<211> LENGTH: 41
<212> TYPE: PRT
<213> ORGANISM: Artificial Sequence
<220> FEATURE:
<223> OTHER INFORMATION: Human TCAP3 (41 a.a.)

<400> SEQUENCE: 86

Arg Gln Leu Leu Ser Ala Gly Lys Val Gln Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Ile Gln Phe Leu Arg Gln Ser Glu Ile
        35                  40

<210> SEQ ID NO 87
<211> LENGTH: 43
<212> TYPE: PRT
<213> ORGANISM: Artificial Sequence
<220> FEATURE:
<223> OTHER INFORMATION: Human preTCAP3 (43 a.a.)

<400> SEQUENCE: 87

Gln Leu Leu Ser Ala Gly Lys Val Gln Gly Tyr Asp Gly Tyr Tyr Val
1               5                   10                  15

Leu Ser Val Glu Gln Tyr Pro Glu Leu Ala Asp Ser Ala Asn Asn Ile
            20                  25                  30

Gln Phe Leu Arg Gln Ser Glu Ile Gly Arg Arg
```

<210> SEQ ID NO 88
<211> LENGTH: 44
<212> TYPE: PRT
<213> ORGANISM: Artificial Sequence
<220> FEATURE:
<223> OTHER INFORMATION: Human preTCAP3 (44 a.a.)

<400> SEQUENCE: 88

Arg Gln Leu Leu Ser Ala Gly Lys Val Gln Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Ile Gln Phe Leu Arg Gln Ser Glu Ile Gly Arg Arg
        35                  40

<210> SEQ ID NO 89
<211> LENGTH: 120
<212> TYPE: DNA
<213> ORGANISM: Artificial Sequence
<220> FEATURE:
<223> OTHER INFORMATION: Human TCAP3 (120 n.a.)

<400> SEQUENCE: 89
cagctgctga gcgccggcaa ggtgcagggc tacgacgggt actacgtact ctcggtggag     60
cagtaccccg agctggccga cagcgccaac aacatccagt tcctgcggca gagcgagatc    120

<210> SEQ ID NO 90
<211> LENGTH: 123
<212> TYPE: DNA
<213> ORGANISM: Artificial Sequence
<220> FEATURE:
<223> OTHER INFORMATION: Human TCAP3 (123 n.a.)

<400> SEQUENCE: 90
cggcagctgc tgagcgccgg caaggtgcag ggctacgacg ggtactacgt actctcggtg     60
gagcagtacc ccgagctggc cgacagcgcc aacaacatcc agttcctgcg gcagagcgag    120
atc                                                                 123

<210> SEQ ID NO 91
<211> LENGTH: 129
<212> TYPE: DNA
<213> ORGANISM: Artificial Sequence
<220> FEATURE:
<223> OTHER INFORMATION: Human preTCAP (129 n.a.)

<400> SEQUENCE: 91
cagctgctga gcgccggcaa ggtgcagggc tacgacgggt actacgtact ctcggtggag     60
cagtaccccg agctggccga cagcgccaac aacatccagt tcctgcggca gagcgagatc    120
ggcaggagg                                                           129

<210> SEQ ID NO 92
<211> LENGTH: 132
<212> TYPE: DNA
<213> ORGANISM: Artificial Sequence
<220> FEATURE:
<223> OTHER INFORMATION: Human preTCAP3 (132 n.a.)

<400> SEQUENCE: 92
cggcagctgc tgagcgccgg caaggtgcag ggctacgacg ggtactacgt actctcggtg     60

```
gagcagtacc ccgagctggc cgacagcgcc aacaacatcc agttcctgcg gcagagcgag    120
atcggcagga gg                                                        132
```

<210> SEQ ID NO 93
<211> LENGTH: 40
<212> TYPE: PRT
<213> ORGANISM: Artificial Sequence
<220> FEATURE:
<223> OTHER INFORMATION: Human TCAP4 (40 a.a.)

<400> SEQUENCE: 93

```
Gln Val Leu Ser Thr Gly Arg Val Gln Gly Tyr Asp Gly Phe Phe Val
1               5                   10                  15

Ile Ser Val Glu Gln Tyr Pro Glu Leu Ser Asp Ser Ala Asn Asn Ile
            20                  25                  30

His Phe Met Arg Gln Ser Glu Met
        35                  40
```

<210> SEQ ID NO 94
<211> LENGTH: 41
<212> TYPE: PRT
<213> ORGANISM: Artificial Sequence
<220> FEATURE:
<223> OTHER INFORMATION: Human TCAP4 (41 a.a.)

<400> SEQUENCE: 94

```
Gln Gln Val Leu Ser Thr Gly Arg Val Gln Gly Tyr Asp Gly Phe Phe
1               5                   10                  15

Val Ile Ser Val Glu Gln Tyr Pro Glu Leu Ser Asp Ser Ala Asn Asn
            20                  25                  30

Ile His Phe Met Arg Gln Ser Glu Met
        35                  40
```

<210> SEQ ID NO 95
<211> LENGTH: 43
<212> TYPE: PRT
<213> ORGANISM: Artificial Sequence
<220> FEATURE:
<223> OTHER INFORMATION: Human preTCAP4 (43 a..a)

<400> SEQUENCE: 95

```
Gln Val Leu Ser Thr Gly Arg Val Gln Gly Tyr Asp Gly Phe Phe Val
1               5                   10                  15

Ile Ser Val Glu Gln Tyr Pro Glu Leu Ser Asp Ser Ala Asn Asn Ile
            20                  25                  30

His Phe Met Arg Gln Ser Glu Met Gly Arg Arg
        35                  40
```

<210> SEQ ID NO 96
<211> LENGTH: 44
<212> TYPE: PRT
<213> ORGANISM: Artificial Sequence
<220> FEATURE:
<223> OTHER INFORMATION: Human preTCAP4 (44 a.a.)

<400> SEQUENCE: 96

```
Gln Gln Val Leu Ser Thr Gly Arg Val Gln Gly Tyr Asp Gly Phe Phe
1               5                   10                  15

Val Ile Ser Val Glu Gln Tyr Pro Glu Leu Ser Asp Ser Ala Asn Asn
            20                  25                  30

Ile His Phe Met Arg Gln Ser Glu Met Gly Arg Arg
        35                  40
```

<210> SEQ ID NO 97
<211> LENGTH: 120
<212> TYPE: DNA
<213> ORGANISM: Artificial Sequence
<220> FEATURE:
<223> OTHER INFORMATION: Human TCAP4 (120 n.a.)

<400> SEQUENCE: 97

```
caggtgctga gcacagggcg ggtgcaaggc tacgacggct ttttcgtgat ctctgtcgag      60
cagtacccag aactgtcaga cagcgccaac aacatccact tcatgagaca gagcgagatg     120
```

<210> SEQ ID NO 98
<211> LENGTH: 123
<212> TYPE: DNA
<213> ORGANISM: Artificial Sequence
<220> FEATURE:
<223> OTHER INFORMATION: Human TCAP4 (123 n.a.)

<400> SEQUENCE: 98

```
cagcaggtgc tgagcacagg gcgggtgcaa ggctacgacg cttttcgt gatctctgtc       60
gagcagtacc cagaactgtc agacagcgcc aacaacatcc acttcatgag acagagcgag    120
atg                                                                  123
```

<210> SEQ ID NO 99
<211> LENGTH: 129
<212> TYPE: DNA
<213> ORGANISM: Artificial Sequence
<220> FEATURE:
<223> OTHER INFORMATION: Human preTCAP4 (129 n.a.)

<400> SEQUENCE: 99

```
caggtgctga gcacagggcg ggtgcaaggc tacgacggct ttttcgtgat ctctgtcgag      60
cagtacccag aactgtcaga cagcgccaac aacatccact tcatgagaca gagcgagatg    120
ggccggagg                                                            129
```

<210> SEQ ID NO 100
<211> LENGTH: 132
<212> TYPE: DNA
<213> ORGANISM: Artificial Sequence
<220> FEATURE:
<223> OTHER INFORMATION: Human preTCAP4 (132 n.a.)

<400> SEQUENCE: 100

```
cagcaggtgc tgagcacagg gcgggtgcaa ggctacgacg cttttcgt gatctctgtc       60
gagcagtacc cagaactgtc agacagcgcc aacaacatcc acttcatgag acagagcgag    120
atgggccgga gg                                                        132
```

<210> SEQ ID NO 101
<211> LENGTH: 41
<212> TYPE: PRT
<213> ORGANISM: Artificial Sequence
<220> FEATURE:
<223> OTHER INFORMATION: G. gallus TCAP-1

<400> SEQUENCE: 101

```
Gln Gln Leu Leu Asn Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30
```

```
Ile His Phe Met Arg Gln Ser Glu Ile
        35                  40
```

<210> SEQ ID NO 102
<211> LENGTH: 41
<212> TYPE: PRT
<213> ORGANISM: Artificial Sequence
<220> FEATURE:
<223> OTHER INFORMATION: Zebrafish TCAP-4

<400> SEQUENCE: 102

```
Gln Gln Leu Leu Ser Ser Gly Arg Val Gln Gly Tyr Glu Gly Phe Tyr
1               5                   10                  15

Ile Val Ser Val Asp Gln Phe Pro Glu Leu Thr Asp Asn Ile Asn Asn
                20                  25                  30

Val His Phe Trp Arg Gln Thr Glu Met
        35                  40
```

<210> SEQ ID NO 103
<211> LENGTH: 37
<212> TYPE: PRT
<213> ORGANISM: Artificial Sequence
<220> FEATURE:
<223> OTHER INFORMATION: D. melanogaster Ten-m gene product

<400> SEQUENCE: 103

```
Glu Leu Val Gln His Gly Asp Val Asp Gly Trp Asn Gly Asp Ile His
1               5                   10                  15

Ser Ile His Lys Tyr Pro Gln Leu Ala Asp Pro Gly Asn Val Ala Phe
                20                  25                  30

Gln Arg Asp Ala Lys
        35
```

<210> SEQ ID NO 104
<211> LENGTH: 41
<212> TYPE: PRT
<213> ORGANISM: Artificial Sequence
<220> FEATURE:
<223> OTHER INFORMATION: Human CRF TCAP like region

<400> SEQUENCE: 104

```
Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
                20                  25                  30

Ser Asn Arg Lys Leu Met Glu Ile Ile
        35                  40
```

<210> SEQ ID NO 105
<211> LENGTH: 40
<212> TYPE: PRT
<213> ORGANISM: Artificial Sequence
<220> FEATURE:
<223> OTHER INFORMATION: Human urocortin TCAP-like region

<400> SEQUENCE: 105

```
Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
                20                  25                  30

Asn Arg Ile Ile Phe Asp Ser Val
        35                  40
```

<210> SEQ ID NO 106
<211> LENGTH: 38
<212> TYPE: PRT
<213> ORGANISM: Artificial Sequence
<220> FEATURE:
<223> OTHER INFORMATION: Human urocortin 2 TCAP-like region

<400> SEQUENCE: 106

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 107
<211> LENGTH: 38
<212> TYPE: PRT
<213> ORGANISM: Artificial Sequence
<220> FEATURE:
<223> OTHER INFORMATION: Human urocortin 3 TCAP=like region

<400> SEQUENCE: 107

Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
            20                  25                  30

His Leu Met Ala Gln Ile
        35

<210> SEQ ID NO 108
<211> LENGTH: 46
<212> TYPE: PRT
<213> ORGANISM: Artificial Sequence
<220> FEATURE:
<223> OTHER INFORMATION: L. migratoria DP

<400> SEQUENCE: 108

Met Gly Met Gly Pro Ser Leu Ser Ile Val Asn Pro Met Asp Val Leu
1               5                   10                  15

Arg Gln Arg Leu Leu Leu Glu Ile Ala Arg Arg Arg Leu Arg Asp Ala
            20                  25                  30

Glu Glu Gln Ile Lys Ala Asn Lys Asp Phe Leu Gln Gln Ile
        35                  40                  45

<210> SEQ ID NO 109
<211> LENGTH: 46
<212> TYPE: PRT
<213> ORGANISM: Artificial Sequence
<220> FEATURE:
<223> OTHER INFORMATION: A. domesticus DP

<400> SEQUENCE: 109

Thr Gly Ala Gln Ser Leu Ser Ile Val Ala Pro Leu Asp Val Leu Arg
1               5                   10                  15

Gln Arg Leu Met Asn Glu Leu Asn Arg Arg Arg Met Arg Glu Leu Gln
            20                  25                  30

Gly Ser Arg Ile Gln Gln Asn Arg Gln Leu Leu Thr Ser Ile
        35                  40                  45

<210> SEQ ID NO 110
<211> LENGTH: 39

```
<212> TYPE: PRT
<213> ORGANISM: Artificial Sequence
<220> FEATURE:
<223> OTHER INFORMATION: T. molitor DP

<400> SEQUENCE: 110

Ser Pro Thr Ile Ser Ile Thr Ala Pro Ile Asp Val Leu Arg Lys Thr
1               5                   10                  15

Trp Glu Gln Glu Arg Ala Arg Lys Gln Met Val Ala Gln Asn Asn Arg
            20                  25                  30

Glu Phe Leu Asn Ser Leu Asn
        35

<210> SEQ ID NO 111
<211> LENGTH: 41
<212> TYPE: PRT
<213> ORGANISM: Artificial Sequence
<220> FEATURE:
<223> OTHER INFORMATION: M. sexta DP-1

<400> SEQUENCE: 111

Arg Met Pro Ser Leu Ser Ile Asp Leu Pro Met Ser Val Leu Arg Gln
1               5                   10                  15

Lys Leu Ser Leu Glu Lys Glu Arg Lys Val His Ala Leu Arg Ala Ala
            20                  25                  30

Ala Asn Arg Asn Phe Leu Asn Asp Ile
        35                  40

<210> SEQ ID NO 112
<211> LENGTH: 30
<212> TYPE: PRT
<213> ORGANISM: Artificial Sequence
<220> FEATURE:
<223> OTHER INFORMATION: M. sexta DP-II

<400> SEQUENCE: 112

Ser Leu Ser Val Asn Pro Ala Val Asp Ile Leu Gln His Arg Tyr Met
1               5                   10                  15

Glu Lys Val Ala Gln Asn Asn Arg Asn Phe Leu Asn Arg Val
            20                  25                  30

<210> SEQ ID NO 113
<211> LENGTH: 45
<212> TYPE: PRT
<213> ORGANISM: Artificial Sequence
<220> FEATURE:
<223> OTHER INFORMATION: P. Americana

<400> SEQUENCE: 113

Thr Gly Ser Gly Pro Ser Leu Ser Ile Val Asn Pro Leu Asp Val Leu
1               5                   10                  15

Arg Gln Arg Leu Leu Leu Glu Ile Ala Arg Arg Met Arg Gln Ser
            20                  25                  30

Gln Asp Gln Ile Gln Asn Arg Glu Ile Leu Gln Thr Ile
        35                  40                  45

<210> SEQ ID NO 114
<211> LENGTH: 41
<212> TYPE: PRT
<213> ORGANISM: Artificial Sequence
<220> FEATURE:
<223> OTHER INFORMATION: O. keta CRP

<400> SEQUENCE: 114
```

```
Ser Asp Asp Pro Pro Ile Ser Leu Asp Leu Thr Phe His Met Leu Arg
1               5                   10                  15

Gln Met Asn Glu Met Ser Arg Ala Glu Gln Leu Gln Gln Gln Ala His
            20                  25                  30

Ser Asn Arg Lys Met Met Glu Ile Phe
        35                  40

<210> SEQ ID NO 115
<211> LENGTH: 40
<212> TYPE: PRT
<213> ORGANISM: Artificial Sequence
<220> FEATURE:
<223> OTHER INFORMATION: R. norvegicus

<400> SEQUENCE: 115

Asp Asp Pro Pro Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 116
<211> LENGTH: 37
<212> TYPE: PRT
<213> ORGANISM: Artificial Sequence
<220> FEATURE:
<223> OTHER INFORMATION: P. sauvageii

<400> SEQUENCE: 116

Gln Gly Pro Pro Ile Ser Ile Asp Leu Ser Leu Glu Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu
        35

<210> SEQ ID NO 117
<211> LENGTH: 41
<212> TYPE: PRT
<213> ORGANISM: Artificial Sequence
<220> FEATURE:
<223> OTHER INFORMATION: C. carpio US

<400> SEQUENCE: 117

Asn Asp Asp Pro Pro Ile Ser Ile Asp Leu Thr Phe His Leu Leu Arg
1               5                   10                  15

Asn Met Ile Glu Met Ala Arg Asn Glu Asn Gln Arg Glu Gln Ala Gly
            20                  25                  30

Leu Asn Arg Lys Tyr Leu Asp Glu Val
        35                  40

<210> SEQ ID NO 118
<211> LENGTH: 38
<212> TYPE: PRT
<213> ORGANISM: Artificial Sequence
<220> FEATURE:
<223> OTHER INFORMATION: M. Musculus UCN2

<400> SEQUENCE: 118

Val Ile Leu Ser Leu Asp Val Pro Ile Gly Leu Leu Arg Ile Leu Leu
1               5                   10                  15
```

```
Glu Gln Ala Arg Tyr Lys Ala Ala Arg Asn Gln Ala Ala Thr Asn Ala
            20                  25                  30

Gln Ile Leu Ala His Val
        35

<210> SEQ ID NO 119
<211> LENGTH: 38
<212> TYPE: PRT
<213> ORGANISM: Artificial Sequence
<220> FEATURE:
<223> OTHER INFORMATION: R. dano UCN2

<400> SEQUENCE: 119

Leu Thr Leu Ser Leu Asp Val Pro Thr Asn Ile Met Asn Val Leu Phe
1               5                   10                  15

Asp Val Ala Lys Ala Lys Asn Leu Arg Ala Lys Ala Ala Glu Asn Ala
            20                  25                  30

Arg Leu Leu Ala His Ile
        35

<210> SEQ ID NO 120
<211> LENGTH: 305
<212> TYPE: DNA
<213> ORGANISM: Artificial Sequence
<220> FEATURE:
<223> OTHER INFORMATION: Hamster 305bp urocortin cDNA probe examples
      "cloning mRNA"

<400> SEQUENCE: 120
attcaccgcc gctcgggatc tgagcctgca ggcgagcggc agcgacggga agaccttccg      60
ctgtccatcg acctcacatt ccacctgcta cggaccctgc tggagatggc ccggacacag     120
agccaacgcg agcgagcaga gcagaaccga atcatactca acgcggtggg caagtgatcg     180
gcccggtgtg ggaccccaaa aggctcgacc ctttccccta cctacccggg ggctgaagtc     240
acgcgaccga agtcggctta gtcccgcggt gcagcgcctc ccagagttac cctgaacaat     300
cccgc                                                                 305

<210> SEQ ID NO 121
<211> LENGTH: 24
<212> TYPE: DNA
<213> ORGANISM: Artificial Sequence
<220> FEATURE:
<223> OTHER INFORMATION: TCAP1 fwd primer

<400> SEQUENCE: 121
acgtcagtgt tgatgggagg acta                                             24

<210> SEQ ID NO 122
<211> LENGTH: 27
<212> TYPE: DNA
<213> ORGANISM: Artificial Sequence
<220> FEATURE:
<223> OTHER INFORMATION: TCAP1 rvs primer

<400> SEQUENCE: 122
cctcctgcct atttcactct gtctcat                                          27

<210> SEQ ID NO 123
<211> LENGTH: 25
<212> TYPE: DNA
<213> ORGANISM: Artificial Sequence
<220> FEATURE:
```

<223> OTHER INFORMATION: TCAP2 Fwd primer

<400> SEQUENCE: 123
tcgagggcaa ggacacacac tactt                                         25

<210> SEQ ID NO 124
<211> LENGTH: 26
<212> TYPE: DNA
<213> ORGANISM: Artificial Sequence
<220> FEATURE:
<223> OTHER INFORMATION: TCAP2 rvs primer

<400> SEQUENCE: 124
aagaactgga tgttgctgct actgtc                                        26

<210> SEQ ID NO 125
<211> LENGTH: 25
<212> TYPE: DNA
<213> ORGANISM: Artificial Sequence
<220> FEATURE:
<223> OTHER INFORMATION: TCAP3 fwd primer

<400> SEQUENCE: 125
caacaacgcc ttctacctgg agaac                                         25

<210> SEQ ID NO 126
<211> LENGTH: 21
<212> TYPE: DNA
<213> ORGANISM: Artificial Sequence
<220> FEATURE:
<223> OTHER INFORMATION: TCAP3 rvs primer

<400> SEQUENCE: 126
tgttgttggc actgtcagcc a                                             21

<210> SEQ ID NO 127
<211> LENGTH: 23
<212> TYPE: DNA
<213> ORGANISM: Artificial Sequence
<220> FEATURE:
<223> OTHER INFORMATION: TCAP4 fwd primer

<400> SEQUENCE: 127
tttgcctcca gtggttccat ctt                                           23

<210> SEQ ID NO 128
<211> LENGTH: 24
<212> TYPE: DNA
<213> ORGANISM: Artificial Sequence
<220> FEATURE:
<223> OTHER INFORMATION: TCAP4 rvs primer

<400> SEQUENCE: 128
tggatattgt tggcgctgtc tgac                                          24

<210> SEQ ID NO 129
<211> LENGTH: 6
<212> TYPE: PRT
<213> ORGANISM: Artificial Sequence
<220> FEATURE:
<223> OTHER INFORMATION: Conserved motif between CRF and TCAP I/L S X X
      (X)-L/V at amino terminus
<220> FEATURE:
<221> NAME/KEY: MISC_FEATURE
<222> LOCATION: (1)..(1)
<223> OTHER INFORMATION: X=I or L
<220> FEATURE:

```
<221> NAME/KEY: MISC_FEATURE
<222> LOCATION: (3)..(3)
<223> OTHER INFORMATION: X=T or A
<220> FEATURE:
<221> NAME/KEY: MISC_FEATURE
<222> LOCATION: (4)..(4)
<223> OTHER INFORMATION: X=L, I or G
<220> FEATURE:
<221> NAME/KEY: MISC_FEATURE
<222> LOCATION: (5)..(5)
<223> OTHER INFORMATION: X=D, R or K
<220> FEATURE:
<221> NAME/KEY: MISC_FEATURE
<222> LOCATION: (6)..(6)
<223> OTHER INFORMATION: X=L or V

<400> SEQUENCE: 129

Xaa Ser Xaa Xaa Xaa Xaa
1               5

<210> SEQ ID NO 130
<211> LENGTH: 4
<212> TYPE: PRT
<213> ORGANISM: Artificial Sequence
<220> FEATURE:
<223> OTHER INFORMATION: Conserved motif between CRF and TCAP - In
      middle L/V-L/I-X-V/ali phatic residue
<220> FEATURE:
<221> NAME/KEY: MISC_FEATURE
<222> LOCATION: (1)..(1)
<223> OTHER INFORMATION: X=V or L
<220> FEATURE:
<221> NAME/KEY: MISC_FEATURE
<222> LOCATION: (2)..(2)
<223> OTHER INFORMATION: X=L, I or F
<220> FEATURE:
<221> NAME/KEY: MISC_FEATURE
<222> LOCATION: (3)..(3)
<223> OTHER INFORMATION: X=E, N, S or P
<220> FEATURE:
<221> NAME/KEY: MISC_FEATURE
<222> LOCATION: (4)..(4)
<223> OTHER INFORMATION: X=M, L Q, I or V

<400> SEQUENCE: 130

Xaa Xaa Xaa Xaa
1

<210> SEQ ID NO 131
<211> LENGTH: 4
<212> TYPE: PRT
<213> ORGANISM: Artificial Sequence
<220> FEATURE:
<223> OTHER INFORMATION: Conserved motif between CRF and TCAP
      N/I/A-H/basic residue -I/L/F/-aliphatic at carboxy terminus
<220> FEATURE:
<221> NAME/KEY: MISC_FEATURE
<222> LOCATION: (2)..(2)
<223> OTHER INFORMATION: X=R, A or I
<220> FEATURE:
<221> NAME/KEY: MISC_FEATURE
<222> LOCATION: (3)..(3)
<223> OTHER INFORMATION: X=H or basic residues, K, I, R or Q
<220> FEATURE:
<221> NAME/KEY: MISC_FEATURE
<222> LOCATION: (4)..(4)
<223> OTHER INFORMATION: X=I, L or F

<400> SEQUENCE: 131

Asn Xaa Xaa Xaa
1

<210> SEQ ID NO 132
```

```
<211> LENGTH: 8964
<212> TYPE: DNA
<213> ORGANISM: Mus musculus
<220> FEATURE:
<221> NAME/KEY: exon
<222> LOCATION: (50)..(8197)

<400> SEQUENCE: 132
```

| | | | | | | | | | | | | |
|---|---|---|---|---|---|---|---|---|---|---|---|---|
| aagttctaag | aagccggacc | gatgtgcaca | gagaaggaat | gaaggaagt | atg | gat | gtg | | | | | 58 |
| | | | | | Met | Asp | Val | | | | | |
| | | | | | | | 1 | | | | | |

| aag | gaa | cgc | agg | cct | tac | tgc | tcc | ttg | acc | aag | agc | aga | cgg | gaa | aag | 106 |
|---|---|---|---|---|---|---|---|---|---|---|---|---|---|---|---|---|
| Lys | Glu | Arg | Arg | Pro | Tyr | Cys | Ser | Leu | Thr | Lys | Ser | Arg | Arg | Glu | Lys | |
| | 5 | | | | 10 | | | | | 15 | | | | | | |

| gaa | agg | cgc | tat | aca | aat | tcg | tcc | gcg | gac | aat | gag | gag | tgt | agg | gtc | 154 |
|---|---|---|---|---|---|---|---|---|---|---|---|---|---|---|---|---|
| Glu | Arg | Arg | Tyr | Thr | Asn | Ser | Ser | Ala | Asp | Asn | Glu | Glu | Cys | Arg | Val | |
| 20 | | | | 25 | | | | | 30 | | | | | 35 | | |

| ccc | acg | cag | aag | tcc | tat | agt | tcc | agt | gaa | acc | ttg | aaa | gct | ttc | gat | 202 |
|---|---|---|---|---|---|---|---|---|---|---|---|---|---|---|---|---|
| Pro | Thr | Gln | Lys | Ser | Tyr | Ser | Ser | Ser | Glu | Thr | Leu | Lys | Ala | Phe | Asp | |
| | | | 40 | | | | | 45 | | | | | 50 | | | |

| cat | gat | tat | tca | cgg | ctg | ctt | tat | gga | aac | aga | gta | aag | gat | ttg | gtc | 250 |
|---|---|---|---|---|---|---|---|---|---|---|---|---|---|---|---|---|
| His | Asp | Tyr | Ser | Arg | Leu | Leu | Tyr | Gly | Asn | Arg | Val | Lys | Asp | Leu | Val | |
| | | | 55 | | | | | 60 | | | | | 65 | | | |

| cac | aga | gaa | gcc | gac | gag | tat | act | aga | caa | gga | cag | aat | ttt | acc | cta | 298 |
|---|---|---|---|---|---|---|---|---|---|---|---|---|---|---|---|---|
| His | Arg | Glu | Ala | Asp | Glu | Tyr | Thr | Arg | Gln | Gly | Gln | Asn | Phe | Thr | Leu | |
| | 70 | | | | | 75 | | | | | 80 | | | | | |

| agg | cag | tta | gga | gtg | tgt | gaa | tcc | gca | act | cga | aga | gga | gtg | gca | ttc | 346 |
|---|---|---|---|---|---|---|---|---|---|---|---|---|---|---|---|---|
| Arg | Gln | Leu | Gly | Val | Cys | Glu | Ser | Ala | Thr | Arg | Arg | Gly | Val | Ala | Phe | |
| | 85 | | | | | 90 | | | | | 95 | | | | | |

| tgt | gcg | gaa | atg | ggg | ctc | cct | cac | aga | ggt | tac | tcc | atc | agt | gca | ggg | 394 |
|---|---|---|---|---|---|---|---|---|---|---|---|---|---|---|---|---|
| Cys | Ala | Glu | Met | Gly | Leu | Pro | His | Arg | Gly | Tyr | Ser | Ile | Ser | Ala | Gly | |
| 100 | | | | | 105 | | | | | 110 | | | | | 115 | |

| tca | gat | gcg | gat | acg | gaa | aac | gaa | gca | gtg | atg | tcc | cct | gag | cat | gcc | 442 |
|---|---|---|---|---|---|---|---|---|---|---|---|---|---|---|---|---|
| Ser | Asp | Ala | Asp | Thr | Glu | Asn | Glu | Ala | Val | Met | Ser | Pro | Glu | His | Ala | |
| | | | | 120 | | | | | 125 | | | | | 130 | | |

| atg | aga | ctt | tgg | ggc | agg | ggg | gtc | aaa | tcg | ggc | cgc | agt | tcc | tgc | ctg | 490 |
|---|---|---|---|---|---|---|---|---|---|---|---|---|---|---|---|---|
| Met | Arg | Leu | Trp | Gly | Arg | Gly | Val | Lys | Ser | Gly | Arg | Ser | Ser | Cys | Leu | |
| | | | 135 | | | | | 140 | | | | | 145 | | | |

| tca | agc | cgg | tcc | aac | tcc | gcc | ctc | acc | ctg | aca | gac | acg | gag | cac | gag | 538 |
|---|---|---|---|---|---|---|---|---|---|---|---|---|---|---|---|---|
| Ser | Ser | Arg | Ser | Asn | Ser | Ala | Leu | Thr | Leu | Thr | Asp | Thr | Glu | His | Glu | |
| | | 150 | | | | | 155 | | | | | 160 | | | | |

| aac | agg | tcg | gac | agt | gag | agc | gag | caa | cct | tca | aac | aac | cca | ggg | caa | 586 |
|---|---|---|---|---|---|---|---|---|---|---|---|---|---|---|---|---|
| Asn | Arg | Ser | Asp | Ser | Glu | Ser | Glu | Gln | Pro | Ser | Asn | Asn | Pro | Gly | Gln | |
| | | | 165 | | | | | 170 | | | | | 175 | | | |

| ccc | acc | ctg | cag | cct | ttg | ccg | cca | tcc | cac | aag | cag | cac | ccg | gcg | cag | 634 |
|---|---|---|---|---|---|---|---|---|---|---|---|---|---|---|---|---|
| Pro | Thr | Leu | Gln | Pro | Leu | Pro | Pro | Ser | His | Lys | Gln | His | Pro | Ala | Gln | |
| 180 | | | | | 185 | | | | | 190 | | | | | 195 | |

| cat | cac | ccg | tcc | atc | act | tcc | ctc | aat | aga | aac | tcc | ctg | acc | aat | aga | 682 |
|---|---|---|---|---|---|---|---|---|---|---|---|---|---|---|---|---|
| His | His | Pro | Ser | Ile | Thr | Ser | Leu | Asn | Arg | Asn | Ser | Leu | Thr | Asn | Arg | |
| | | | | 200 | | | | | 205 | | | | | 210 | | |

| agg | aac | cag | agt | ccg | gcc | ccg | ccg | gct | gct | ttg | ccc | gcc | gag | ctg | caa | 730 |
|---|---|---|---|---|---|---|---|---|---|---|---|---|---|---|---|---|
| Arg | Asn | Gln | Ser | Pro | Ala | Pro | Pro | Ala | Ala | Leu | Pro | Ala | Glu | Leu | Gln | |
| | | | 215 | | | | | 220 | | | | | 225 | | | |

| acc | aca | ccc | gag | tcc | gtc | cag | ctg | cag | gac | agc | tgg | gtc | ctt | ggc | agt | 778 |
|---|---|---|---|---|---|---|---|---|---|---|---|---|---|---|---|---|
| Thr | Thr | Pro | Glu | Ser | Val | Gln | Leu | Gln | Asp | Ser | Trp | Val | Leu | Gly | Ser | |
| | | 230 | | | | | 235 | | | | | 240 | | | | |

| aat | gta | cca | ctg | gaa | agc | agg | cat | ttc | cta | ttc | aaa | aca | ggg | aca | ggg | 826 |
|---|---|---|---|---|---|---|---|---|---|---|---|---|---|---|---|---|
| Asn | Val | Pro | Leu | Glu | Ser | Arg | His | Phe | Leu | Phe | Lys | Thr | Gly | Thr | Gly | |
| | 245 | | | | | 250 | | | | | 255 | | | | | |

| acg | acg | cca | ctg | ttc | agt | acg | gca | acc | ccg | gga | tac | aca | atg | gca | tct | 874 |
|---|---|---|---|---|---|---|---|---|---|---|---|---|---|---|---|---|
| Thr | Thr | Pro | Leu | Phe | Ser | Thr | Ala | Thr | Pro | Gly | Tyr | Thr | Met | Ala | Ser | |

```
          260              265                270              275
ggc tct gtt tat tct ccg cct acc cgg cca ctt cct aga aac acc cta    922
Gly Ser Val Tyr Ser Pro Pro Thr Arg Pro Leu Pro Arg Asn Thr Leu
                280                285                290 tca aga agt gct ttt aaa ttc aag aag tct tca aag tac tgc agc tgg    970
Ser Arg Ser Ala Phe Lys Phe Lys Lys Ser Ser Lys Tyr Cys Ser Trp
                295                300                305 agg tgc acc gca ctg tgt gct gta ggg gtc tca gtg ctc ctg gcc att   1018
Arg Cys Thr Ala Leu Cys Ala Val Gly Val Ser Val Leu Leu Ala Ile
                310                315                320 ctc ctc tcc tat ttt ata gca atg cat cta ttt ggc ctc aac tgg cac   1066
Leu Leu Ser Tyr Phe Ile Ala Met His Leu Phe Gly Leu Asn Trp His
                325                330                335 tta cag cag acg gaa aat gac aca ttc gag aat gga aaa gtg aat tct   1114
Leu Gln Gln Thr Glu Asn Asp Thr Phe Glu Asn Gly Lys Val Asn Ser
340                345                350                355 gac acc gtg cca aca aac act gta tcg tta cct tct ggc gac aat gga   1162
Asp Thr Val Pro Thr Asn Thr Val Ser Leu Pro Ser Gly Asp Asn Gly
                360                365                370 aaa tta ggt gga ttt aca cat gaa aat aac acc ata gat tcc gga gaa   1210
Lys Leu Gly Gly Phe Thr His Glu Asn Asn Thr Ile Asp Ser Gly Glu
                375                380                385 ctt gat att ggc cgg aga gca att caa gag gtt ccc ccc ggg atc ttc   1258
Leu Asp Ile Gly Arg Arg Ala Ile Gln Glu Val Pro Pro Gly Ile Phe
                390                395                400 tgg aga tcg cag ctc ttt att gat cag cca cag ttt ctt aag ttc aac   1306
Trp Arg Ser Gln Leu Phe Ile Asp Gln Pro Gln Phe Leu Lys Phe Asn
                405                410                415 atc tct ctt cag aag gat gca ttg atc gga gtg tac ggc cgg aag ggc   1354
Ile Ser Leu Gln Lys Asp Ala Leu Ile Gly Val Tyr Gly Arg Lys Gly
420                425                430                435 tta ccg cct tcc cat act cag tac gac ttt gtg gaa cta ctg gat ggt   1402
Leu Pro Pro Ser His Thr Gln Tyr Asp Phe Val Glu Leu Leu Asp Gly
                440                445                450 agc agg tta att gcg aga gag cag cgg aac ctg gtg gag tcc gaa aga   1450
Ser Arg Leu Ile Ala Arg Glu Gln Arg Asn Leu Val Glu Ser Glu Arg
                455                460                465 gcc ggg cgg cag gcg aga tct gtc agc ctg cac gaa gct ggc ttc atc   1498
Ala Gly Arg Gln Ala Arg Ser Val Ser Leu His Glu Ala Gly Phe Ile
                470                475                480 cag tac ttg gat tct gga atc tgg cat ctg gct ttt tat aac gac ggg   1546
Gln Tyr Leu Asp Ser Gly Ile Trp His Leu Ala Phe Tyr Asn Asp Gly
                485                490                495 aaa aac cca gag cag gtc tcc ttt aac acg atc gtt ata gag tct gtg   1594
Lys Asn Pro Glu Gln Val Ser Phe Asn Thr Ile Val Ile Glu Ser Val
500                505                510                515 gtg gaa tgc ccc cga aat tgc cat gga aat gga gag tgt gtt tct gga   1642
Val Glu Cys Pro Arg Asn Cys His Gly Asn Gly Glu Cys Val Ser Gly
                520                525                530 act tgc cat tgt ttc ccc ggg ttt cta ggt ccg gat tgt tca aga gca   1690
Thr Cys His Cys Phe Pro Gly Phe Leu Gly Pro Asp Cys Ser Arg Ala
                535                540                545 gcc tgt ccg gtg ctc tgt agt ggc aac ggg caa tac tcc aag ggc cgc   1738
Ala Cys Pro Val Leu Cys Ser Gly Asn Gly Gln Tyr Ser Lys Gly Arg
                550                555                560 tgc ctg tgc ttc agt ggc tgg aag ggc acc gag tgt gac gtg ccg acg   1786
Cys Leu Cys Phe Ser Gly Trp Lys Gly Thr Glu Cys Asp Val Pro Thr
                565                570                575 acc cag tgc att gac ccg cag tgc ggg ggt cgt ggg att tgc atc atg   1834
```

```
                Thr Gln Cys Ile Asp Pro Gln Cys Gly Gly Arg Gly Ile Cys Ile Met
                580             585                 590                 595
ggc tct tgc gct tgt aac tcg gga tac aaa gga gaa aac tgt gag gaa              1882
Gly Ser Cys Ala Cys Asn Ser Gly Tyr Lys Gly Glu Asn Cys Glu Glu
                        600                 605                 610 gcg gac tgt cta gac cct gga tgt tct aat cac ggg gtg tgt atc cat              1930
Ala Asp Cys Leu Asp Pro Gly Cys Ser Asn His Gly Val Cys Ile His
                615                 620                 625 ggg gaa tgt cac tgc aat cca ggc tgg ggt ggc agc aac tgt gaa ata              1978
Gly Glu Cys His Cys Asn Pro Gly Trp Gly Gly Ser Asn Cys Glu Ile
            630                 635                 640 ctg aag act atg tgt gca gac cag tgc tca ggc cac ggg act tac ctt              2026
Leu Lys Thr Met Cys Ala Asp Gln Cys Ser Gly His Gly Thr Tyr Leu
        645                 650                 655 caa gaa agc ggc tcc tgc act tgc gac cca aat tgg act ggc ccc gac              2074
Gln Glu Ser Gly Ser Cys Thr Cys Asp Pro Asn Trp Thr Gly Pro Asp
660                 665                 670                 675 tgc tca aat gaa ata tgt tca gtg gac tgc ggc tca cac ggc gtc tgc              2122
Cys Ser Asn Glu Ile Cys Ser Val Asp Cys Gly Ser His Gly Val Cys
                680                 685                 690 atg ggg ggc tcc tgt cgc tgt gaa gaa ggc tgg acc ggc ccg gcg tgt              2170
Met Gly Gly Ser Cys Arg Cys Glu Glu Gly Trp Thr Gly Pro Ala Cys
            695                 700                 705 aat cag aga gct tgc cac cct cgc tgt gct gag cac ggg acg tgc aag              2218
Asn Gln Arg Ala Cys His Pro Arg Cys Ala Glu His Gly Thr Cys Lys
        710                 715                 720 gac ggc aag tgc gag tgc agc caa gga tgg aac gga gag cac tgc aca              2266
Asp Gly Lys Cys Glu Cys Ser Gln Gly Trp Asn Gly Glu His Cys Thr
725                 730                 735 att gct cac tat ttg gat aag ata gtt aaa gag ggt tgc ccc ggc ttg              2314
Ile Ala His Tyr Leu Asp Lys Ile Val Lys Glu Gly Cys Pro Gly Leu
740                 745                 750                 755 tgc aac agc aat ggg aga tgc aca ctg gac caa aac ggc tgg cac tgc              2362
Cys Asn Ser Asn Gly Arg Cys Thr Leu Asp Gln Asn Gly Trp His Cys
                760                 765                 770 gtt tgc cag cca ggg tgg aga gga gca ggc tgt gac gta gcc atg gag              2410
Val Cys Gln Pro Gly Trp Arg Gly Ala Gly Cys Asp Val Ala Met Glu
            775                 780                 785 acc ctc tgt aca gac agc aaa gac aac gaa gga gac gga ctc att gac              2458
Thr Leu Cys Thr Asp Ser Lys Asp Asn Glu Gly Asp Gly Leu Ile Asp
        790                 795                 800 tgc atg gat cct gat tgc tgc ctc cag agc tcc tgc caa aac cag ccc              2506
Cys Met Asp Pro Asp Cys Cys Leu Gln Ser Ser Cys Gln Asn Gln Pro
805                 810                 815 tac tgt cgt ggc ttg cct gat cct cag gat atc att agc caa agc ctt              2554
Tyr Cys Arg Gly Leu Pro Asp Pro Gln Asp Ile Ile Ser Gln Ser Leu
820                 825                 830                 835 cag aca cca tct cag caa gct gcc aag tcc ttc tat gac cga atc agt              2602
Gln Thr Pro Ser Gln Gln Ala Ala Lys Ser Phe Tyr Asp Arg Ile Ser
                840                 845                 850 ttc ctg att gga tcg gat agc acc cac gtg ctc cct gga gaa agt ccg              2650
Phe Leu Ile Gly Ser Asp Ser Thr His Val Leu Pro Gly Glu Ser Pro
            855                 860                 865 ttc aat aag agt ctt gcg tcc gtc atc aga ggc caa gta cta aca gct              2698
Phe Asn Lys Ser Leu Ala Ser Val Ile Arg Gly Gln Val Leu Thr Ala
        870                 875                 880 gat gga acc cca ctt att ggc gtc aac gtg tcg ttt tta cac tac tcg              2746
Asp Gly Thr Pro Leu Ile Gly Val Asn Val Ser Phe Leu His Tyr Ser
885                 890                 895
```

```
gaa tat gga tat acc att acc cgc cag gat gga atg ttt gac ttg gtg    2794
Glu Tyr Gly Tyr Thr Ile Thr Arg Gln Asp Gly Met Phe Asp Leu Val
900                 905                 910                 915 gca aat ggt ggc gct tct ctg act ttg gta ttt gag cgt tcc cca ttc    2842
Ala Asn Gly Gly Ala Ser Leu Thr Leu Val Phe Glu Arg Ser Pro Phe
            920                 925                 930 ctc act cag tac cac act gtg tgg att ccc tgg aat gtc ttt tat gtg    2890
Leu Thr Gln Tyr His Thr Val Trp Ile Pro Trp Asn Val Phe Tyr Val
        935                 940                 945 atg gat acc ctt gtc atg aag aaa gag gag aac gac att ccc agc tgt    2938
Met Asp Thr Leu Val Met Lys Lys Glu Glu Asn Asp Ile Pro Ser Cys
    950                 955                 960 gac ctc agt ggc ttt gtg agg cca agt ccc atc att gtg tct tca ccg    2986
Asp Leu Ser Gly Phe Val Arg Pro Ser Pro Ile Ile Val Ser Ser Pro
965                 970                 975 tta tcc acc ttc ttc agg tct tcc cct gag gac agc ccc atc atc ccc    3034
Leu Ser Thr Phe Phe Arg Ser Ser Pro Glu Asp Ser Pro Ile Ile Pro
980                 985                 990                 995 gag aca cag gtc ctg cat gaa gaa acc aca att cca gga aca gat        3079
Glu Thr Gln Val Leu His Glu Glu Thr Thr Ile Pro Gly Thr Asp
                    1000                1005                1010 ttg aaa ctt tcc tac ctg agt tcc aga gcg gca ggg tac aag tca        3124
Leu Lys Leu Ser Tyr Leu Ser Ser Arg Ala Ala Gly Tyr Lys Ser
                1015                1020                1025 gtt ctt aag att acc atg acc cag gcc gtc ata ccg ttt aac ctc        3169
Val Leu Lys Ile Thr Met Thr Gln Ala Val Ile Pro Phe Asn Leu
                1030                1035                1040 atg aag gtc cat ctg atg gtg gcc gtg gtt ggg aga ctc ttc cag        3214
Met Lys Val His Leu Met Val Ala Val Val Gly Arg Leu Phe Gln
                1045                1050                1055 aag tgg ttt cct gcc tcg cca aac ttg gcc tac acg ttc atc tgg        3259
Lys Trp Phe Pro Ala Ser Pro Asn Leu Ala Tyr Thr Phe Ile Trp
                1060                1065                1070 gat aag acg gac gca tat aat cag aaa gtc tac ggc ttg tca gag        3304
Asp Lys Thr Asp Ala Tyr Asn Gln Lys Val Tyr Gly Leu Ser Glu
                1075                1080                1085 gca gtt gtg tcc gtc gga tac gag tac gag tcg tgc ttg gac ctg        3349
Ala Val Val Ser Val Gly Tyr Glu Tyr Glu Ser Cys Leu Asp Leu
                1090                1095                1100 act ctc tgg gaa aag agg act gcc gtt ttg caa ggc tat gag ttg        3394
Thr Leu Trp Glu Lys Arg Thr Ala Val Leu Gln Gly Tyr Glu Leu
                1105                1110                1115 gat gct tcg aac atg ggc ggc tgg acg ttg gac aag cac cat gta        3439
Asp Ala Ser Asn Met Gly Gly Trp Thr Leu Asp Lys His His Val
                1120                1125                1130 ctg gac gtt cag aac ggt ata cta tac aaa gga aat gga gaa aat        3484
Leu Asp Val Gln Asn Gly Ile Leu Tyr Lys Gly Asn Gly Glu Asn
                1135                1140                1145 cag ttc atc tct cag cag cct ccg gtg gtc agc agc atc atg ggt        3529
Gln Phe Ile Ser Gln Gln Pro Pro Val Val Ser Ser Ile Met Gly
                1150                1155                1160 aat ggt cgg agg cgt agc atc tca tgc cca agt tgc aat ggt caa        3574
Asn Gly Arg Arg Arg Ser Ile Ser Cys Pro Ser Cys Asn Gly Gln
                1165                1170                1175 gct gac ggg aac aaa ctc ctg gca ccc gtg gcg ctt gcc tgt ggg        3619
Ala Asp Gly Asn Lys Leu Leu Ala Pro Val Ala Leu Ala Cys Gly
                1180                1185                1190 atc gac ggc agt cta tac gta ggg gat ttc aat tac gtc cgg cgg        3664
Ile Asp Gly Ser Leu Tyr Val Gly Asp Phe Asn Tyr Val Arg Arg
                1195                1200                1205
```

| | | |
|---|---|---|
| ata ttc ccg tct ggg aat gtg aca agt gtt tta gaa cta aga aat<br>Ile Phe Pro Ser Gly Asn Val Thr Ser Val Leu Glu Leu Arg Asn<br>1210                  1215                 1220 | | 3709 |
| aaa gat ttt aga cat agt agc aac cca gct cac aga tac tac ctg<br>Lys Asp Phe Arg His Ser Ser Asn Pro Ala His Arg Tyr Tyr Leu<br>1225                  1230                 1235 | | 3754 |
| gct acg gac cca gtc acc gga gat ttg tac gtc tct gat act aac<br>Ala Thr Asp Pro Val Thr Gly Asp Leu Tyr Val Ser Asp Thr Asn<br>1240                  1245                 1250 | | 3799 |
| acc cgc aga atc tat cgg ccg aaa tca ctc acg gga gcc aaa gac<br>Thr Arg Arg Ile Tyr Arg Pro Lys Ser Leu Thr Gly Ala Lys Asp<br>1255                  1260                 1265 | | 3844 |
| ctg act aaa aac gct gaa gtg gtg gca ggg acc ggg gaa cag tgc<br>Leu Thr Lys Asn Ala Glu Val Val Ala Gly Thr Gly Glu Gln Cys<br>1270                  1275                 1280 | | 3889 |
| ctt ccc ttt gac gag gcc agg tgt ggg gat gga ggc aag gct gtg<br>Leu Pro Phe Asp Glu Ala Arg Cys Gly Asp Gly Gly Lys Ala Val<br>1285                  1290                 1295 | | 3934 |
| gaa gca acg ctc atg agt ccc aaa gga atg gca atc gat aag aac<br>Glu Ala Thr Leu Met Ser Pro Lys Gly Met Ala Ile Asp Lys Asn<br>1300                  1305                 1310 | | 3979 |
| gga ctg atc tac ttt gtt gat gga acc atg atc aga aag gtt gat<br>Gly Leu Ile Tyr Phe Val Asp Gly Thr Met Ile Arg Lys Val Asp<br>1315                  1320                 1325 | | 4024 |
| caa aat gga atc ata tca act ctc ctg ggc tcc aac gac ctc acg<br>Gln Asn Gly Ile Ile Ser Thr Leu Leu Gly Ser Asn Asp Leu Thr<br>1330                  1335                 1340 | | 4069 |
| tca gct cga cct tta acc tgt gat act agc atg cat atc agc cag<br>Ser Ala Arg Pro Leu Thr Cys Asp Thr Ser Met His Ile Ser Gln<br>1345                  1350                 1355 | | 4114 |
| gtg cgt ctg gaa tgg ccc act gac ctc gcg atc aac ccc atg gat<br>Val Arg Leu Glu Trp Pro Thr Asp Leu Ala Ile Asn Pro Met Asp<br>1360                  1365                 1370 | | 4159 |
| aac tcc atc tac gtc ctg gat aat aac gta gtt tta cag atc act<br>Asn Ser Ile Tyr Val Leu Asp Asn Asn Val Val Leu Gln Ile Thr<br>1375                  1380                 1385 | | 4204 |
| gaa aac cgt cag gtc cgc atc gct gcc ggg cgg ccc atg cac tgt<br>Glu Asn Arg Gln Val Arg Ile Ala Ala Gly Arg Pro Met His Cys<br>1390                  1395                 1400 | | 4249 |
| cag gtc cct gga gtg gaa tac ccg gtg ggg aag cac gcg gtt cag<br>Gln Val Pro Gly Val Glu Tyr Pro Val Gly Lys His Ala Val Gln<br>1405                  1410                 1415 | | 4294 |
| acc acc ctg gag tca gcc acg gcc att gct gtg tcc tac agc ggg<br>Thr Thr Leu Glu Ser Ala Thr Ala Ile Ala Val Ser Tyr Ser Gly<br>1420                  1425                 1430 | | 4339 |
| gtc ctt tac atc acg gaa act gat gag aag aag atc aac cga ata<br>Val Leu Tyr Ile Thr Glu Thr Asp Glu Lys Lys Ile Asn Arg Ile<br>1435                  1440                 1445 | | 4384 |
| agg cag gtc acg aca gac ggg gag atc tcc tta gtg gct ggg ata<br>Arg Gln Val Thr Thr Asp Gly Glu Ile Ser Leu Val Ala Gly Ile<br>1450                  1455                 1460 | | 4429 |
| cct tcg gaa tgt gac tgc aag aac gac gcc aac tgt gac tgc tac<br>Pro Ser Glu Cys Asp Cys Lys Asn Asp Ala Asn Cys Asp Cys Tyr<br>1465                  1470                 1475 | | 4474 |
| caa agc gga gac ggc tac gcc aaa gat gcc aaa ctc aat gcg ccg<br>Gln Ser Gly Asp Gly Tyr Ala Lys Asp Ala Lys Leu Asn Ala Pro<br>1480                  1485                 1490 | | 4519 |
| tcc tcc ctg gcc gcc tcg cca gat ggc act ctg tac att gca gat<br>Ser Ser Leu Ala Ala Ser Pro Asp Gly Thr Leu Tyr Ile Ala Asp<br>1495                  1500                 1505 | | 4564 |

-continued

| | |
|---|---|
| ctg gga aat atc agg atc cgg gcc gtt tcg aag aat aaa cct tta<br>Leu Gly Asn Ile Arg Ile Arg Ala Val Ser Lys Asn Lys Pro Leu<br>          1510                       1515                      1520 | 4609 |
| ctg aac tca atg aac ttt tac gaa gtt gcc tct cca act gat caa<br>Leu Asn Ser Met Asn Phe Tyr Glu Val Ala Ser Pro Thr Asp Gln<br>                    1525                      1530                    1535 | 4654 |
| gag ctc tac atc ttt gac atc aac ggt act cac cag tac acc gtg<br>Glu Leu Tyr Ile Phe Asp Ile Asn Gly Thr His Gln Tyr Thr Val<br>          1540                     1545                     1550 | 4699 |
| agc ctg gtc acg ggt gac tac cta tat aat ttt agt tac agc aat<br>Ser Leu Val Thr Gly Asp Tyr Leu Tyr Asn Phe Ser Tyr Ser Asn<br>          1555                     1560                     1565 | 4744 |
| gac aat gac gtc acc gct gta act gac agc aat ggc aac acc ctc<br>Asp Asn Asp Val Thr Ala Val Thr Asp Ser Asn Gly Asn Thr Leu<br>                    1570                      1575                    1580 | 4789 |
| cga atc cga agg gat ccg aat cgg atg ccg gtg cgg gtg gtg tct<br>Arg Ile Arg Arg Asp Pro Asn Arg Met Pro Val Arg Val Val Ser<br>          1585                     1590                     1595 | 4834 |
| cct gat aac cag gtg ata tgg ttg acc ata ggc acc aac ggg tgt<br>Pro Asp Asn Gln Val Ile Trp Leu Thr Ile Gly Thr Asn Gly Cys<br>                    1600                      1605                    1610 | 4879 |
| ctg aaa agc atg acc gct cag ggc ctg gaa ctg gtt ttg ttt act<br>Leu Lys Ser Met Thr Ala Gln Gly Leu Glu Leu Val Leu Phe Thr<br>          1615                     1620                     1625 | 4924 |
| tac cat ggc aac agt ggg ctt tta gcc acc aaa agt gac gaa act<br>Tyr His Gly Asn Ser Gly Leu Leu Ala Thr Lys Ser Asp Glu Thr<br>                    1630                      1635                    1640 | 4969 |
| gga tgg aca aca ttt ttt gac tat gac agt gaa ggt cgc ctg acg<br>Gly Trp Thr Thr Phe Phe Asp Tyr Asp Ser Glu Gly Arg Leu Thr<br>          1645                     1650                     1655 | 5014 |
| aat gtt acc ttc ccc act ggg gtg gtt aca aac ctg cac ggg gac<br>Asn Val Thr Phe Pro Thr Gly Val Val Thr Asn Leu His Gly Asp<br>                    1660                      1665                    1670 | 5059 |
| atg gac aag gct atc acg gtg gac atc gag tca tcc agc aga gag<br>Met Asp Lys Ala Ile Thr Val Asp Ile Glu Ser Ser Ser Arg Glu<br>          1675                     1680                     1685 | 5104 |
| gaa gat gtc agc atc act tcg aac ttg tcc tcc atc gat tcc ttc<br>Glu Asp Val Ser Ile Thr Ser Asn Leu Ser Ser Ile Asp Ser Phe<br>                    1690                      1695                    1700 | 5149 |
| tac acc atg gtc caa gac cag tta aga aac agt tac cag att ggg<br>Tyr Thr Met Val Gln Asp Gln Leu Arg Asn Ser Tyr Gln Ile Gly<br>          1705                     1710                     1715 | 5194 |
| tat gat ggc tcc ctt aga atc ttc tat gcc agt ggt ctg gac tct<br>Tyr Asp Gly Ser Leu Arg Ile Phe Tyr Ala Ser Gly Leu Asp Ser<br>                    1720                      1725                    1730 | 5239 |
| cac tac cag aca gag ccc cac gtt ctg gct ggc acg gcg aat ccc<br>His Tyr Gln Thr Glu Pro His Val Leu Ala Gly Thr Ala Asn Pro<br>          1735                     1740                     1745 | 5284 |
| aca gta gcc aaa aga aac atg act ctt ccc ggt gag aac ggg cag<br>Thr Val Ala Lys Arg Asn Met Thr Leu Pro Gly Glu Asn Gly Gln<br>                    1750                      1755                    1760 | 5329 |
| aat ctg gtg gag tgg aga ttc cga aaa gaa caa gcc cag ggc aaa<br>Asn Leu Val Glu Trp Arg Phe Arg Lys Glu Gln Ala Gln Gly Lys<br>          1765                     1770                     1775 | 5374 |
| gtc aac gta ttc ggc cgg aag ctc agg gtc aat ggg cgc aac cta<br>Val Asn Val Phe Gly Arg Lys Leu Arg Val Asn Gly Arg Asn Leu<br>                    1780                      1785                    1790 | 5419 |
| ctc tca gtg gac ttt gat cgg acc acc aag acg gaa aag atc tat<br>Leu Ser Val Asp Phe Asp Arg Thr Thr Lys Thr Glu Lys Ile Tyr<br>          1795                     1800                     1805 | 5464 |

```
gat gac cac cgg aaa ttt ctc ctg agg atc gct tac gac acg tcg      5509
Asp Asp His Arg Lys Phe Leu Leu Arg Ile Ala Tyr Asp Thr Ser
            1810                1815                1820 ggg cac ccg act ctc tgg ctg ccg agt agc aag cta atg gca gtg      5554
Gly His Pro Thr Leu Trp Leu Pro Ser Ser Lys Leu Met Ala Val
            1825                1830                1835 aac gtc acc tac tca tcc acc ggt caa att gcc agc atc cag aga      5599
Asn Val Thr Tyr Ser Ser Thr Gly Gln Ile Ala Ser Ile Gln Arg
            1840                1845                1850 ggg acc acg agc gaa aag gtg gac tat gac agc cag ggg agg atc      5644
Gly Thr Thr Ser Glu Lys Val Asp Tyr Asp Ser Gln Gly Arg Ile
            1855                1860                1865 gta tct cgg gtc ttt gcc gat ggg aaa aca tgg agt tac acg tac      5689
Val Ser Arg Val Phe Ala Asp Gly Lys Thr Trp Ser Tyr Thr Tyr
            1870                1875                1880 ttg gaa aag tcc atg gtt ctt ctg ctc cat agc cag cgg cag tac      5734
Leu Glu Lys Ser Met Val Leu Leu Leu His Ser Gln Arg Gln Tyr
            1885                1890                1895 atc ttc gaa tac gac atg tgg gac cgc ctg tcc gcc atc acc atg      5779
Ile Phe Glu Tyr Asp Met Trp Asp Arg Leu Ser Ala Ile Thr Met
            1900                1905                1910 ccc agt gtg gct cgc cac acc atg cag acc atc cgg tcc att ggc      5824
Pro Ser Val Ala Arg His Thr Met Gln Thr Ile Arg Ser Ile Gly
            1915                1920                1925 tac tac cgc aac atc tac aat ccc cca gaa agc aat gcc tct atc      5869
Tyr Tyr Arg Asn Ile Tyr Asn Pro Pro Glu Ser Asn Ala Ser Ile
            1930                1935                1940 atc acc gac tac aac gag gaa ggg ctg ctt ctg caa aca gct ttc      5914
Ile Thr Asp Tyr Asn Glu Glu Gly Leu Leu Leu Gln Thr Ala Phe
            1945                1950                1955 ctg gga acg agt cgg agg gtc tta ttc aag tat aga agg cag acc      5959
Leu Gly Thr Ser Arg Arg Val Leu Phe Lys Tyr Arg Arg Gln Thr
            1960                1965                1970 agg cta tca gaa att tta tac gac agc aca aga gtc agt ttt acc      6004
Arg Leu Ser Glu Ile Leu Tyr Asp Ser Thr Arg Val Ser Phe Thr
            1975                1980                1985 tac gac gaa aca gcg gga gtc ctg aaa aca gta aac ctt cag agt      6049
Tyr Asp Glu Thr Ala Gly Val Leu Lys Thr Val Asn Leu Gln Ser
            1990                1995                2000 gat ggt ttt att tgc acc att aga tac agg caa att ggt ccc ctg      6094
Asp Gly Phe Ile Cys Thr Ile Arg Tyr Arg Gln Ile Gly Pro Leu
            2005                2010                2015 att gac aga cag att ttc cgc ttc agc gag gat gga atg gta aat      6139
Ile Asp Arg Gln Ile Phe Arg Phe Ser Glu Asp Gly Met Val Asn
            2020                2025                2030 gcg aga ttt gac tat agc tac gac aac agc ttt cga gtg acc agc      6184
Ala Arg Phe Asp Tyr Ser Tyr Asp Asn Ser Phe Arg Val Thr Ser
            2035                2040                2045 atg cag ggt gtc atc aat gaa aca cca ctg ccc att gat cta tac      6229
Met Gln Gly Val Ile Asn Glu Thr Pro Leu Pro Ile Asp Leu Tyr
            2050                2055                2060 cag ttt gat gac atc tct ggc aaa gtc gag cag ttt gga aaa ttc      6274
Gln Phe Asp Asp Ile Ser Gly Lys Val Glu Gln Phe Gly Lys Phe
            2065                2070                2075 gga gtg ata tac tac gac atc aac caa atc att tcc acg gcc gtg      6319
Gly Val Ile Tyr Tyr Asp Ile Asn Gln Ile Ile Ser Thr Ala Val
            2080                2085                2090 atg act tat aca aag cac ttt gat gct cat ggg cgc atc aag gag      6364
Met Thr Tyr Thr Lys His Phe Asp Ala His Gly Arg Ile Lys Glu
            2095                2100                2105
```

|     |     |     |     |     |     |     |     |     |     |     |     |     |     |     |      |
| --- | --- | --- | --- | --- | --- | --- | --- | --- | --- | --- | --- | --- | --- | --- | ---- |
| atc | caa | tat | gag | ata | ttt | agg | tca | ctc | atg | tac | tgg | att | aca | att | 6409 |
| Ile | Gln | Tyr | Glu | Ile | Phe | Arg | Ser | Leu | Met | Tyr | Trp | Ile | Thr | Ile |      |
|     |     |     |     | 2110 |   |   |     | 2115 |   |     |     |     |     | 2120 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| caa | tat | gat | aat | atg | ggc | cgg | gta | acc | aag | aga | gag | att | aaa | att | 6454 |
| Gln | Tyr | Asp | Asn | Met | Gly | Arg | Val | Thr | Lys | Arg | Glu | Ile | Lys | Ile |      |
|     |     |     |     | 2125 |   |   |     | 2130 |   |     |     |     |     | 2135 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| ggg | cct | ttt | gcc | aac | act | acc | aaa | tac | gcg | tac | gag | tac | gac | gtc | 6499 |
| Gly | Pro | Phe | Ala | Asn | Thr | Thr | Lys | Tyr | Ala | Tyr | Glu | Tyr | Asp | Val |      |
|     |     |     |     | 2140 |   |   |     | 2145 |   |     |     |     |     | 2150 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| gat | gga | cag | ctc | caa | aca | gtt | tac | cta | aac | gaa | aag | atc | atg | tgg | 6544 |
| Asp | Gly | Gln | Leu | Gln | Thr | Val | Tyr | Leu | Asn | Glu | Lys | Ile | Met | Trp |      |
|     |     |     |     | 2155 |   |   |     | 2160 |   |     |     |     |     | 2165 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| cgg | tac | aac | tac | gac | cta | aat | gga | aac | ctc | cac | ttg | ctc | aac | ccc | 6589 |
| Arg | Tyr | Asn | Tyr | Asp | Leu | Asn | Gly | Asn | Leu | His | Leu | Leu | Asn | Pro |      |
|     |     |     |     | 2170 |   |   |     | 2175 |   |     |     |     |     | 2180 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| agc | agc | agc | gcc | cgc | ctg | acc | cct | ctg | cgc | tat | gac | ctg | cgc | gac | 6634 |
| Ser | Ser | Ser | Ala | Arg | Leu | Thr | Pro | Leu | Arg | Tyr | Asp | Leu | Arg | Asp |      |
|     |     |     |     | 2185 |   |   |     | 2190 |   |     |     |     |     | 2195 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| aga | atc | acc | cgc | ctg | ggc | gat | gtt | cag | tac | cgg | ctg | gat | gaa | gat | 6679 |
| Arg | Ile | Thr | Arg | Leu | Gly | Asp | Val | Gln | Tyr | Arg | Leu | Asp | Glu | Asp |      |
|     |     |     |     | 2200 |   |   |     | 2205 |   |     |     |     |     | 2210 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| ggt | ttc | ctg | cgt | cag | agg | ggc | act | gaa | att | ttt | gaa | tac | agc | tcc | 6724 |
| Gly | Phe | Leu | Arg | Gln | Arg | Gly | Thr | Glu | Ile | Phe | Glu | Tyr | Ser | Ser |      |
|     |     |     |     | 2215 |   |   |     | 2220 |   |     |     |     |     | 2225 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| aaa | ggg | ctt | ctg | act | cga | gtc | tac | agt | aaa | ggc | agt | ggc | tgg | aca | 6769 |
| Lys | Gly | Leu | Leu | Thr | Arg | Val | Tyr | Ser | Lys | Gly | Ser | Gly | Trp | Thr |      |
|     |     |     |     | 2230 |   |   |     | 2235 |   |     |     |     |     | 2240 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| gtg | atc | tat | cgg | tac | gac | ggc | ctg | gga | aga | cgt | gtt | tct | agc | aaa | 6814 |
| Val | Ile | Tyr | Arg | Tyr | Asp | Gly | Leu | Gly | Arg | Arg | Val | Ser | Ser | Lys |      |
|     |     |     |     | 2245 |   |   |     | 2250 |   |     |     |     |     | 2255 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| acc | agc | ctg | gga | cag | cac | ctt | cag | ttt | ttc | tac | gcc | gac | ctg | aca | 6859 |
| Thr | Ser | Leu | Gly | Gln | His | Leu | Gln | Phe | Phe | Tyr | Ala | Asp | Leu | Thr |      |
|     |     |     |     | 2260 |   |   |     | 2265 |   |     |     |     |     | 2270 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| tac | ccc | acg | aga | att | act | cac | gtc | tac | aac | cat | tcc | agt | tca | gaa | 6904 |
| Tyr | Pro | Thr | Arg | Ile | Thr | His | Val | Tyr | Asn | His | Ser | Ser | Ser | Glu |      |
|     |     |     |     | 2275 |   |   |     | 2280 |   |     |     |     |     | 2285 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| atc | acc | tcc | ctg | tac | tat | gac | ctc | caa | gga | cat | ctc | ttc | gcc | atg | 6949 |
| Ile | Thr | Ser | Leu | Tyr | Tyr | Asp | Leu | Gln | Gly | His | Leu | Phe | Ala | Met |      |
|     |     |     |     | 2290 |   |   |     | 2295 |   |     |     |     |     | 2300 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| gag | atc | agc | agt | ggg | gat | gag | ttc | tac | atc | gcc | tcg | gac | aac | acg | 6994 |
| Glu | Ile | Ser | Ser | Gly | Asp | Glu | Phe | Tyr | Ile | Ala | Ser | Asp | Asn | Thr |      |
|     |     |     |     | 2305 |   |   |     | 2310 |   |     |     |     |     | 2315 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| ggg | aca | ccg | ctg | gct | gtt | ttc | agc | agc | aac | ggg | ctc | atg | ctg | aaa | 7039 |
| Gly | Thr | Pro | Leu | Ala | Val | Phe | Ser | Ser | Asn | Gly | Leu | Met | Leu | Lys |      |
|     |     |     |     | 2320 |   |   |     | 2325 |   |     |     |     |     | 2330 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| cag | acc | cag | tac | act | gcc | tat | ggt | gag | atc | tac | ttt | gac | tcc | aac | 7084 |
| Gln | Thr | Gln | Tyr | Thr | Ala | Tyr | Gly | Glu | Ile | Tyr | Phe | Asp | Ser | Asn |      |
|     |     |     |     | 2335 |   |   |     | 2340 |   |     |     |     |     | 2345 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| gtc | gac | ttt | cag | ctg | gta | att | gga | ttc | cac | ggg | ggc | ttg | tat | gac | 7129 |
| Val | Asp | Phe | Gln | Leu | Val | Ile | Gly | Phe | His | Gly | Gly | Leu | Tyr | Asp |      |
|     |     |     |     | 2350 |   |   |     | 2355 |   |     |     |     |     | 2360 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| ccg | ctc | acc | aaa | cta | atc | cac | ttt | gga | gaa | aga | gat | tat | gac | att | 7174 |
| Pro | Leu | Thr | Lys | Leu | Ile | His | Phe | Gly | Glu | Arg | Asp | Tyr | Asp | Ile |      |
|     |     |     |     | 2365 |   |   |     | 2370 |   |     |     |     |     | 2375 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| ttg | gcg | gga | aga | tgg | acc | aca | ccg | gac | att | gaa | atc | tgg | aaa | agg | 7219 |
| Leu | Ala | Gly | Arg | Trp | Thr | Thr | Pro | Asp | Ile | Glu | Ile | Trp | Lys | Arg |      |
|     |     |     |     | 2380 |   |   |     | 2385 |   |     |     |     |     | 2390 |   |

|     |     |     |     |     |     |     |     |     |     |     |     |     |     |     |      |
| --- | --- | --- | --- | --- | --- | --- | --- | --- | --- | --- | --- | --- | --- | --- | ---- |
| atc | gga | aag | gac | cct | gct | cct | ttt | aac | ctg | tat | atg | ttt | cgg | aat | 7264 |
| Ile | Gly | Lys | Asp | Pro | Ala | Pro | Phe | Asn | Leu | Tyr | Met | Phe | Arg | Asn |      |
|     |     |     |     | 2395 |   |   |     | 2400 |   |     |     |     |     | 2405 |   |

```
aac aac ccc gcg agc aaa atc cat gat gtg aaa gat tac atc acg      7309
Asn Asn Pro Ala Ser Lys Ile His Asp Val Lys Asp Tyr Ile Thr
            2410                2415                2420 gat gtt aac agc tgg ctg gtg acg ttt ggc ttc cat ctg cac aat      7354
Asp Val Asn Ser Trp Leu Val Thr Phe Gly Phe His Leu His Asn
            2425                2430                2435 gct att cct gga ttc cct gtt ccc aaa ttt gat tta act gag cct      7399
Ala Ile Pro Gly Phe Pro Val Pro Lys Phe Asp Leu Thr Glu Pro
            2440                2445                2450 tcc tat gag ctt gtg aag agt caa cag tgg gaa gat gtg ccg ccc      7444
Ser Tyr Glu Leu Val Lys Ser Gln Gln Trp Glu Asp Val Pro Pro
            2455                2460                2465 atc ttt gga gtt cag cag caa gtg gca agg caa gcc aag gcc ttc      7489
Ile Phe Gly Val Gln Gln Gln Val Ala Arg Gln Ala Lys Ala Phe
            2470                2475                2480 ttg tcc ctg ggg aag atg gcc gag gtg cag gtg agc cga cgc aaa      7534
Leu Ser Leu Gly Lys Met Ala Glu Val Gln Val Ser Arg Arg Lys
            2485                2490                2495 gct ggc gcc gag cag tcg tgg ctg tgg ttc gcc acg gtc aag tcg      7579
Ala Gly Ala Glu Gln Ser Trp Leu Trp Phe Ala Thr Val Lys Ser
            2500                2505                2510 ctc atc ggc aag ggc gtc atg ctg gcc gtg agc caa ggc cgc gtg      7624
Leu Ile Gly Lys Gly Val Met Leu Ala Val Ser Gln Gly Arg Val
            2515                2520                2525 cag acc aac gtg ctc aac atc gcc aac gag gac tgc atc aag gtg      7669
Gln Thr Asn Val Leu Asn Ile Ala Asn Glu Asp Cys Ile Lys Val
            2530                2535                2540 gcg gcg gtg ctc aac aac gcc ttc tac ctg gag aac ctg cac ttc      7714
Ala Ala Val Leu Asn Asn Ala Phe Tyr Leu Glu Asn Leu His Phe
            2545                2550                2555 acc atc gag ggc aag gac aca cac tac ttc atc aag acc acc aca      7759
Thr Ile Glu Gly Lys Asp Thr His Tyr Phe Ile Lys Thr Thr Thr
            2560                2565                2570 ccc gag agc gac ctg ggc aca ctg cgg ctg acg agc ggt cgc aag      7804
Pro Glu Ser Asp Leu Gly Thr Leu Arg Leu Thr Ser Gly Arg Lys
            2575                2580                2585 gcc ctg gag aac ggg atc aac gtg acc gtg tct cag tcc acc acg      7849
Ala Leu Glu Asn Gly Ile Asn Val Thr Val Ser Gln Ser Thr Thr
            2590                2595                2600 gtg gtg aac ggc agg act cgc agg ttc gcc gac gtg gag atg cag      7894
Val Val Asn Gly Arg Thr Arg Arg Phe Ala Asp Val Glu Met Gln
            2605                2610                2615 ttc ggt gcc ctg gca ctg cat gtg cgc tat ggc atg acg ctg gac      7939
Phe Gly Ala Leu Ala Leu His Val Arg Tyr Gly Met Thr Leu Asp
            2620                2625                2630 gag gag aag gcg cgc att ctg gag cag gcg cgc cag cgc gcg ctc      7984
Glu Glu Lys Ala Arg Ile Leu Glu Gln Ala Arg Gln Arg Ala Leu
            2635                2640                2645 gcc cgg gcg tgg gca cgg gag cag cag cgc gtg cgc gac ggc gag      8029
Ala Arg Ala Trp Ala Arg Glu Gln Gln Arg Val Arg Asp Gly Glu
            2650                2655                2660 gag ggt gcg cgc ctc tgg acg gag ggt gag aaa cgg cag ctg ctg      8074
Glu Gly Ala Arg Leu Trp Thr Glu Gly Glu Lys Arg Gln Leu Leu
            2665                2670                2675 agc gct ggc aag gtg cag ggc tac gat ggg tac tac gta ctg tcg      8119
Ser Ala Gly Lys Val Gln Gly Tyr Asp Gly Tyr Tyr Val Leu Ser
            2680                2685                2690 gtg gag cag tac ccc gag ctg gct gac agt gcc aac aac atc cag      8164
Val Glu Gln Tyr Pro Glu Leu Ala Asp Ser Ala Asn Asn Ile Gln
            2695                2700                2705
```

| | |
|---|---|
| ttc ttg cga caa agt gag atc ggc aag agg taa ccccgggcc<br>Phe Leu Arg Gln Ser Glu Ile Gly Lys Arg<br>2710                       2715 | 8207 |
| accctgtgc agattctcct gtagcacaat ccaaaccgga ctctccaaag agccttccaa | 8267 |
| aatgacactg ctctgcagac agacacatcg cagatacaca cgcaacacaa accagaaaca | 8327 |
| aagacaactt ttttttttt ctgaatgacc ttaaaggtga tcggctttaa agaatatgtt | 8387 |
| tacatacgca tatcgctgca ctcaattgga ctggaagtat gagaaaggaa aaaaaagcat | 8447 |
| taaaaaggc aacgttttgc catgacccct ctgtaccttc gaggcactgt atttaacaaa | 8507 |
| ggttttaaaa aggaaaaaaa aatgcgtaca atgtttccag atattactga attgtcgacc | 8567 |
| tttgcttaca ggaagtaatc tctacttagg atgtgatata tatagatctg ttcattttaa | 8627 |
| aatgtgggc aaagttactg tttatagaac ccaactgctt tcccgtgctg ctttgtaaaa | 8687 |
| ggacactggc acaagggacg tctgcttcgg cggggattta ataatggatt ttactaacat | 8747 |
| ggcttgccct gggagggaaa aactgacgaa tagaatcctt gtcactgata agcaaaggaa | 8807 |
| accctgattt ttttgtaaat tatgtgagac aagttgttta tggattttta tatgaattac | 8867 |
| aatttactgt acatcaaata ttagtctcag aggagttaat ttatgtaaag tgtttaaaaa | 8927 |
| gtttatactt aaaataaaa tgataaaaac aaaaaa | 8964 |

<210> SEQ ID NO 133
<211> LENGTH: 2253
<212> TYPE: DNA
<213> ORGANISM: Homo sapiens
<220> FEATURE:
<221> NAME/KEY: exon
<222> LOCATION: (107)..(1090)

<400> SEQUENCE: 133

| | |
|---|---|
| gtgccccgga tgtgcccagc tggctcctgg ccccacccct cgggcctttg ggctggacca | 60 |
| gccacctctg cctgagacct ccggtcgccg caagaagctg gagagg atg tac agc<br>                                                                    Met Tyr Ser<br>                                                                    1 | 115 |
| gtt gac cgt gtg tct gac gac atc cct att cgt acc tgg ttc ccc aag<br>Val Asp Arg Val Ser Asp Asp Ile Pro Ile Arg Thr Trp Phe Pro Lys<br>5                    10                   15 | 163 |
| gaa aat ctt ttc agc ttc cag aca gca acc aca act atg caa gcg gtg<br>Glu Asn Leu Phe Ser Phe Gln Thr Ala Thr Thr Thr Met Gln Ala Val<br>20                  25                   30                   35 | 211 |
| ttc agg ggc tac gcg gag agg aag cgc cgg aaa cgg gag aat gat tcc<br>Phe Arg Gly Tyr Ala Glu Arg Lys Arg Arg Lys Arg Glu Asn Asp Ser<br>                   40                   45                   50 | 259 |
| gcg tct gta atc cag agg aac ttc cgc aaa cac ctg cgc atg gtc ggc<br>Ala Ser Val Ile Gln Arg Asn Phe Arg Lys His Leu Arg Met Val Gly<br>55                    60                   65 | 307 |
| agc cgg agg gtg aag gcc cag acg ttc gct gag cgg cgc gag cgg agc<br>Ser Arg Arg Val Lys Ala Gln Thr Phe Ala Glu Arg Arg Glu Arg Ser<br>                  70                   75                   80 | 355 |
| ttc agc cgg tcc tgg agc gac ccc acc ccc atg aaa gcc gac act tcc<br>Phe Ser Arg Ser Trp Ser Asp Pro Thr Pro Met Lys Ala Asp Thr Ser<br>85                    90                   95 | 403 |
| cac gac tcc cga gac agc agt gac ctg cag agc tcc cac tgc acg ctg<br>His Asp Ser Arg Asp Ser Ser Asp Leu Gln Ser Ser His Cys Thr Leu<br>100                  105                 110               115 | 451 |
| gac gag gcc ttc gag gac ctg gac tgg gac act gag aag ggc ctg gag<br>Asp Glu Ala Phe Glu Asp Leu Asp Trp Asp Thr Glu Lys Gly Leu Glu<br>                  120                 125               130 | 499 |

| | | |
|---|---|---|
| gct gtg gcc tgc gac acc gaa ggc ttc gtg cca cca aag gtc atg ctc<br>Ala Val Ala Cys Asp Thr Glu Gly Phe Val Pro Pro Lys Val Met Leu<br>              135                    140                  145 | | 547 |
| att tcc tcc aag gtg ccc aag gct gag tac atc ccc act atc atc cgc<br>Ile Ser Ser Lys Val Pro Lys Ala Glu Tyr Ile Pro Thr Ile Ile Arg<br>        150                    155                    160 | | 595 |
| cgg gat gac ccc tcc atc atc ccc atc ctc tac gac cat gag cac gca<br>Arg Asp Asp Pro Ser Ile Ile Pro Ile Leu Tyr Asp His Glu His Ala<br>  165                    170                    175 | | 643 |
| acc ttc gag gac atc ctt gag gag ata gag agg aag ctg aac gtc tac<br>Thr Phe Glu Asp Ile Leu Glu Glu Ile Glu Arg Lys Leu Asn Val Tyr<br>180                    185                    190                  195 | | 691 |
| cac aag gga gcc aag atc tgg aaa atg ctg att ttc tgc cag gga ggt<br>His Lys Gly Ala Lys Ile Trp Lys Met Leu Ile Phe Cys Gln Gly Gly<br>              200                    205                    210 | | 739 |
| cct gga cac ctc tat ctc ctc aag aac aag gtg gcc acc ttt gcc aaa<br>Pro Gly His Leu Tyr Leu Leu Lys Asn Lys Val Ala Thr Phe Ala Lys<br>        215                    220                    225 | | 787 |
| gtg gag aag gaa gag gac atg att cac ttc tgg aag cgg ctg agc cgc<br>Val Glu Lys Glu Glu Asp Met Ile His Phe Trp Lys Arg Leu Ser Arg<br>  230                    235                    240 | | 835 |
| ctg atg agc aaa gtg aac cca gag ccg aac gtc atc cac atc atg ggc<br>Leu Met Ser Lys Val Asn Pro Glu Pro Asn Val Ile His Ile Met Gly<br>245                    250                    255 | | 883 |
| tgc tac att ctg ggg aac ccc aat gga gag aag ctg ttc cag aac ctc<br>Cys Tyr Ile Leu Gly Asn Pro Asn Gly Glu Lys Leu Phe Gln Asn Leu<br>260                    265                    270                  275 | | 931 |
| agg acc ctc atg act cct tat agg gtc acc ttc gag tca ccc ctg gag<br>Arg Thr Leu Met Thr Pro Tyr Arg Val Thr Phe Glu Ser Pro Leu Glu<br>                  280                    285                  290 | | 979 |
| ctc tca gcc caa ggg aag cag atg atc gag acg tac ttt gac ttc cgg<br>Leu Ser Ala Gln Gly Lys Gln Met Ile Glu Thr Tyr Phe Asp Phe Arg<br>        295                    300                    305 | | 1027 |
| ttg tat cgc ctg tgg aag agc cgc cag cac tcg aag ctg ctg gac ttt<br>Leu Tyr Arg Leu Trp Lys Ser Arg Gln His Ser Lys Leu Leu Asp Phe<br>  310                    315                    320 | | 1075 |
| gac gac gtc ctg tga ggggcagagg cctccgccca gtcaccatca ggccactccc<br>Asp Asp Val Leu<br>    325 | | 1130 |
| tctgcaccgg gacctggggc tgggccgcct cgtgctcccc gggactgtgt agctccggtc | | 1190 |
| tcgcctggag ccacttcagg gcacctcaga cgttgctcag gttcccctg tgggttccgg | | 1250 |
| tcctcgctgc acccgtggcc gcagaggctg cagtccctgg gggccgggag gatcccgccc | | 1310 |
| tgtggcccgt ggatgctcag cggccaggca ctgacctgcc atgcctcgcc tggaggctca | | 1370 |
| gctgtgggca tccctccatg gggttcatag aaataagtgc aatttctaca cccccgaaac | | 1430 |
| aattcaaagg gaagcagcat ttcttgttaa ctagttaagc actatgctgc tagttacagt | | 1490 |
| gtaggcaccc cggcccagca gcccagcagc ccacatgtgt tcaggaccct ccctgcccac | | 1550 |
| cccctccctg ccgtatcgat caccagcacc agggtggccc gtgtgcgtgg ggccagcgtc | | 1610 |
| gccgggctgc ccagcctggc tctgtctaca ctggccgagt ctctgggtct gtctacactg | | 1670 |
| gccgagtctc cgactgtctg tgctttcact tacactcctc ttgccacccc ccatccctgc | | 1730 |
| ttacttagac ctcagccggc gccggacccg gtaggggcag tctgggcagc aggaaggaag | | 1790 |
| ggcgcagcgt ccctccttc agaggaggct ctgggtgggg cctgctcctc atcccccaa | | 1850 |
| gcccacccag cactctcatt gctgctgttg agttcagctt ttaccagcct cagtgtggag | | 1910 |
| gctccatccc agcacacagg cctggggctt ggcaggggcc cagctggggc tgggccctgg | | 1970 |

```
gttttgagaa actcgctggc accacagtgg gccctggac ccggccgcgc agctggtgga    2030
ctgtaggggc tcctgactgg gcacaggagc tcccagcttt tgtccacggc cagcaggatg    2090
ggctgtcgtg tatatagctg gggcgagggg gcaggccccc cttgtgcaga gccagggtc    2150 tgagggcacc tggctgtgtt cccagctgag ggagggctgg ggcggggggcc gggcttggaa    2210 cgatgtacga taccctcata gtgaccatta aacctgatcc tcc                      2253
```

<210> SEQ ID NO 134
<211> LENGTH: 2253
<212> TYPE: DNA
<213> ORGANISM: Danio rerio
<220> FEATURE:
<221> NAME/KEY: exon
<222> LOCATION: (1)..(298)

<400> SEQUENCE: 134

```
gtg ccc cgg atg tgc cca gct ggc tcc tgg ccc cac ccc tcg ggc ctt    48
Val Pro Arg Met Cys Pro Ala Gly Ser Trp Pro His Pro Ser Gly Leu
 1               5                  10                  15 tgg gct gga cca gcc acc tct gcc tga gac ctc cgg tcg ccg caa gaa    96
Trp Ala Gly Pro Ala Thr Ser Ala     Asp Leu Arg Ser Pro Gln Glu
             20                  25                  30 gct gga gag gat gta cag cgt tga ccg tgt gtc tga cga cat ccc tat   144
Ala Gly Glu Asp Val Gln Arg     Pro Cys Val     Arg His Pro Tyr
         35                  40                  45 tcg tac ctg gtt ccc caa gga aaa tct ttt cag ctt cca gac agc aac   192
Ser Tyr Leu Val Pro Gln Gly Lys Ser Phe Gln Leu Pro Asp Ser Asn
             50                  55                  60 cac aac tat gca agc ggt gtt cag ggg cta cgc gga gag gaa gcg ccg   240
His Asn Tyr Ala Ser Gly Val Gln Gly Leu Arg Gly Glu Glu Ala Pro
 65                  70                  75 gaa acg gga gaa tga ttc cgc gtc tgt aat cca gag gaa ctt ccg caa   288
Glu Thr Gly Glu     Phe Arg Val Cys Asn Pro Glu Glu Leu Pro Gln
 80                      85                  90 aca cct gcg c atggtcggca gccggagggt gaaggcccag acgttcgctg          338
Thr Pro Ala
         95 agcggcgcga gcggagcttc agccggtcct ggagcgaccc cacccccatg aaagccgaca    398 cttcccacga ctcccgagac agcagtgacc tgcagagctc ccactgcacg ctggacgagg    458 ccttcgagga cctggactgg gacactgaga agggcctgga ggctgtggcc tgcgacaccg    518 aaggcttcgt gccaccaaag gtcatgctca tttcctccaa ggtgcccaag ctgagtaca     578 tccccactat catccgccgg gatgacccct ccatcatccc catcctctac gaccatgagc    638 acgcaacctt cgaggacatc cttgaggaga tagaggaa gctgaacgtc taccacaagg     698 gagccaagat ctggaaaatg ctgattttct gccagggagg tcctggacac ctctatctcc    758 tcaagaacaa ggtggccacc tttgccaaag tggagaagga agaggacatg attcacttct    818 ggaagcggct gagccgcctg atgagcaaag tgaacccaga gccgaacgtc atccacatca    878 tgggctgcta cattctgggg aaccccaatg agagaagct gttccagaac ctcaggaccc    938 tcatgactcc ttatagggtc accttcgagt caccctgga gctctcagcc caagggaagc    998 agatgatcga gacgtacttt gacttccggt tgtatcgcct gtggaagagc cgccagcact   1058 cgaagctgct ggactttgac gacgtcctgt gaggggcaga ggcctccgcc cagtcaccat   1118 caggccactc cctctgcacc gggacctggg gctgggccgc ctcgtgctcc ccgggactgt   1178 gtagctccgg tctcgcctgg agccacttca gggcacctca gacgttgctc aggttcccc    1238
```

-continued

```
tgtgggttcc ggtcctcgct gcacccgtgg ccgcagaggc tgcagtccct gggggccggg    1298
aggatcccgc cctgtggccc gtggatgctc agcggccagg cactgacctg ccatgcctcg    1358
cctggaggct cagctgtggg catccctcca tggggttcat agaaataagt gcaatttcta    1418
cacccccgaa acaattcaaa gggaagcagc atttcttgtt aactagttaa gcactatgct    1478
gctagttaca gtgtaggcac cccggcccag cagcccagca gcccacatgt gttcaggacc    1538
ctccctgccc accccctccc tgccgtatcg atcaccagca ccagggtggc ccgtgtgcgt    1598
ggggccagcg tcgccgggct gcccagcctg gctctgtcta cactggccga gtctctgggt    1658
ctgtctacac tggccgagtc tccgactgtc tgtgctttca cttacactcc tcttgccacc    1718
ccccatccct gcttacttag acctcagccg gcgccggacc cggtaggggc agtctgggca    1778
gcaggaagga agggcgcagc gtcccctcct tcagaggagg ctctgggtgg ggcctgctcc    1838 tcatccccccc aagcccaccc agcactctca ttgctgctgt tgagttcagc ttttaccagc    1898
ctcagtgtgg aggctccatc ccagcacaca ggcctgggc ttggcagggg cccagctggg    1958
gctgggccct gggttttgag aaactcgctg gcaccacagt gggcccctgg acccggccgc    2018
gcagctggtg gactgtaggg gctcctgact gggcacagga gctcccagct tttgtccacg    2078
gccagcagga tgggctgtcg tgtatatagc tggggcgagg gggcaggccc ccttgtgca    2138 gagccagggg tctgagggca cctggctgtg ttcccagctg agggagggct ggggcggggg    2198
ccgggcttgg aacgatgtac gatacccctca tagtgaccat taaacctgat cctcc        2253
```

<210> SEQ ID NO 135
<211> LENGTH: 40
<212> TYPE: PRT
<213> ORGANISM: Artificial Sequence
<220> FEATURE:
<223> OTHER INFORMATION: TCAP 3 General Motif
<220> FEATURE:
<221> NAME/KEY: MISC_FEATURE
<222> LOCATION: (5)..(5)
<223> OTHER INFORMATION: X=G, S or A
<220> FEATURE:
<221> NAME/KEY: MISC_FEATURE
<222> LOCATION: (6)..(6)
<223> OTHER INFORMATION: X=G or R
<220> FEATURE:
<221> NAME/KEY: MISC_FEATURE
<222> LOCATION: (9)..(9)
<223> OTHER INFORMATION: X=L or Q
<220> FEATURE:
<221> NAME/KEY: MISC_FEATURE
<222> LOCATION: (19)..(19)
<223> OTHER INFORMATION: X=V or I
<220> FEATURE:
<221> NAME/KEY: MISC_FEATURE
<222> LOCATION: (32)..(32)
<223> OTHER INFORMATION: X=V or I

<400> SEQUENCE: 135

Gln Leu Leu Ser Xaa Xaa Lys Val Xaa Gly Tyr Asp Gly Tyr Tyr Val
1               5                   10                  15

Leu Ser Xaa Glu Gln Tyr Pro Glu Leu Ala Asp Ser Ala Asn Asn Xaa
            20                  25                  30

Gln Phe Leu Arg Gln Ser Glu Ile
            35                  40

<210> SEQ ID NO 136
<211> LENGTH: 36
<212> TYPE: PRT
<213> ORGANISM: Artificial Sequence

```
<220> FEATURE:
<223> OTHER INFORMATION: G. gallus TCAP2

<400> SEQUENCE: 136

Thr Gly Arg Val Gln Gly Tyr Glu Gly Tyr Tyr Val Leu Pro Val Glu
1               5                   10                  15

Gln Tyr Pro Glu Leu Ala Asp Ser Ser Asn Ile Gln Phe Leu Arg
            20                  25                  30

Gln Asn Glu Met
        35

<210> SEQ ID NO 137
<211> LENGTH: 251
<212> TYPE: PRT
<213> ORGANISM: Artificial Sequence
<220> FEATURE:
<223> OTHER INFORMATION: Human Ten M1

<400> SEQUENCE: 137

Thr Ile Leu Gly Ile Gln Cys Glu Leu Gln Lys Gln Leu Arg Asn Phe
1               5                   10                  15

Ile Ser Leu Asp Gln Leu Pro Met Thr Pro Arg Tyr Asn Asp Gly Arg
            20                  25                  30

Cys Leu Glu Gly Gly Lys Gln Pro Arg Phe Ala Ala Val Pro Ser Val
        35                  40                  45

Phe Gly Lys Gly Ile Lys Phe Ala Ile Lys Asp Gly Ile Val Thr Ala
    50                  55                  60

Ile Ile Gly Val Ala Asn Glu Asp Ser Arg Arg Leu Ala Ala Ile Leu
65                  70                  75                  80

Asn Asn Ala His Tyr Leu Glu Asn Leu His Phe Thr Ile Glu Gly Arg
                85                  90                  95

Asp Thr His Tyr Phe Ile Lys Leu Gly Ser Leu Glu Glu Asp Leu Val
            100                 105                 110

Leu Ile Gly Asn Thr Gly Gly Arg Arg Ile Leu Glu Asn Gly Val Asn
        115                 120                 125

Val Thr Val Ser Gln Met Thr Ser Val Leu Asn Gly Arg Thr Arg Arg
    130                 135                 140

Phe Ala Asp Ile Gln Leu Gln His Gly Ala Leu Cys Phe Asn Ile Arg
145                 150                 155                 160

Tyr Gly Thr Thr Val Glu Glu Lys Asn His Val Leu Glu Ile Ala
                165                 170                 175

Arg Gln Arg Ala Val Ala Gln Ala Trp Thr Lys Glu Gln Arg Arg Leu
            180                 185                 190

Gln Glu Gly Glu Glu Gly Ile Arg Ala Trp Thr Glu Gly Lys Gln
        195                 200                 205

Gln Leu Leu Ser Thr Gly Arg Val Gln Gly Tyr Asp Gly Tyr Phe Val
    210                 215                 220

Leu Ser Val Glu Gln Tyr Leu Glu Leu Ser Asp Ser Ala Asn Asn Ile
225                 230                 235                 240

His Phe Met Arg Gln Ser Glu Ile Gly Arg Arg
                245                 250

<210> SEQ ID NO 138
<211> LENGTH: 40
<212> TYPE: PRT
<213> ORGANISM: Artificial Sequence
<220> FEATURE:
<223> OTHER INFORMATION: G. gallus TCAP-1
```

```
<400> SEQUENCE: 138

Gln Leu Leu Asn Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile
        35                  40

<210> SEQ ID NO 139
<211> LENGTH: 41
<212> TYPE: PRT
<213> ORGANISM: Artificial Sequence
<220> FEATURE:
<223> OTHER INFORMATION: scrambled TCAP (scTCAP) sequence
<220> FEATURE:
<221> NAME/KEY: MOD_RES
<222> LOCATION: (1)..(1)
<223> OTHER INFORMATION: pyroglutamic acid

<400> SEQUENCE: 139

Glu Thr His Ser Leu Glu Leu Arg Val Ser Leu Ile Gly Glu Val Gln
1               5                   10                  15

Gln Phe Ile Gly Tyr Glu Asn Gln Ser Asp Gln Asn Tyr Gly Leu Leu
            20                  25                  30

Ala Tyr Phe Asp Arg Val Gly Met Ser
        35                  40

<210> SEQ ID NO 140
<211> LENGTH: 25
<212> TYPE: PRT
<213> ORGANISM: Artificial Sequence
<220> FEATURE:
<223> OTHER INFORMATION: sequence used as hapten
<220> FEATURE:
<221> NAME/KEY: MOD_RES
<222> LOCATION: (1)..(1)
<223> OTHER INFORMATION: pyroglutamic acid

<400> SEQUENCE: 140

Glu Gln Leu Leu Gly Thr Gly Arg Val Gln Gly Tyr Asp Gly Tyr Phe
1               5                   10                  15

Val Leu Ser Val Glu Gln Tyr Leu Glu
            20                  25

<210> SEQ ID NO 141
<211> LENGTH: 25
<212> TYPE: PRT
<213> ORGANISM: Artificial Sequence
<220> FEATURE:
<223> OTHER INFORMATION: sequence used as hapten

<400> SEQUENCE: 141

Val Leu Ser Val Glu Gln Tyr Leu Glu Leu Ser Asp Ser Ala Asn Asn
1               5                   10                  15

Ile His Phe Met Arg Gln Ser Glu Ile
            20                  25
```

METHOD FOR MODULATING INSULIN-INDEPENDENT GLUCOSE TRANSPORT USING TENEURIN C-TERMINAL ASSOCIATED PEPTIDE (TCAP)

RELATED APPLICATIONS

This patent application claims priority from U.S. Provisional Patent Application No. 62/026,346, filed Jul. 18, 2014, entitled, "METHOD FOR MODULATING GLUCOSE TRANSPORT USING TENEURIN C-TERMINAL ASSOCIATED PEPTIDE (TCAP)", which is incorporated herein by reference in its entirely.

FIELD OF THE INVENTION

This invention relates to a method for modulating insulin-independent glucose transport using Teneurin C-Terminal Associated Peptide (TCAP). In one aspect, the invention provides a method to increase energy available to skeletal muscle cells. In some embodiments, it further relates to methods and uses and compositions of Teneurin C-Terminal Associated Peptide (TCAP) as an agent to increase glucose uptake by skeletal muscle cells under conditions where increased intracellular glucose in skeletal muscle cells is advantageous. In other embodiments it relates to methods, uses and compositions of TCAP for modulating, in one aspect lowering plasma glucose levels.

INCORPORATION BY REFERENCE STATEMENT

All references noted herein are incorporated by reference. The paper copy and computer-readable form (CRF) are identical. Further the sequence listing is being submitted through EFS-Web compliant with ASCII text and is also herein incorporated by reference. The name of the text file is T8476302WO_ST25.txt, created on Jul. 20, 2015 and the size of the text file is 128 kilobytes.

BACKGROUND OF THE INVENTION

The teneurins are a family of four vertebrate type II transmembrane proteins preferentially expressed in the central nervous system (Baumgartner et al., 1994). The teneurins are about 2800 amino acids long and possess a short membrane spanning region. The extracellular face consists of a number of structurally distinct domains suggesting that the protein may possess a number of distinct functions (Minet and Chiquet-Ehrismann, 2000; Minet et al., 1999; Oohashi et al., 1999). The gene was originally discovered in Drosophila as a pair rule gene and was named tenascin-major (Ten-M) or Odz (Baumgartner et al., 1994; Levine et al., 1994). It is expressed in the Drosophila nervous system and targeted disruption of the genes leads to embryonic lethality (Baumgartner et al., 1994). In immortalized mouse cells, expression of the teneurin protein led to increased neurite outgrowth (Rubin et al., 1999).

The extracellular C-terminal region of each teneurin is characterized by a 40 or 41 amino acid sequence flanked by enzymatic cleavage sites, which predicts the presence of an amidated cleaved peptide (Qian et al., 2004; Wang et al., 2004). A synthetic version of this peptide was named teneurin C-terminus associated peptide (TCAP) and is active in vivo and in vitro. The mouse TCAP from teneurin-1 (TCAP-1) can modulate cAMP concentrations and proliferation in mouse hypothalamic cell lines as well as regulate the teneurin protein in a dose-dependent manner (Wang et al, 2004). Intracerebroventricular injection of TCAP-1 into rats can induce changes in the acoustic startle response three weeks after administration (Wang et al., 2004). [Also see, PCT/CA2003/000622, filed May 2, 2003, herein incorporated by reference; PCT/CA200300621, filed May 2, 2003, herein incorporated by reference; U.S. Ser. No. 11/706,376, filed Feb. 15, 2007, which claims the benefit and priority of provisional application No. 60/773,309, filed on Feb. 15, 2006, and provisional application No. 60/783,821, filed on Mar. 21, 2006, all of which are incorporated in their entirety by reference.]

Skeletal muscle is a critical regulator of glucose homeostasis. Skeletal muscle comprises the bulk of the body's insulin-sensitive tissue and is where insulin-induced glucose uptake is quantitatively most important (Wasserman et al., 2010; Abdul-Ghani and DeFronzo, 2010). Impairment in the response to insulin in skeletal muscle (i.e. an "insulin-resistant" state) leads to a marked reduction in glucose uptake (Brozimck et al., 1992; Wasserman et al., 2010; Abdul-Ghani and DeFronzo, 2010). Skeletal muscle insulin resistance is considered to be the initiating or primary defect for development of type 2 diabetes, sometimes evident years before failure of pancreatic β cells and onset of overt hyperglycemia (DeFronzo and Tripathy, 2009; Petersen et al., 2007; Wasserman et al., 2011).

Further, Type 1 diabetes is characterised by the absence of circulating insulin due to the autoimmune destruction of beta-cells in the pancreas. Patients are traditionally treated with multiple daily injections of exogenous insulin analogues. However, although these therapies improve quality of life, they are associated with the risk of hypoglycemic episodes and do not prevent the development of debilitating secondary complications. For these reasons, there is increasing demand for new therapies and preventions. Mann et al. (Curr Pharm Des. 2010; 16(8):1002-20-http://www.ncbi.nlm.nih.gov/pubmed/20041826) describe one approach, which is to the use of viral or non-viral gene therapy to modify skeletal muscle to produce and secrete insulin into the circulation and/or to increase muscle glucose uptake. Skeletal muscle is a desirable target tissue for the treatment of diabetes, including Type 1 diabetes) not only for its central role in whole body metabolism and glucose homeostasis, but also for its accessibility and amenability to many potential gene therapy technologies. However, gene therapy is quite complex, expensive and not optimal route.

Some glycogen storage diseases are also associated with improper glucose homeostasis in skeletal muscle cells. For example, glycogen storage disease type V (McArdle disease) results from a deficiency of the muscle isoform of the enzyme glycogen phosphorylase, which catalyzes glycogen to glucose for use in muscle (Robertshaw et al., 2007). In another example, glycogen storage disease type III is characterized by a deficiency in glycogen debranching enzymes which results in excess amounts of abnormal glycogen to be deposited in the liver and muscles (Preisler et al., 2013).

Skeletal muscle is also the primary site of glucose uptake during exercise (Wasserman et al., 2010; Richter and Hargreaves, 2013). Carbohydrate in the form of glucose becomes an increasingly important energy substrate with rising exercise intensity (Jensen and Richter, 2012; Holloszy and Kohrt, 1996). Blood glucose uptake into skeletal muscle cells can account for up to 40% of oxidative metabolism during exercise, and enhancing the availability of glucose delays muscle fatigue and increases performance (Richter and Hargreaves, 2013; Coyle et al., 1983).

In light of the above, there is a need to develop methods and compounds to stimulate glucose uptake by skeletal muscle cells and thereby increase the energy available to skeletal muscle cells in diseased and normal states.

SUMMARY OF THE INVENTION

In one aspect the invention provides a method for increasing energy available to a skeletal muscle cells. The inventors have surprisingly found that TCAP induces muscle cells to take up glucose.

As such, in one aspect the invention provides a method for increasing energy available to skeletal muscle cells by administering to a patient in need thereof an effective amount of TCAP, pharmaceutically acceptable salt or ester thereof or obvious chemical equivalent thereof. In another embodiment, administration of TCAP to the cells is administration of TCAP to a patient in need thereof comprising said cells. In one aspect the patient in need thereof is a patient with skeletal muscle cells exhibiting insulin resistance. In one aspect, a pharmaceutical composition comprising TCAP, pharmaceutically acceptable salt or ester or obvious chemical equivalent thereof and a pharmaceutically acceptable carrier is administered.

In one aspect, the invention provides a method of increasing energy available to skeletal muscle cells, the method comprising administering to a patient in need thereof an effective amount of an isolated teneurin c-terminal associated peptide (TCAP peptide), or a pharmaceutically acceptable salt thereof, wherein the amino acid sequence of said TCAP peptide consists essentially of: (i) au amino acid sequence having at least 95% identity to an amino acid sequence selected from the group consisting of SEQ ID NOs: 13, 14, 21, 22, 29, 30, 37, 38, 45, 46, 53, 54, 61, 62, 69, 70, 77, 78, 85, 86, 93, 94, and 101; or (ii) a 38 amino acid sequence from the carboxy terminal end of a peptide having at least 95% identity to an amino acid sequence selected from the group consisting of SEQ ID NOs: 13, 14, 21, 22, 29, 30, 37, 38, 45, 46, 53, 54, 61, 62, 69, 70, 77, 78, 85, 86, 93, 94, and 101; optionally wherein: (a) the carboxy terminal end of said TCAP peptide is amidated or comprises an amidation signal sequence; or (b) when the amino terminal amino acid of said TCAP peptide is glutamine, it is in the form of pyroglutamic acid.

In one embodiment, increasing energy available to a muscle cell comprises increasing glucose uptake by the cell under conditions where increased energy is advantageous, such as to protect against, inhibit/prevent, and/or treat muscle trauma or muscle fatigue.

In one embodiment, a condition where increased energy is advantageous is the increased rate of muscle fiber contractions associated with exercise. As such in one aspect the invention provides a method of increasing energy available to a skeletal muscle cell before, during, or following exercise by administering to the cell an effective amount of TCAP, a pharmaceutically acceptable salt or ester thereof or obvious chemical equivalent thereof.

In another embodiment, a condition where increased energy is advantageous is selected from the group consisting of: injury, hypoxia, a glycogen storage disease, and a myopathy.

In another embodiment, the invention provides a method of increasing energy available to a muscle cell over a long term. In various aspects, the long term is at least one day, al least three days, at least five days, or at least seven days.

In one embodiment, the invention provides a method for using TCAP, for instance TCAP-1 (human or mouse, or preferably human), to prevent or treat diabetes. In another embodiment the diabetes is Type 1 diabetes. In another embodiment the diabetes is Type 2 diabetes.

In one embodiment of the aforementioned methods of the invention, the muscle cell is a mouse myocyte.

In one embodiment the findings show that TCAP-1 results in a 20-30% decrease in plasma glucose levels in rats one week alter administration. In another embodiment there was an increases in $^{18}$F-2-deoxyglucose uptake into the cortex of TCAP-1 treated rats. In vitro, TCAP-1 also induces 3H-deoxyglucose transport into hypothalamic neurons via an insulin-independent manner. This is correlated with an increase in membrane levels of GLUT3 protein and immunoreactivity. In one embodiment a deduced pathway by which, TCAP-1 signals in vitro was used to establish a link between the MEK-ERK1/2 pathway and glucose uptake as well as a connection between the MEK-ERK1/2 and AMPK pathways. In another embodiment, the immunoreactivity studies herein indicate that the TCAP-1 system exists in muscle and plays a part in skeletal muscle metabolism and physiology.

In another aspect, the invention relates to a method for modulating insulin-independent glucose transport using Teneurin C-Terminal Associated Peptide (TCAP) as defined herein. In one aspect, the invention provides a method to increase energy available to skeletal muscle cells. In one embodiment, it further relates to methods and uses and compositions of Teneurin C-Terminal Associated Peptide (TCAP) as an agent to increase glucose uptake by skeletal muscle cells under conditions where increased intracellular glucose in skeletal muscle cells is advantageous such as to protect against, inhibit/prevent, and/or treat insulin resistance or muscle fatigue.

In other embodiments the invention provides a method for controlling plasma glucose levels. In one embodiment, the invention provides a method for decreasing plasma glucose levels using and/or administering an effective amount of TCAP (as defined herein) or a composition comprising TCAP or a salt thereof and a pharmaceutically acceptable carrier. In some embodiments, the invention provides a composition comprising TCAP, in other embodiments TCAP-1 or a salt or amide or pyroglutamic acid derivative thereof as described herein for use in the embodiments of this invention. In one embodiment the use is for controlling plasma glucose levels, in one aspect, lowering plasma glucose levels in patients in need thereof, such as diabetics, in one embodiment Type 2 diabetics.

Additional aspects and advantages of the present invention will be apparent in view of the description which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The invention will now be described in relation to the drawings, in which.

FIG. 6A Haemoglobin concentrations in vivo. Hemoglobin concentrations were generated using plasma collected from male Wistar rats given a single injection of saline (n=5), 1 nmole/kg TCAP-1 (n=4), or 10 nmole/kg TCAP-1 (n=4), and no injection (Control; n=2). No significant results were observed in haemoglobin concentrations following TCAP-1 administration. (Mean±SEM; 1-way ANOVA and Bonferonni's post hoc test.) FIG. 6B Hematocrit of rats in vivo. Hematocrit counts were generated using plasma collected from male Wistar rats given a single injection of saline (n=5), 1 nmole/kg TCAP-1 (n=4), or 10 nmole/kg TCAP-1 (n=4), and no injection (Control; n=2). No significant results were observed in the hematocrit counts following TCAP-1 administration. (Mean±SEM; 1-way ANOVA and Bonferonni's post hoc test.) FIG. 6C Platelet counts of rats in vivo. Platelet/thrombocyte counts were generated using plasma collected from male Wistar rats given a single injection of saline (n=5), 1 nmole/kg TCAP-1 (n=4), or 10 nmole/kg TCAP-1 (n=4), and no injection (Control; n=2). No significant results were observed in platelet counts following TCAP-1 administration. (Mean±SEM; 1-way ANOVA and Bonferonni's post hoc test.) FIG. 6D Red blood cell counts of rats in vivo. Red blood cell counts were generated using plasma collected from male Wistar rats given a single injection of saline (n=5), 1 nmole/kg TCAP-1 (n=4), or 10 nmole/kg TCAP-1 (n=4) and no injection (Control; n=2). No significant results were observed in red blood cell counts following TCAP-1 administration. (Mean±SEM; 1-way ANOVA and Bonferonni's post hoc test) FIG. 6E White blood cells (WBC), neutrophils (NE), or lymphocytes (LY) in vivo. Levels of immune factors were generated using plasma collected from male Wistar rate given a single injection of saline (n=5), 1 nmole/kg TCAP-1 (n=4), or 10 nmole/kg TCAP-1 (n=4) and no injection (Control; n=2). No significant results were observed in the levels of white blood cells, neutrophils or lymphocytes following TCAP-1 administration. (Mean±SEM; 1-way ANOVA and Bonferonni's post hoc test). FIG. 6F Monocytes (MO), basophils (BA), or eosinophils (EO) in vivo. Levels of immune factors were generated using plasma collected from male Wistar rats given a single injection of saline (n=5), 1 nmole/kg TCAP-1 (n=4), or 10 nmole/kg TCAP-1 (n=4) and no injection (Control; n=2). No significant results were observed in monocytes, basophils or eosinophils following TCAP-1 administration. (Mean±SEM; 1-way ANOVA and Bonferonni's post hoc test.) FIG. 6G Haemoglobin concentration in spontaneously diabetic Gogo-Kakizaki (GK) rats in vivo. Hemoglobin concentrations were generated using plasma collected from male GK. Wistar rats given a single injection of saline (n=10), or 10 nmole/kg TCAP-1 (n=8). No significant results were observed in haemoglobin concentrations following TCAP-1 administration. (Mean±SEM; 1-way ANOVA and Bonferonni's post hoc test.) FIG. 6H Hematocrit in spontaneously diabetic Goto-Kakizaki (GK) rats in vivo. Hematocrit counts were generated using plasma collected from male GK Wistar rats given a single injection of saline (n=10), or 10 nmole/kg TCAP-1 (n=8). No significant results were observed in hematocrit counts following TCAP-1 administration, (Mean±SEM; 1-way ANOVA and Bonferonni's post hoc test) FIG. 6I Platelet counts of spontaneously diabetic Goto-Kakizaki (GK) rats in vivo. Platelet/thrombocyte counts were generated using plasma collected from male GK Wistar rats given a single injection of saline (n=10), or 10 nmole/kg TCAP-1 (n=8). No significant results were observed in platelet counts following TCAP-1 administration. (Mean±SEM; 1-way ANOVA and Bonferonni's post hoc test.) FIG. 6J Red blood cell counts of spontaneously diabetic Goto-Kakizaki (GK) rats in vivo. Red blood cell counts were generated using plasma collected from male GK Wistar rats given a single injection of saline (n=10), or 10 nmole/kg TCAP-1 (n=8). No significant results were observed in red blood cell counts following TCAP-1 administration. (Mean±SEM; 1-way ANOVA and Bonferonni's post hoc test.) FIG. 6K White blood cells (WBC), neutrophils (NE), or lymphocytes (LY) in spontaneously diabetic Goto-Kakizaki (GK) rats in vivo. Levels of immune factors were generated using plasma collected from male GK Wistar rats given a single injection of saline (n=10), or 10 nmole/kg TCAP-1 (n=8). No significant results were observed in the levels of white blood cells, neutrophils or lymphocytes following TCAP-1 administration. (Mean±SEM; 1-way ANOVA and Bonferonni's post hoc test.) FIG. 6L Monocytes (MO), basophils (BA), or eosinophils (EO) in spontaneously diabetic Goto-Kakizaki (GK) rats in vivo. Levels of immune factors were generated using plasma collected from male GK Wistar rats given a single injection of saline (n=10), or 10 nmole/kg TCAP-1 (n=8). No significant results were observed in monocytes, basophils or eosinophils following TCAP-1 administration. (Mean±SEM; 1-way ANOVA and Bonferonni's post hoc test.)

Phosphorylation of AMPK is inhibited by application of 10 µM MEK inhibitor (U0126) suggesting a MEK/ERK1-2 dependent signalling.

Figure 19:
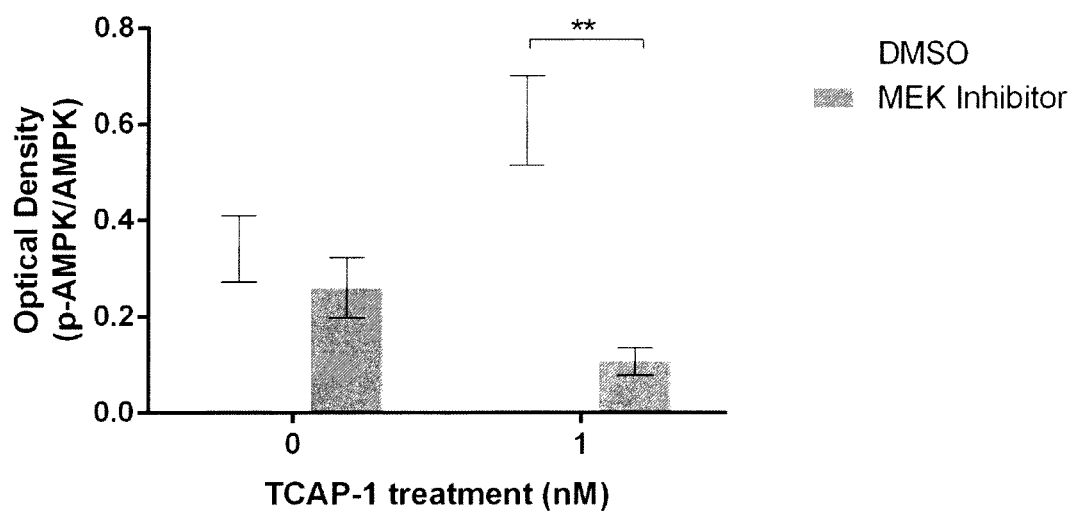

FIG. 19. TCAP-1 induces MEK-dependent AMPK phosphorylation in mHypoE-38 neurons. Analyses of western blots from FIG. 3.15 for vehicle and 1 nM TCAP-1 treated cells at 1 minute (n=3 for each group). Each p-AMPK band intensity was normalized to total AMPK at each corresponding treatment point. There was a significant (p<0.01) inhibition of AMPK phosphorylation in the presence of 10 µM MEK inhibitor (U0126) with TCAP-1 treatment Values are mean±SEM, two-way ANOVA and Bonferonni's post hoc test. Band intensity was measured by quantifying the integrated optical intensity using LabWorks (UVP Bio-imaging systems v4.0.0.8).

Figure 20:
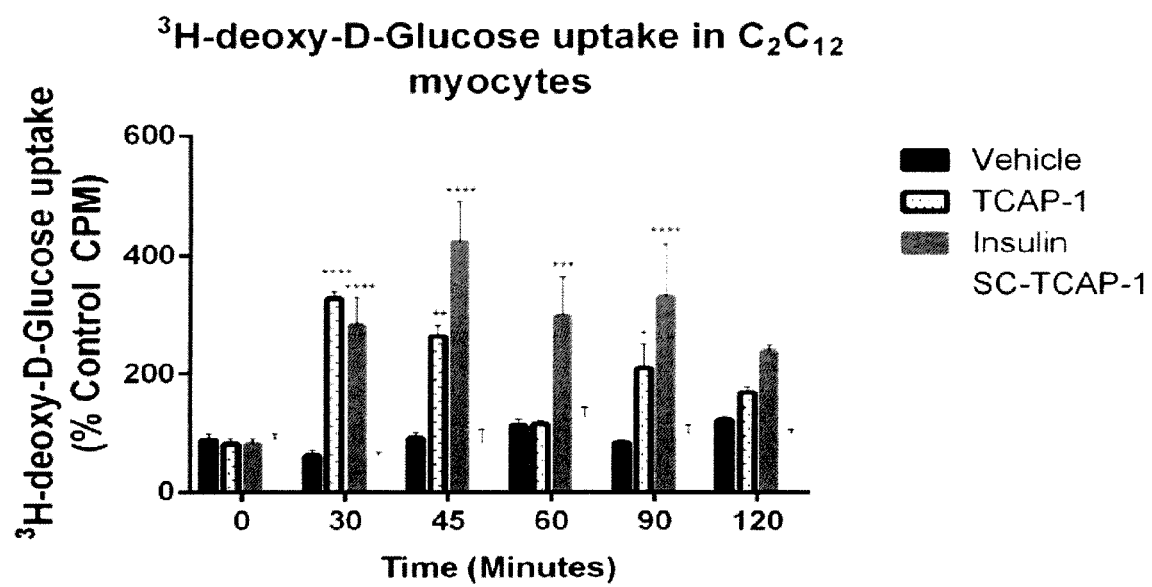

FIG. 20. Insulin and TCAP-1 treatments cause an increase in $^3$H-2-deoxyglucose transport in $C_2C_{12}$ myocytes over the course of two hours. Cells were treated with 100 nM insulin, 100 nM TCAP-1, 100 nM SC-TCAP-1, or saline then exposed to 0.5 µCi/well 3H-2-deoxyglucose, and subsequently lysed with 50 mM NaOH. Radioactivity in cell lysates was counted using a liquid scintillation counter. The level of significance was determined by two-way ANOVA and Bonferonni's post hoc test.

Figure 21:
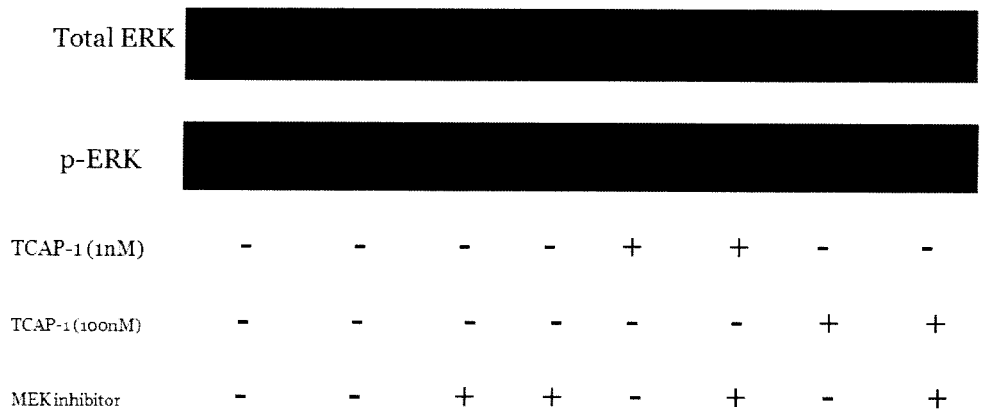

FIG. 21. TCAP-1 treatment does not significantly change levels of p-ERK expression in C2C12 myocytes. C2C12 cells were treated with 1 nM or 100 nM TCAP-1 for 1 minute and levels of p-ERK and total ERK was compared. Representative western blots show that TCAP-1 treatment did not significantly change p-ERK levels suggesting that TCAP-1 acts via an alternate signalling pathway. Phosphorylation of ERK is inhibited by application of MEK inhibitor (positive control).

Figure 22:
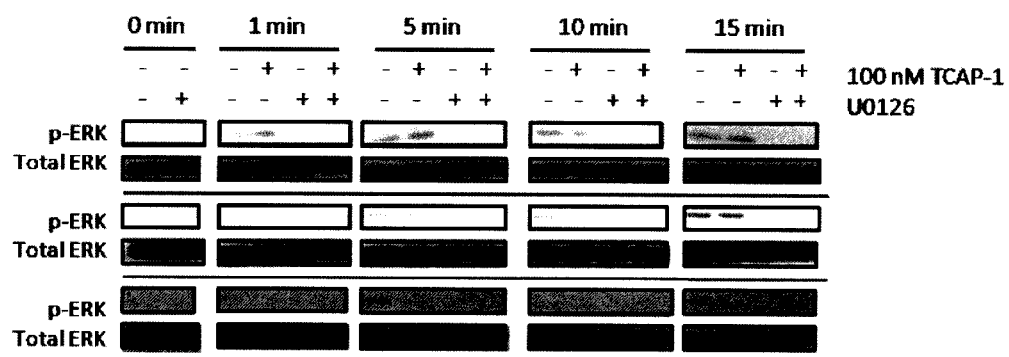

FIG. 22. 100 nM TCAP-1 treatment on pERK levels in C2C12 myocytes is not altered across 15 minutes. C2C12 cells were treated with 100 nM TCAP-1 for 0 (Vehicle), 1, 5, 10 and 15 minutes and levels of p-ERK and total ERK was compared. Representative western blots show that TCAP-1 treatment did not significantly change p-ERK levels suggesting that TCAP-1 acts via an alternate signalling pathway. Phosphorylation of ERK is inhibited by application of 10 µM MEK inhibitor (positive control; U0126).

Figure 23:
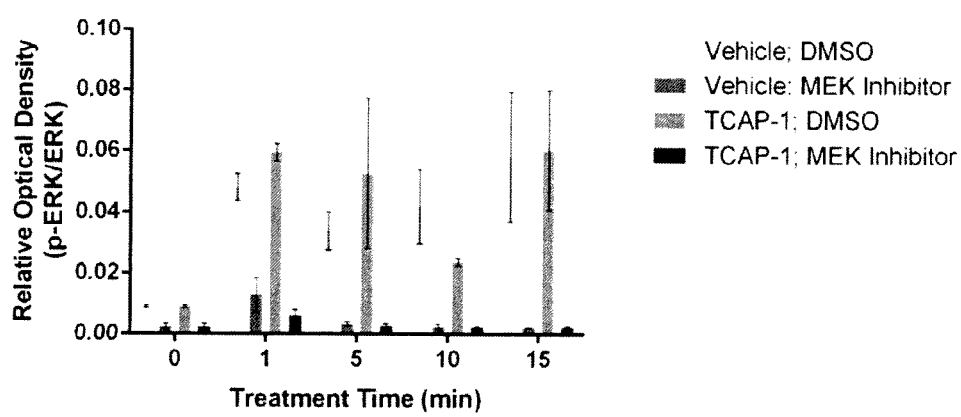

FIG. 23 Western blot analyses quantification of TCAP-1 treatment on ERK, phosphorylation in C2C12 myocytes. Analyses of western blots from FIG. 15 for vehicle and 100 nM TCAP-1 treated cells at 0, 1, 5, 10, and 15 minutes (n=3 for each group). Each p-ERK band intensity was normalized to total ERK at each corresponding treatment time. There was no significant change in ERK phosphorylation in response to TCAP-1 at any time points. There was significant inhibition of ERK phosphorylation in the presence of 10 µM MEK inhibitor (U0126). (Values are mean±SEM, two-way ANOVA and Bonferonni's post hoc test). Band intensity was measured by quantifying the integrated optical intensity using Lab Works (UVP Bio-imaging: systems V4.0.0.8).

DETAILED DESCRIPTION OF THE INVENTION

As described herein, teneurin C-terminus associated peptide (TCAP) increases energy available to muscles, such as to protect against, inhibit/prevent, and/or treat muscle fatigue or insulin resistance. In another aspect, TCAP treatment produces a significant decrease in blood glucose after one week. In the examples described herein, treatment with TCAP-1 induced glucose uptake in two distinct cell types: a mouse myocyte cell line ($C_2C_{12}$) and an immortalized hypothalamic mouse cell line (N38). Upregulated glucose uptake is associated with other metabolic changes including mitochondrial activation and glucose transporter translocation to membranes and regions of cellular growth. Further, TCAP is found on sarcolemma of skeletal muscle and localizes to neuromuscular junctions. As such, TCAP can be used to increase energy available to muscles where increased energy is advantageous, such as to protect against, inhibit/prevent, and/or treat muscle trauma or muscle fatigue.

The present inventors are the first to show that the teneurin proteins play a significant role in the regulation of energy metabolism in mammals and in plasma glucose specifically in a recognized diabetes Type II animal model. Specifically, the C-terminal peptide region, termed teneurin C-terminal associated peptide (TCAP)-1 as defined herein or compositions comprising same can carry out these actions. It has been shown herein that single administrations of TCAP-1 at nanomolar concentrations can taken up in the blood stream and brain. Further, a single injection results in significant uptake in brain glucose after 3 days and decreased plasma glucose occurs after one week in rats. This is corroborated by decreased plasma levels of insulin and increased levels of glucagon. Using an arcuate nucleus neuronal cell model, our studies indicate that the increased uptake of glucose into brain tissues is associated in part by increased glucose transporters into the plasma membrane in a manner distinct from insulin. This increased glucose results in increased aerobic activity leading to increased mitochondrial ATP production. The actions of TCAP-1 are effected via the latrophilin and dystroglycan complex to stimulate a MEK-ERK/1/2 pathway leading to the phorphorylation of AMPK and AKT to regulate glucose transporter residency time in the plasma. The increase energy in the animal by TCAP-1 is reflected by behavioural studies that indicate an excess of energy production and usage. The teneurin/TCAP-latrophilin system is one of the oldest known in multicellular organisms and may reflect one of the first mechanisms that evolved to regulate glucose and nutrient uptake. Moreover, TCAP-1 regulates the behavioural actions of energy usage in rats indicating that it may play a significant role in the treatment of major depression.

The present inventor(s) have also shown that TCAP can lower plasma glucose levels in an insulin independent manner in a diabetic mouse model. Thus TCAP can be used in the treatment of diabetes. In another aspect it can be used in the prevention and/or treatment of hypoglcemia, such as common in diabetics, such as insulin dependent Type I diabetics.

Definitions

"Administering to the cell(s)" as used herein means both in vitro and in vivo administration to the cells and can be direct or indirect administration, as long as the cells are at some point exposed to the substance being administered.

"Effective Amount" and "Therapeutically Effective Amount" as used herein means an amount effective, at dosages and for periods of time necessary to achieve the desired results. For example, an effective amount of a substance may vary according to factors such as the disease state, age, sex, and weight of the individual, and the ability of the substance to elicit a desired response in the individual. Dosage regimes may be adjusted to provide the optimum therapeutic response. For example, several divided doses may be administered daily or the dose may be proportionally reduced as indicated by the exigencies of the therapeutic situation.

"Homeostasis" as used herein means the inherent tendency in an organism or cell toward maintenance of physiological stability and making automatic adjustments in relation to its environment. Otherwise known as normal stability of the internal environment (Sapolsky, 1992).

"Insulin Resistance" as used herein means a reduced response of skeletal muscle cells to insulin as compared with skeletal muscle cells of a subject with normal glucose tolerance.

"Muscle Fatigue" as used herein means the decline in the ability of a muscle fiber to generate force as a result of depletion of energy substrates within the fiber.

"Muscle Trauma" as used herein means any injury to one or more skeletal muscle cells.

"Neuronal Cells" as used herein includes, but is not limited to, immortalized mouse hypothalamic neurons.

"Obvious Chemical Equivalents" as used herein means, in the case of TCAP, any variant that does not have a material effect upon the way the invention works and would be known to a person skilled in the art. For instance, this could include but not necessarily be limited to any salts, esters, conjugated molecules comprising TCAP, truncations or additions to TCAP.

"Pharmaceutically Acceptable Carrier" as used herein means any medium which does not interfere with the effectiveness or activity of an active ingredient and which is not toxic to the hosts to which it is administered. It includes any carrier, excipient, or vehicle, which further includes diluents, binders, adhesives, lubricants, disintegrates, bulking agents, wetting or emulsifying agents, pH buffering agents, and miscellaneous materials such as absorbants that may be needed in order to prepare a particular composition. Examples of carriers, excipient or vehicles include but are not limited to saline, buffered saline, dextrose, water, glycerol, ethanol, and combinations thereof. The use of such media and agents for an active substance is well known in the art (e.g., "Remington: The Sciences and Practice of Pharmacy, 21$^{st}$ Edition", (University of the Sciences in Philadelphia, 2005).

"Skeletal Muscle Cells" as used herein includes, but is not limited to, $C_2C_{12}$ myocytes.

"TCAP" as used herein means a 38-41 amino acid sequence, or in one embodiment a 40-41 amino acid sequence, from the C-terminal end of a teneurin peptide and all analogs, homologs, fragments, derivatives, salts, esters of the TCAP peptide which have the desired activity, and obvious chemical equivalents thereto, as described in PCT/CA2003/000622, filed May 2, 2003, published Nov. 13, 2003, and which is herein incorporated by reference. For instance, in one embodiment, TCAP includes human or mouse TCAP, such as TCAP-1, such as SEQ. ID. NOs. 37-44 (mouse) or 69-76 (human) of PCT/CA2003/000622 and analogs, homologs, fragments, derivatives, salts, esters and obvious chemical equivalents thereof. In one embodiment the TCAP is mouse TCAP-1 having the amino acid sequence: QQLLGTGRVQGYDGYFVLSVEQYLELSDSANNUHF-MRQSEI-NH2 (accession number nm 011855 (SEQ. ID. NO. 38)). In another embodiment the TCAP is human TCAP-1. In another embodiment the "Q" at the C-terminal of the TCAP, for instance in TCAP-1 can be a glutamic acid or a pyroglutamic add. In another embodiment the TCAP peptide consists essentially of:
(i) an amino acid sequence having at least 95% identity to an amino acid sequence selected from the group consisting of SEQ ID NOs: 13, 14, 21, 22, 29, 30, 37, 38, 45, 46, 53, 54, 61, 62, 69, 70, 77, 78, 85, 86, 93, 94, and 101; or
(ii) a 38 amino acid sequence from the carboxy terminal end of a peptide having at least 95% identity to an amino acid sequence selected from the group consisting of SEQ ID NOs: 13, 14, 21, 22, 29, 30, 37, 38, 45, 46, 53, 54, 61, 62, 69, 70, 77, 78, 85, 86, 93, 94, and 101;
optionally wherein:
(a) the carboxy terminal end of said TCAP peptide is amidated or comprises an amidation signal sequence; or
(b) when the amino terminal amino acid of said TCAP peptide is glutamine, it is in the form of pyroglutamic acid.

In one embodiment the TCAP is TCAP-1, in another mouse or human TCAP-1, or a sequence with 95% identity to an amino acid sequence of mouse or human TCAP-1 (SEQ. ID NO. 37, 38, 69 or 70 or in other embodiments SEQ. ID. NO. 38 or 70), optionally wherein:
(a) the carboxy terminal end of said TCAP peptide is amidated or comprises an amidation signal sequence; or
(b) when the amino terminal amino acid of said TCAP peptide is glutamine, it is in the form of pyroglutamic acid.

In one embodiment TCAP is prepared by solid phase synthesis and stored as a lyophilized powder at −80° C. reconstituted by alkalinizing with ammonium hydroxide and dissolved into physiological saline at $10^{-4}$ M stock solution. In one embodiment the TCAP-1 is expressed in separate transcript from the teneurins, such as in adults.

"A nucleotide encoding TCAP" as used herein means a nucleotide sequence that encodes TCAP, including DNA and RNA. Such suitable sequences are described in PCT/CA2003/000622, which is herein incorporated by reference.

Applications: The use of TCAP to Increase Energy Available to Skeletal Muscle Cells The invention broadly contemplates the use of TCAP, including an isolated TCAP, and a nucleotide encoding TCAP, to increase energy available to skeletal muscle cells.

(a) Applications of Increasing Glucose Uptake in Skeletal Muscle Cells

Uptake of glucose into skeletal muscle cells is critical for carbohydrate storage and to provide energy for muscle contractions (e.g. during exercise) (Wasserman et al., 2011). During exercise, higher skeletal muscle glucose uptake and carbohydrate oxidation delays muscle fatigue by enabling carbohydrate oxidation from sources other than glycogen (Coyle et al., 1986; McConell et al., 1999, 2000). As a regulator of glucose homeostasis, skeletal muscle comprises the bulk of insulin-sensitive tissue. In insulin resistance states, such as type 2 diabetes and obesity, insulin-stimulated glucose disposal in skeletal muscle is markedly impaired (DeFronzo and Tripathy, 2009; Petersen et al., 2007; Wasserman et al., 2011). Insulin resistance in skeletal muscle can precede development of hyperglycemia and type 2 diabetes, and in the event that these states develop, skeletal muscle continues to exhibit insulin resistance (DeFronzo and Tripathy, 2009; Petersen et al., 2007). Insulin resistance in skeletal muscle is associated with a variety of conditions, including obesity, hypertension, heart disease, dyslipidemia, and ageing, as well as many disease states including type 2 diabetes, polycystic ovary syndrome, chronic kidney failure, heart failure, myotonic dystrophy, and lipodystrophy (Abdul-Ghani and DeFronzo, 2010).

Further, skeletal muscle is a desirable target tissue for the treatment of diabetes, including Type 1 diabetes) not only for its central role in whole body metabolism and glucose homeostasis. (Mann et al. (Curr Pharm Des. 2010; 16(8): 1002-20-http://www.ncbi.nlm.nih.gov/pubmed/20041826).

As a result, the ability to enhance glucose uptake in skeletal muscle cells and correspondingly lower blood plasma glucose levels has potential applications to enhance performance during exercise (e.g. by delaying onset of muscle fatigue), to counteract skeletal muscle insulin resistance, and as a treatment for a variety of disorders associated with insulin resistance, including type 1 and type 2 diabetes. The present inventors herein describe a method of increasing energy available to skeletal muscle cells using TCAP.

A method for increasing glucose uptake in muscle cells also has potential applications for promoting recovery from muscle trauma or exercise-induced injury, and/or as a treatment for glycogen storage disorders or hypoxia.

Glycogen storage disease type V (McArdle's disease) results from a deficiency of the muscle isoform of glycogen phosphorylase, which is responsible for glycogenolysis. At the protein level, skeletal muscle adaptations suggest an augmented glucose transport and glycolytic flux as a compensatory metabolic strategy to a chronic absence of the enzyme (Robertshaw et al., 2007). Due to virtually absent myocellular glycogenolysis, patients with the disorder rely heavily on blood-borne fuels, and increased availability of glucose during exercise has a marked and prolonged effect on exercise tolerance in patients with McArdle's disease (Vissing et al., 1992; Andersen et al., 2008).

Glycogen storage disease type III results from a deficiency in glycogen branching enzymes resulting in deposition of abnormal glycogen in muscle cells. Although myopathic symptoms in this disorder are often ascribed to the muscle wasting these patients suffer in adult life, a recent study suggests that the inability to debranch glycogen also has an impact on muscle energy metabolism. In particular, patients experience exercise-related symptoms of muscle fatigue likely related to insufficient energy production in muscle (Preisler et al., 2013). Patients may therefore benefit from increased availability of glucose to muscle cells.

Exercise-induced skeletal muscle injury also impairs glucose uptake, likely via disturbance of the insulin signaling pathway (Aoi et al., 2012). Increased glucose uptake in skeletal muscle tissue is also a hallmark of hypoxia (Zierath et al., 1998). These results suggest that increased availability of glucose to skeletal muscle cells after injury or during hypoxia may be beneficial.

Further in some embodiments one can control glucose uptake by skeletal muscle cells by varying amount of TCAP administered and timing.

(b) Effect of TCAP in Increasing Energy Available to Skeletal Muscle Cells

The potential for natural peptides to regulate skeletal muscle glucose uptake is an important paradigm in the search for novel ways of normalizing energy homeostasis, enhancing muscle fiber performance and recovery from injury, and coping with disorders of skeletal muscle carbohydrate metabolism. The TCAP peptides increase the energy available to skeletal muscle cells by increasing intracellular glucose concentrations and reducing plasma glucose levels. The present inventors herein describe a method of treatment or use of TCAP in increasing available energy to skeletal muscle cells to address and treat such concerns.

Pharmaceutical Compositions and Modes of Administration

TCAP, pharmaceutically acceptable salts or esters thereof or obvious chemical equivalents thereof as defined herein can be used in the methods and use of the invention described herein. In some embodiments it can be administered by any means that produce contact of said active agent with the agent's sites of action in the body of a subject or patient to produce a therapeutic effect, in particular a beneficial effect, in particular a sustained beneficial effect. The active ingredients can be administered simultaneously or sequentially and in any order at different points in time to provide the desired beneficial effects. A compound and composition of the invention can be formulated for sustained release, for delivery locally or systemically. It lies with the capability of a skilled physician or veterinarian to select a form and route of administration that optimizes the effects of the compositions and treatments of the present invention to provide therapeutic effects, in particular beneficial effects, more particularly sustained beneficial effects.

In one embodiment, administration of TCAP includes any mode that produce contact of said active agent with the agent's sites of action in vitro or in the body of a subject or patient to produce the desired or therapeutic effect, as the case may be. As such it includes administration of the peptide to the site of action—directly or through a mode of delivery (e.g. sustained release formulations, delivery vehicles that result in site directed delivery of the peptide to a particular cell or site in the body. It also includes administration of a substance that enhances TCAP expression and leads to delivery of TCAP to a desired cell or site in the body. This would include but is not limited to the use of a nucleotide encoding TCAP, e.g. via gene therapy or through a TCAP expression system in vitro or in vivo, as the case may be that results in enhanced expression of TCAP. It can also include administration of a substance to the cell or body that enhances TCAP levels at the desired site.

The above described substances including TCAP and nucleic acids encoding TCAP or other substances that enhance TCAP expression may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals.

Thus in one embodiment, the invention provides the use of TCAP or modulator thereof in the preparation of a medicament for the inhibition of neuronal cell death and/or the treatment of related conditions. In one embodiment, a therapeutically effective amount of TCAP or a pharmaceutical composition as described herein is administered to a patient in need thereof. A patient in need thereof is any animal, in one embodiment a human, that may benefit from TCAP and its effect on inhibition of neuronal cell death.

An active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions that may inactivate the compound. In one embodiment, TCAP is administered directly t or proximate to the desired site of action, by injection or by intravenous. If the active substance is a nucleic acid encoding, for example, a TCAP peptide it may be delivered using techniques known in the art.

The compositions described herein can be prepared by per se known methods for the preparation of pharmaceutical acceptable compositions which can be administered to subjects, such that an effective quantity of the active substance is combined in a mixture with a pharmaceutical acceptable vehicle or carrier. Suitable vehicles or carriers are described, for example, in Remington's Pharmaceutical Sciences (Remington's Pharmaceutical Sciences, Mack Publishing Company, Easton, Pa., USA 1985 or Remington's The Sciences and Practice of Pharmacy, 21$^{st}$ Edition", (University of the Sciences in Philadelphia, 2005) or Handbook of Pharmaceutical Additives (compiled by Michael and Irene Ash, Gower Publishing Limited, Aldershot, England (1995)). On this basis, the compositions include, albeit not exclusively, solutions of the substances in association with one or more pharmaceutical acceptable vehicles, carriers or diluents, and may be contained in buffered solutions with a suitable pH and/or be iso-osmotic with physiological fluids. In this regard, reference can be made to U.S. Pat. No. 5,843,456.

As will also be appreciated by those skilled, administration of substances described herein may be by an inactive viral carrier. In one embodiment TCAP can be administered in a vehicle comprising saline and acetic acid.

Further, in one embodiment, TCAP may be administered in a form that is conjugated to another peptide to facilitate delivery to a desired site, or in a vehicle, eg. a liposome or other vehicle or carrier for delivery.

The present invention is described in the following Examples, which are set forth to aid in the understanding of the invention, and should not be construed to limit in any way the scope of the invention as defined in the claims which follow thereafter.

EXAMPLES

Example 1—Peptide Synthesis

Mouse TCAP-1 (such as SEQ. ID. NO. 38) was prepared by solid phase synthesis as previously described (Qian et al., 2004). The peptide was solubilized in phosphate buffered saline (PBS) at a concentration of $2 \times 10^{-7}$ M before being diluted in the appropriate medium.

The sequence of the mouse TCAP-1 (SEQ. ID NO. 38) was determined by examining the carboxy terminal exon region of mouse teneurin-1 (accession number: NM011855). A mouse paralogue of the putative peptide sequence from teneurin-1 was synthesized on an automated peptide synthesizer, Model Novayn Crystal (NovaBiochem, UK Ltd., Nottingham, UK) on PEG-PS resin using continuous flow Fmoc chemistry (Calbiochem-Novabiochem Group, San Diego, Calif.) Eight times excess diisopropyl ethyl amine (Sigma-Aldrich Canada Ltd.) and four times excess Fmoc-amino acid activated with HATU (O-(7-azabenzotriazol)-1-3, 3-tetramethyluronium hexfluorophosphate; Applied Bio systems, Foster City, Calif.) at a 1:1 (mol/mol) ratio were used during the coupling reaction. The reaction time was 1 h. A solution of 20% piperidine (Sigma-Aldrich Canada Ltd.) in N,N-dimethylformide (DMF; Caledon Laboratories Ltd., Canada) was used for the deprotection step in the synthesis cycle. The DMF was purified in-house and used fresh each time as a solvent for the synthesis. The cleavage/deprotection of the final peptide was carried out with trifluoroacetic acid (TFA), thioanisole, 1, 2 ethandithiol, m-cresole, triisopropylsilane, and bromotrimethyl silane (Sigma-Aldrich Canada Ltd.) at a ratio of 40:10:5:1:1:5. Finally, it was desalted on a Sephadex G-10 column using aqueous 0.1% TFA solution and lyophilized.

Synthetic rat $K_{37}$- or $K_8$-TCAF-1 (TCAP with an R to K substitution at position 37 or position 8) was synthesized by the University of Toronto as previously described [2]; Briefly, $K_{37}$-TCAP-1 was dissolved in PBS at 2 mg/ml and $K_{37}$-TCAP-1 was biotinylated using the EZ-Link Sulfo-NHFS-LC Biotinylation kit (Pierce, Rockford, Ill.) and purified with a D-salt polyacrilamide desalting column (ThermoFisher, Toronto, ON).

For use as a control, a scrambled TCAP (scTCAP) was made that was non-junctional in every test relative to TCAP-1 where each residue in mouse TCAP1 was assigned a random number from 1 to 41 using excells random number function. Then the sequence was reconstructed except that a pyroglutamic acid was placed in the first position. Hence the scTCAP has the same amino acid composition but a different order. The scTCAP used in the experiments noted herein had the amino acid sequence: pETHSLELRVSLIGEVQQFIGY-ENQSDQNYGLLAYFDRVGMS-NH2, wherein the pE is pyroglutamic acid.

Other Materials and Methods

TCAP-1 Antisera Production:

The sequences used as haptens were KLH-pEQLLGT-GRVQGYDGYFVLSVEQYLE-OH (pE: pyroglutamic acid) and KLH-VLSVEQYLELSDSANNIHFMRQSEI-NH2. The purity of fragments was measured by high performance liquid chromatography (HPLC) at over 80% using a Vydac C18 reverse-phase column. Two un-conjugated peptide sequences of N-TCAP-1 and C-TCAP-1 were used far antisera specificity studies. Two rabbits were each immunized with one of the conjugated peptides. The pre-immune sera were collected to assess the background immunoreactivity before immunization. The conjugated peptides were emulsified with Freund's complete adjuvant (FCA) in 1:1 ratio (V/V) at a final peptide concentration of 100 µg/ml. Four weeks after the injection, the rabbits received a booster injection of peptides with Freund's incomplete adjuvant. Periodic blood samples were collected to assess antibody titer. Booster injections were repeated until antibody titers were sufficient as determined by dot and western blotting.

The binding specificity of the antisera was determined by an enzyme-linked immunosorbent assay (ELISA). Nunc Maxisorp flat-bottom plates were coated with goat anti-rabbit IgG Fc fragment (Pierce Biotechnology) at 10 µg/ml overnight at 4° C. The remaining binding sites were blocked with 1% bovine serum albumin (BSA) in PBS 0.05% Tween-20 (PBS-T) for 2-16 h and the wells then washed with PBS-T. TCAP-specific antisera, at 1:1000 dilution in PBS-T with 1% BSA, were bound to the goat anti-rabbit IgG Fc fragment-coated plates for 2 h. The wells were washed 3× with PBS-T, [K8]- and [K37]-TCAP-1 variants were labeled with biotin using EZ-Link Sulfo-NHS-LC-Biotinylation Kit (Pierce Biotechnology). Serial dilutions of unlabelled TCAP and 10 µg/ml biotinylated TCAP in PBS-T 1% BSA were incubated for 4 h at room temperature (RT). The wells were washed 4× with PBS-T and incubated with streptavidin-44 HRP (Pierce Boitechnology) at 0.1 µg/ml in PBS-T 1% BSA for 25 min. After 3 washes with PBS-T, the substrate Super Signal TMB (Pierce Biotechnology) was added for 10-30 min, the reaction was stopped with sulfuric acid, and HRP activity measured at 450 nm. The competition curves and 50% binding values were calculated with GraphPad Prism 4 (San Diego, Calif.) software using variable slope sigmoidal regression and F test to compare the 50% binding values.

FITC-TCAP-1 Conjugation:

The [$K_8$]-TCAP-1 peptide was labeled with fluorescein isothiocyanate (FITC) according to the EZ-label TITC Protein labeling kit (Pierce Biotechnology, Rockford Ill.). FITC was dissolved in dimethylformamide, mixed with the [$K_8$]-TCAP-1 at a 24:1 excess molar ratio and incubated for 2 h at RT in the dark to allow for the conjugation of the primary amine of the lysine group. A dextran column was used to remove the unconjugated FITC and the absorbance of each fraction was measured at 280 nm to determine the elution point of the conjugated peptide in phosphate buffered saline (PBS; 0.1M phosphate, 0.15 M NaCl, pH7.2). The four fractions with the highest protein absorbance readings were combined and sterilize-filtered using an Acrodisc Syringe 0.2 µm Supor low protein binding filter (Pall Life Sciences, Ann Arbor, Mich.). The filtrate was concentrated using a Microsep 1K Omega centrafuge (Pall Life Sciences) at 4 C. The samples were stored at 4 C. To confirm the size of the FITC-[$K_8$]-TCAP-1, 5 and 10 ul aliquots of the concentrated filtrate were run on a 10-20% gradient Tris-Tricine gel. The amount of the FITC required to be injected as a control was determined by applying different PBS-diluted preparations of FITC on a nitrocelluose membrane. The level of fluorescence was directly compared to that of a spot of the FITC-[$K_8$]-TCAP-1 conjugate to be administered and that dilution was used for the administration after sterilize-filtration indicated above. Fluorescence was measured using an EP Chemi II Darkroom system (UVP, Upland, Calif.) with the sequential integration function of LabWorks Image acquisition and analysis software.

Uptake of TCAP-1 in Plasma:

Male Wistar rats weighing 400-450 g were obtained from Charles River Laboratories (Montreal, Canada). Rats were singly-housed in standard Plexiglas shoebox cages under standard laboratory conditions, (12 h light:dark cycle, lights on at 0700) with food and water available ad libitum. Testing took place between 0900 and 1200 hours. Rats were given one week to acclimatize to the laboratory before surgery. Rats were anesthetized with isoflurane (2-3% in 100% $O_2$) and a catheter was implanted into the jugular vein.

TCAP Biotinylation:

The K37 biotinylated TCAP was diluted into 200 ul physiological saline to contain 10.5 ug for 5 nM/kg dose and 52.5 ug for 25 nM/kg dose. The rats weighed 400-450 g. 200 ul of peptide containing solution was delivered through the cannula, different syringe containing saline was connected and 200 ul of saline was delivered to push the peptide into the bloodstream. The third syringe containing the heparin solution was used to fill the line with the lock, 150-200 ul. After 5 min, the lock solution was aspirated into the syringe, and also about 150 ul of the blood were aspirated and disposed off in case of the local contamination with high peptide concentrations. 200 ul of the blood was sampled in a fresh syringe, line flushed with saline first (200 ul) and heparin saline next (150-200 ul).

Intravenous Studies:

Rats were gently restrained, cannula clamped and unplugged, 1 ml syringe with blunt needle attached to the end of the polyethylene 50 line and the lock solution containing heparin 50-100 U/ml was removed. The line was clamped and a new syringe with a blunt needle attached for withdrawing about 200 ul blood. The line was clamped and syringe removed to recover the blood. This blood sample was used to determine a baseline level of activity. All blood samples were incubated at a room temperature for 10-20 min and centrifuged at 3000 rpm for 5 min to recover the serum. The serum was frozen on dry ice and kept at −80° C. until the assay.

Subcutaneous Studies:

K37 TCAP was biotin labeled according to the biotinylation method above. Rats were gently restrained, cannula clamped and unplugged, 1 ml syringe with blunt needle attached to the end of the polyethylene 50 line and the lock solution containing heparin 50-100 U/ml was removed. The line was clamped and a new syringe with a blunt needle attached for withdrawing about 200 ul blood. The line was clamped and syringe removed to recover the blood. This blood sample was used to determine a baseline level of activity. All blood samples were incubated at a room temperature for 10-20 min and centrifuged at 3000 rpm for 5 min to recover the serum. The serum was frozen on dry ice and kept at −80° C. until the assay.

For IV administration, rats were gently restrained during the injection procedure. The IV cannula was unplugged and the lock solution (150-200 µl of 50-100 U/ml of heparin, Sigma Scientific) was removed. To obtain a baseline level of activity, 200 µl of blood was withdrawn prior to injection. 200 µl of TCAP-containing solution was delivered through the cannula, followed by 200 µl of saline to push the TCAP solution through the cannula. 150-200 µl of lock solution was injected to fill the catheter. For subcutaneous (SC) administration, rats were gently restrained and injected under the skin with 200 µl of TCAP-1-containing solution with a 23 gauge needle Blood Sampling Procedures:

Blood samples were obtained from the jugular catheter. Rats were gently restrained, and the IV cannula was unplugged. The lock solution was aspirated along with 150 µl of blood. This mixture was discarded in case of local contamination with high peptide concentrations. A sample of200 µl of blood was obtained in a fresh syringe. The catheter was then flushed with 200 µl of saline and then filled with 150-200 µl of lock solution. Lateral tail vein blood samples were obtained from lightly restrained rats whereby 200 µl of blood was obtained using a 23-gauge needle. A final bleed was achieved via cardiac puncture. All collected blood samples were allowed to clot for 15 min at room temperature and centrifuged for 5 min at 3000 rpm to recover the serum. The serum was frozen on dry ice and stored at −80° C. until the assay.

TCAP Enzyme-Linked Immunosorbent Assay (ELISA):

Nunc Maxisorp Flat bottom plates (VWR, Mississauga, ON) were coated with 100 µl of goat anti-rabbit IgG Fc fragment (Pierce, Rockford, Ill.) at 10 µg/ml in PBS overnight at 4° C. The remaining binding sites were blocked with 1% bovine serum albumen (BSA; Sigma) with thimerosal (Sigma) in PBS with 0.05% Tween-20 (PBS-T) for 2-24 h. TCAP-1-specific antisera (1:1000; [3]) in PBS-T with 1% BSA was bound to the goat anti-rabbit IgG Fc fragment-coated plates for 2 h. Serial dilutions of unlabelled TCAP (0.1-100 ng/ml) and 20% blood serum were incubated for 4 h. Each blood serum sample was run in triplicate, Streptavidin-HRP (1:10000) in PBS-T with 1% BSA was added to the wells and incubated for 25 min. Substrate Super Signal TMB (Pierce, Rockford, Ill.) was added and incubated for 10-30 min, and the reaction was stopped with 2 M sulfuric acid. HRP absorbance was read at 450 nm in a Molecular Devices UV-Vis spectrophotometer.

Autoradiography:

For the TCAP-1 radioiodination, 5 µl iodogen was added to 50 µl dichloromethane and allowed to dry. 30 µl of ammonium bicarbonate buffer was added, followed by 15 µg of TCAP. The solution was incubated with 1.5 mCi Na$^{115}$I in 40 µl phosphate buffer, pH 7.8 for 15 min at RT. The reaction was stopped with 2 µl TFA and purified by HPLC. A radioactive peak eluting between 13.8-15 min was collected and 870 µCi of radiolabeled peptide was obtained. $^{125}$I-TCAP-1 was stored in the mobile phase with 1% BSA and 0.1% mercaptoethanol. Prior to injection, $^{125}$I-TCAP-1 was dried under nitrogen, redissolved in 0.1% TFA and loaded onto a C-18 Seppak cartridge. Following washing, the peptide was eluted with 50% acetonitrile with 0.1% TFA, evaporated to dryness and redissolved in 0.1 ml of ammonium bicarbonate and diluted in 0.5 ml ddH$_2$O. For the intranasal preparation, the peptide was redissolved in 20 μl ammonium bicarbonate solution with 20 μl water and 1 μl enhancer (10% DDM in water, total concentration 0.25%). Male Sprague-Dawley rats (n=3) (160-280 g; Charles River) were weighed and injected with 0.2 ml 0.9% sodium iodide (IP) prior to tail vein injection with $^{125}$I-TCAP-1 radiotracer. The dose (80-174 μCi) was proportional to the rat weight. Rats were sacrificed 30 min after radiotracer injection. Following sacrifice, brains were dissected out and weighed. Brains were cooled in ice-cold saline and sectioned in 300-μm slices on a vibratome. Sections were dried on a slide warmer and exposed to a phosphor screen for 7-15 days for the IV-administered animals and 6 days for the intranasally-administered animal and scanned. Areas of $^{125}$I-mTCAP-1 binding were analyzed according to the atlas of Paxinos and Watson.

Functional Positronic Emission Tomography Studies:

TCAP-1 and scrambled TCAP-1 were stored at −80° C. and protected from the light. On the day of administration, just prior to injection, one vial of either TCAP-1 or scrambled TCAP-1 was removed from the freezer and placed on wet ice to thaw. Once the vial was thawed, it was warmed to room temperature by hand and vortexed for approximately 20 s. Each injection consisted of 100 μl (3000 pmol) or either the TCAP-1 or scrambled TCAP-1. A new aliquot was used for per injection per rat.

Male Harlan Wistar rats (Hsd:WI) were used in this study. They were approximately 325 g on Day 1 of the experiment. The rats were fed irradiated Harlan 2918.15 Rodent Diet and water ad libitum. Rats were housed in static cages with Bed-O'Cobs™ bedding inside Biobubble® Clean Rooms that provide H.E.P.A filtered air into the bubble environment at 100 complete air changes per hour. All treatments, body weight determinations, and tumor measurements were carried out in the bubble environment. The environment was controlled to a temperature range of 70°±2° F. and a humidity range of 30-70%. The rats were randomized into treatment groups based on body weight on Day 0. All rats weighed ≥333 g. Mean group body weights at the start of treatment were well matched (range of group means, 348-356 g). Each rat was given a fixed volume subcutaneous injection of 0.1 ml of either saline, TCAP-1, or scrambled TCAP-1 as indicated.

PET Image Acquisition and Analysis;

Positron emission tomography (PET) was performed using a Siemens Inveon microPET small animal PET scanner, and [18F]fluorodeoxyglucose (FDG) radiotracer (IBA Molecular). PET scans were acquired on all of the animals 4.5 hrs post dosing and 3 days post dosing. The animals were not fasted before the start of imaging as per the protocol. The animals were injected intravenously with approximately 1 mCi of FDG. The FDG uptake occurred under anesthesia for 90 minutes. All the animals were imaged in the prone position. Body temperature was maintained with a thermostat-regulated recirculating water heated pad. Individual body weights were recorded before each imaging session. Static emission data was acquired for 20 minutes.

The PET list mode data was converted to 2-dimensional (2D) sinograms, corrected for random coincidences, and normalized for scanner uniformity. PET images were reconstructed using an iterative 3D ordered subsets expectation maximization followed by a maximum a posteriori reconstruction (OSEM3D/MAP). PET image analysis was performed using the Amira 5.5.0 analysis software package. For whole body ROIs, a low threshold was set to delineate specific signals in the whole body while eliminating background. Regions of interest (ROIs) were drawn in three orthogonal planes on the whole body, cerebral cortex, rostral cortex, scapular region, lower and upper right/left forearm, heart, ganglion, upper and lower hind limbs, testes, bladder and hypothalamic region, and then interpolated by the software. The total PET counts were calculated from all voxels within the segmented volumes of interest Percent injected dose (% ID) was calculated by normalizing the total counts in each tissue of interest at each time point, to the whole body total counts calculated over 1 minute from the whole body max uptake time point, for each animal, during the first 90 minutes post 18F-FDG administration.

All animals were observed for clinical signs at least once daily. The rats were weighed on each day of treatment and at least twice weekly thereafter. Treatment-related weight loss in excess of 20% is generally considered unacceptably toxic. In this report, a dosage level is described as tolerated if treatment-related weight loss (during and two weeks after treatment) is <20% and mortality during this period in the absence of potentially lethal tumor burdens is ≤10%.

RT-PCR: RNA Extraction:

After serum-depriving a 6-well plate of E14 and N38 cells for 3 hours, Trizol reagent was added to the plate to maintain RNA integrity. Once at room temperature, chloroform was added and each sample was centrifuged at 12,000 rpm for 15 min. at 4° C. Then, the supernatant containing RNA was transferred to new sample tubes, 2-propanol was added, and each sample was centrifuged at maximum rpm (14000) for 10 min. at 4° C. The supernatant was then discarded, pellets were washed with 75% ethanol, and samples were centrifuged at 7400 rpm for 5 min. at 4° C. This process was repeated. Once the ethanol was removed, pellets were resuspended in diethylpyrocarbonate (DEPC) H$_2$O, incubated in a 60° C. water bath and incubated to room temperature. RNA concentration was assessed using a Thermo Scientific Nanodrop 2000 Spectrophotometer.

Reverse Transcription and PCR:

Total RNA (0.49 μg) from mouse E14 and N38 cells was reverse transcribed into complementary DNA (cDNA). RNA-free H$_2$O, random primers, and dNTP were added to sample RNA and the mix was heated to 65° C. for 5 min, put on ice for 1 min., then 5× first strand buffer and 0.1 M DTT was added. Then, the following protocol was performed: samples were cooled to 25° C. for 2 min., Superscript II Reverse Transcriptase (RT) was added, heated at 25° C. for 10 min., 42° C. for 50 min., and 70° C. for 15 min. Polymerase Chain Reaction (PCR) for cDNAs of interest was carried out in the following conditions: denaturation for 7 min. at 95° C. 1 min. at 95° C. then annealing at 60° C. for 1 min. 30 s. The extension phase occurred at 72° C. for 35 s and 5 min. at 72° C. Primer pairs used in the PCRs are found in Table 1. Gel electrophoresis was done using a 3% agarose gel. A gel doc system (BioRad Molecular Image Gel Doc XR+) was used to image teneurin-1 and TCAP-1 mRNA expression.

Signal Transduction Studies:

MEK-ERK-AMPK Phosphorylation: Following TCAP-1 treatments, mHypoE-38 immortalized hypothalamic neurons were lysed with 500 μL of RIPA buffer. Cells were harvested using a cell scraper and centrifuged at 14 000 rpm for 20 minutes at 4° C. The pellet was discarded and supernatant aliquoted into two tubes, 30 μL for protein quantification and the remainder ~450 μL for western blot analysis, and stored in −20° C. A Pierce BCA protein assay (Thermo Fischer Scientific, Cat. No. 23225) was performed to quantify protein concentrations for standardizing dilutions of respective supernatant samples. Samples (15 μg) were resuspended in sample buffer and size fractioned by SDS-PAGE (10%) at 100V for approximately 1 hour. Proteins were then electro-transferred to Hybond-ECL nitrocellulose membranes (Amersham, Cat No. RPN303D) for approximately 2 hours at 100 V. Membranes were washed with PBS and blocked in 5% milk-PBST (5% w/v non-fat milk powder in PBS with 0.2% Tween®20) at room temperature for 1 hour on a lab rotator (Thermo Scientific). Afterwards, membranes with incubated with rabbit primary antibodies in 1% milk-PBST overnight at 4° C. with gentle agitation. Following 24 hours, the membranes were given three 5-minute washes in fresh PBST at room temperature and 42 incubated with anti-rabbit horseradish peroxidase (HRP)-conjugated secondary antibody (VWR Cat. No. RPN2135 or Amersham, Cat. No. NIF824) diluted to 1:7500 in 1% milk-PBST for 1 hour at room temperature with gentle agitation. The membranes underwent three more 5-minute washes in fresh PBST at room temperature. Subsequently, proteins were detected by adding chemiluminescence detection reagent (ECL Amersham, Cat. No. RPN2232) to the membranes and exposing onto ECL Hyperfilm (VWR, Cat. No. 95017-653L) for 10-60 minutes. For analysis of AMPK phosphorylation signals, cells were pre-treated with either DMSO or MEK inhibitor (New England Biolabs, Cat. No. U0126) for 1 hour followed by saline or 100 nM TCAP-1 for a further 1 hour. Cells were harvested and western blot analyses were performed using a AMPK Rabbit mAb and p-AMPK Rabbit mAb. Antibody optimizations were achieved to maximize the band intensity while ensuring the absence of nonspecific bands. The primary antibodies for AMPK, p-AMPK, ERK, and p-ERK gave the best results at a dilution of 1:1000. The experimental band for AMPK and p-AMPK is 62 kDa, consistent with experimental results. However, p-AMPK was difficult to detect. The experimental bands for ERK and p-ERK are 44 ka and 42 kDa, consistent with experimental results.

DAG IP3 Assays: Bicinchoninic Acid (BCA) Assay:

To determine the protein concentration in the lysed samples, I used the Pierce BCA Protein assay kit (Thermo Fischer Scientific, Cat. No. 23225). Diluted bovine serum albumin (BSA) standards were prepared according to kit instructions, and both the diluted standards and the supernatant were added in 25 uL duplicates to a 96 well plate. Then 200 uL of working reagent was added to each well. The plate was incubated for 30 min. at 37° C. Absorbance levels were measured at λ=562 nm using a Spectramax Plus (Molecular Devices, USA).

Enzyme-linked Immunosorbent Assays (ELISAs):

Treatment was performed as described above, except that E14 and N38 cells were treated with either 100 nM of TCAP-1 or vehicle (distilled water) for 0, 5, 15, 30, 60 or 120 min. To quantify the protein concentration in E14 and N38 cell lysates, a Pierce BCA Protein Assay was performed as described above. Lysates were then diluted in RIPA buffer so that each sample had equal protein concentration.

Diacylglycerol (DAG) Assay:

The protocol for the Mouse DAG ELISA kit (MyBioSource.com, Cat No. MBS029616) was followed, in which an antibody-antigen-antibody-enzyme complex was formed. 50 uL of each sample was added in quadruplicate to a 96-well plate, and then incubated with an HRP-linked antibody. The plate was then washed and 3,3', 5,5'-tetramethylbenzidine (TMB) was added creating a blue solution indicating a HRP enzyme-catalyzed reaction. Once TMB was added, the plate was incubated for 15 min. at 37° C. The reaction was terminated with a sulphuric acid solution and colour was measured at λ=450 nm using a Spectramax Plus 384 (Molecular devices, USA). DAG standards of 0.625, 1.25, 2.5, 5, 10, and 20 umol/well were prepared, as per kit instructions, and added in 50 uL duplicates allowing a standard curve to be generated.

Inositol Triphosphate (IP3) Assay:

The protocol for the Mouse IP3 ELISA kit (MyBioSource.com, Cat No. MBS744522) was performed as described in the above DAG assay section. However, 100 uL of each sample was added in quadruplicate to a 96-well plate, and IP3 standards of 2.5, 5, 10, 25, and 50 ng/mL were prepared to create a standard curve. Colour was also measured at λ=450 nm using a Spectramax Plus 384 (Molecular devices, USA).

Fluo-4 Fluorescence Measurements for $[Ca^{2+}]_i$:

For fluorescence experiments, N38 cells were grown on Poly-D-lysine coated 25 mm round No. 1 glass coverslips (Warner Instruments, Hamden, Conn., USA) and placed in a flow-through bath chamber (RC-40HP, Warner Instruments, Hamden, Conn., USA) of an inverted microscope (Axio Observer Z1, Zeiss, Toronto, ON, Canada) equipped with a Zeiss 40× oil immersion objective. Dyes were imaged using a FITC filter set (Semrock, Rochester, N.Y., USA) and a X-Cite 120 fluorescence illumination system (Excelitas Technologies, Mississauga, ON, Canada), controlled by Volocity imaging software (Quorum Technologies Inc., Guelph, ON, Canada.). Fluorescence emissions were detected with an Orca-ER Hamamatsu B/W CCD digital camera (Hamamatsu, Middlesex, N.J., USA). Neurons were excited for 100 ms every 1 min to prevent bleaching of the dye and permit experiments of up to an hour in length. To assess whether endogenous fluorescence of cortical sheets affects fluorescence measurements, control cortical sheets were exposed to each treatment in the absence of fluorophores. The background fluorescence was minimal and remained constant with each treatment; therefore, background fluorescence was not subtracted from fluorescent data. For statistical analysis, 10 neurons per coverslip were chosen at random and the average change in regions of interest from the center of the cell body was used as a single replicate. Brightly fluorescing cells were avoided. Traces were drift corrected to a linear regression line fit to the normoxic portion of the trace to enable comparison and produce average traces Example 2—In-Vivo Experiments Animals:

All animal studies performed in Canada followed the requirements set out by the Canadian Council for Animal Care (CCAC). The University of Toronto is a CCAC accredited facility. For studies performed in United States, all procedures were conducted in compliance with all the laws, regulations and guidelines of the National Institutes of Health (NIH) and with the approval of Molecular Imaging. Inc.'s Animal Care and Use Committee. Molecular Imagine. Inc. is an AAALAC accredited facility.

Example 2A—TCAP Uptake in Plasma and Brain and Glucose Uptake

The first goal of establishing the in vivo actions of teneurin C-terminal associated peptide (TCAP)-1 was to determine its longevity in plasma and ability to be taken up into key regions of the brain associated with glucose and behavioural regulation. In the first set of studies, synthetic TCAP-1 was administered by either intravenous (IV, FIG. 1A) or subcutaneous (SC, FIG. 1B) injection. Both approaches showed a significant uptake of TCAP-1 into the systemic plasma, as measured by an in-dwelling canula, however the rate of uptake and clearance differed markedly. In IV-treated animals, TCAP-1 was cleared from plasma within about 100 min, whereas, the SC treated animals showed clearance within about 170 min for the highest dose of 125 ng/kg. The plasma clearance half-life for IV-administered TCAP was ranged from 4±1 min for the lowest dose, 7±2 for the mid dose and 16±4 for the highest dose. In comparison, the clearance time in the SC-treated rats was prolonged due to the absorbance time required for the peptide to enter the blood stream and ranged from 40±4 for the lowest dose, 50±11 for the mid dose and 36±20 for the highest dose. There were no significant differences among the doses. Despite the differences in the plasma clearance half-life between the IV and SC-treated animals, the area under the curve (AUC) was similar with values of 1867±58 and 1355±374 at the low dose for IV and SC-treated animals, 5529±1002 and 5445±482 respectively for the middle dose and 12805±1691 and 19633±4354 respectively for the highest dose. Although the IV-treated animals at the lowest dose of 5 ng/kg was significantly (p<0.05, t-test) greater than the SC results, there were no significant differences between the AUC for IV and SC at the middle and high doses. On the basis of these studies, SC doses near the middle and higher concentrations were used for the physiological studies (see below).

Example 2B—$^{125}$I TCAP-1 Uptake into the Brain

Having established that high concentrations of TCAP-1 could be detected in the bloodstream, a second study utilizing $^{125}$I-labelled TCAP-1 was injected IV to determine the uptake into the brain (FIG. 1C). An IV-administration protocol was utilized for direct comparison with a previous study (Al Chawaf et al., 2007) using FITC-labeled TCAP, and also to maximize the amount of material that could gain entry into the brain. Strong concentration of the label was found in a number of limbic regions including the nucleus accumbens, amygdala and hippocampus. A strong signal was also shown in the arcuate nucleus, consistent with the concept of TCAP playing a role in energy metabolism. Uptake was also observed in the periaqueductal grey and Substantia nigra indicating potential interaction with 5-HT and dopaminergic regulation (see discussion). These data are consistent with previous studies oil IV administered FITC-labelled TCAP-1 showing uptake into the brain. In another fPET scan, 2-deoxyglucose allows for an accurate depiction of the levels of glucose uptake as the missing hydroxyl group at the 2' position renders the molecule unusable by tissues. fPET scans offer high-resolution images showing distinct uptake into regions of the rat with the magnitude of uptake (image not shown). Adult male Wistar rats injected with a single dose (vehicle, 10 nmole/kg TCAP-1 or 10 nmole/kg scTCAP-1) subcutaneously into the interscapular region showed no significant effect in the mean differences among 18F-2-deoxyglucose uptake in any tissues at 3 hours. However, TCAP-1 treated animals showed a high variability in the uptake into the cortical regions of the brain (data not shown). At three days after treatment, the trends were apparent. In the cortex, TCAP-1 induced a 42% increase (P=0.0374; two-tailed t-test) over the vehicle response, and a 65% increase (P=0.0243; two-tailed t-test) over the scTCAP-1-induced uptake. Using a two-tailed one-way ANOVA, the effect of treatment was P=0.0348. The data was analyzed both by t-test and ANOVA because of the potential difference in effect due to a specific receptor for TCAP-1 and the possibility of an oligopeptide transporter effect of the scTCAP-1. Regardless however, a two-tailed, two way ANOVA using all three regions of the brain yielded a significant effect of treatment (P=0.0008) indicating a strong effect of TCAP-1 to increase glucose uptake into these regions. Moreover, there was no significant effect of regions or interaction as shown by the ANOVA analysis. Taken together, these data indicated that with respect to an acute administration, the brain showed the most enhanced uptake of glucose relative to the other tissue regions (such as the pectoral region, intercostal muscles, heart, sympatheitc ganglia, bladder, pelvic region and testes, which showed no significant effect.

Figure 1:
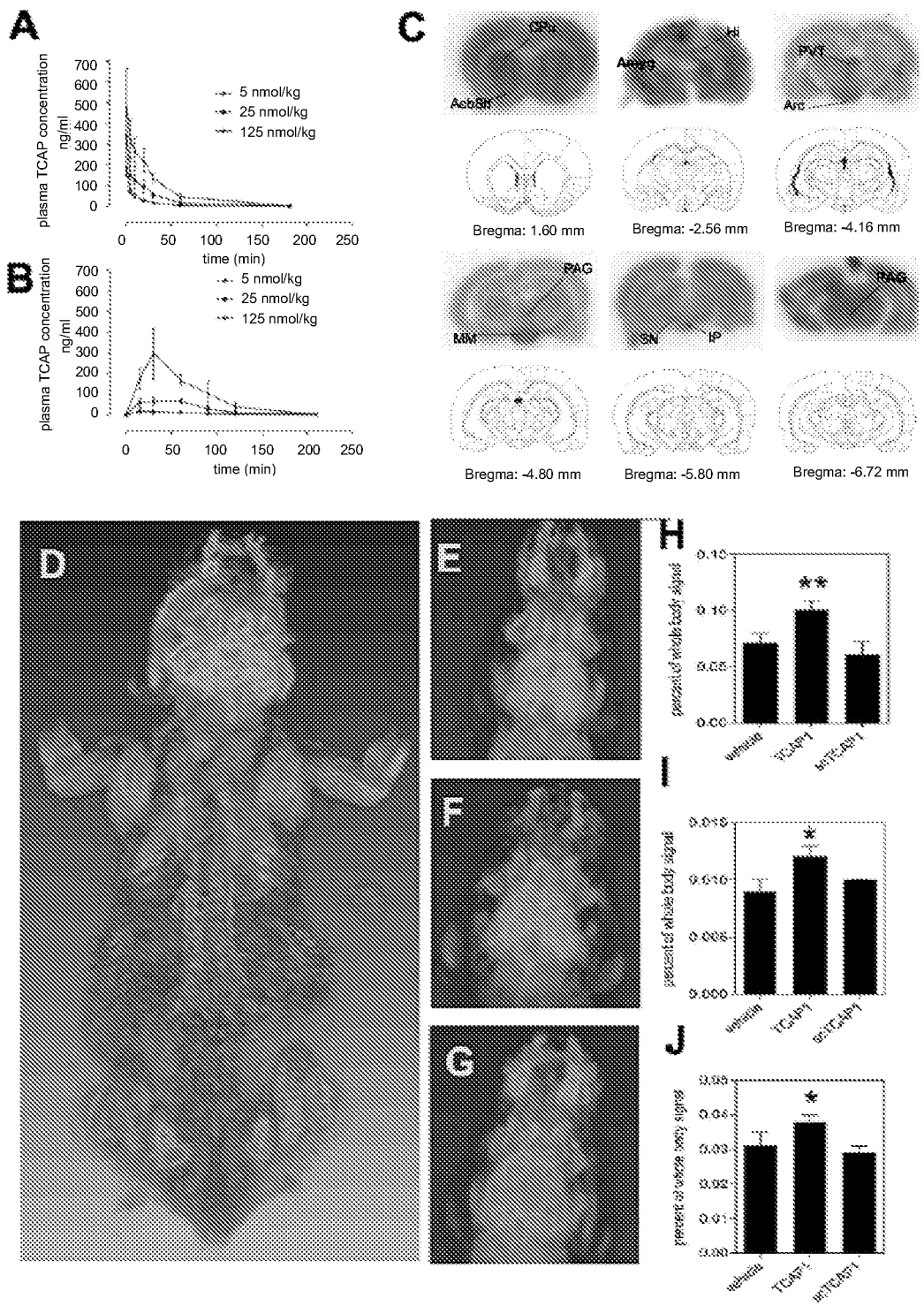
FIG. 1 depicts TCAP-1 action in plasma and brain. A. IV administered TCAP-1 is rapidly cleared from plasma with a peak occurring with 1 min. B. SC administered TCAP-1 shows a peak plasma concentration at 30 to 30 min with a 50% loss occurring within about 90 min. C. IV administered $^{125}$I-TCAP-1 showed concentration in a number of regions of the brain. D. Control animal with SC-administered $^{18}$Fluro-2-deoxyglucose (F2DG) after positron emission tomography (PET) imaging. E. Saline control of rat showing F2DG activity. F. Control animal with scrambled TCAP-1 showing F2DG activity. G. TCAP-1 administered animal showing F2DG activity. H. Comparative uptake of TCAP-1 and controls in total brain region. I. Comparative uptake of TCAP-1 and controls to cortical regions, J. Comparative uptake of TCAP-1 and controls in subcortical regions. **p<0.01, *p<0.05. AcbSh, nucleus accumbens, shell; Amyg, amygdala; CB, cerebellum; CPu, caudate putamen; Hi, hippocampus; IC, inferior colliculus; mGN, medial geniculate nucleus; MN, mammillary nucleus; PAG, periaqueductal grey; SC, superior colliculus; SN, *Substantia nigra*.

Functioned Positron Emission Tomography (fPET)

fPET studies discussed above were conducted through a collaboration with Molecular Imaging, Inc. (Ann Arbor Mich. USA). Normal adult male Wistar rats (approximately 350 g) were acclimated for one week, then injected with vehicle (saline), 10 nmole/kg TCAP-1 or 10 nmole/kg scrambled (SC)-TCAP-1 subcutaneously in the interscapular region. The animals were allowed to equilibrate for 3 hours and 3 days when they were injected with 200 μCu of 18F-2-deoxyglucose under halothane anesthesia 30 minutes before imaging. Animals were imaged with a Siemens microPET scanner. Positron emission was determined using the bundled software and the regions of uptake were determined as a percentage of local emission relative to total body emission. Data was analyzed by two-tailed t-tests, one and two-way ANOVAs where necessary Example 2C—Glucose Uptake into the Brain Given the prolonged residency time of TCAP-1 in the plasma, an SC-administration was used to investigate whether the increase in TCAP-1 into the brain induced increased neurological activity. Using positron emission tomography (PET), neurological activity was assessed using $^{18}$Fluorine-2-deoxyglucose (F2DG) uptake into the brain and examined at 3 hours post TCAP injection and 3 days post injection. A Single SC administration of 3000 pmol/kg of TCAP-1 induced a significant uptake of F2DG into the forebrain in comparison to the saline control or the scrambled TCAP-1 analogue (FIG. 1, D-G). Overall uptake showed about a 35% uptake (p<0.01) in F2DG over the controls (FIG. 1H). Separate examination of cortical (FIG. 1I) and subcortical (FIG. 1J) regions showed increases of about 25% in each region. Uptake after 3 hours, in comparison, was not significant but showed similar trends (data not shown). Although there was major uptake of F2DG in the sympathetic ganglia, heart and bladder, there were no significant differences in these regions between the vehicle, scrambled TCAP or TCAP administered groups.

Example 3—Effect of TCAP an Blood Glucose Levels

A series of three in vivo experiments were performed in which male rats (Rattus norvegicus) were given a single injection of saline, 1 nmole/kg TCAP-1, 1 nmole/kg TCAP-1, or 10 nmole/kg TCAP-1. Plasma glucose levels were measured using the OneTouch Ultra 2 Blood Glucose Monitoring System (accurate to 0.1 mM) during the first week and second week after administration.

In Vivo TCAP-1 Administration

Male Wistar rats pre-catheterized in the jugular vein were obtained from Charles River Laboratories (n=30; 6-8 weeks old) and were divided into three treatment groups: saline (n=10), 1 nmol/kg TCAP-1 (n=10) and 10 nmol/kg TCAP-1 (n=10). Rats were housed in Plexiglass shoebox cages under standard laboratory conditions (12:12 h light:dark cycle, lights on at 0700 h, temperature 21±1° C.) with unrestricted access to food and water. Upon arrival, the rats underwent one week of handling. All procedures were approved by the University of Toronto Animal Care Committee in accordance with the Canadian Council on Animal Care.

In Experiment 1 (An in vivo administration of TCAP-1 in male Wistar rats to measure acute changes in blood glucose and glycogen stores), after acclimation, three animals from each group were injected subcutaneously with TCAP-1 in the scapular region with 100 µLs of vehicle (saline) or the appropriate dose of TCAP-1. Blood was collected and glucose was analyzed at 0, 1, 2, and 4 hours on day 1 of experimenting. On day 2, the next set of 3 animals from each group were treated and blood collected and analyzed in the same manner. On day 3, the final 4 animals from each group were processed in the same manner. For the next week, the blood collection procedure was repeated again. However, at the end of the final 4 hour blood collection, the animals were anesthetized with isoflurane, blood collected by cardiac puncture, then euthanized with carbon dioxide. Tissues (brain, testes, heart, skeletal muscle from gastrocnemius, adipose and liver) were collected, flash frozen, and stored in −80° C. In objective 1; Experiment 2 (An in vivo administration of TCAP-1 in male Wistar rats to measure the long term changes in blood glucose), after acclimation, all animals from each group were injected subcutaneously with TCAP-1 as above. Blood was collected and glucose was analyzed everyday at 10 am for 10 days. On the last day, the animals were sacrificed and tissues were collected as above. Experiment 3 (An in vivo administration of TCAP-1 in male GK rats to measure changes in blood glucose) was performed the same way as Experiment 2.

Glucose Level Determination

Blood collected from each sample was immediately assayed using the ONE TOUCH Ultra®2 Blood Glucose Monitoring System (ONE TOUCH). The precision of this test was accurate to 0.1 mmol/L and intra-assay variation was determined to be 3.32%.

Serum Processing and Haematology Analysis

Whole blood samples were collected into plastic microcentrifuge tubes with EDTA-coated capillary tubes. A minimum sample volume of 20 µL was required for the analyses by the Toronto Centre for Phenogenomics (Mount Sinai Hospital, Toronto) using the Hemavet 950Fs Hematology Analyzer. From the whole blood samples, serum was separated from the cells and fibrin by centrifuging the collection tubes for five minutes at 7000 g at 25° C. Afterwards, immediately following collection of serum, the samples were stored and maintained at a freezing temperature of −80° C.

Muscle, and Liver Tissue Processing and Glycogen Assays

Gastrocnemius muscle and liver samples were immediately extracted following cessation of life. The muscle tissue was washed in 0.1M PBS, pH 7.4 and flash frozen in liquid nitrogen before being sealed in aluminum foil and stored at −80° C.

A portion of the frozen tissue was separated and ground up in liquid nitrogen to a powder form. Ground up tissue was dissolved in radio-immunoprecipitation assay (RIPA) buffer, containing 1% Triton X-100, 50 mM TRIS-HCl (pH 7.4), 150 nM NaCl, 0.1% SDS, 0.5% Sodium deoxycholate, 1 mM EDTA, 1% Protease Inhibitor Cocktail Set III (Calbiochem, Cat. No. 539134), and 25 mM DTT. Tissues was dissolved at a 1-5 mg/ml ratio at 4° C. for 2 hours on a lab rotator (Thermo Scientific). The solution was subsequently centrifuged for 15 minutes at 13 000 rpm to remove the indigestible tissue. The colorimetric protocol for the Glycogen Assay Kit (Biovision, Cat. No. K646-100) was followed. Briefly, the enzyme mix included in the assay contains a glucoamylase enzyme that breaks down glycogen into glucose which is then specifically oxidized to react with a probe in the mix to produce a measurable colour at $\lambda=570$ nm.

Results

Figure 2:
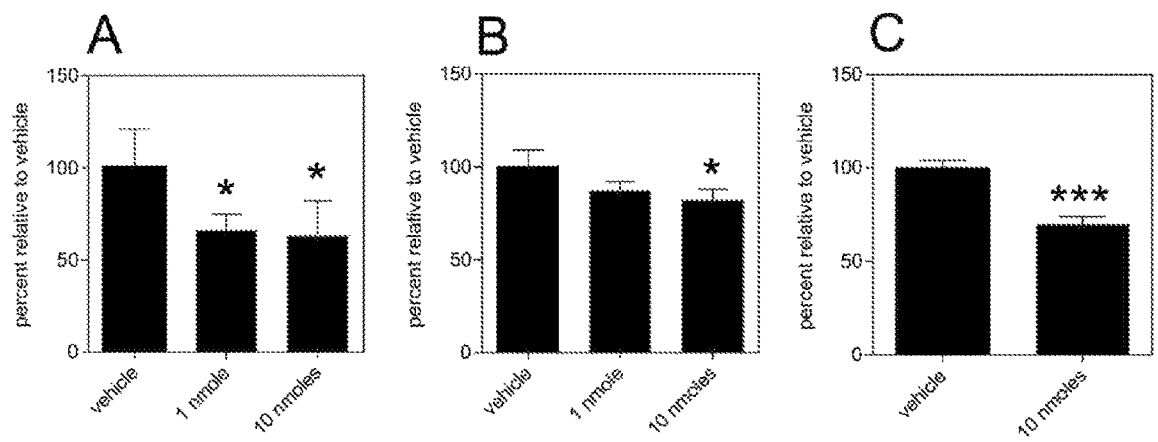
FIG. 2. Subcutaneous TCAP-1 injections decrease plasma glucose levels in normal Wistar rats (A, B) and Type II diabetic GK rats (C) after one week. Male Wistar rats were given a single injection of saline, 1 nmole/kg TCAP-1, 1 nmole/kg TCAP-1, or 10 nmole/kg TCAP-1. Plasma glucose levels were measured using the OneTouch Ultra 2 Blood Glucose Monitoring System (accurate to 0.1 mM) during the first week and second week after administration. The level of significance was determined by a one-way ANOVA and Bonferonni's post hoc test (A,B) and student's t-test (C).

Analysis revealed a significant decrease in blood glucose ($p<0.05$) between week 1 and week 2 for rats injected with both a low and high dose of TCAP-1 (1 nmole/kg and 10 nmole/kg, respectively) (FIG. 2A). Hourly results indicate that blood glucose is not significantly affected by TCAP-1 administration within 4 hours (data not shown). FIG. 2A shows that 1 nmole/kg TCAP-1 treated rats (n=7) exhibited a significant decrease in blood glucose relative to vehicle (n=6) (*$p<0.05$). 10 nmole/kg TCAP-1 treated rats (n=7) exhibited a significant decrease in blood glucose levels relative to vehicle (*$p<0.05$)

To confirm the results from the first experiment, a second repeat of the same experimental design was performed. Again, male rats (*Rattus norvegicus*) were given injection(s) of varying doses of TCAP-1 and blood glucose levels were monitored daily for one week and once the second week. Daily glucose levels showed no significant changes during week 1 (data not shown). A comparison of the terminal glucose levels during week 2 relative to the vehicle shows a significant lowering of blood glucose in the 10 nmole/kg TCAP-1-injected rats ($p<0.05$; FIG. 2B). FIG. 2B shows that 1 mnole/kg TCAP-1 treated rats (n=4) exhibited no significant change, 10 nmole/kg TCAP-1 treated rats (right, n=3) exhibited a significant decrease in blood glucose levels compared to vehicle (*$p<0.05$)

To determine the effect of TCAP-1 on blood glucose in the pathological model of diabetic GK male rats, rats were given a weekly injection for two weeks of saline or 10 nmole/kg TCAP-1. Blood glucose was monitored daily for one week. Results indicate that TCAP-1 significantly decreases plasma glucose levels by day 4 of week 1 ($p<0.001$; FIG. 2C), FIG. 2C shows that 10 nmole/kg TCAP-1 treated rats (n=7) exhibited a significant decrease in blood glucose levels relative to vehicle (***$p<0.001$). The study was terminated after day 4 of week 1 due to catheterization issues. (For all studies values were normalized as a percentage relative to the vehicle of each experiment. Mean±SEM; *$p<0.05$; $p<0.01$, *$p<0.001$; A+B) 1-way ANOVA and Bonferonni's post hoc test C) Student's t-test).

Example 4—Glucose Insulin and Glucagon Changes in Blood

The previous experiments confirmed that IV and SC TCAP-1 uptake was into plasma was equivalent and that plasma TCAP can be taken up into the brain inducing glucose uptake into the brain. These findings suggested that increased transport of glucose via TCAP-1 into tissues may result in decreased plasma glucose. Therefore, the acute effect of TCAP-1 on plasma glucose changes was investigated in normal Wistar and diabetic Goto-Kakizaki rats. The first set of studies using normal Wistar rats showed that upon a single SC injection of TCAP-1, both concentrations of the peptide (1 nmole and 10 nmols/kg) reduced plasma glucose levels by about 40% (p<0.05; 1 nmole; one-way ANOVA, Dunnett's Multiple Comparison Test) one week after the TCAP-1 injection (FIG. 3A). An examination of insulin showed that in normal wistar rats plasma insulin was reduced by 45-50% (p<0.05, one-way ANOVA) in low and high concentrations respectively (FIG. 3B). Glucagon concentrations showed the opposite trend with the 10 nmol dose of TCAP inducing at 100% increase in normal animals at the highest dose (p<0.05, one-way ANOVA) (FIG. 3C). Similarly, in Goto-Kakizaki rats, plasma glucose was reduced about 35% after one week (p<0.05; Student's T-test) (FIG. 3D). Plasma insulin and glucagon changes reflected that of the normal Wistar rats with insulin concentrations decreasing about 40% (FIG. 3E) and glucagon levels increasing about 38% over the vehicle administered animals (p<0.05; Student's T-test) (FIG. 3F).

Figure 3:
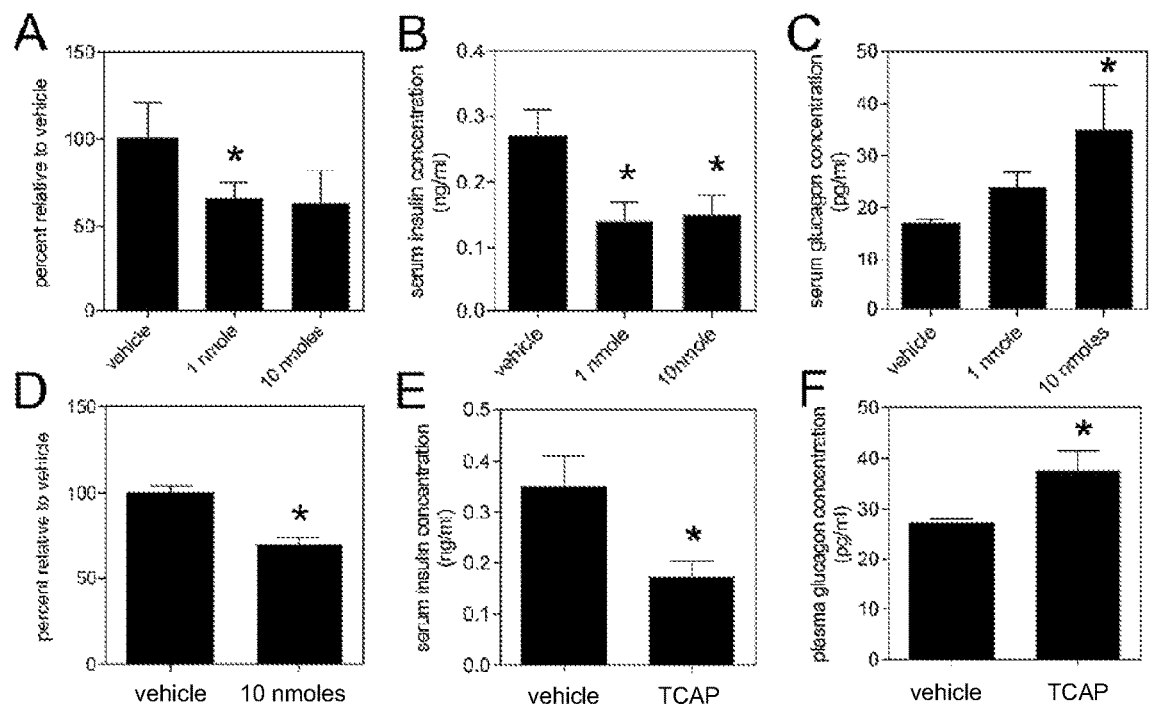
FIG. 3 TCAP-1 induced changes in plasma glucose, insulin and glucagon. A. Normal rats with acute SC TCAP-1 administration showing the decrease in plasma glucose after 1 week. B. Decrease in plasma insulin after 1 week in normal Wistar animals. C. Increase in plasma glucagon after 1 week in normal Wistar rats. D. Decrease in plasma glucose after 1 week in Goto-Kakazaki (GK) rats. E. Decrease in plasma insulin in GK rats. F. Increase in plasma glucagon in GK rats after 1 week of treatment. *p<0.05 as determined by a one-way ANOVA (FIGS. 23A-C) and Students T-test (FIGS. 23D-F).

Example 5—Liver and Muscle Glycogen Content in Extracted Liver of TCAP-1 Treated Wistar Rats Glycogen content in excised gastrocnemius muscle and liver was measured and results indicate no significant change between TCAP-1 treated rats and control rats (p>0.05) (FIGS. 3.2 and 3.3). Average muscle glycogen levels in the vehicle, 1 nmole/kg TCAP-1, and 10 nmole/kg TCAP-1 groups were 0.03836±0009150 µg/µg protein, 0.02634±0.003573 µg/µg protein, 0.03854±0.01146 µg/µg protein, respectively. Average liver glycogen levels in the vehicle, 1 nmole/kg TCAP-1, and 10 nmole/kg TCAP-1 groups were 0.02233±0.002131 µg/µg protein, 0.02318±0.0001932 µg/µg protein, 0.0.01674±0.0.001783 µg/µg protein, respectively.

Figure 4:
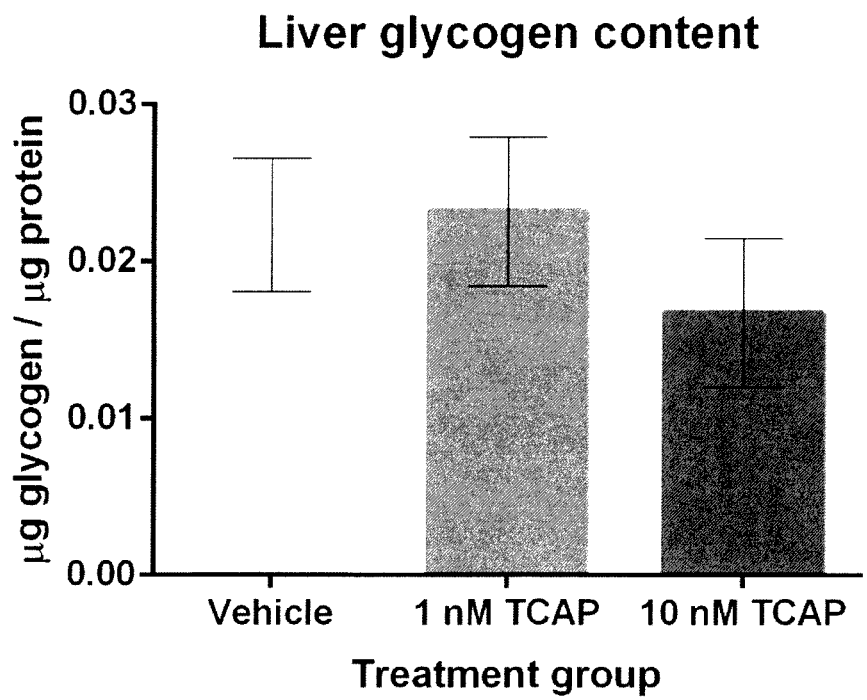
FIG. 4 Liver glycogen content in extracted liver of TCAP-1 treated Wistar rats. Wistar rats were given injections of 0 nmole/kg (n=6), 1 nmole/kg (n=7), or 10 nmole/kg (n=7) of TCAP-1. During the second week, liver tissue was extracted and glycogen content was analyzed using a colorimetric glycogen assay. There is no significant change in liver glycogen content as a result of TCAP-1 treatment p>0.05. (Mean±SEM; *p<0.05, p<0.01, *p<0.001; 1-way ANOVA and Bonferonni's post hoc test).

FIG. 4 illustrates the liver glycogen content in extracted liver of TCAP-1 treated Wistar rats. As noted above, Wistar rats were given injections of 0 nmole/kg (n=6), 1 nmole/kg (n=7), or 10 nmole/kg (n=7) of TCAP-1. During the second week, liver tissue was extracted and glycogen content was analyzed using a colorimetric glycogen assay. There is no significant change in liver glycogen content as a result of TCAP-1 treatment p>0.05. (Mean±SEM; *p<0.05, p<0.01, *p<0.001; 1-way ANOVA and Bonferonni's post hoc test).

Figure 5:
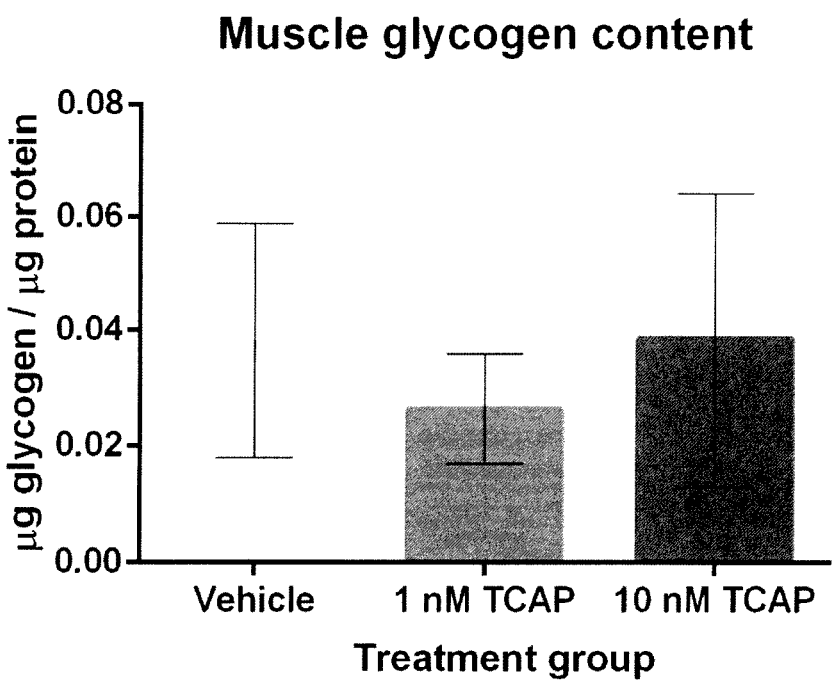
FIG. 5 Muscle glycogen content in extracted gastrocnemius muscle of TCAP-1 treated Wistar rats. Wistar rats were given injections of 0 nmole/kg (n=6), 1 nmole/kg (n=7), or 10 nmole/kg (n=7) of TCAP-1. During the second week, muscle tissue was extracted and glycogen content was analyzed using a colorimetric glycogen assay. There is no significant change in muscle glycogen content as a result of TCAP-1 treatment p>0.05. (Mean±SEM; *p<0.05, p<0.01, *p<0.001; 1-way ANOVA and Bonferonni's post hoc test).
Figure 6A:
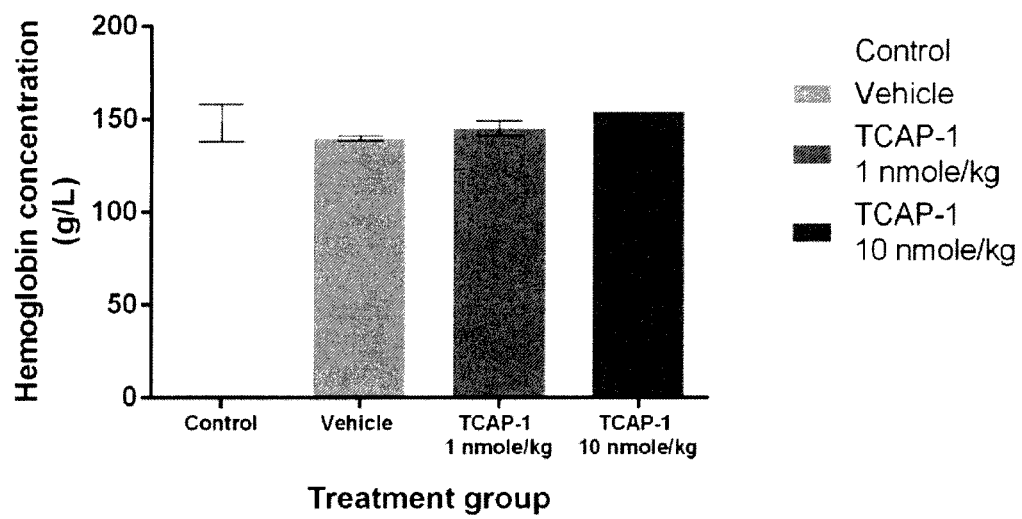
FIG. 6A to 6L are results of assays illustrating the lack of effect on various immune factors and blood characteristics in vivo.
Figure 6B:
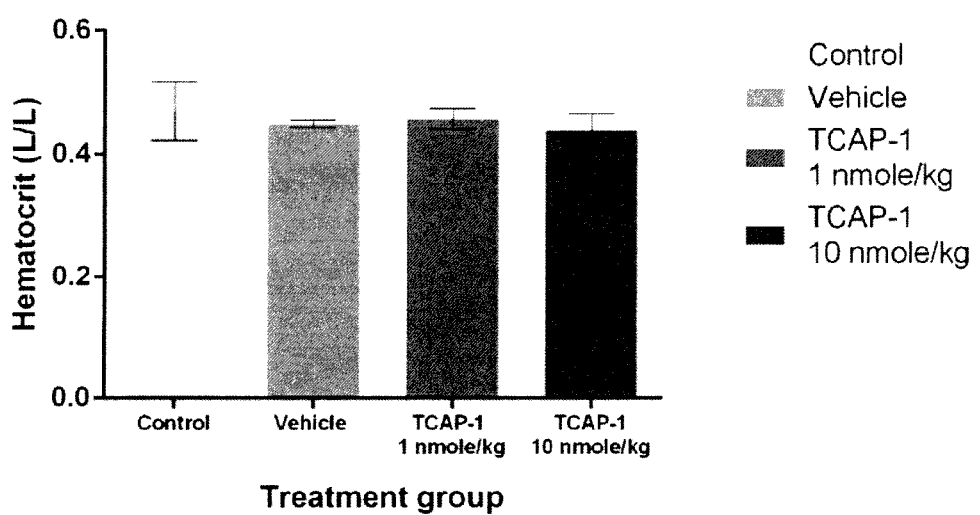
Figure 6C:
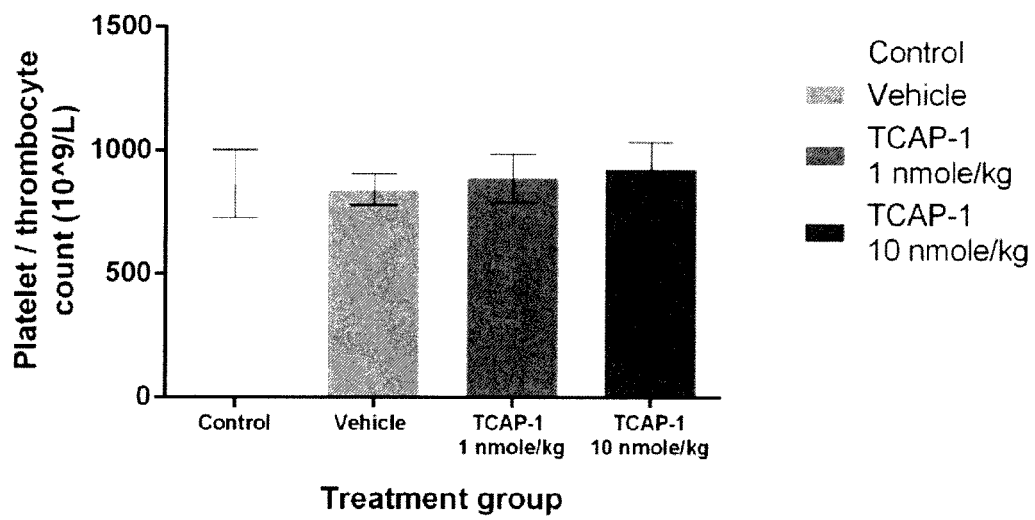
Figure 6D:
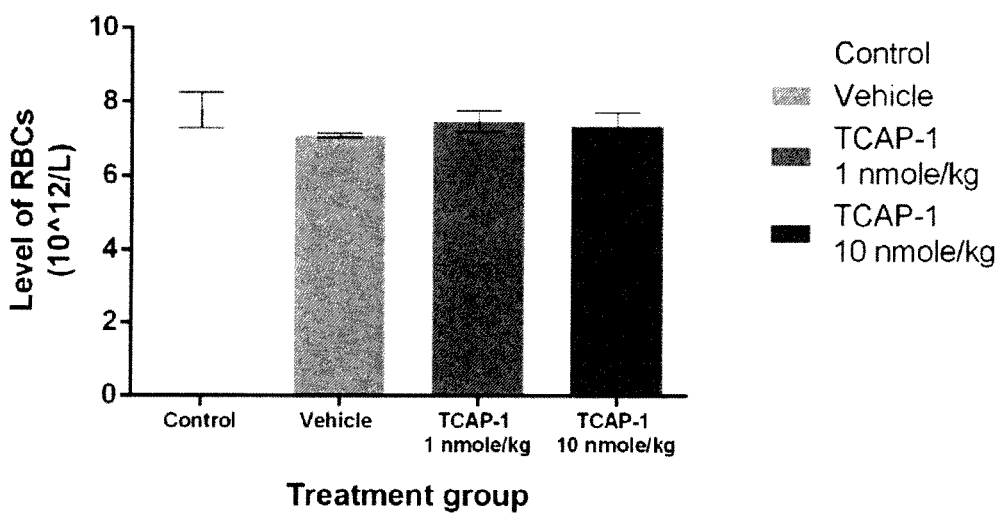
Figure 6E:
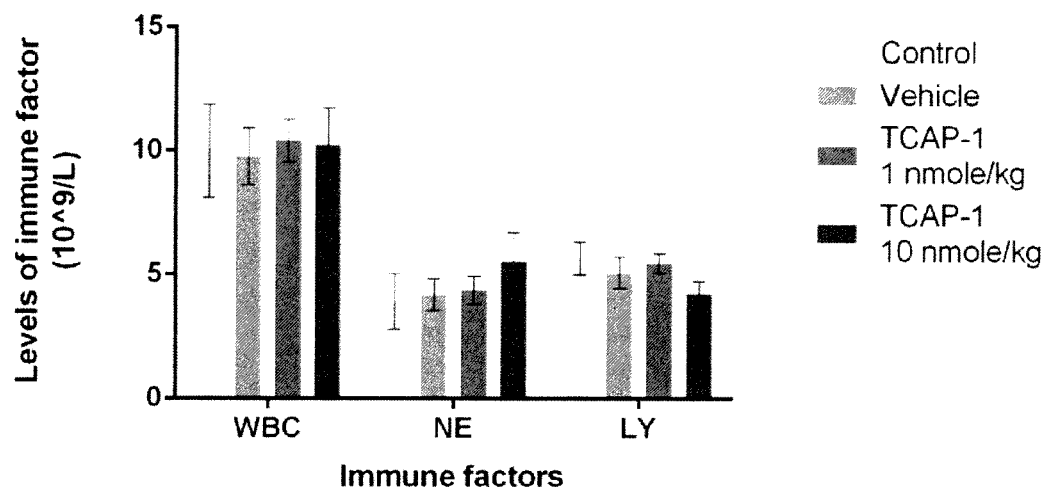
Figure 6F:
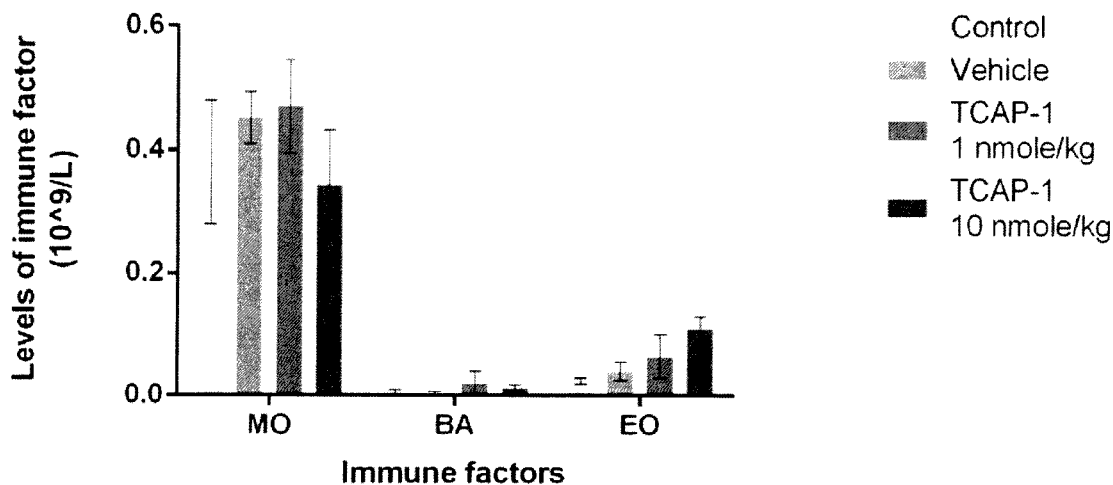
Figure 6G:
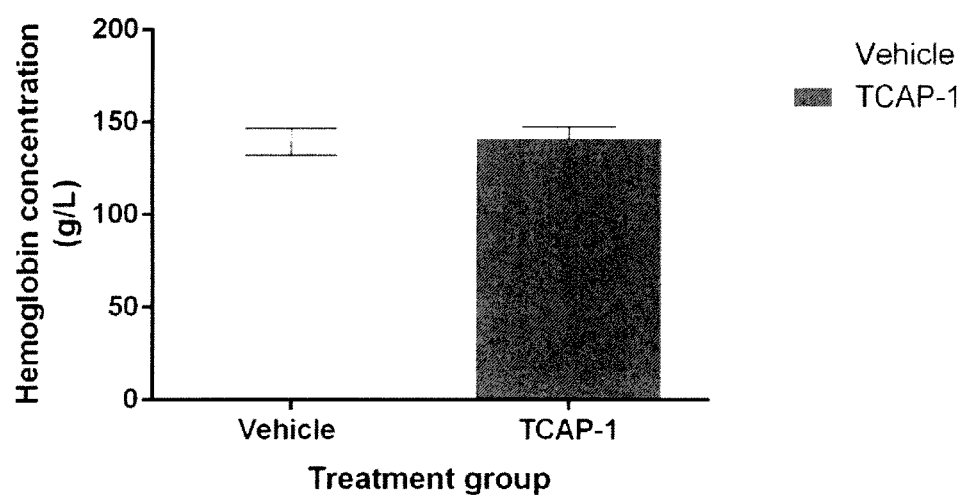
Figure 6H:
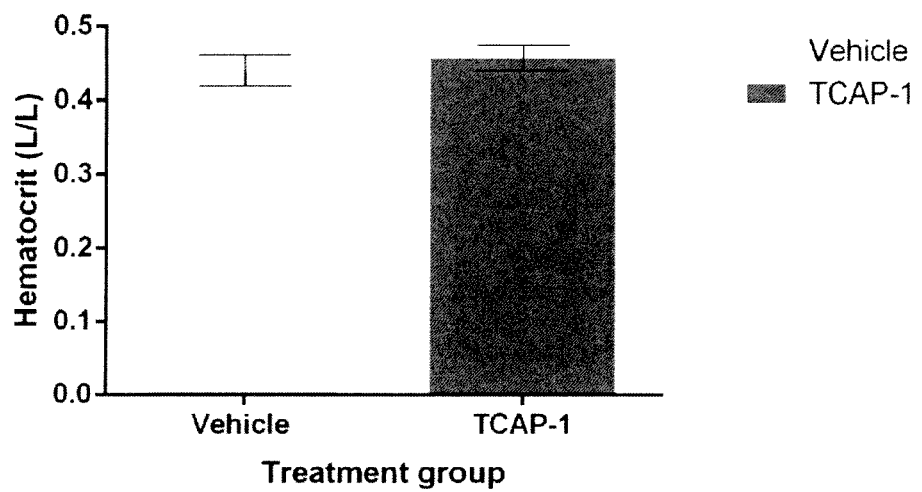
Figure 6I:
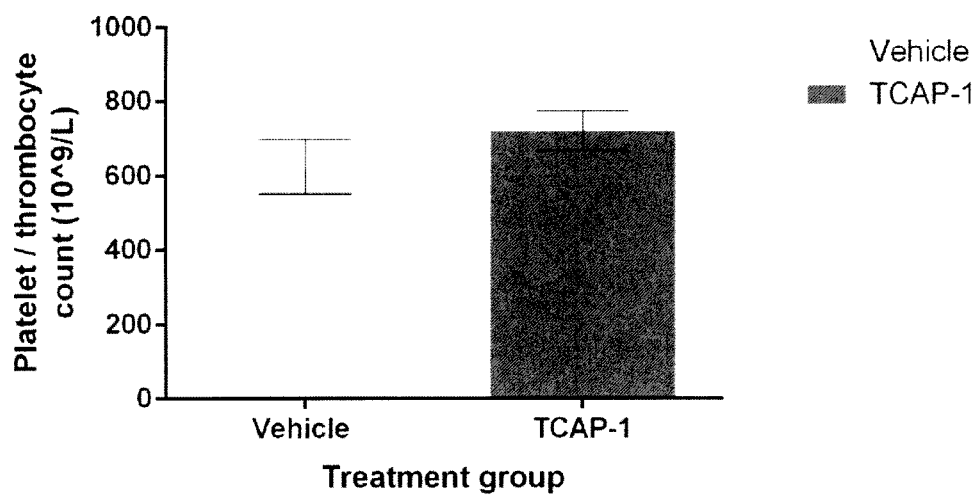
Figure 6J:
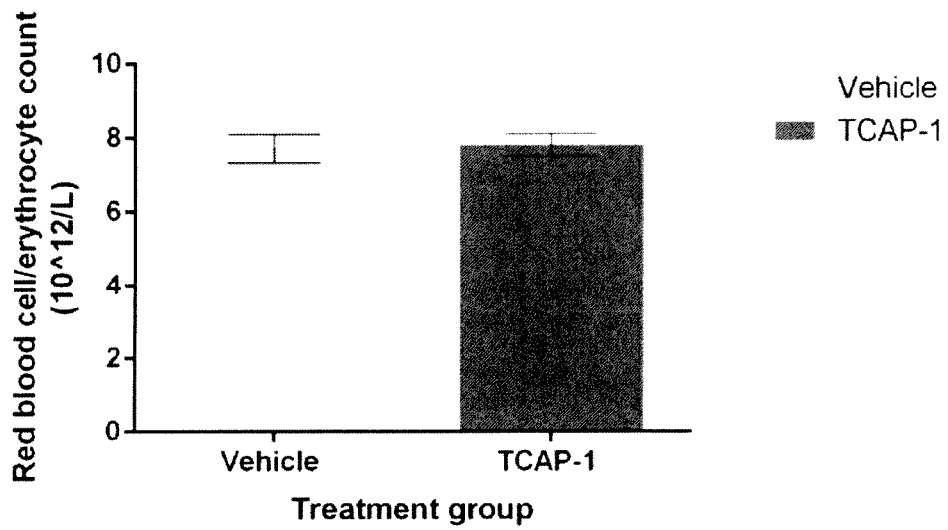
Figure 6K:
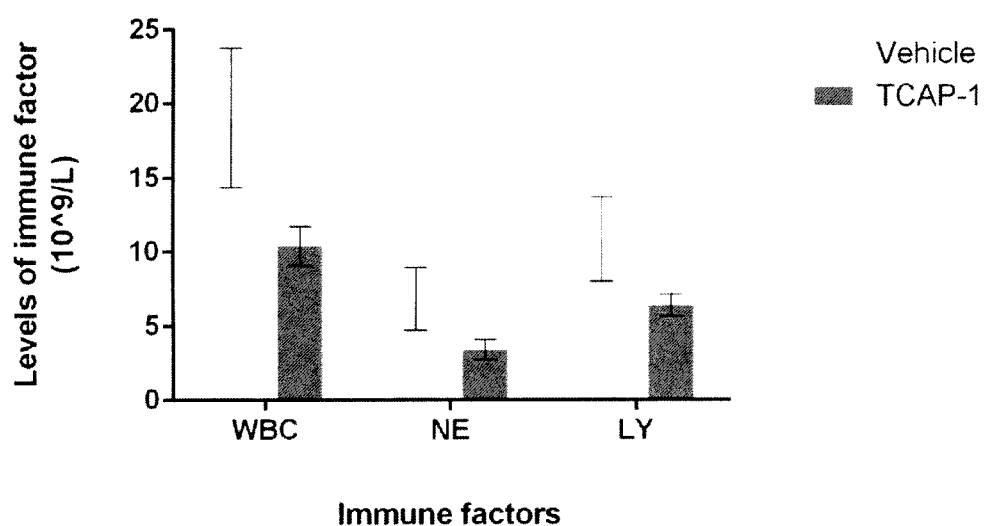
Figure 6L:
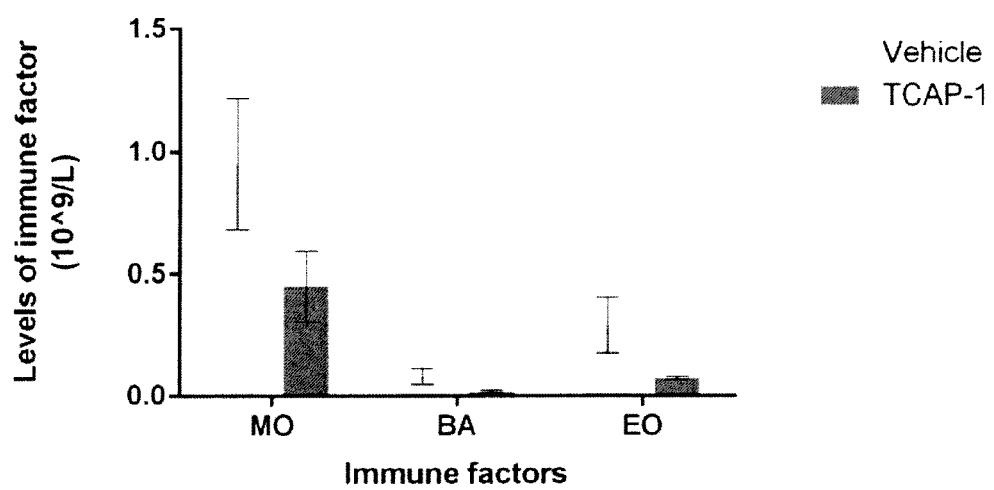

FIG. 5 illustrates muscle glycogen content in extracted gastrocnemius muscle of TCAP-1 treated Wistar rats. Wistar rats were given injections of 0 nmole/kg (n=6), 1 nmole/kg (n=7), or 10 nmole/kg (n=7) of TCAP-1. During the second week, muscle tissue was extracted and glycogen content was analyzed using a colorimetric glycogen assay. There is no significant change in muscle glycogen content as a result of TCAP-1 treatment p>0.05. (Mean±SEM; *p<0.05, p<0.01, *p<0.001; 1-way ANOVA and Bonferonni's post hoc test).

Example 6—Haematology Assays

Haematology assays were performed on physiological normal rat serum and from Type II Diabetic GK rats obtained at the end of the in vivo studies noted herein in which TCAP-1 was administered to the normal rats and plasma glucose levels were monitored over the course of 1-2 weeks. The assays were performed to determine whether TCAP-1 had an effect on immune factors and blood characteristics: Hemoglobin concentration, hematocrit, as well as platelet, red blood cell, white blood cell, neutrophil, lymphocyte, monocyte, basophi and eosinophil counts. Results are illustrated in FIGS. 6A to 6L. As can be seen by the figures, TCAP-1 did not have affect a change in these immune factors and blood characteristics.

Example 7—Localization of TCAP in Muscle Tissue

Figure 7:
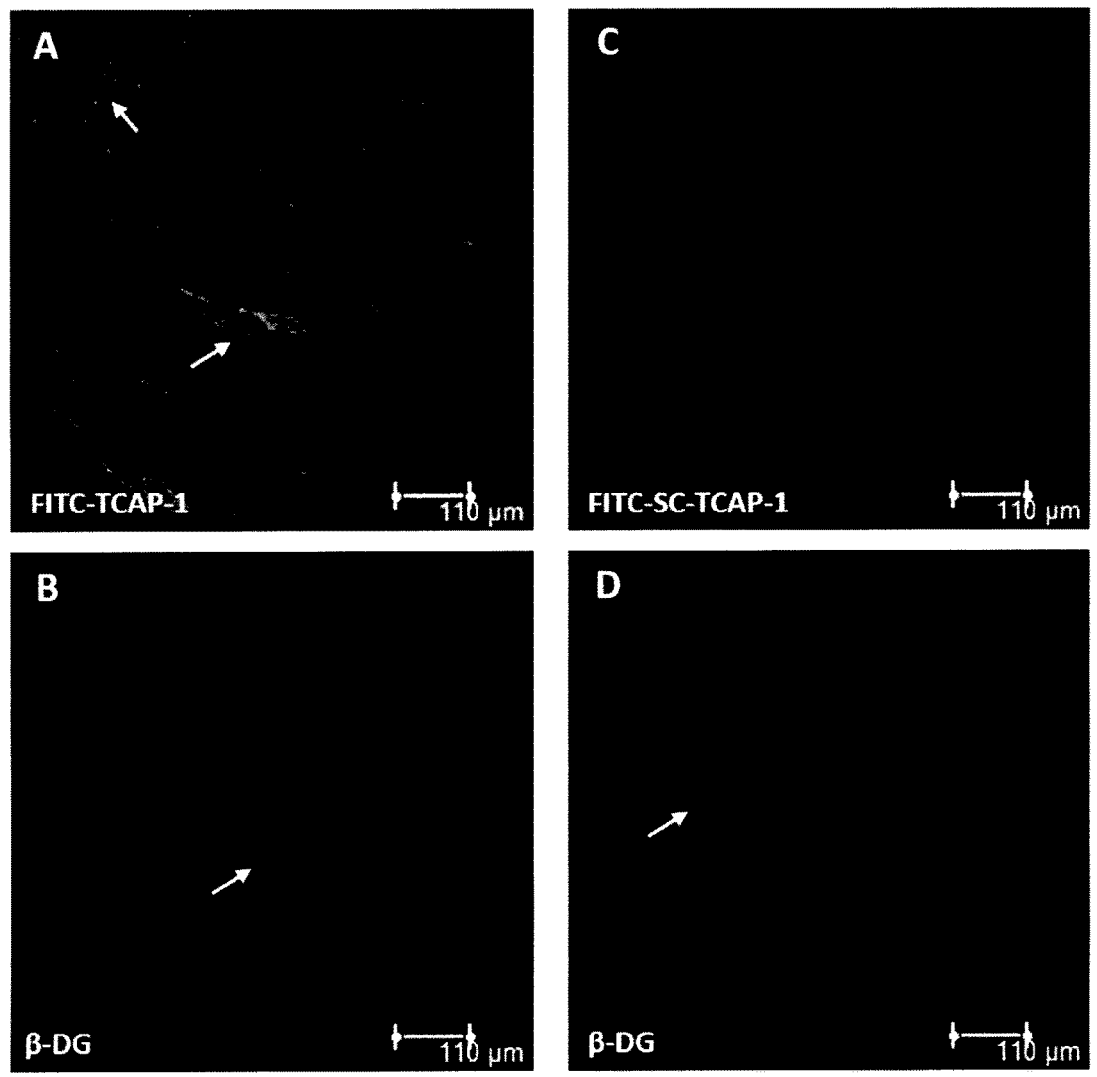
FIG. 7. Immunohistochemistry of β-dystroglycan (β-DG; red) and FITC-TCAP-1/FITC-SC-TCAP-1 (green) co-staining on 5 μm sections of skeletal mouse muscle. A) FITC-TCAP-1 binding is seen ubiquitously at low concentrations and on sarcolemmas in high concentrations; B+D) β-DG expression localized to the sarcolemma; C) FITC-SC-TCAP-1 binding shows non-specific localization. Images were obtained using a WaveFX spinning-disk confocal microscope (Quorum Technologies, Canada). Images were taken using a 20× confocal. Scale bar: 110 μm FIG. 8. 19Immunohistochemistry of co-staining of β-dystroglycan (β-DG; red) and TCAP-1 (green) on 5 μm sections of skeletal mouse muscle showing high sarcolemma localization of β-DG and TCAP-1. A) TCAP-1 is localized to the sarcolemma of muscle tissue; B) β-DG localization mainly on sarcolemma; C) A merge of TCAP-1 and β-DG localizations shows strong co-localization. Images were obtained using a WaveFX spinning-disk confocal microscope (Quorum Technologies, Canada), Images were taken using a 20× confocal. Scale bar: 110 μm.

Previous binding assays on brain tissue slices and embryonic hippocampal cells showed that FITC-TCAP-1 bound and co-localized with β-DG on cell membranes (Chand et al., 2012). The dystroglycan complex is implicated in muscle development and maintenance and is expressed ubiquitously on skeletal muscle fibers (Hughes et al., 2006). To determine whether the TCAP-1 system was present in skeletal muscle, mouse gastrocnemius muscle were sectioned into 5 µm slices and a fluorescent immunohistochemistry study for β-DG was performed together with a FITC-TCAP-1 binding assay.
Results
FITC-labelled TCAP-1 preferentially binds to the membranes of individual skeletal mouse muscle fibers and also exhibited a weaker, patchy localization across a slice of tissue (FIG. 7A). Consistent with the known localization of β-DG on muscle, β-DG showed strong localization to the sarcolemma as well (FIGS. 7B and D). A parallel FITC-labelled scrambled-TCAP-1 binding assay was perforated and results indicate weak, nonspecific binding (FIG. 7C).

Example 8—Localization of TCAP-1 Relative to β-Dystroglycan in Skeletal Cells

Figure 8:
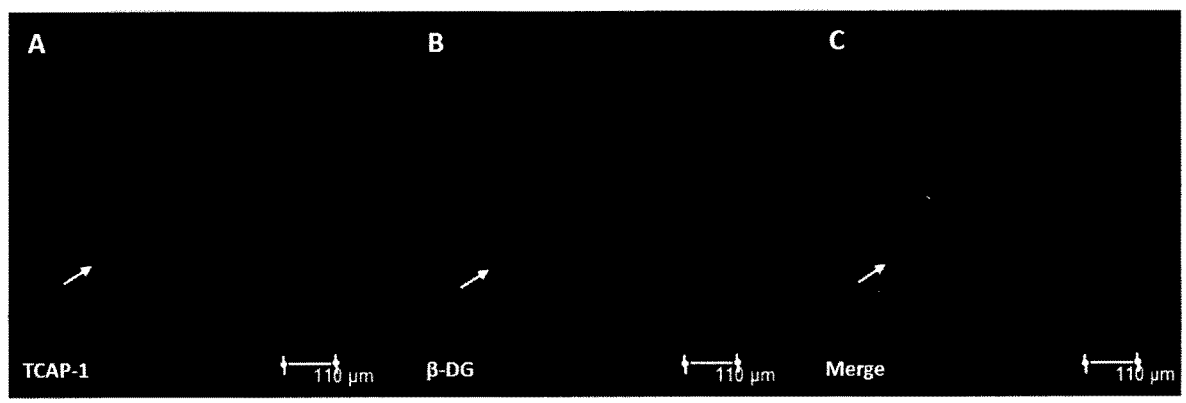

TCAP-1 can be expressed as part of the entire teneurin-1 gene or as a separate transcript independent of the teneurin-1 gene (Chand et al., 2012). Since FITC-TCAP-1 shows binding on skeletal muscle tissue with the dystroglycan complex, endogenous TCAP-1 may also be localized similarly on skeletal muscle. To determine if endogenous TCAP-1 existed on skeletal muscle, mouse gastrocnemius muscle was sectioned into 5 nm slices and a fluorescent immunohistochemistry study was performed with TCAP-1 TNR308 antiserum and β-DG.
Results
TCAP-1 localized to the sarcolemma of muscle tissue (FIG. 8A) as did β-DG (FIG. 8B); there was strong co-localization of both TCAP-1 and β-DG (FIG. 8C).

Figure 9:
FIG. 9. Immunohistochemistry of co-staining of rapsyn (red) and TCAP-1 (green) on 5 μm sections of skeletal mouse muscle shows patch distributions. A) DIC; B) TCAP-1; C) Rapsyn; D) Merge of TCAP-1 and Rapsyn. Images were obtained using a WaveFX spinning-disk confocal microscope (Quorum Technologies, Canada). Magnification of 40×. Scale bar: 15 μm.
Figure 9:
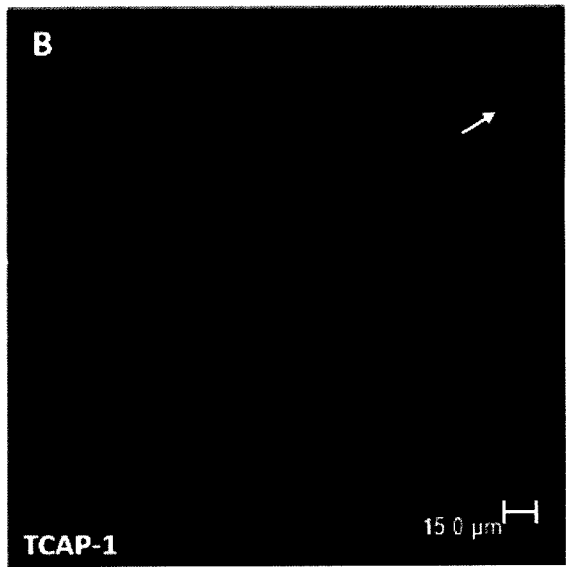
Figure 9:
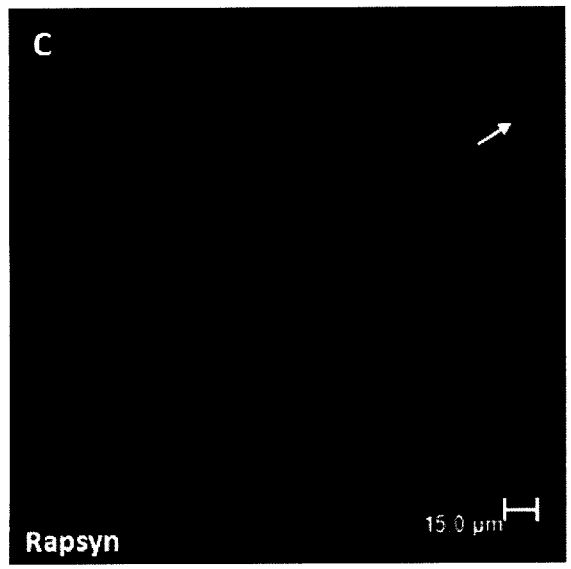
Figure 9:
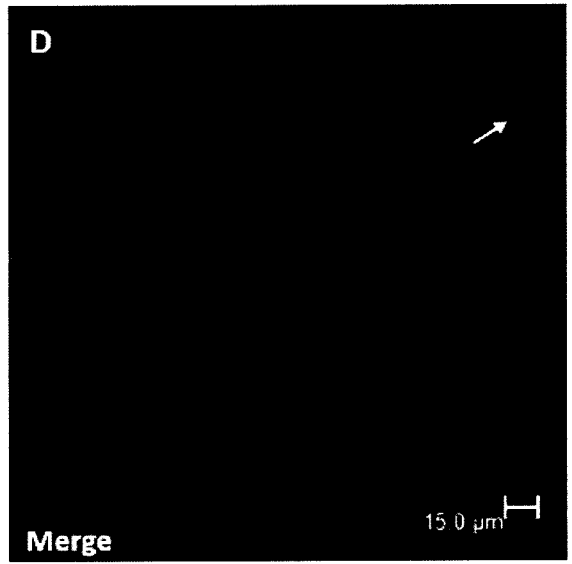

Example 9—Localization of TCAP-1 Relative to Rapsyn in Skeletal Cells

β-DG plays an integral role in the signalling at the neuromuscular junction of skeletal muscle (Hughes et al., 2006). Given that TCAP-1 upregulates β-DG gene expression in the brain and appears to be present in the skeletal muscle system, TCAP-1 may be playing a role in neuromuscular signaling. The first step in determining whether this is the case was to perform a preliminary immunoreactivity co-staining of TCAP-1 and the neuromuscular junction marker rapsyn.
Result
This experiment shows TCAP-1 immunoreactivity on the sarcolemma and in specific regions of the sarcolemma (FIG. 9B). Rapsyn localized to distinct regions of the sarcolemma (FIG. 9C). Co-localization of TCAP-1 and rapsyn occurred in a patchy distribution where TCAP-1 is consistently localized adjacent to rapsyn (FIG. 9D). FIG. 9A is DIC.

Example 10—Defining the Hypo e-38 Cells as a Model

As noted herein it was established that $^{125}$I-TCAP-1 can betaken up into the arcuate nucleus of the brain (see above), confirming previous studies that TCAP-1 can cross the blood-brain barrier (Al Chawaf et al., 2007). Because the hypo-E38 cell is derived from the mouse arcuate nucleus and we have previously established that this cell line is responsive to TCAP treatment, it was chosen as a model to investigate glucose metabolism. To further characterize this cell line, the expression of teneurins, TCAP and its putative receptor, latrophilin-1 was investigated (FIG. 10A, B). PCR-based expression showed that teneurins 3 and 4, and TCAPs 3 and 4 were highly expressed in the hypo-E38 cells whereas teneurin and TCAP-2 were less expressed. Unequivocal expression of either teneurin-1 or TCAP-1 could not be ascertained. These studies were compared to mouse brain that showed that all components of teneurins and TCAP's were present. With respect to the putative receptors, latrophilins, only latrophilin 1 and 3 could be detected in this cell line or in the intact mouse brain. Thus these findings suggested that the Hypo-E38 cell line was particularly appropriate for treatments of TCAP-1 as it did not express the peptide or proprotein endogenously. To confirm previously published studies that the TCAP region of teneurins could bind with latrophilin-1, the co-localization of FITC-TCAP-1 with latrophilin-1 immunoreactivity was examined (FIG. 10B). This showed a strong co-localization between the labelled TCAP-1 and the latrophilin-1 immunoreactivity consistent with the previous studies that TCAP binds with latrophilin.

Figure 10:
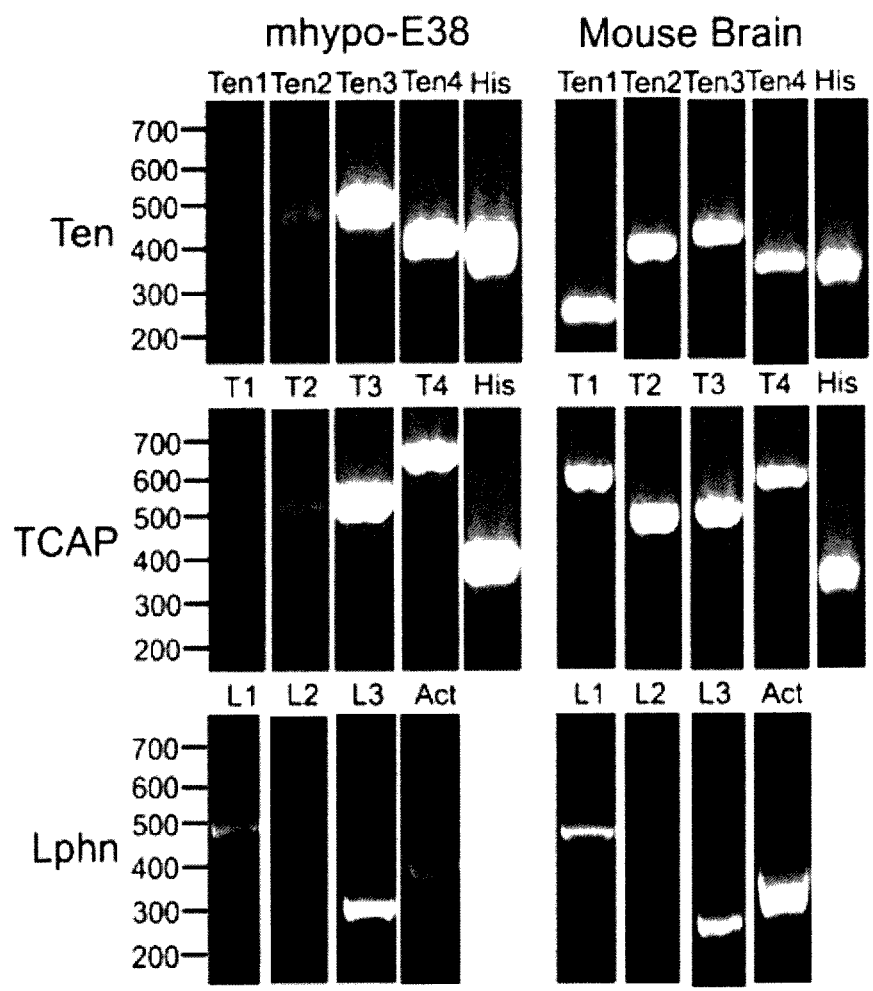
FIG. 10. Defining the Hypo e-38 Cells as a Model immortalized Cell Line: A. Expression of Teneurin (Ten), TCAP and Latrophilin-1 (Lphn) in Hypo E-38 cells and whole mouse brain. B. Co-localization of FITC-TCAP-1 (green) with Lphn-1 (red) in two representative Hypo E-38 cells. Yellow regions indicate regions of overlap.

FIG. 10: Defining the Hypo e-38 Cells as a Model immortalized Cell Line: A. Expression of Teneurin (Ten), TCAP and Latrophilin-1 (Lphn) in Hypo E-38 cells and whole mouse brain. B. Co-localization of FITC-TCAP-1 (green) with Lphn-1 (red) in two representative Hypo E-38 cells. Yellow regions indicate regions of overlap.

Glucose Uptake in Cells:

Having established that the Hypo-E38 cells possess the key components of the teneurin-TCAP-latrophilin interactive complex, they were used to examine glucose uptake. These studies indicated that TCAP-1 had the potential to increase glucose transport into neurons. Initially, The amount of glucose uptake was examined (FIG. 11A) however, there were no significant differences. However, because glucose is rapidly converted to glucose-6-phosphate (G6P) by hexokinase II, intracellular G6P was subsequently examined (FIG. 11B). A 10 nM concentration increased intracellular G6P concentrations by 150% ($p<0.05$, one-way ANOVA). Given these findings, the study was repeated using 3H-deoxyglucose (3HDG), which is not hydrolyzed by hexokinase II and, therefore, provides a more accurate indication of glucose uptake into cells.

In these studies, 3HDGglucose uptake was measured in whole cells after TCAP-1, insulin or control administration. Insulin, used as the positive control showed a significant ($p=0.0363$; one-way ANOVA) uptake in 3HDGlucose within 30 min and remained high until after 60 min ($p<0.05$ Dunnett's Multiple Comparison Test) (FIG. 11C). TCAP-1 also showed a significant effect of treatment ($p=0.0005$, one-way ANOVA) showed a significant uptake at 60 mm ($p<0.01$, Dunnett's Test) (FIG. 11E). The scTCAP-1 showed no significant glucose uptake (FIG. 11D). Moreover, because insulin has been established to be potassium (K-) dependent, the study was repeated potassium-free media. Although the lack of potassium decreased insulin-dependent glucose uptake to baseline levels, the decreased potassium concentration in the medium had no effect of TCAP-1 stimulated glucose uptake ($p<0.001$; FIG. 11F, G).

Glucose entry into cells is passive and is dependent on the number of glucose transporters resident in the cell membrane. Therefore, it was likely that the ability of TCAP-1 to increase the amount of glucose into the cell could be due in part to increased glucose transporter insertion into the plasma membrane. The glucose transporter, GLUT3 is the major transporter of glucose in neurons and therefore was examined in the Hypo E38 cells (FIG. 11H). In untreated cells, most of the GLUT3 immunoreactivity was found around the nucleus, however after 1 h following TCAP-1 treatment, there was a significant ($p<0.05$) increase (25%) in the amount of immunoreactivity in the cytoplasm (FIG. 11I), and by 3 h, a 40% increase ($p<0.001$) could be detected in the cytosol. Further examination showed increased ($p<0.05$) presence in the membrane regions (FIG. 11J). A further study was performed to establish whether TCAP-1 could also induce glucose transporters in the growing neurites, as previous studies (Chand et al., 2012, Al Chawaf et al., 2007) showed that TCAP-1 has a major effect on neuronal process formation (FIG. 11K). In the current experiment, TCAP-1 induced a significant ($p<0.01$) uptake of GLUT3 immunoreactivity in growth cones of extending neurites (FIG. 11L).

Figure 11:
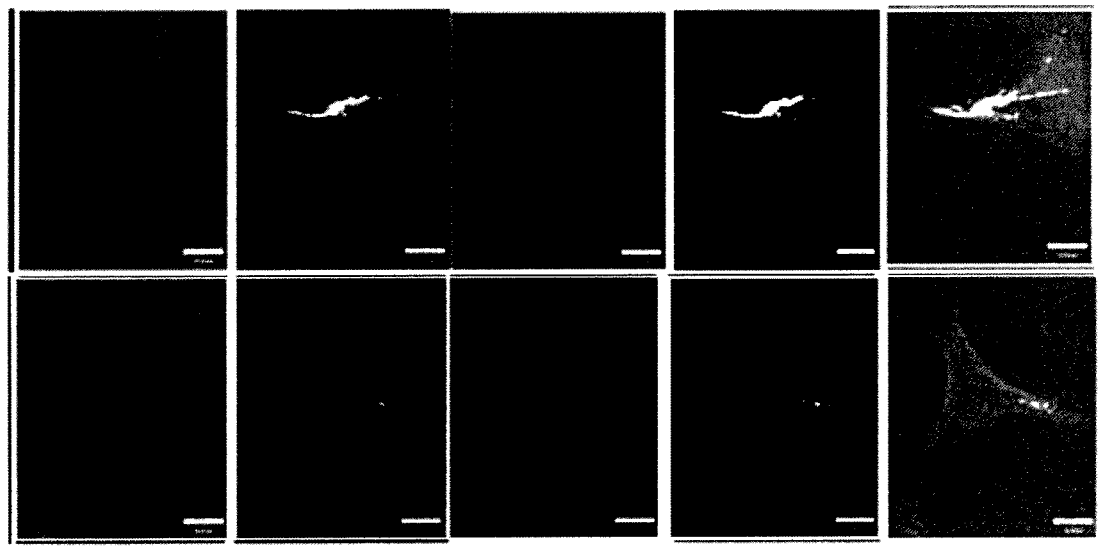
FIG. 11. Increased glucose uptake and glucose transporter translocation in immortalized neurons. A. Glucose uptake in Hypo-E38 cells. B. Glucose-6-phosphate conversion in Hypo E38 cells following TCAP-1 treatment. TCAP-1 at 10 nmoles shows a significant increase in G6P. C. Uptake of 3HDG following insulin administration to the cell. Significant increases were noted between 30-60 min. D. Uptake of 3HDG following scrambled TCAP administration to the cell. There were no significant differences. E. Uptake of3HDG following TCAP-1 administration to the cells. TCAP-1 shows a significant uptake in 3H-deoxyglucose in immortalized neurons with an uptake profile distinct from insulin peaking at 60 min. F. TCAP-1 associated glucose uptake is independent from potassium which is required for insulin uptake. H. TCAP-1 induces GLUT3 translocation to the membrane H-ABC, micrograph images over 3 h; H-DEF, GLUT3 immunofluorescent images over 3 h. H-GHI, combined images with DAPI. I. Increase in cytosolic GLUT3 immunoreactivity over 3 hours. J. Increase in GLUT3 immunoreactivity in membrane regions over 3 hours. K. Examination of GLUT3 in neurites and growth cones. K-ABC; wheat-germ agglutinin immunoreactivity changes over 2 hours. K-DEF; changes in GLUT3 immunoreactivity over 2 hours. K-GHI, combined images for K-A to F. L. Quantification of GLUT3 in neurites and growth cones over 2 hours.

FIG. 11: Increased glucose uptake and glucose transporter translocation in immortalized neurons. A. Glucose uptake in Hypo-E38 cells. B. Glucose-6-phosphate conversion in Hypo E38 cells following TCAP-1 treatment. TCAP-1 at 10 nmoles shows a significant increase in G6P, C. Uptake of 3HDG following insulin administration to the cell. Significant increases were noted between 30-60 min. D. Uptake of 3HDG following scrambled TCAP administration to the cell. There were no significant differences. E. Uptake of 3HDG Mowing TCAP-1 administration to the cells, TCAP-1 shows a significant uptake in 3H-deoxyglucose in immortalized neurons with an uptake profile distinct from insulin peaking at 60 min. F. TCAP-1 associated glucose uptake is independent from potassium which is required for insulin uptake. H. TCAP-1 induces GLUT3 translocation to the membrane H-ABC, micrograph images over 3 h; H-DEF, GLUT3 immunofluorescent images over 3 h. H-GHI, combined images with DAPI. I. Increase in cytosolic GLUT3 immunoreactivity over 3 hours. J. Increase in GLUT3 immunoreactivity in membrane regions over 3 hours. K. Examination of GLUT3 in neurites and growth cones. K-ABC; wheat-germ agglutinin immunoreactivity changes over 2 hours. K-DEF; changes in GLUT3 immunoreactivity over 2 hours. K-GHI, combined images for K-A to F. L. Quantification of GLUT3 in neurites and growth cones over 2 hours.

Example 11—Effect of TCAP on Cellular Glucose Uptake in Brain Cells

The effect of TCAP-1 on glucose uptake in brain cells was examined in immortalized N38 hypothalamic cells. Immortalized mHypoE-38 hypothalamic embryonic mouse neurons (gift from Dr. Denise Belsham, University of Toronto) were grown in Dulbecco's Modified Eagle Medium (DMEM) containing 4500 mg/L D-glucose, L-glutamine, and 25 mM HEPES buffer, without sodium pyruvate or phenol red (Gibco, Cat. No. 21063029), supplemented with 5% heat-inactivated fetal bovine serum (FBS), 100 U/ml penicillin and 100 µg/ml streptomycin. Cells were maintained at 60-70% confluency at 37° C. in a humidified $CO_2$ incubator. To passage, cells were washed once in sterile PBS, trypsinized and seeded at a density of 100,000 cells per 3.5 cm plate and allowed to grow for 2-3 days. 24 hours prior to experimentation, medium was changed. mHypoE-38 hypothalamic cells were grown in 6-well tissue culture dishes (Corning Incorporated, Cat. No. 3516) at a seeding density of 200 000 cells/9.5 cm² well in a 37° C. normoxic incubator. Cultures were grown for 36 hours to ~85% confluence prior to experimentation.

At day 3 post-plating, cells were washed twice with Locke's buffer (154 mM NaCl, 5.6 mM KCl, 2.3 mM CaCl2, 3.6 mM NaHCO3, 5 mM HEPES) without serum and glucose. The culture was incubated in the Locke's buffer for 1 hour at 37° C. followed by exposure to 100 nM insulin, 100 nM TCAP-1, 100 nM SC-TCAP-1, or saline. KCl (40 mM) and ³-2-deoxyglucose (0.5 µCi/ml) were added to culture 5 minutes before termination of treatment exposure. Uptake of ³H-2-deoxyglucose was stopped immediately after 5 minutes with three washes of ice-cold 0.9% NaCl solution. Parallel experiments with 5 µM of cytochalasin B were performed to ensure that glucose uptake was of transporter-inhibitable transport. The cells were digested with 1 ml of 0.05 N NaOH at 0, 15, 30, 45, 60, 90 and 120 minutes after treatment. Cell lysates were used for determination of radioactivity by a beta liquid scintillation counter. Experiments were repeated three times with 3 wells pear condition per replication.

Results

Figure 12A:
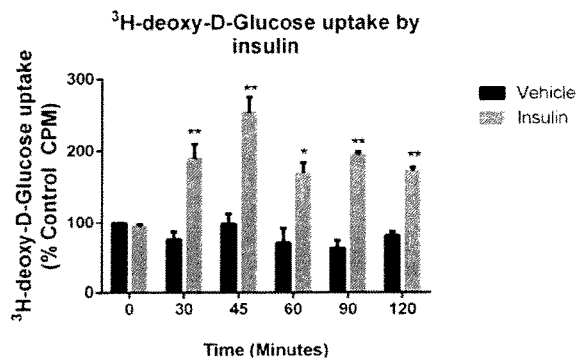
FIG. 12A. Insulin treatment causes an increase in $^3$H-2-deoxyglucose transport after 30 minutes b mHypoE-38 neurons. Cells were treated with 100 nM insulin, exposed to 0.5 μCi/well 3H-2-deoxy glucose and 40 mM KCl, and subsequently lysed with 50 mM NaOH. Radioactivity in cell lysates was counted using a liquid scintillation counter. The level of significance was determined by two-way ANOVA using Bonferonni's post hoc test.
Figure 12B:
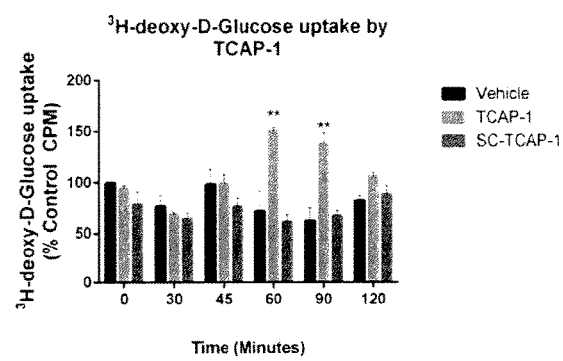
FIG. 12B. TCAP-1 treatment results in an initial decrease in $^3$H-2-deoxyglucose uptake but an increase with an increased treatment time of 60 minutes in mHypoE-38 neurons. Cells were treated with 100 nM TCAP-1, 100 nM SC-TCAP-1, or saline, exposed to 0.5 μCi/well 3H-2-deoxyglucose and 40 mM KCl, and subsequently lysed with 50 mM NaOH. Radioactivity in cell lysates was counted using a liquid scintillation counter. The level of significance was determined by two-way ANOVA using Bonferonni's post hoc test.

For immortalized N38 hypothalamic cells, results indicate a significant signal for positive control insulin treatments ($p<0.001$) (FIG. 12A), a significant signal for TCAP-1 treatment ($p<0.001$) and a lack of a significant signal for scrambled-TCAP-1 (SC-TCAP-1) treatments ($p>0.05$) (FIG. 12B). All results in FIGS. 12A and 12B were obtained from cells stimulated with 40 mM of KCl for 5 minutes. Insulin treated mHypoE-38 hypothalamic cells exhibited an increase in ³H-2-deoxyglucose uptake compared to control after 30 minutes with gradual decreases in glucose uptake at time points leading up to 2 hours. The maximal glucose uptake for insulin-treated cells was at 45 minutes resulting in an uptake value of 253±21.38% relative to baseline (vehicle at 45 minutes=98-27±14.828%). TCAP-1 treatment of mHypoE-38 hypothalamic cells resulted in an initial decrease in ³H-2-deoxyglucose transport after 30 minutes and then a significant increase over the vehicle after 60 minutes (FIG. 12B). The maximal glucose uptake for TCAP-1 treated cells was at 60 minutes resulting in an uptake value of 150.553±3.609% relative to baseline ($p<0.001$; vehicle at 60 minutes=72.247±19.677%; SC-TCAP-1 at 60 minutes=61.523±7.545%). This enhanced uptake persists until 90 minutes when there is an increased glucose uptake up to 137.511±10.893% relative to baseline ($p<0.001$) (vehicle at 90 minutes=62.813±12.728%; SC-TCAP-1 at 90 minutes=68.020±4.812%). (Mean±SEM; n=3; *$p<0.05$, $p<0.01$, *$p<0.001$; 2-way ANOVA and Bonferonni's test).

Example 12—Effect of TCAP on KCl-Independent Glucose Transport

N38 hypothalamic cells were cultured as above and treated with 100 nM insulin, 100 nM TCAP-1 or saline, exposed to 5.6 mM or 40 mM KCl and 0.5 µCi/well 3H-2-deoxy glucose, and subsequently lysed with 50 mM NaOH. Radioactivity in cell lysates was counted using a liquid scintillation counter.

Results

Figure 13:
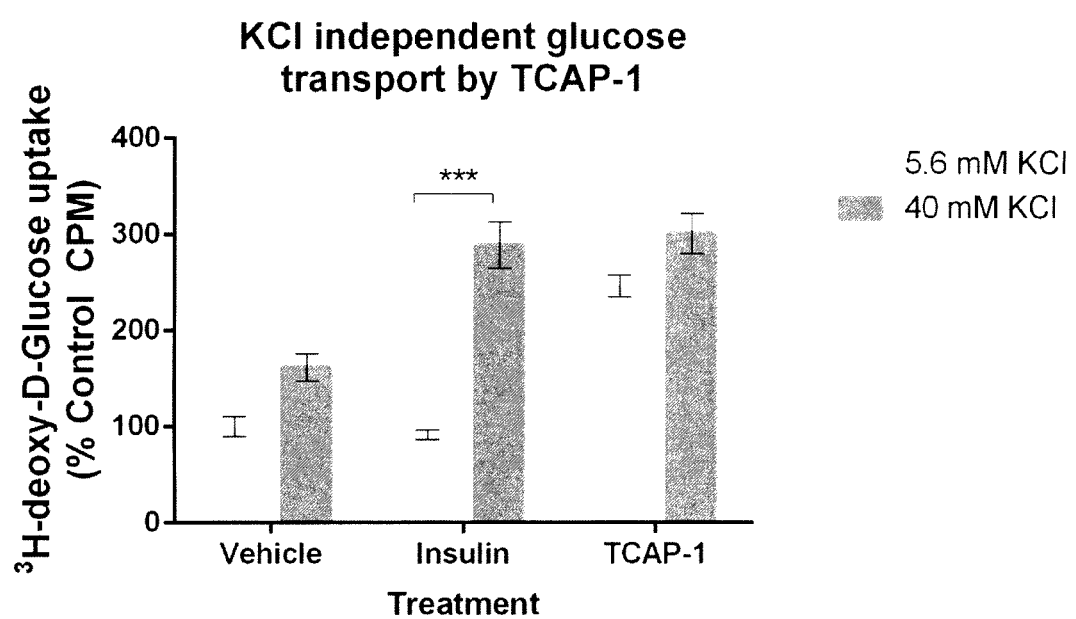
FIG. 13. Insulin mediates KCl-dependent increases in 3H-2-deoxyglucose and TCAP-1 mediates KCl-independent transport of 3H-2-deoxyglucose in mHypoE-38 neurons. Cells were treated with 100 nM insulin, 100 nM TCAP-1 or saline, exposed to 5.6 mM or 40 mM KCl and 0.5 μCi/well 3H-2-deoxyglucose, and subsequently lysed with 50 mM NaOH. Radioactivity in cell lysates was counted using a liquid scintillation counter. The level of significance was determined by two-way ANOVA using Bonferonni's post hoc test.

Results are shown in FIG. 13 where Insulin-treated cells exposed to low KCl concentrations did not show significantly increased ³H-2-deoxyglucose uptake (91.423±5.226% vs. 99.964±10.340%; $p>0.05$). However, 40 mM KCl exposure and 100 nM insulin together caused a significant increase in ³H-2-deoxyglucose uptake both compared to insulin-treatment alone (288.572±24.527% vs. 91.423±5.226%) and 40 mM KCl exposure in the vehicle (288.572±24.527% vs. 161.565±14.238%; FIG. 13). This significant potentiation by KCl was not seen in TCAP-1 Heated cells (300.601±20.753% for 40 mM KCl vs, 246.261±11.387% for 5.6 mM KCl). (Mean±SEM; n=3; *$p<0.05$, $p<0.01$; *$p<0.001$; 2-way ANOVA and Bonferonni's post hoc test).

Therefore insulin treatment of 30 minutes alone does not cause an increase in glucose transport in mHypoE-38cells, KCl potentiates the insulin effect confirming the dependence of insulin on KCl to stimulate glucose uptake in neurons. Exposure to high KCl concentrations does not potentiate the TCAP-1 effect. Results demonstrate that unlike insulin, TCAP-1 increases ³H-2-deoxyglucose uptake in a KCl-independent manner, likely through a different pathway.

Example 13—Effect of TCAP on Mitochondrial Activation

A key component of energy production in cells is the activation of mitochondria. TOM20, an outer membrane RNA transporter in mitochondria, was used as a marker for mitochondrial activation. The effect of TCAP-1 treatment on mitochondrial activity in mouse immortalized N38 hypothalamic cells was assessed using antibodies specific for TOM20 (red). An antibody specific for hexokinase (green) was also used.

Results

Figure 14:
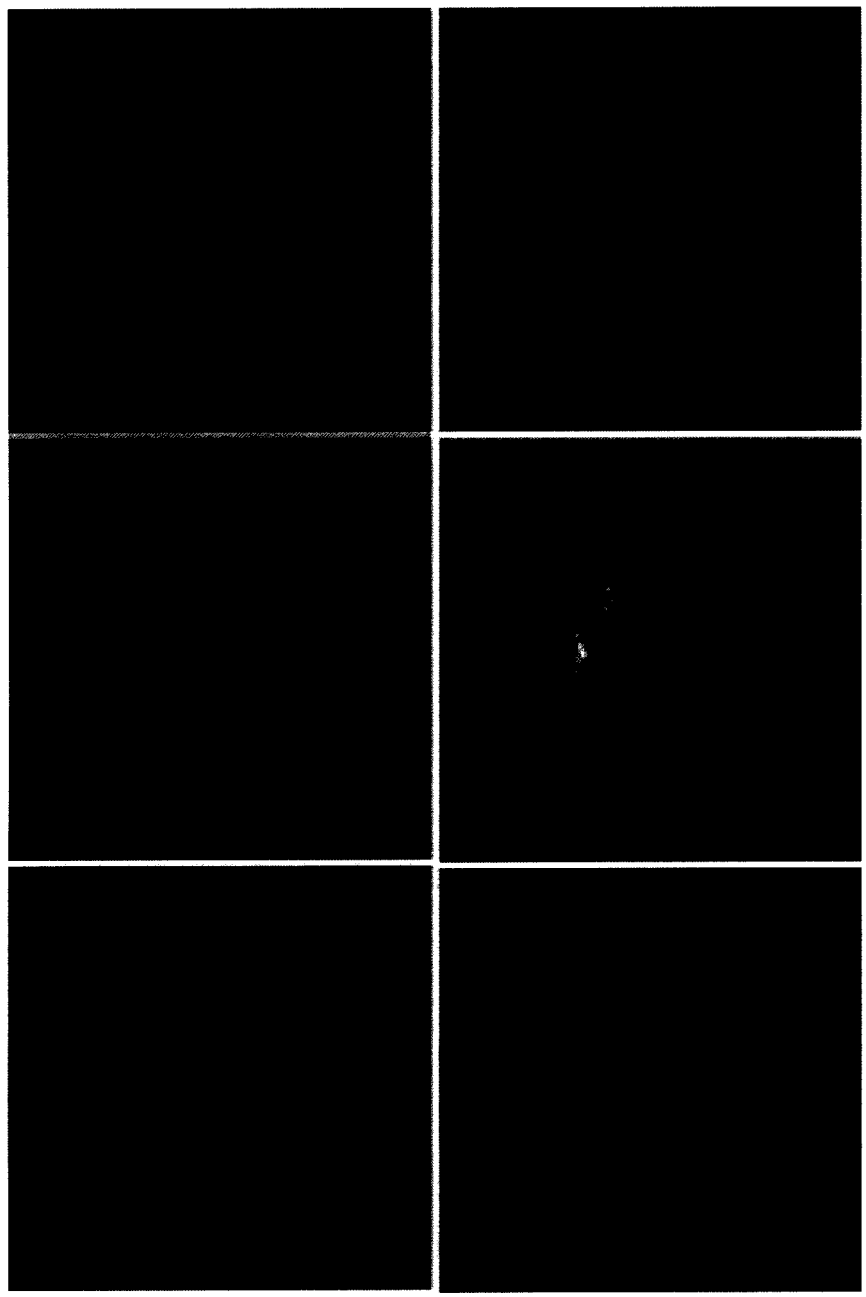
FIG. 14. Localization of TOM20 (red) and hexokinase (green) as a function of duration of TCAP-1 treatment in mouse immortalized N38 hypothalamic cells.

TOM20 was upregulated after 3 hours of TCAP-1 treatment (FIG. 14).

Example 14—Effect of TCAP on Intracellular Lactate and Pyruvate Concentrations in mHypoE-38 Cells Effect of TCAP-1 Treatments of 0 nM (Vehicle) and 100 nM on Intracellular Lactate Concentrations in mHypoE-38 Immortalized Embryonic Hypothalamic Neurons.

Figure 15:
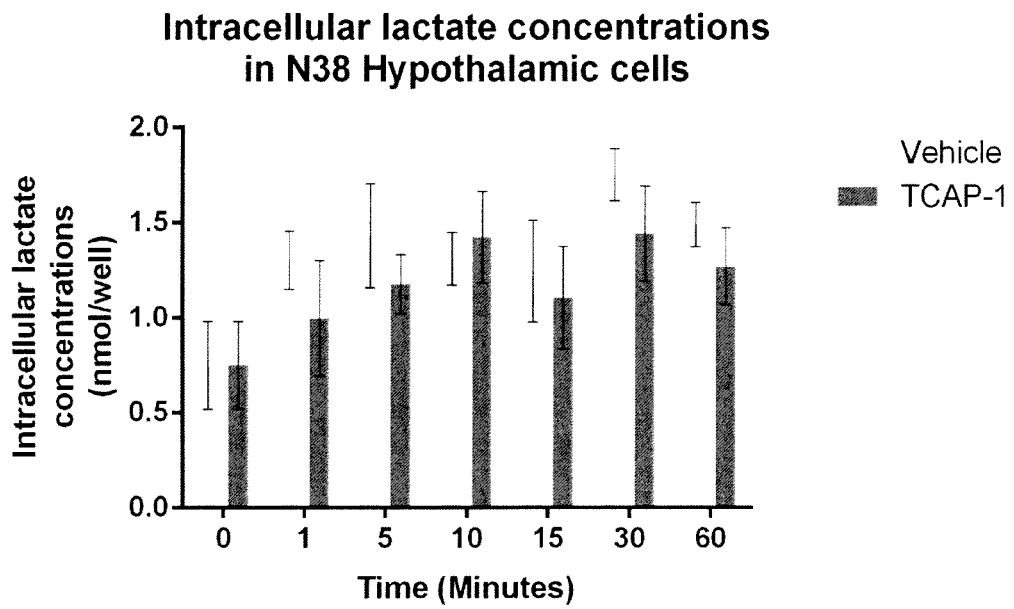
FIG. 15. Intracellular lactate levels show no significant change following an acute 100 nM TCAP-1 treatment in mHypoE-38 neurons. Immortalized hypothalamic neurons were given acute treatments of 100 nM TCAP-1 or vehicle (saline), (Mean±SEM; n=3, *p<0.05, p<0.01, *p<0.001; 2-way ANOVA and Bonferonni's post hoc test).

Lactate is required to generate NAD+ from NADH as a result of sustained glycolysis (Kolev et al., 2008). Thus, a decrease in lactate would suggest that there is a metabolic shift favouring non-glycolytic metabolism. Chronic 100 nM TCAP-1 treatment of mHypoE-38 neurons for 3-12 hours decreased intracellular lactate in a dose-dependent fashion (Xu, 2012). Results are shown in FIG. 15. These acute studies showed no significant changes in the intracellular lactate concentrations between TCAP-1 and vehicle ($p=0.1877$; FIG. 15). Immortalized hypothalamic neurons were given acute treatments of 100 nM TCAP-1 or vehicle (saline). (Mean±SEM; n=3, *$p<0.05$: $p<0.01$; *$p<0.001$; 2-way ANOVA and Bonferonni's post hoc test).

Effect of TCAP-1 Treatments of 0 nM (Vehicle) and 100 nM on Intracellular Pyruvate Concentrations in mHypoE-38 Immortalized Embryonic Hypothalamic Neurons.

To comply with the supply and demand principle for glucose as cellular energy, an increase in glucose uptake into the cell could result in acute changes in the metabolism of pyruvate. Pyruvate is actively converted from glucose through glycolysis and provides cells with energy through the Krebs cycle during aerobic metabolism (Pelicano et al., 2001). Thus, a decrease in pyruvate levels would indicate decreased glycolysis or increased oxidative phosphorylation by virtue of the Krebs cycle.

mHypoE-38 cells were cultured as above except that, 24 hours prior to experimentation the medium was changed and cells were grown in 10 cm tissue culture treated polystyrene plates (Corning Incorporated, Cat. No. 430293) at a seeding density of 400 000 cells/55 cm2 dish in a 37° C. normoxic incubator. Cultures were grown for 36 hours to 85% confluence and subsequently synchronized for 3 hours, in serum-free media with penicillin and streptomycin antibiotics, prior to acute TCAP-1 treatments.

Cells were lysed with 200 µL of Pyruvate assay buffer containing a proprietary protease inhibitor cocktail. Cells were harvested using a cell scraper and centrifuged at 14 000 rpm for 20 minutes at 4° C. The pellet was discarded and supernatant aliquoted into two tubes, 30 µL for protein quantification and the remainder for the lactate assay kit A Pierce BCA Protein Assay (Thermo Fischer Scientific, Cat. No. 23225) was performed to quantify protein concentrations for standardizing dilutions of respective supernatant samples. Diluted samples were deproteinized using disposable ultrafiltration 10 Kd spin columns (Biovision, Cat. No 1997-25) at 10000 g for 10 minutes at 4° C. The colorimetric protocol for the Pyruvate assay kit (Biovision, Cat. No. K609-100-1) was followed, in which an enzyme mix reacts with pyruvate and the product then interacts with a probe to generate a measurable color measurable at $\lambda=570$ nm. Briefly, 50 µL of each deproteinized sample was added in triplicates to a 96-well plate. Pyruvate standards of 0, 2, 4, 6, 8, and 10 nmol/well were prepared, as per kit instructions, and added in 50 µL triplicates to generate a standard curve. A pyruvate reaction mix, containing 46 µL of the assay buffer, 2 µL of the probe and 2 µL of the enzyme, was prepared and 50 µL mixed to each sample or standard for a total volume of 100 µL/well. The reaction was incubated for 30 minutes at room temperature, protected from light. An absorbance reading was obtained at $\lambda=570$ nm using a SpectramaxPlus 384 (Molecular devices, USA).

Results

Figure 16:
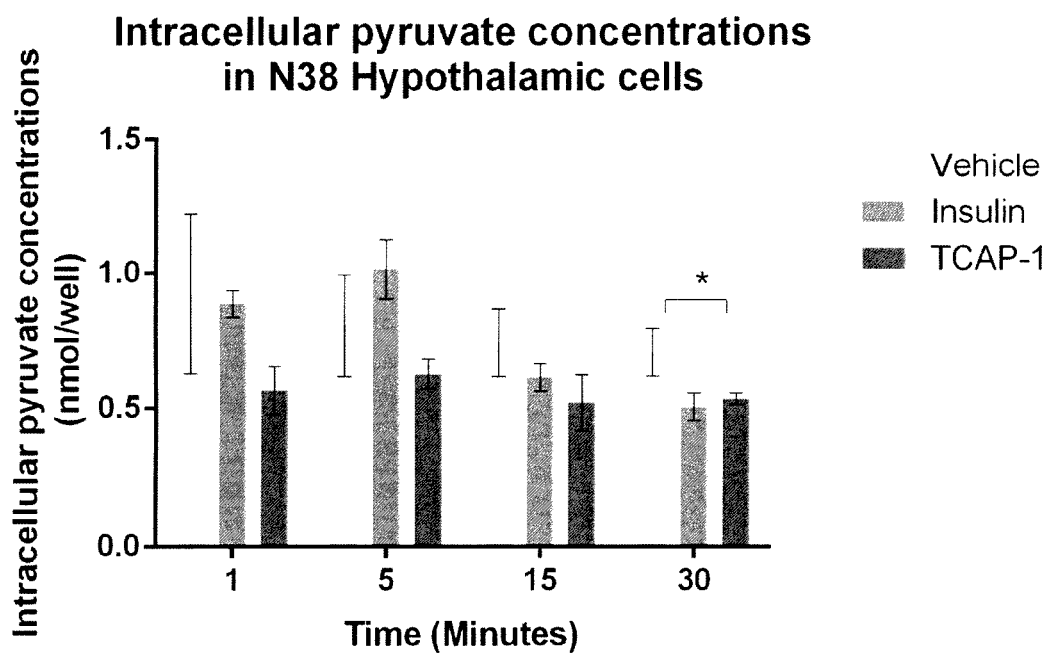
FIG. 16. Intracellular pyruvate levels decrease following an acute 100 nM TCAP-1 treatment in mHypoE-38 neurons. Immortalized hypothalamic neurons were given acute treatments of 100 nM TCAP-1, insulin or vehicle (saline). The level of significance was determined by two-way ANOVA using Bonferonni's post hoc test.

Results show that 100 nM TCAP-1 treatment in mHypoE-38 cells result in a general decrease in intracellular pyruvate levels that was significant at 30 minutes (0.536±0.012 nmole/well vs. 0.706±0.050 nmole/well; FIG. 16). It should be noted that a non-significant decrease in pyruvate levels can be observed at 1 minute with TCAP-1 treatment This stays constant across 30 minutes. The effect of insulin appears nearing 15-30 minutes of treatment The decrease in intracellular pyruvate may suggest that oxidative phosphorylation is enhanced, causing a depletion of pyruvate. Main effect of TCAP-1 significant p=0.0012 (**). TCAP-1 treatment significant at 30 minutes (p=0.030425*). (Mean±SEM; n=3, *p<0.05, p<0.01, *p<0.001; 2-way ANOVA and Bonferonni's post hoc test).

TCAP1 treatment of N38 cells increased ATP production in a dose dependent manner with 1 nmole concentration increasing ATP production by 18% (p<0.01), 10 nmoles by 25% (p<0.01) and 100 nmoles by about 40% (p<0.01) (FIG. 4). If an anaerobic pathway was utilized this should translate into increased lactate production. In fact, TCAP-1 administration decreased lactate production in a dose-dependent manner with 1 nmole decreasing lactate by about 20% (p<0.05), 10 nmoles by 25% (p<0.001) and 100 nmoles by 40% (p<0.0001). As such, the lack of lactate production has many benefits for instance in one aspect it can be used to protect against, inhibit/prevent and or treat muscle fatigue or assist in muscle recovery.

Experimental design for the determination of intracellular pyruvate and lactate concentrations upon TCAP-1 treatment on mHypoE-38 immortalized embryonic hypothalamic neurons: Cells were grown to ~80% confluence and serum deprived for 3 hours to synchronize. TCAP-1 treatment of 0 nM (vehicle) and 100 nM were administered at 0 min and cultures lysed at 1, 5, 10, 15, 30, 45, and 60 minutes. Colorimetric assays were subsequently conducted.

Lactate Assays

The mHypoE-38 cultures were lysed with 200 µL of Lactate assay buffer containing a protease inhibitor cocktail. Cells were harvested using a cell scraper and centrifuged at 14 000 rpm for 20 minutes at 4° C. The pellet was discarded and supernatant aliquoted into two tubes, 30 µL for protein quantification and the remainder for the lactate assay kit A Pierce BCA Protein Assay (Thermo Fischer Scientific, Cat. No. 23225) was performed to quantify protein concentrations for standardizing dilutions of respective supernatant samples. Diluted samples were deproteinized using disposable ultrafiltration 10 Kd spin columns (Biovision, Cat. No 1997-25) at 10000 g for 10 minutes at 4° C. The colorimetric protocol for the Lactate Assay Kit (Biovision, Cat. No. K607-100) was followed, in which an enzyme mix reacts with lactate and the product then interacts with a probe to generate a measurable color. Briefly, 50 µL of each deproteinized sample was added in triplicates to a 96-well plate. Lactate standards of 0, 2, 4, 6, 8, and 10 nmol/well were prepared, as per kit instructions, and added in 50 µL triplicates to generate a standard curve. A lactate reaction mix, containing 46 µL of the assay buffer, 2 µL of the probe and 2 µL of the enzyme mix, was prepared and 50 µL mixed to each sample or standard for a total volume of 100 µL/well. The reaction was incubated for 30 minutes at room temperature, protected from light. An absorbance reading was obtained at $\lambda=570$ nm using a SpectramaxPlus 384 (Molecular devices, USA).

2.2.6 Pyruvate Assays

The previous protocol was also utilized for the colorimetric Pyruvate assay kit (Biovision, Cat. No. K609-100-1), in which an enzyme mix reacts with pyruvate and the product then interacts with a probe to generate a measurable color measurable at $\lambda=570$ nm. A pyruvate assay buffer containing a proprietary protease inhibitor cocktail, was used. Additionally, the pyruvate reaction mix contained 46 µL of the assay buffer, 2 µL of the probe and 2 µL of the enzyme.

Example 15—Effect of MEK Inhibition on TCAP-1-Induced Increases on 3H-2-deoxyglucose Uptake in mHypoE-38 Immortalized Embryonic Hypothalamic Neurons The MEK-ERK1/2 pathway has been established to be downstream of TCAP-1 and β-DG in hippocampal cells (Chand et al., 2012). MEK inhibition has also been shown to inhibit glucose uptake increases in adipocytes and regulate expressions of genes critical for organismal metabolism and homeostasis in mHypoE-46 hypothalamic neurons (Harmon et al., 2004; Mayer and Belsham, 2009). Insulin signaling normally downregulates NPY and AgRP gene expressions. In mHypoE-46 neurons, the addition of MEK inhibitor resulted in a prevention of the repression of NPY and AgRP transcription suggesting that the MEK-ERK1/2 pathway may play a direct role in metabolic signaling in hypothalamic cells (Mayer and Belsham, 2009). Results suggest that insulin signals for increases in glucose uptake into mHypoE-38 neurons through MEK as MEK inhibition resulted in a decrease in 3H-2-deoxyglucose uptake compared to insulin, non-MEK-inhibited cells that was significant (p=0.0438; 108.069±13.671 vs. 162.846±1.813; FIG. 3.14). The effect of TCAP-1 was not significant in these experiments (p=0.1499; 124.809±26.063 vs. 67.770±1.151). However, a decrease can be seen in the glucose uptake amount following treatment with MEK inhibitor, suggesting the possibility of a strong dependence on the MEK/ERK1-2 pathway.

Figure 17:
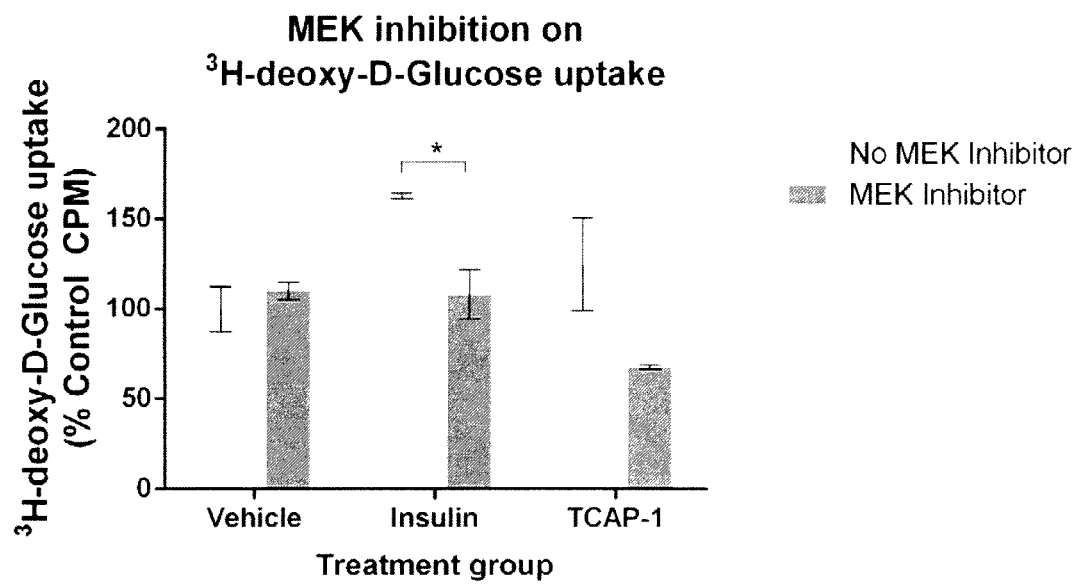
FIG. 17. Addition of 10 μM of MEK inhibitor for 60 minutes prior to farther treatment resulted in a decrease in 3H-2-deoxyglucose transport in insulin and TCAP-1 treated mHypoE-38 neurons. MEK inhibitor did not alter vehicle glucose uptake significantly. Cells were pretreated with 10 μM MEK inhibitor (U0126, New England Biolabs) for 1 hour prior to treatment with insulin, TCAP, or saline, exposed to 40 mM KCl and 0.5 μCi/well 3H-2-deoxyglucose, and subsequently lysed with 50 mM NaOH. Radioactivity in cell lysates was counted using a liquid scintillation counter. (Mean±SEM; n=3; *p<0.05, p<0.01, *p<0.001; 2-way ANOVA and Bonferonni's post hoc test).

FIG. 17: Addition of 10 µM of MEK inhibitor for 60 minutes prior to further treatment resulted in a decrease in 3H-2-deoxyglucose transport in insulin and TCAP-1 treated mHypoE-38 neurons, MEK inhibitor did not alter vehicle glucose uptake significantly. Cells were pretreated with 10 nM MEK inhibitor (U0126, New England Biolabs) for 1 hour prior to treatment with insulin, TCAP, or saline, exposed to 40 mM KCl and 0.5 µCi/well 3H-2-deoxyglucose, and subsequently lysed with 50 mM NaOH. Radioactivity in cell lysates was counted using a liquid scintillation counter. (Mean±SEM; n=3; *p<0.05, p<0.01, *p<0.001; 2-way ANOVA and Bonferonni's post hoc test).

Effect of TCAP-1 Treatments of 0 nM (Vehicle) and 1 nM on MEK-Dependent AMPK Phosphorylation in mHypoE-38 Immortalized Embryonic Hypothalamic Neurons.

Previous unpublished results indicate that TCAP-1 induces increased phosphorylation of AMPK (AMP activated kinase). AMPK phosphorylation activates the metabolic regulator and promotes ATP-generating processes such as glucose uptake and fatty acid oxidation (Mihaylova and Shaw, 2011). Western blot analyses indicate that TCAP-1-induced AMPK-phosphorylation is inhibited upon the addition of MEK inhibitor, suggesting a link between the two in the TCAP-1 signalling mechanism (FIG. 3.15). These results also confirm that TCAP-1 induces AMPK-phosphorylation.

Figure 18:
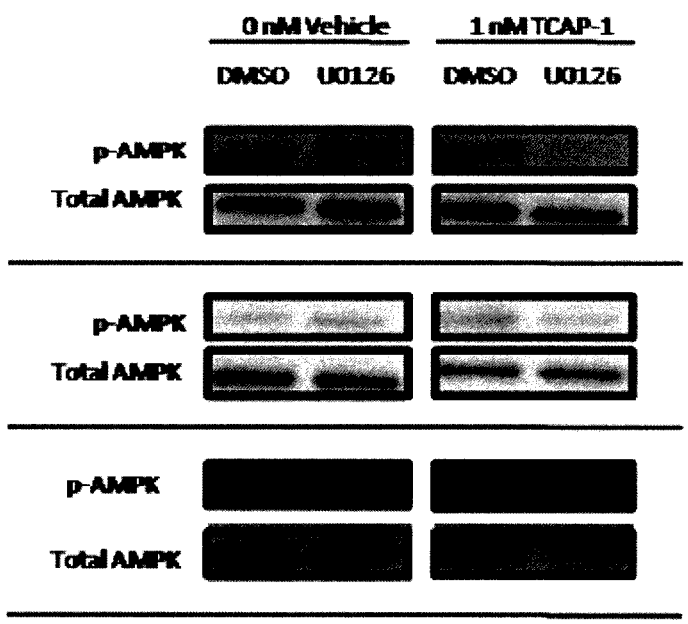
FIG. 18. TCAP-1 signalling through the MEK/ERK1-2 pathway is upstream of AMPK signalling in mHypoE-38 neurons. AMPK phosphorylation is enhanced by 1 nM treatment of TCAP-1 for 1 minute to mHypoE-38 cells.

FIG. 18: TCAP-1 signalling through the MEK/ERK1-2 pathway is upstream of AMPK signalling in mHypoE-38 neurons. AMPK phosphorylation is enhanced by 1 nM treatment of TCAP-1 for 1 minute to mHypoE-38 cells. Phosphorylation of AMPK is inhibited by application of 10 nM MEK inhibitor (U0126) suggesting a MEK/ERK1-2 dependent signalling.

FIG. 19: TCAP-1 induces MEK-dependent AMPK phosphorylation in mHypoE-38 neurons. Analyses of western blots from FIG. 3.15 for vehicle and 1 nM TCAP-1 treated cells at 1 minute (n=3 for each group). Each p-AMPK band intensity was normalized to total AMPK at each corresponding treatment point. There was a significant (p<0.01) inhibition of AMPK phosphorylation in the presence of 10 nM MEK inhibitor (U0126) with TCAP-1 treatment. Values are mean±SEM, two-way ANOVA and Bonferonni's post hoc test. Band intensity was measured by quantifying the integrated optical intensity using Lab Works (UVP Bio-imaging systems V4.0.0.8).

Example 16—Effect of TCAP on Cellular Glucose Uptake in Muscle Cells

The effect of TCAP-1 on glucose uptake in muscle cells was examined in a $C_2C_{12}$ mouse myocyte cell line. $C_2C_{12}$ myocytes were cultured in Dulbecco's Modified Eagle Medium (DMEM) containing 4500 mg/L D-glucose, L-glutamine, and 25 mM HEPES buffer, without sodium pyruvate or phenol red (Gibco, Cat. No. 21063029), supplemented with 20% heat-inactivated fetal bovine serum (FBS), 100 U/ml penicillin and 100 µg/ml streptomycin. Cells were maintained at 80% confluency at 37° C. in a humidified $CO_2$ incubator. To initiate differentiation, myocytes were further cultured in DMEM supplemented with 10% heat-inactivated horse serum (HS), transferrin, 100 U/ml penicillin and 100 µg/ml streptomycin. Myocytes were allowed to differentiate into multi-nucleated myotubes for 5 days before experimentation. 24 hours prior to experimentation, medium was changed.

At day 5 of differentiation, cells were deprived of serum and incubated in Minimal Essential Medium containing 1000 mg/L D-glucose, L-glutamine, without nucleosides (Gibco, Cat. No. 12561049) for 5 hours at 37° C. prior to incubation with insulin, TCAP-1, or saline. Cells were washed twice in glucose-free HEPES-buffered solution (HBS), containing 140 mM NaCl, 20 mM HEPES, 5 mM KCl, 2.5 mM MgSO4 and 1 mM CaCl2, followed by determinations of transport of 3H-2-deoxyglucose for 10 minutes at 0.5 µCi/ml at room temperature. Uptake of 3H-2-deoxyglucose was stopped immediately after 10 minutes with three washes of ice-cold 0.9% NaCl solution. Parallel experiments with 5 µM of cytochalasin B were done to ensure that glucose uptake was of transporter-inhibitable transport The cells were digested with 1 ml of 0.05 N NaOH. Cell lysates were used for determination of radioactivity by a beta liquid scintillation counter. Experiments were repeated three times with 3 wells per condition per replication.

Culturing of the C2C12 Cell Line

C2C12 myocytes were cultured in Dulbecco's Modified Eagle Medium (DMEM) containing 4500 mg/L D-glucose, L-glutamine, and 25 mM HEPES buffer, without sodium pyruvate or phenol red (Gibco, Cat. No. 21063029), supplemented with 20% heat-inactivated fetal bovine serum (FBS), 100 U/ml penicillin and 100 µg/ml streptomycin. Cells were maintained at 80% confluency at 37° C. in a humidified CO2 incubator. Protocol for cell passage described above. Protocols for the seeding of cells for various experimental purposes were followed as in section 2.2.1. To initiate differentiation, myocytes were further cultured in DMEM supplemented with 10% heat-inactivated horse serum (HS), transferrin, 100 U/ml penicillin and 100 µg/ml streptomycin. Myocytes were allowed to differentiate into multi-nucleated myotubes for 5 days before experimentation, 24 hours prior to experimentation, medium was changed.

2.2.4 2-Deoxy-D-Glucose Uptake Assays in C2C12 Myocytes

At day 5 of differentiation, cells were deprived of serum and incubated in Minimal Essential Medium containing 1000 mg/L D-glucose, L-glutamine, without nucleosides (Gibco, Cat. No. 12561049) for 5 hours at 37° C. prior to incubation with insulin, TCAP-1, or saline. Cells were washed twice in glucose-free HEPES-buffered solution (HBS), containing 140 mM NaCl, 20 mM HEPES, 5 mM KCl, 2.5 mM MgSO4 and 1 mM CaCl2, followed by determinations of transport of 3H-2-deoxyglucose for 10 minutes at 0.5 µCi/ml at room temperature. Uptake of 3H-2-deoxyglucose was stopped immediately after 10 minutes with three washes of ice-cold 0.9% NaCl solution. Parallel experiments with 5 nM of cytochalasin B were done to ensure that glucose uptake was of transporter-inhexplicabletable transport. The cells were digested with 1 ml of 0.05 N NaOH. Cell lysates were used for determination of radioactivity by a beta liquid scintillation counter. Experiments were repeated three times with 3 wells per condition per replication.

Results

For $C_2C_{12}$ myocytes, results indicate a positive signal for positive control insulin treatments, a significant signal for TCAP-1 treatment and a lack of positive signal for scrambled-TCAP-1 (SC-TCAP-1) treatments (FIG. 20). Insulin treated $C_2C_{12}$ myocytes exhibited an increase in $^3$H-2-deoxyglucose uptake compared to control after 30 minutes (284.520±47.129% vs. 61.518±8.637; p<0.0001) that is sustained until 90 minutes (332.321±87.296% vs. 84.050±4.480%; p<0.001). TCAP-1 treatment of $C_2C_{12}$ myocytes resulted in a significant increase in $^3H$-2-deoxyglucose transport after 30 minutes compared to the vehicle (329.124±10.817% vs. 61.518±7.545%; p<0.0001). This significant increase is sustained until 90 minutes compared to vehicle (209.702±40.436% vs. 84.050±4.480%; p<0.05). (Mean±SEM; n=3; *p<0.05, p<0.01, *p<0.001; 2-way ANOVA and Bonferonni's post hoc test).

Example 17—Elucidating Candidate Signalling Proteins Downstream of TCAP-1 in C2C12 Myocytes Effect of TCAP-1 Treatments of 0 nM (Vehicle), 1 nM and 100 nM on ERK Phosphorylation in C2C12 Myocytes.

TCAP-1 activates the MEK-ERK1/2 pathway in neurons (Chand et al., 2012). In skeletal muscle, exercise has been associated with an increase in ERK1/2 phosphorylation and activation of the MAPK pathway, leading to upregulation of GLUT4 expression (Aronson et al., 1997; Widgren et al., 1998). If TCAP-1 treatment results in increased levels of ERK in vitro in C2C12 myocytes, it would suggest that TCAP-1 plays a role in activating the MEK-ERK1/2 pathway in muscle and further experiments centered on this pathway can be performed to elucidate further details. Initial results indicated that TCAP-1 does not activate the MEK-ERK1/2 pathway after 1 minute of TCAP-1 treatment at both 1 nM and 100 nM concentrations (FIG. 21). Further repeats with 1, 5, 10 and 15 minute treatment times revealed similar results indicating no effect of TCAP-1 on the activation of ERK in C2C12 myocytes (FIG. 22).

FIG. 21: TCAP-1 treatment does not significantly change levels of p-ERK expression in C2C12 myocytes. C2C12 cells were treated with 1 nM or 100 nM TCAP-1 for 1 minute and levels of p-ERK and total ERK was compared. Representative western blots show that TCAP-1 treatment did not significantly change p-ERK levels suggesting that TCAP-1 acts via an alternate signalling pathway. Phosphorylation of ERK is inhibited by application of MEK inhibitor (positive control).

FIG. 22: 100 nM TCAP-1 treatment on pERK levels in C2C12 myocytes is not altered across 15 minutes. C2C12 cells were treated with 100 nM TCAP-1 for 0 (Vehicle), 1, 5, 10 and 15 minutes and levels of p-ERK and total ERK was compared. Representative western blots show that TCAP-1 treatment did not significantly change p-ERK levels suggesting that TCAP-1 acts via an alternate signalling pathway. Phosphorylation of ERK is inhibited by application of 10 μM MEK inhibitor (positive control; U0126).

FIG. 23: Western blot analyses quantification of TCAP-1 treatment on ERK phosphorylation in C2C12 myocytes. Analyses of western blots from FIG. 15 for vehicle and 100 nM TCAP-1 treated cells at 0, 1, 5, 10, and 15 minutes (n=3 for each group). Each p-ERK band intensity was normalized to total ERK at each corresponding treatment time. There was no significant change in ERK phosphorylation in response to TCAP-1 at any time points. There was significant inhibition of ERK phosphorylation in the presence of 10 μM MEK inhibitor (U0126). (Values are mean±SEM, two-way ANOVA and Bonferonni's post hoc test). Band intensity was measured by quantifying the integrated optical intensity using LabWorks (UVP Bio-imaging systems v4.0.0.8).

Example 18—Energy Associated Behaviour in Rats

Having established that TCAP-1 increases glucose uptake and energy production, behavioral studies were conducted to see if it translate to energy associated behaviour in animals.

The forced swim test was used as a model because of the energy demands this test places on the animal. Although this behavioural model has been utilized as a standard test for the incidence of depressive-like symptoms (REFS), in fact the behaviour of the animal in the test reflects its energy reserves. Herein it is utilized as a homeostatic model of low energy. In this interpretation, animals displaying low energy metabolism will act to increase intake of high energy compounds, whereas active animals at high levels of energy metabolism are less likely to take in high energy nutrients because of the high level of activity. If the animal has a high energy reserve, it is likely to increase escape behaviour, on the other band, with low energy reserves, it is likely to conserve energy until an escape situation occurs. A number of other studies have discussed this aspect of the forced swim test.

Two behavioural tests were conducted: sucrose preference and forced swim test. Mature male rats treated with TCAP-1 showed that in the low sucrose preference group that TCAP-1 induced a significant increase in sucrose preference, whereas those that showed high sucrose preference showed not significant change in sucrose preference. With respect to the forced swim test, TCAP-1 increased swimming and climbing behaviour, while decreasing immobility time.

Discussion of Results

In summary, in one aspect, the findings of this study indicate that there is a glucose-lowering effect of TCAP-1 administration in vivo. This is observed both in physiologically normal Wistar rats as well as spontaneously Type II diabetic Goto-Kakizaki rats one week after the initial peptide administration, 18F-DG uptake into rats 3 days after TCAP-1 treatment was enhanced in the brain, corroborating the glucose data. The in vitro glucose uptake into hypothalamic neurons and skeletal myocytes increased in response to TCAP-1 treatment. In hypothalamic neurons, the enhanced glucose uptake in response to TCAP-1 occurs in the absence of potassium stimulating, differentiating the TCAP-1 mechanism from that of insulin. The increase in glucose uptake is corroborated with an increase in GLUT3 expression in the membranes of hypothalamic neurons. TCAP-1 treatment further decreased pyruvate levels in hypothalamic neurons and did not change lactate levels. MEK inhibition prevented the enhanced glucose uptake into hypothalamic neurons as well as the phosphorylation of AMPK. In skeletal muscle, FITC-TCAP-1 ubiquitously bound to muscle fibers but is strongly localized to the sarcolemma where it co-localizes with β-DG. Endogenous TCAP-1 localized exclusively to the sarcolemma and showed similar co-localizations. Immunoreactivity studies with rapsyn shows that TCAP-1 localizes near rapsyn at the neuromuscular junctions.

TCAP-1 is also shown herein to increase mitochondrial activity, as depicted by an increase in Hexokinase II immunoreactivity following 1-2 hours of TCAP-1 treatment in mHypoE-38 neurons (Lovejoy et al., unpublished findings). These findings suggest that TCAP-1 is able to achieve metabolic optimization both through an increasing the intake of energy substrates into cells as well as shifting metabolic machinery to upregulate the more efficient energy production pathways. The commonality amongst this evidence comes down to increasing glucose uptake into cells and maximizing the efficiency of glucose utilization.

Skeletal muscle is the largest organ of the body and is the most important site for glucose uptake by insulin stimulation (DeFronzo et al., 1981; Hegarty et al., 2009; Alberts et al., 2008). Skeletal muscle acts as one of two main storage sites of glycogen; the other being the liver. Most of the imported glucose in skeletal muscle is then stored as glycogen and the rest is metabolized to meet energy demands (Alberts et al., 2008). Skeletal muscle glucose transport is largely mediated by GLUT1 and GLUT4 (Barnard and Youngren, 1992). Like in neurons, GLUT1 is responsible for glucose transport under basal conditions in muscle. Under insulin stimulation, GLUT4 transporters will translocate out of T-tubules and onto the sarcolemma to increase glucose transport (Barnard and Youngren, 1992). Insulin stimulation will also activate insulin-sensitive kinases that mediate a response to activate glycogen synthase (Kruszynska et al., 2001).

There are primarily two mechanisms by which skeletal muscle fibers uptake, glucose; 1) through an insulin-dependent mechanism or 2) through an insulin-independent contraction-stimulated mechanism involving the AMPK pathway (Jessen and Goodyear, 2005; Nobuham et al., 2006). Contraction-stimulated glucose uptake is dependent on the intensity of exercise and duration (Richter and Hargreaves, 2013). In the contracting muscle, glucose uptake occurs through facilitated diffusion through GLUT4. The rate of this diffusion can be regulated through glucose delivery from surrounding blood vessels, the level of GLUT activity, and by the level of metabolic activity. Through increased blood flow of up to 20-fold during exercise as well as capillary recruitment, glucose uptake can be increased. During rest, GLUT1 is the most abundantly expressed transporter in skeletal muscle as GLUT4 remains in higher abundance in intracellular vesicles, ready to be transported to the sarcolemma and T-tubules. There has been debate as to the translocation of GLUT4 is the major contributor of contraction-stimulated glucose transport or whether an increase in GLUT4 intrinsic activity is also significant. Nevertheless, GLUT4 translocation to the sarcolemma is regulated by exocytosis and endocytosis of the transporter vesicles and guided by interaction between SNARE proteins (soluble N-ethylmaleimide-sensitive factor-attachment protein receptors). After recruitment of GLUT4 vesicles during intense exercise, the rate limiting step in glucose uptake into skeletal muscle is the phosphorylation of glucose into glucose-6-phosphate (G6P). Glucose transport into skeletal muscle is then regulated by the activity of Hexokinase II and other mitochondria enzymes (FIG. 1.8; Richter and Hargreaves, 2013). Studies with AMPK activator amino-imidazole-carboxamide-ribonucleoside (AICAR) suggest that targeting AMPK in skeletal muscle counteracts aspects of type 2 diabetes such as insulin resistance (Taylor and Goodyear, 2007). Thus, proteins upregulating AMPK in skeletal muscle could be potential candidates for treating pathologies associated with type 2 diabetes. AMPK is known to be involved in the docking of GLUT4 vesicles during translocation to the sarcolemma and T-tubules; its role in glucose metabolism is for the most part, insulin-independent (Hegarty et al., 2009). Preliminary in vitro studies show that TCAP-1 administration increased AMPK activation in hypothalamic cells. Another preliminary in vivo experiment showed that TCAP-1 administration resulted in changes in skeletal muscle morphology hypertrophy.

Based on experimental evidence that support the role of the dystroglycan complex in neuron morphology and cellular activity, testing whether TCAP-1 is present and physiologically active with the dystroglycan complex in muscle may yield novel data that can improve our understanding of the physiology of this hormone system in skeletal muscle. The MEK-ERK1/2 pathway is activated in response to TCAP-1 treatment in vitro, as such it may also have a role in muscle physiology by activating the ERK-dependent mechanical stress signalling cascade in skeletal muscle.

The purpose of this study was to examine the roles of TCAP-1 on glucose metabolism in vivo and the associated mechanism by which TCAP-1 regulates cellular metabolism in vitro using the mHypoE-38 hypothalamic cells as a model for the brain and the C2C12 myocytes as a model for skeletal muscle. The chief goals and findings for each project objective are as follows:

The first objective was to determine whether TCAP-1 affects glucose levels in vivo. Through a series of TCAP-1 in vivo administration experiments, a significant decrease in plasma glucose that was dose dependent on TCAP-1 treatment in adult male Wistar rats was observed. As per this finding, the same experiment was done on a pathological model, the type II diabetic Goto-Kakizaki (GK) rats. Similar results were seen in that TCAP-1 treatment relieved hyperglycemia in diabetic rats during the first week of treatment. To corroborate this with changes in glucose uptake into tissues, another in vivo study was performed where TCAP-1 was administered to male Wistar rats and the 18F-DG uptake into tissues was quantified. Results show that TCAP-1 significantly increased glucose uptake into the brain.

The second objective was to determine the mechanism by which TCAP-1 affected glucose metabolism and in particular, uptake into the brain. In vitro glucose uptake studies were performed using 3H-2-deoxyglucose in both the mHypoE-38 and C2C12 cell lines as representative neuron and skeletal muscle cell models, respectively. TCAP-1 treatment was shown to increase cellular glucose uptake as measured by the increase in radioactivity in cell lysates post-treatment The glucose uptake profile in response to TCAP-1 exhibited a different time course than that of insulin treatment in both cell lines. In the case of neurons, insulin requires a depolarizing boost of KCl in order to exhibit its actions on increasing glucose transporter activity and glucose uptake into the cells (Uemura and Greenlee, 2006). However, TCAP-1 treatment did not depend on KCl to exhibit this increase in cellular glucose uptake into neurons, suggesting for the first time an insulin-independent mechanism by which TCAP-1 acts to enhance metabolism. Further immunocytochemistry studies on mHypoE-38 cells show that TCAP-1 treatment increases membrane expression of GLUT3 after 2 hours. Colorimetric data indicate that TCAP-1 decreases intracellular pyruvate levels while keeping intracellular lactate levels constant. Western blot analyses show that TCAP-1 treatment of mHypoE-38 neurons increases AMPK phosphorylation. This is also dependent on the MEK-ERK pathway; a glucose uptake assay with MEK inhibitor further confirmed this result.

The third and fourth goals of this study were to characterize the presence and understanding the roles of TCAP-1 on skeletal muscle physiology. The first of these two goals was to determine whether the TCAP-1 system existed in skeletal muscle and the latter was to delineate a potential pathway by which TCAP-1 signals in skeletal muscle to induce its effects. Immunohistochemical studies were performed on sectioned mice gastrocnemius muscle using TCAP-1 antisera TCAP-1 localizes to the sarcolemma of skeletal muscle and shows co-localization with the β-DG receptor. FITC-TCAP-1 binding studies also showed increased uptake into skeletal muscle, indicative of the presence of TCAP-1 in this muscle system. However, results from in vitro analysis revealed inconclusive results on whether TCAP-1 enhances metabolism via the MEK-ERK1/2 pathway.

TCAP-1 has been found to enhance survivability both at the in vitro level by inducing stress coping mechanisms such as activation of the MEK/ERK1-2 pathway (Chand et al., 2012) as well as at the in vivo level such as the modulation of stress behaviours and enhancement of the male reproduction system in rats (Tan et al., 2011; Chand et al., 2013). The brain is heavily reliant on glucose as its primary energy source and is responsible for 20% of the body's glucose metabolism (Baker and Tarnopolsky, 2003; Duelli and Kuschinsky, 2001). Thus, an increased level of glucose uptake into the brain could cause a decrease in plasma glucose levels of the animal. The in vivo data obtained for plasma glucose levels following a single acute dose of 1 nmole/kg and 10 nmole/kg TCAP-1 treatment yielded a significant decrease of ~20% ($p<0.05$) in blood glucose levels one week after the initial administration. In the first in vivo study performed, blood glucose was also monitored within the first few hours after TCAP-1 administration to monitor for acute changes. It was observed that TCAP-1 resulted in no significant acute changes to blood glucose. However, the effective lowering of blood glucose one week after the initial administration corroborates previous studies showing that the behaviour attenuating effects of TCAP-1 are likely slow and chronic, sometimes persisting up to 21 days after peptide injection (Wang et al., 2005). It also suggests that the effects of TCAP-1 on regulating blood glucose is to ultimately lower circulating glucose, possibly to divert glucose to tissues in need for storage as a way of preparing the animal for future energetically-demanding activities. This same in vivo study was repeated once again to confirm the result and a similar trend was observed for this second study in which a significant decrease in blood glucose of ~20% ($p<0.05$) was observed one week after the initial injection for rats injected with TCAP-1 compared with the vehicle rats.

As part of the role of TCAP-1 in attenuating the CRF stress response, it can be expected that TCAP-1 may have an effect on behaviour in vivo. Previous studies have shown that acute administration of TCAP-1 decreases the acoustic startle response in high-anxiety rats (Wang et al., 2005). Also, a CRF and TCAP-1 co-administration resulted in an attenuation of the CRF stress response, suggesting a neuromodulatory role of TCAP-1 (Al Chawaf et al., 2007). In addition to the changes in glucose seen between the treatment groups, a modulated stress-response to the injections in the TCAP-1 treated rats was observed (data not shown). The modulation of the stress response by TCAP-1 is dose dependent and can be observed as a smaller change in plasma glucose levels within the initial hour of injection during week 2. For rats treated with the higher dose of 10 nmole/kg of TCAP-1, the injection stress was nearly absent following the second injection, suggesting a behavioural habituation that supports previous studies on the modulation of CRF activity in rats (Al Chawaf et al., 2007; Tan et al., 2009; Tan et al, 2008; Kupferschmidt et al., 2010). The second in vivo study was a repeat of the first experiment to confirm our results of the long-term changes observed in plasma glucose. Because no significant changes in blood glucose were observed within the first 4 hours post-injection from the first in vivo study, acute effects of TCAP-1 on plasma glucose were not made.

Stress has been long known to suppress immune function and contribute to the aging of the immune system (Bauer et al., 2009). Thus, if TCAP-1 modulates the CRF stress response, it may also be contributing to haematological changes in the rat plasma. This in turn, may be related to the significant changes in blood glucose observed in these studies. To rule out the possibility of an immune effect, haematology assays were done on blood samples of the rats (see Appendix 1). Levels of red blood cells, white blood cells, platelets, neutrophils, lymphocytes, monocytes, basophils, and eosinophils showed no significant changes between the TCAP-1 and vehicle groups. The haemoglobin concentration, hematocrit, mean platelet volume and red cell volumes were also similar between the two groups. The haematology assays were performed on blood samples that did not experience clotting. When possible, the clots were removed although the platelet counts were significantly altered. These samples were noted and omitted from the statistical analysis. An observation made from these data was that clots formed more frequently in the blood samples of TCAP-1 treated rats. On average, the size of the clots were also larger for TCAP-1 treated rats suggesting a possible immune effect that is represented by changes in parameters other than the ones tested. For future analysis, clotting time should be tested and compared.

Glycogen is a readily utilized form of glucose that is stored mainly in the skeletal muscle and liver (Berg et al, 2002). Since TCAP-1 administration resulted in significant changes in plasma glucose levels, it is important to consider other forms of glucose and changes associated with stored energy reserves. From the first TCAP-1 in vivo administration study, it can be concluded that TCAP-1 does not significantly change glycogen levels of rats given a single acute dose of the peptide. Previous in vivo data show that repeated TCAP-1 administration daily for 9 days resulted in an increase in adipocyte density associated with decreasing adipocyte size (Xu, 2012). In addition, muscle hypertrophy was observed with a repeated TCAP-1 administration study, perhaps due to an increase in glycogen reserves (Lovejoy et al. unpublished findings). Thus, the insignificance in changes in stored glycogen levels of this study could be attributed to the relatively infrequent TCAP-1 administrations. As well, because glycogen is broken down into glucose more readily than fatty acids, it serves as a better buffer for maintaining plasma and cerebral glucose levels. Taken together, it is likely that the actions of TCAP-1 on metabolism are to decrease obesity while maintaining a balance with decreased plasma glucose levels.

From the first two in vivo studies, it is apparent that TCAP-1 induces a lowering of blood glucose and could serve as therapeutic usages in cases of hyperglycemia related to metabolic syndrome or diabetes. Thus for the third in vivo experiment, spontaneously diabetic Goto-Kakizaki (GK) rats that are hyperglycaemic were treated with TCAP-1. The Goto-Kakizaki (GK) rats were chosen for this study as they are spontaneously diabetic and exhibit hyperglycemia in the absence of obesity. From the culmination of previous in vivo studies, it was decided that a high dose of TCAP-1 (10 nmole/kg) would serve as a suitable dosage over the low dose of 1 nmole/kg. It was expected that a sustained lowering of plasma glucose would ensue with TCAP-1 administration. Following four days post-injection, it was observed that TCAP-1 induced a significant decrease in plasma glucose levels, supporting the hypothesis. The glucose levels were observed for a week following, during which time the plasma glucose levels returned to initial values, suggesting that multiple doses of TCAP-1 may be required for a long term effect on relieving hyperglycemia in diabetic animals. GK rats begin exhibiting diabetic symptoms after 28 days from birth when hepatic glucose production increases, and defects begin developing in the β-cells of the pancreas leading to impaired insulin secretion (Portha et al., 2012). Around 65 days, the rats experience peripheral insulin resistance, attributing to the further complications that follow a few months after. Due to the increase in peripheral insulin resistance over time, glucose uptake by the whole body (GUR) in these rats is significantly decreased compared with age-matched wild type Wistar rats. Although the GK rats are considered a non-obese Type II Diabetic (T2D) model, adipose accumulation does increase through the progression of insulin resistance (Portha et al., 2012). The progressively decreasing GUR in these rats may account for the short-lived decrease in plasma glucose levels upon TCAP-1 administration. A longer term study with chronic treatments of TCAP-1 daily or weekly may yield more significant long lasting suppressions in plasma glucose levels. Nonetheless, this experiment show for the first time the therapeutic potential of TCAP-1 in managing hyperglycemia in diabetic animals.

The GK rats also exhibited no significant changes in blood parameters following TCAP-1 administration (see Appendix 1). Unlike the normal Wistar rats, there appears to be a decrease in white blood cells, neutrophils and lymphocytes in TCAP-1 administered GK rats. However, due to the complications of increased blood clotting (mainly in the TCAP-1 administered group), results are variable and thus inconclusive.

To understand the physiology behind the apparent decrease in plasma glucose after TCAP-1 administration, a fPET study was performed on male Wistar rats injected with either TCAP-1, SC-TCAP-1 or saline. In this study, 18F-DG was used as a marker for glucose and uptake into the tissues was measured as a function of the radioactivity. The functional positron emission tomography studies indicated that the brain was the only region that showed enhanced glucose uptake after a single acute administration of TCAP-1. There was consistent glucose uptake across the three regions measured: cortex, frontal cortex and subcortical regions. Although the resolution of the fPET instrumentation was limited to 1.5 to 2 mm, this study confirms previous experiments showing the sites of TCAP-1 action in the brain. Al Chawaf and associates (2007) showed that FITC labelled TCAP-1 could cross the blood-brain-barrier and could discern labelled material crossing the endothelial layer of capillaries in the subcortical regions, ventral to the hippocampus in rats. A second study using 125I-labelled TCAP-1 showed uptake in a number of subcortical regions including the nucleus accumbens, arcuate nucleus and the ventral midbrain regions (Tan, 2011). Interestingly, the nucleus accumbens is a major region for the integration of the hedonic actions of glucose, whereas the arcuate nucleus is one of the key regions of the hypothalamus associated with the regulation of energy metabolism in the organism (Rorabaugh et al., 2014; Goldstone et al., 2014; Carey et al., 2013; Sohn et al., 2013). The neural perception of blood glucose concentrations are found in a number of subcortical regions including the dentate gyrus and CA fields of the hippocampus (Ren et al., 2009; Boubaker et al., 2012). The fPET studies of enhanced glucose uptake in the forebrain and subcortical regions is consistent with these previous studies. These findings provide a hypothesis to explain the long term actions of TCAP-1 on blood glucose concentrations after a single acute administration. It is possible that TCAP-1 increases the transport of glucose into these critical regions of the brain indicating a greater need for neurological activity and hence a greater need for glucose. Consequently, horaeostatic regulation in the form of modifications to neuronal communication results in increased uptake of glucose from the blood until negative feedback to these regions of the brain from the result of lower than normal blood glucose, decreased insulin and perhaps increased glucagon. Although the exact mechanism has not been ascertained, TCAP-1 interacts with a number of cell adhesion systems associated with synaptic plasticity in the form of dystroglycans (Chand et al., 2012), latrophilins (Boucard et al., 2014) and teneurins (Mosca et al., 2012).

The in vivo experiments of this study utilized ~10 week old, male Wistar rats to examine effects of TCAP-1 on whole-body glucose metabolism and utilization. Wistar rats are a strain of albino rats that were originally bred out of the Wistar institute (Portha et al., 2012). The particular colony used for this study was selected as it had a low incidence of hydronephrosis. For the first two in vivo studies, normal Wistar rats were chosen as no previous studies were done on rats for the purpose of measuring metabolic parameters and plasma glucose levels. Thus, the use of this strain of normal Wistar rats allowed for preliminary studies to be conducted in the most ideal manner. The initial findings of the in vivo studies done on normal Wistar rats prompted experiments done on pathological models to further the investigation. Thus, the Goto-Kakizaki (GK) Wistar rats were chosen as our next in vivo model. The GK rats are an inbred strain of Wistar rats that exhibit non-obese Type II diabetes with mild hyperglycemia, hyperinsulinemia and insulin resistance. Because previous results suggests an effect of TCAP-1 on lowering of plasma glucose levels, the GK rats were the next logical step in furthering this investigation. Due to the uncertain kinetics of TCAP-1 actions on metabolic parameters, the milder degree of hyperglycemia experienced by the GK rats allowed for an initial test of whether the dosage given to Type II diabetic rats in these experiments was appropriate and effective. Previous studies with mice showed that TCAP-1 injections decreases serum leptin and insulin levels (Xu; 2012). The GK rats' innate high levels of insulin coupled with insulin resistance allows for a convenient corroboration of the previous data. As these in vivo studies indicate that TCAP-1 plays an active role in enhancing whole-body metabolism through a global lowering of plasma glucose levels in both normal and non-obese diabetic rats, examining the roles of TCAP-1 on obesity in the obese Zucker Diabetic (Type II) Fatty (ZDF) rats may unveil further functions of TCAP-1.

For all in vivo studies, the animals were handled as consistently with previous studies performed as possible. A recent study shows that male researchers induces a stress response in lab rodents that results in stressed-induced analgesia (Sorge et al., 2014). This stress response is male specific and is not reproduced with female experimenters. The conditions of the animal facility were kept as consistent as possible in terms of personnel. However, exposure to unfamiliar males was inevitable and should be taken into consideration for data analysis, particularly for any conclusions to be drawn regarding the rats' stress response, or stress-mediated changes in glucose levels. The recent studies did however, mention that the phenomenon they discovered appeared to be olfactory in nature and were not significantly affected by the personnel responsible for husbandry, i.e. the technicians (Sorge et al., 2014). For all three in vivo studies in which blood glucose measurements were taken, all experimenters during the handling procedures were female.

The first three in vivo experiments employed usage of the jugular vein catheter for repeated blood sampling of plasma glucose. A study examining the efficacy of using the jugular vein catheter for experimentation outlines the striking benefits of the technique as it is minimally invasive for the rats, convenient for researchers, and there is also no compromise of blood volumes (Thrivikraman et al., 2002). This was especially optimal as it ensured the lowest levels of stress for the rats. However, usage of the catheters was only suggested for a limited length of time due to the gradual attrition of jugular vein catheters. For the purposes of this study, the rats were kept and blood was drawn from the catheters at least once a day for two weeks. With increased catheter usage, there is always a risk of infection, thrombosis, or mechanical damage to the catheter with increased usage (Galloway and Bodenham, 2004). The gradual attrition of the catheters was observed; one catheter a day was blocked throughout the three in vivo studies, rendering lower than intended sample sizes for statistical analysis. Future studies should look into the feasibility of using the saphenous vein as a site of collection (Parasuraman et al., 2010). The saphenous vein is a reasonable alternative that does not require anesthesia while still allowing for repeated sampling of small amounts of blood (Beeton et al., 2007; Parasuraman et al., 2010). However, collecting from the saphenous vein involves restraining the rat, thus possibly producing immobilization stress. A way of avoiding this confounding factor could be to habituate the rats to this stressor. A second confounding factor in using the saphenous vein as a collection site is the possibility of wound healing affecting the experimental data. Thus, haematology assays would need to be performed to ensure no changes in blood parameters for consistency with the previous in vivo experiments.

Glucose is the primary source of energy for the brain. Neuroprotection in vitro entails increasing glucose uptake into the brain for metabolism or for storage as glycogen in astrocytes to prepare neurons for stress. The actions of TCAP-1 for the purposes of neuroprotection all aim in the direction of metabolic optimization (Trubiani et al., 2007; Xu et al., 2012). Changes associated with metabolic optimization include the acquisition of glucose and therefore, TCAP-1 may induce increased glucose uptake into neurons as a method of protecting the brain from a future insult. Using 3H-2-deoxyglucose (2DG) uptake as a measure of glucose uptake ensures an accurate profile of glucose currents in cultured cells since 2DG is not metabolized after being taken up in the cell. Because TCAP-1 modulates cytoskeletal activity through the activation of the MEK/ERK1-2 pathway within the first hour of treatment in vitro, it was expected that a single acute administration of TCAP-1 would effectively alter cellular metabolism within the same time frame. The uptake studies on mHypoE-38 cells suggest that TCAP-1 mediates a significant increase in neuronal glucose uptake in an insulin-independent manner. The increase is most prominent 30 minutes into TCAP-1 treatment and gradually decreases to baseline levels after 2 hours. The half-life of TCAP-1 suggests that its effects are likely acute, as observed in several previous studies (Chand et al., 2012). This increase in cellular glucose uptake into cells as a result of TCAP-1 administration supports the in vivo studies in that TCAP-1 is lowering plasma glucose levels of an organism by effectively increasing cellular glucose uptake. In particular, the increase in FDG uptake into the brain corroborates evidence supporting the roles of TCAP-1 in neuroprotection. Although results indicate clear significant increases in 2DG uptake at various time points of treatment, there was a decrease, though insignificant, of uptake into neuronal cells during the first half hour of treatment. This is possibly due to the effect of peptide administration to the cultured cells.

Insulin mediates increases in glucose transport via GLUT3 upon stimulation with potassium depolarization in neurons (Uemura and Greenlee, 2006). This study confirms that insulin-mediated increases in 2DG uptake are potassium-dependent unlike TCAP-1, which shows an independence of potassium-mediated depolarization in stimulating glucose uptake into neurons. Insulin treatment alone resulted in no changes in 2DG uptake into mHypoE-38 neurons whereas a pre-treatment with high potassium buffer resulted in a significant increase in 2DG uptake. TCAP-1 treatment resulted in a significant increase in 2DG uptake in the presence or absence of the buffer containing a high potassium concentration. Considering the sole effect of 40 mM of KCl, it can be observed that the depolarization resulting from potassium ion stimulation causes a roughly 50% increase in 2DG uptake in saline treated cells (Vehicle). A similar, though smaller, effect of KCl is observed in the TCAP-1 treated cells suggesting that the mechanism by which depolarization stimulates release of GLUT3 from the intracellular vesicles is likely exclusive from the mechanism by which TCAP-1 increases glucose transport. These studies indicate for the first time that TCAP-1 may be acting in an insulin-independent mechanism. A study shows that leptin infusion into the brain of an uncontrolled diabetes mellitus model of rat results in a lowering of plasma glucose levels via insulin-independent mechanisms (German et al., 2011). The circuitry by which leptin relieves hyperglycemia is likely through the PI3K pathway by targeting nuclei of the hypothalamic POMC cells of the arcuate nucleus. Insulin also activates the PI3K pathway to increase metabolism and glucose transport; however insulin and leptin appear to be targeting different nuclei within the arcuate nucleus (German et al., 2011). Chronic in vivo TCAP-1 administration resulted in a lowering of leptin levels (Xu, 2012), suggesting that TCAP-1 and leptin may have complimentary actions on glucose metabolism irrespective of insulin signalling. As well, the mHypoE-38 hypothalamic neurons used in these studies were derived from the acruate nucleus (Pick and Belsham, 2010). However, unpublished results suggest that TCAP-1 does not significantly alter the activation of PI3K in mHypoE-38 hypothalamic neurons and the exact mechanism of TCAP-1 increases in glucose uptake has yet to be elucidated.

Imported cellular glucose has multiple fates; one of which includes the conversion into pyruvate and then into lactate. Lactate is a metabolite used as currency for exchange of energy between cells and is linked to neuronal metabolism through pyruvate and the redox enzyme lactate dehydrogenase (LDH) (Barros, 2013). LDH controls the ratio of pyruvate to lactate in cells and ensures a near equilibrium at all times. During times of high neural activity, the lactate levels spike, signifying a misbalance between glycolytic activity and mitochondrial activity (Barros, 2013). Studies show that upon neuron excitation, lactate transients increase to ~150% that of baseline levels between 1-5 minutes (Hu and Wilson, 1997; Barros, 2013). Acute TCAP-1 treatment of mHypoE-38 hypothalamic neurons resulted in no significant changes in intracellular levels of lactate. This could potentially be due to the relatively low levels of neuronal excitation during treatment and adequate LDH activity. As well, the majority of neuronal intracellular lactate is controlled through the ANLS and increases with glycogenolysis in astrocytes (Dringen et al., 1993; Dienel, 2012). Thus, the contribution of TCAP-1 treatment to neuronal lactate stores should be considered in a model representing the glial-neuronal network that exists in vivo. Results obtained from the lactate assays resulted in highly variable numbers with no clear trend. Further experiments may look into the roles of TCAP-1 in regulating LDH activity.

Evidence exists supporting the role of pyruvate in neuroprotection from hypoglycaemia through changes in glycogen synthesis (Shetty et al., 2012; Amaral, 2013). Lactate in neurons can be converted back into pyruvate by LDH, which also catalyzes the reverse reaction (Gjedde et al., 2002). Pyruvate has two potential fates once in the cytoplasm; it may be transported to the mitochondria where it is converted into malate to enter the tricarboxylic acid (TCA) cycle or be transported out of the cell through MCTs (Hassel, 2001; Gjedde et al., 2002). The carboxylation of pyruvate is thought to mainly be due to need for compensation of alpha-ketoglutarates that occur through the release of the signalling molecule glutamate during neuronal activity (Hassel, 2001). TCAP-1 treatment of cells resulted in a significant, although weak, decrease in intracellular pyruvate levels. A possible explanation for this decrease could be due to the neuroprotective effects of TCAP-1 bypassing the need for neuroprotection against hypoglycaemia since TCAP-1 administration both in vitro and in vivo appear to increase the amount of glucose available for brain metabolism. As well, the decrease in pyruvate levels could be an indication of increases in oxidative phosphorylation. This would corroborate immunoreactivity studies showing an increase in mitochondrial activity following an acute TCAP-1 treatment in mHypoE-38 neurons (Xu, unpublished). In addition, a quicker decrease in pyruvate levels was observed in response to TCAP-1 treatment compared to the vehicle and insulin treatments. This may be attributable to the independent mechanisms that TCAP-1 relies on to regulate cellular metabolism. As well, this may indicate that TCAP-1 regulates pyruvate levels and thus oxidative phosphorylation quicker than insulin.

GLUT3 is the main isoform of glucose transporters present in the brain (Duelli and Kuschinsky, 2004), TCAP-1 was previously shown to induce an increase in total cell GLUT3 fluorescence following 3 hours of TCAP-1 treatment (Xu, 2012), A similar trend was observed for GLUT1 fluorescence at 1 hour of TCAP-1 treatment; however the total cell fluorescence decreased back to baseline at 3 hours. Compared with GLUT1, which regulates basal glucose input under resting conditions, GLUT3 has a much higher affinity for glucose. This suggests that its roles in augmenting glucose homeostasis may be more prominent due to stress or when exposed to inducing peptides like TCAP-1. Therefore, GLUT3 was the main candidate of focus for this present study. In this study, GLUT3 shows a significantly increased level of membrane fluorescence following 1 and 2 hours of TCAP-1 treatment, corroborating the increases in cellular 2DG uptake into mHypoE-38 neurons and increased FDG uptake into brain tissue of Wistar rats. As per the Astrocyte-Neuron-Lactate Shuttle (ANLS) model of glucose transport in the brain, GLUT3 is mainly expressed in neurons compared with glial in a co-culture while GLUT1 is more heavily expressed in glial cells compared with neurons (Maher, 1995; Yu et al., 2005). The finding that TCAP-1 targets GLUT3 more significantly than GLUT1 gives clues on the possible mechanism of action. If TCAP-1 preferentially targeted GLUT3, it would suggest that TCAP-1 may act as a direct signalling peptide targeted towards neurons of the arcuate nucleus and not through the ANLS. Further experiments examining the mHypoE-38 membrane expressions of GLUT1 should be done to provide more insight on this speculation.

TCAP-1 regulates cytoskeletal changes by activating the MEK/ERK1-2 pathway (Chand et al., 2012). Therefore, it was intuitively the first candidate under consideration for the elucidation of the mechanism for TCAP-1 mediated metabolic optimization in neurons. A 2DG uptake assay with the application of 10 µM of MEK inhibitor (U0126, New England Biolabs) inhibited TCAP-1-mediated increases in glucose uptake. Due to the high variances in repeals, the TCAP-1 effect was not significant, however, the trend shows that TCAP-1 is likely to signal for an increase in GLUT3 transporter activity and thereby increases in glucose uptake through a MEK/ERK1-2 dependent mechanism. A parallel experiment with insulin treatment resulted in significantly lower levels of 2DG uptake with the addition of MEK inhibitor. This is consistent with the roles of insulin in activating both the PI3K/Akt and MEK/ERK1-2 pathways to induce metabolic effects and promote cell growth (Biddinger and Kahn, 2006; Dominici et al., 2005; Taniguchi et al., 2006; Xu and Messina, 2009). The similar trend between insulin and TCAP-1 suggests that TCAP-1 may play a complimentary role to insulin in signalling for increases in glucose uptake and may serve as a potential alternative to insulin.

The AMPK pathway is crucial in the regulation of lipid and glucose metabolism (Hegarty et al., 2009), In skeletal muscle, it plays a role in the regulation of contraction-mediated increases in glucose uptake. Previous unpublished results show that 1 minute of 1 nM treatment of TCAP-1 to mHypoE-38 neurons resulted in an increase in AMPK phosphorylation, suggesting that TCAP-1 likely mediates changes in cellular metabolism through the AMPK pathway. Western blot analyses show that with the addition of MEK inhibitor to mHypoE-38 neurons, TCAP-1 mediated increases in AMPK phosphorylation is inhibited. This suggests for the first time that TCAP-1 activation of the AMPK pathway is likely dependent on the MEK/ERK1-2 pathway.

These studies utilized immortalized embryonic mouse hypothalamic skeletal muscle cell models to examine the mechanism by which TCAP-1 enhances neuronal and muscular metabolism. Due to the complex interactions of cells, tissues, organs and organ systems in vivo, individual cell lines representing a homogenous collection of cells representative of tissues of interest were used to understand the physiological mechanisms of TCAP-1. The mHypoE-38 hypothalamic cell line was used as a model for neurons. These neurons were developed from primary cell cultures of fetal mouse hypothalamus derived during a period of neurogenesis (Belsham et al., 2004). These hypothalamic cultures were transformed with a vector containing SV40 T-Ag as an immortalization factor. Of the total 38 cell lines that were generated from further subcloning, the mHypoE-38 cell line was used for further characterization. These mHypoE-38 neurons express neuronal markers and have demonstrated ability to respond to neuropeptides, particularly those involved in the regulation of metabolism. This was particularly important as the mHypoE-38 neurons are a representative cell line that exhibits the normal neuroendocrine functions of cells of the hypothalamus in mouse, such as leptin sensing. This cell line was used as previous experiments established its ability to respond to neuroprotective actions of TCAP-1 treatment in vitro (Trubiani et al., 2007). As well, unpublished results supporting the hypothesis of TCAP-1's role in optimizing neuron metabolism were also generated through in vitro experiments done on the mHypoE-38 cell line (Xu, 2012). For all in vitro studies involving the mHypoE-38 neurons, the cells were cultured and treated in the same fashion as previously by Trubiani et al (2007), Ng (2010), and Xu (2012).

The C2C12 is a line of immortalized mouse myoblasts. The C2C12 cells represent myogenic muscle cells and were originally derived by Yaffe and Saxel from a heterogeneous cell population in adult dystrophic mouse thigh muscle (Yaffe and Saxel, 1977). For in vitro studies involving the C2C12 myocytes, the cells were cultured, differentiated, and treated in the same fashion as previously by Klip and Ramlal (1987). This way of culturing the C2C12 myocytes had been used for assessing glucose uptake kinetics using 3H-2-deoxyglucose by Klip and Ramlal. Since glucose uptake experiments were the first of experiments to be conducted in this study on the C2C12 myocytes, the rest of the work done on these cells employed the same culturing and treatment technique.

TCAP-1 treatment to C2C12 myocytes resulted in a similar trend of glucose uptake compared to that for the mHypoE-38 neurons. The magnitude of increase in uptake was 2-3 fold compared to the uptake in neurons, as expected by the muscle's increased capacity for glucose transport. Unlike the glucose uptake study on mHypoE-38 cells, results for the C2C12 myocytes were more variable, resulting in larger standard errors as well as a break in the glucose uptake trend by TCAP-1 at 60 minutes, during which time the glucose uptake level returned to baseline. A potential cause for the increased variability of these data is the significantly higher level of glucose in the culturing medium of the C2C12 myocytes compared to that of the mHypoE-38 neurons. The C2C12 myocytes were synchronized for 5 hours in Minimum Essential Medium containing 1000 mg/dL before experimentation whereas the mHypoE-38 neurons were deprived of serum in a buffer containing 0 mg/dL of glucose as per the protocol in Uemura and Greenlee (2006). This high level of surrounding glucose is higher than the physiological range of 70-180 mg/dL. Due to this inconsistency, the C2C12 myocytes may have experienced insulin-insensitivity, leading to variable results. Using the C2C12 myocytes as a model for skeletal muscle, the mechanism by which TCAP-1 stimulates glucose transport can either be by activating an insulin-dependent mechanism or by stimulating a contraction-mediated signal to increase glucose uptake (Richter and Hargreaves, 2013).

FITC-TCAP-1 binding studies on sectioned mouse gastrocnemius muscle indicate that binding sites exist primarily in regions around the sarcolemma. Binding sites are also weakly and ubiquitously spread across the entire section of muscle. This is consistent with the FITC-TCAP-1 binding studies performed on hippocampal E14 cells in which FITC-TCAP-1 bound to cell membranes (Chand et al., 2012). A co-staining with β-DG shows strong co-localization in regions where FITC-TCAP-1 bind.

Immunoreactivity studies show that endogenous TCAP-1 is expressed mainly on the sarcolemma and less so within each myocyte. So far this suggests that the TCAP-1 signalling system exists in mice muscle, at least in part, TCAP-1 has been shown to be an independently functioning peptide after cleavage from the teneurin-1 protein (Chand et al., 2013). However, in the case of skeletal muscle, the absence of endogenous TCAP-1 in skeletal muscle in areas outside of the sarcolemma suggests that TCAP-1 may be dependent on its transmembrane component, teneurin-1. Thus, distinguishing the presence of all teneurin proteins on skeletal muscle may provide insight for delineating the TCAP-1 signalling pathway in muscle. As well, its effects in skeletal muscle may be extended to other systems in which the TCAP-teneurin system exists. Immunoreactivity studies also show a strong association between TCAP-1 and the neuromuscular junction marker, rapsyn. The localization of TCAP-1 relative to rapsyn suggests that TCAP-1 is adjacent to rapsyn at the neuromuscular junctions. This supports the potential role of TCAP-1 in the modulation of neuromuscular signalling and not necessarily in the maintenance or integrity of the neuromuscular junction.

The MEK-ERK1/2 pathway, as part of the RAS/RAF/MEK/ERK pathway, signals to prevent or induce apoptosis or cell cycle progression by regulating the transcription of cell cycle and apoptotic genes (Chang et al., 2003). Western blot analyses performed with TCAP-1 treatment of C2C12 myocytes revealed no significant changes in the activation of ERK1/2. The results of these studies were not in accordance with similar studies done on E14 hippocampal cells (Chand et al., 2012). The co-localization of TCAP-1 and the β-DG complex on the sarcolemma of muscle tissue suggested that TCAP-1 may signal through the same receptor complex to possibly activate the MEK/ERK1-2 pathway. The MAPK signalling pathways are expressed in all mammalian muscle cell types (i.e. skeletal, cardiac, and smooth) (Yamazaki et al., 1995; Goodyear et al., 1996; Force and Bonventre, 1998; Widgren et al., 2002). However, the data on hand suggests that perhaps the complexity of the MEK/ERK1-2 signalling pathway renders this study insufficient. During exercise or muscle contraction, Mitogen-activated protein kinase (MAPK) activation activates three main further downstream signalling molecules; 1) ERK1/2; 2) JNK/P38; and 3) ERK5 (Brunet and Pouyssegur, 1997; Widmann et al., 1999; Widgien et al., 2002). Thus if the role of TCAP-1 is to mediate exercise-like effects on skeletal muscle, further investigation in the other components of the RAS/RAF/MEK/ERK pathway may provide more insight on the mechanism by which TCAP-1 mediates increases in glucose uptake in C2C12 myocytes. As well, it is important to consider the overall complexity of metabolic regulation of skeletal muscle. As the largest contributor of glucose uptake in mammals, skeletal muscle relies on numerous interdependent factors to regulate the molecular responses to stress and increased activity (Widgren et al., 2002). These factors include cues of fatigue, ATP depletion, reduced calcium cycling, pH changes associated with lactate accumulation and glycogen depletion (Shoubridge et al., 2005; Hermansen and Osnes, 1972; Bergstrom et al., 1967). All of these factors alter the signalling of the MEK/ERK1-2 pathway in vivo during exercise and therefore ERK1/2 has only been shown to be activated during exercise in vivo and not in in vitro models (Aronson et al., 1997; Widgren et al., 1998). Thus, the implications of in vitro experiments on the effects of TCAP-1 on cultured skeletal myocytes may be limited.

Preliminary studies (data not shown) suggest that TCAP-1 does not activate the AMPK pathway in C2C12 myocytes (Chen et al., unpublished). The negative results of the western blot analyses of both ERK1/2 and AMPK phosphorylation suggest that TCAP-1 may act through a different receptor system in skeletal muscle than in neurons. This may also suggest that TCAP-1 may be mediating glucose uptake into skeletal muscle via an insulin-dependent mechanism; this is contrary to what is observed in neurons. Future immunoreactivity studies on C2C12 myocytes using TCAP-1 antisera may give further insight on whether TCAP-1 is consistently present in mammalian skeletal muscle models. Subsequent pull-down assays may also provide more information on the receptor system that TCAP-1 relies on for signalling in the in vitro modal of skeletal muscle.

This invention demonstrated that TCAP-1 impacts the glucose homeostasis in vivo by decreasing plasma glucose and increasing uptake of the glucose into key organs of interest, particularly the brain. Additionally, the in vitro data suggest that TCAP-1 mediates these in vivo augmentations in glucose metabolism through an insulin-independent increased cellular uptake of glucose both in neurons and skeletal myocytes.

Over 300 million people in the world suffer from Type II diabetes (World Health Organization, 2009). A risk factor in the development of Type II diabetes (T2D) is insulin resistance, resulting in hyperglycemia. Thus, newest therapeutic treatments are gearing towards pancreatic treatments to alleviate the body's lack of insulin signal. Recent studies show that roughly 50% of glucose disposal occurs through insulin-independent mechanisms; these mechanisms are highly reliant on the brain-centered glucoregulatory system (BCGS) (Schwartz et al., 2013). With the prevailing evidence suggesting that TCAP-1 decreases plasma glucose levels in normal animals and returning plasma glucose to near normal levels in spontaneously diabetic non-obese rats. This study examines whether this impact is present in obese T2D rats. Both insulin-independent and insulin-dependent mechanisms of glucose homeostasis may be compromised in diabetics. Although deficits in one may be compensated by the other, the two mechanisms of glucose homeostasis do not exist in exclusion of one another in vivo. Thus, the study also explores the role of TCAP-1 in vivo and long-term analyses of pancreatic islet cell morphology, insulin responsiveness, and adipocyte changes.

It was previously thought that neurons were the main regulators of brain metabolism and that surrounding glial cells perform other housekeeping functions (Tarczyluck et al., 2013). More recent evidence suggests that a cohort of glial cells, astrocytes, are regulators of neuronal energy supply by sensing levels of neuronal activity and have a symbiotic relationship with neurons to maintain neural activity (Stobart and Anderson, 2013; Turner and Adamson, 2011; Hertz et al., 2007; Sokoloff L, 1999; Verkhrastky and Toescu, 2006). Astrocytes sense neuron activity through increases in extracellular glutamate at synapses during excitation. Much of the brain's glucose metabolism goes towards synaptic transmission and maintaining basal connections between neurons. Adjustments to the metabolism as a result of increased neurotransmission must then be carefully monitored so as to ensure the proper amount of energy intake (Stobart and Anderson, 2013; Pellerin and Magistretti, 1994; Cholet et al., 2001). Certain glial cells, like astrocytes are sensors that ensheath synapses to detect the occurrence of synaptic activity. In response to an increase in synaptic glutamate, astrocytes respond with an increase in glycolysis and glucose utilization, thereby activating GLUT1. GLUT1 transports glucose molecules from the cerebral blood flow into astrocytes, making up the first step of the Astrocyte-Neuron-Lactate Shuttle (ANLS) (FIG. 4.1; Stobart and Anderson, 2013). Astrocytes metabolize the imported glucose into pyruvate, which can then be stored as glycogen, used as a source of energy by the mitochondria, or converted into lactate. Lactate is shuttled out of astrocytes by monocarboxylate transporters MCT-1 and MCT-4. It is taken up by neighbouring neurons through MCT2 (high-affinity for lactate) and is converted back into pyruvate by lactate dehydrogenase (LDH)-1 to be metabolized as a source of energy. Oxygen transported through the blood is used up during oxidative phosphorylation (Stobart and Anderson, 2013).

The regulation of glucose metabolism in skeletal muscle accounts for the majority of physiological glucose usage of an animal. Increased glucose uptake is increased with exercise and during times of muscle growth. TCAP-1 administration shows no significant changes in glycogen storage after two weeks. As such, it may affect the acute contraction strength of skeletal muscle as a consequence of the increases in glucose intake. This can be examined using an appropriate in vivo set up to measure the strength of a contraction before and after TCAP-1 administration. As well, an appropriate muscle recovery assay can be performed to determine whether TCAP-1 has any immediate or long-term effects on recovery from muscle injury. Duchenne's Muscular Dystrophy (DMD) is an X-linked disease resulting in the loss of dystrophin and consequently, muscle integrity. Muscle atrophy is significantly increased in the mdx mouse models of DMD than wild-type mice (Partridge, 2013). Should TCAP-1 have a role in muscle growth and the prevention of atrophy, the phenotype of mdx mice may be alleviated to a certain extent.

In conclusion, the findings of this study show that the effect of TCAP-1 to decrease plasma glucose and consequently increase glucose uptake into tissues is mediated by mechanisms that act to increase cellular metabolism and glucose intake (FIG. 4.2). At the cellular level, TCAP-1 activates the MEK/ERK1-2-dependent AMPK pathway. This then signals to increase GLUT3 expression in the cell membrane; this increased glucose transporter activity is sustained for over two hours. With increased GLUT3 expression in neurons, there is an increase in cellular glucose uptake in an insulin-independent manner that is evident in both the distinct glucose uptake profile as well as the independence of potassium-mediated increases in glucose uptake. TCAP-1 administration in vitro yielded a decrease in acute levels of pyruvate and no changes in the acute levels of lactate. This is consistent with findings of TCAP-1 neuroprotection studies (Xu, 2012) as it is likely that TCAP-1 mediates a stronger chronic effect that is only visible after 3 hours.

In skeletal muscle, similar increases in glucose uptake can be observed though to a much larger degree. The glucose uptake profile also suggests a differential mechanism than that of insulin. In the brain, all findings suggest that TCAP-1 optimizes neuron metabolism by increasing glucose uptake coupled with increased mitochondrial activity and a shift from anaerobic glycolysis to oxidative phosphorylation. This overall increase in energy for the brain would increase the likelihood of the animal to survive oxidative stress and future energy deficits. The increased glucose uptake into skeletal muscle indicates the roles of TCAP-1 in growth and mobility. This is consistent with previous unpublished observations of increased muscle hypertrophy in vivo and represents a beneficial augmentation of the animal's metabolism.

TCAP-1 is shown herein to play a role in the augmentation of muscle metabolism. Understanding the in vitro mechanisms of action could serve for uses in clinical cases of metabolic syndrome and diabetes where TCAP-1 may serve as an alternative to insulin. As well, owing to the role of TCAP-1 in enhancing brain vitality through its neuroprotective capabilities, the usages of TCAP-1 for neurodegenerative diseases will also be beneficial. The discovery of the existence of the TCAP-1 system in skeletal muscle also may have applications in the treatment of muscular diseases and neurodegenerative diseases associated with impaired muscle function.

While the foregoing invention has been described in some detail for purposes of clarity and understanding, it will be appreciated by one skilled in the art, from a reading of the disclosure, that various changes in form and detail can be made without departing from the true scope of the invention in the appended claims.

All publications, patents, and patent applications are herein incorporated by reference in their entirety to the same extent as if each individual publication, patent or patent application was specifically and individually indicated to be incorporated by reference in its entirety.

REFERENCES

1. Abdul-Ghani, M. A. and DeFronzo, R. A. Pathogenesis of insulin resistance in skeletal muscle. J. Biomed. Biotechnol. 2010 (2010): 1-19.
2. Andersen, S. T., Haller, R. G. and Vissing, J. Effect of oral sucrose shortly before exercise on work capacity in McArdle disease. Arch Neurol. 65 (2008): 786-789.
3. Aoi, W., Naito, Y., Tokuda, H., Tanimura, Y., Oya-Ito, T. and Yoshikawa, T. Exercise-induced muscle damage impairs insulin signaling pathway associated with IRS-1 oxidative modification. Physiol. Res, 61 (2012); 81-88.
4. Baumgartner, S., Martin, D., Hagios, C. and Chiquet-Ehrismann, R. Tenm, a Drosophila gene related to tenascin, is a new pair rule gene. EMBO J. 13 (1994): 3728-3740.
5. Brozinick, J. T., Etgen, G. J., Yaspelkis, B. B. and Ivy, J. L. Contraction-activated glucose uptake is normal in insulin-resistant muscle of the obese Zucker rat. J. Appl. Physiol. 73 (1985): 382-387.
6. Chand, D., Song, L., Delannoy, L., Barsyte-Lovejoy, D., Ackloo, S., Boutros, P. C., Evans, K., Belsham, D. D. and Lovejoy, D. A. C-terminal region of teneurin-1 co-localizes with dystroglycan and modulates cytoskeletal organization through an extracellular signal-related kinase-dependent stathmin- and filamin A-mediated mechanism in hippocampal cells. Neuroscience 219 (2012): 255-270.
7. Coyle, E. F., Hagberg, J. M., Hurley, B. F., Martin, W. H., Ehsani, A. A. and Holloszy, J. O, Carbohydrate feeding during prolonged strenuous exercise can delay fatigue. J. Appl. Physiol. Respir. Environ. Exerc. Physiol. 55 (1983): 230-235.
8. DeFronzo, R. A. and Tripathy, D. Skeletal muscle insulin resistance is the primary defect in type 2 diabetes. Diabetes Care 32 (2009): S157-S163.
9. Holloszy, J. O. and Kohrt, W. M., Regulation of carbohydrate and fat metabolism during and after exercise. Annu. Rev. Nutr. 16 (1996): 121-138.
10. Hughes, B. W., Kusner, L. L., Kaminski, H. J. Molecular architecture of the neuromuscular junction. Muscle & Nerve 33 (2006): 445-461.
11. Jensen, T. E, and Richter, E. A. Regulation of glucose and glycogen metabolism during and after exercise. J. Physiol. 590.5 (2012): 1069-1076.
12. Kang Y. S., Bickel, U. and Pardridge, W. M. Pharmacokinetics and saturable blood brain barrier transport of biotin bound to a conjugate of avidin and a monoclonal antibody to the transferring receptor Drug Metab. Dispos. 22 (1994): 99-105.
13. Levine, A., Bashan-Ahrend, O., Budai-Hadrian, D., Gartenberg, S., Menasherow, R and Wides, R. Odd Oz: a novel Drosophila pair rule gene. Cell 77 (1994); 587-598.
14. Minet, A. and Chiquet-Ehrismann, R. Phylogenetic analysis of teneurin genes and comparison to the rearrangement hot spot elements of E. coli. Gene 257 (2000): 87-89.
15. Minet, A., Rubin, B., Tucker, R., Baumgartner, S. and Chiquet-Ehrismann, R. Teneurin-1, a vertebrate homologue of the Drosophilapair-rule gene Ten-m, is a neuronal protein with a novel type of heparin-binding domain. Journal of Cell Science 112 (1999): 2019-2032.
16. Oohashi, T., Zhou, K., Feng, B., Richter, M., Morgelin, M., Perez, W., Su, R., Chiquet-Ehrismann, R., Rauch, U. and Fassler, R. Mouse ten-m/Odz is a new family of dimeric type II transmembrane proteins expressed in many tissues. J. Cell Biol. 145 (1999): 563-577.
17. Pelicano, H., Martin, D. S., Xu, R. H. and Huang, P. Glycolysis inhibition for anticancer treatment. Oncogene 25 (2006): 4633-4646.
18. Petersen, K. F., Dufour, S., Savage, D. B., Bilz, S., Solomon, G., Yonemitsu, S. Cline, G. W., Befroy, D., Zemany, L., Kahn, B. B., Papademetris, X., Rothman, D. L. and Sbulman, G. I. The role of skeletal muscle insulin resistance in the pathogenesis of the metabolic syndrome. PNAS 104 (2007): 12587-12594.
19. Preisler, N., Pradel, A., Husra, E., Madsen, K. L., Becquemin, M. H., Mollet, A., Labrone, P., Petit, F., Hogrel, J. Y., Jardel, C., Maillot, F., Vissing, J. and Laforet, P. Exercise intolerance in glycogen storage disease type III: weakness or energy deficiency Mol. Genet. Metab. 109 (2013): 14-20.
20. Qian, X., Barsyte-Lovejoy, D., Wang, L., Chewpoy, B., Gautam, N., Al Chawaf, A. and Lovejoy, D. A, Cloning and characterization of teneurin C-terminus associated peptide (TCAP)-3 from the hypothalamus of an adult rainbow trout (Oncorhynchus mykiss). Gen Comp Endocrinol. 137 (2004): 205-16.
21. Richter, E. A. and Hargreaves, M. Exercise, GLUT4 and skeletal muscle glucose uptake. Physiol. Rev. 93 (2013); 993-1017.
22. Robertshaw, H. A., Raha, S., Kaczor, J. J. and Tamopolsky, M. A. Increased PFK activity and GLUT4 protein content in McArdle's disease. Muscle & Nerve 37 (2008): 431-437.
23. Rubin, B., Tucker, P., Martin, D. and Chiquet-Ehrismann, R. Teneurins: a novel family of neuronal cell surface proteins in vertebrates, homologous to the Drosophila pair-rule gene product, Ten-m. Dev Biol. 216 (1999): 195-209.
24. Sapolsky, R. M. (1992) Stress, the aging brain and the mechanisms of neuronal death. MIT Press. Cambridge Mass. 428 pages.
25. Vissing, J. and Haller, R. G. The effect of oral sucrose on exercise tolerance in patients with McArdle's disease. New England Journal of Medicine 349 (2003): 2503-2509.
26. Vuisser, C. C., Stevanovic, S., Voorwindem, L., Gaillard, P. J., Connmelin, D. J., Danhof, M. and DeBoer A. G. Validation of the transferring receptor for drug targeting to brain capillary endothelial cells in vitro. J. Drug Target 12 (2004): 145-150.
27. Wang, L., Rotzinger, S., Al Chawaf, A., Elias, C. F., Barsyte-Lovejoy, D., Qian, X., Wan, N-C., De Cristofaro, A., Belsham, D., Bittencourt, J. C., Vaccarino, F. and Lovejoy, D. A. Teneurin proteins possess a carboxy terminal sequence with neuromodulatory activity. Mol. Brain Res. 133 (2005): 253-265.

28. Wasserman, D. H., Kang, L., Ayala, J. E., Fueger, P. T., and Lee-Young, R. S. The physiological regulation of glucose flux into muscle in vivo. J. Exp. Biol. 214 (2011): 254-262.
29. Zhang Y. and Pardridge, W. M. Conjugation of brain-derived neurotrophic factor to a blood-brain barrier drug targeting system enables neuroprotection in regional brain ischemia following intravenous injection of the neurotrophic. Brain Res. 889 (2001): 49-56.
30. Zierath, J. R., Tsao, T. S., Steonbit, A. E., Ryder, J. W., Galuska, D. and Chairon, M. J. Restoration of hypoxia-stimulated glucose uptake in GLUT4-deficient muscles by muscle-specific GLUT4 transgenic complementation. J. Biol. Chem. 273 (1998): 20910-20915.
31. Xu, M. A novel pathway for enhanced metabolic capacities underlies the neuroprotective actions of Teneurin C-Terminal Associated Peptide (TCAP)-1. PhD Thesis, University of Toronto (2012).
Abi-Saab W M, Maggs D G, Jones T, Jacob R, Srihari V, Thompson J, Kerr D, Leone P, Krystal J H, Spencer D D, During M J, Sherwin R S. (2002). Striking differences in glucose and lactate levels between brain extracellular fluid and plasma in conscious human subjects: effects of hyperglycemia and lypoglycaemia. *J Careb Blood Flow Metab* 22:271-279.
Al Chawaf A, St Amant K, Belsham D, Lovejoy D A. (2007a). Regulation of neurite outgrowth in immortalized mouse hypothalamic neurons and rat hippocampal primary cultures by teneurin C-terminal-associated peptide-1. *Neuroscience* 144:1241-1254.
Al Chawaf A, Xu K, Tan L, Vaccarino F J. Lovejoy D A, Rotzinger S. (2007b). Corticotropin-releasing factor (CRF)-induced behaviors are modulated by intravenous administration of teneurin C-terminal associated peptide-1 (TCAP-1). *Peptides* 28:1406-1415.
Alberts et al. (2008). Molecular Biology of the Cell. Garland Science, New York N.Y. 180.
Alquier F, Leloup C, Lorsignol A, Penicaud L. (2006). Translocable Glucose Transporters in the Brain. Where are we in 2006? *Diabetes* 55:5131-5138.
Airley R E, Mobasheri A. (2007). Hypoxic regulation of glucose transport, anaerobic metabolism and angiogenesis in cancer novel pathways and targets for anticancer therapeutics. *Chemotherapy* 53(4):233-256.
Andersson J O. (2005). Lateral gene transfer in eukaryotes. *Cell Mol Life Sci* 62:1182-1197.
Aravind L, Anantharaman V, Zhang D, de Souza R F, Iyer L M. (2012). Gene flow and biological conflict systems in the origin and evolution of eukaryote. *Front Cell Infect Microbiol* 2:89.
Aronson D, Violan M A, Dufresue S D, Zangen D. Fielding R A, Goodyear. (1997). Exercise stimulates the mitogen-activated protein kinase pathway in human skeletal muscle. *J Clin Invest* 99:1251-1257.
Bady I, Matty N, Daltaporfa M, Emery M, Gyger J, Tarussio D, Foretz M, Thoreos B. (2006). Evidence from glut2-null mice that glucose is a critical physiological regulator of feeding. *Diabetes* 55:988-95.
Bajor M, Kaczmarek L. (2013). Proteolytic Remodeling of the Synaptic Cell Adhesion Molecules (CAMS) by Metziocins in Synaptic Plasticity. *Neurochem Res* 38:1113-1121.
Barnard R J, Youngren J F. (1992). Regulation of glucose transport m skeletal muscle. *The FASEB Journal* 6(14): 3238-3244.
Barnes K, Ingram J C, Porras O H, Barros L F, Hudson E R, Fryer L G, Fonfelle F. Carling D, Hardie D G, Baldwin S A. (2002). Activation of GLUT1 by metabolic and osmotic stress: potential involvement of AMP-activated protein kinase (AMPK). *J Cell Sci* 115:2433-2442.
Barros L F. (2013). Metabolic signaling by lactate in the brain. *Trends Neurosci* 36:396-404.
Barsyte D. Tipping D R, Smart D, Conloa J M, Baker B I, Lovejoy D A. (1999). Rainbow trout (*Oncorhynchusmykiss*) urotensin-I: structural differences between uroteosins-I and crocortins. *Gen Comp Endocrinol* 115: 169-177.
Baumgartner S, Martin D, Hagios C, Chiquet-Ehrismann R. (1994). Team, a *Drosophila* gene related to tenacin is a new pair-rule gene. *EMBO J* 13:3728-3740.
Burcelin R, Thorens B. (2001). Evidence that extrepancreahc GLUT2-dependent glucose sensors control glucagon secretion. *Diabetes* 50:1252-9.
Carey M, Kehlenbrink S, Hawkins M. (2013). Evidence for Central Regulation of Glucose Metabolism. *Journal of Biological Chemistry* 288:34981-34988.
Chand D, Casatti C A, de Lannoy L, Song L, Kollara A, Barsyte-Lovejoy D, Brown T J, Lovejoy D A. (2013a). C-terminal processing of the teneurin proteins: Independent actions of a teneurin C-terminal associated peptide in hippocampal cells. *Mol Cell Neurosci* 52:38-50.
Chaned D, de Lannoy L, Tucker R, Lovejoy D A (2013b). Origin of chordate peptides by horizontal protozoan gene transfer in early metazoans and protists: Evolution of the teneurin C-terminal associated peptides (TCAP). *Gen Comp Endocrinol* 183:144-150.
Chand D, Song L, Delannoy L, Barsyte-Lovejoy D, Ackloo S, Boutros P C. Evans K, Belsham D D, Lovejoy D A (2012). C-terminal region of teneurin-1 co-localizes with dystroglycan and modulates cytaskeletal organization through an extracellular signal-related kinase-dependent stafhnin- and filamin A-mediated mechanism in hippocampal cells. *Neuroscience* 219:255-270.
Chang C L, Hsu S Y. (2004). Ancient evolution of stress-regulating peptides in vertebrates. *Peptides* 25:1681-1688.
Chen Y, Xu M, De Almeida R, Lovejoy D A. (2013). Teneorin C-Terminal associated peptides (TCAP): Modulators of corticotropin-releasing factor (CRF) physiology and behavior. *Frontiers in Neuroscience* 7:1-6.
Chung W, Campanelli J T. (1999). WW and EF hand domains of dystrophin-family proteins mediate dystroglycan binding. *Mol Cell Biol Res Commun* 2:162-171.
Cohn, R D. (2004). Dystroglycan: important player in skeletal muscle and beyond. *Neuromuscular Disorders* 15:207-217.
Condeelis J. (1995) Elongation factor 1 alpha, translation and the cytoskeletan. *Trends Biochem Sci* 5:169-70.
De Almeida R. (2012). Modulation of Hypothalamic-Pituitary-Adrenal Axis Parameters by Teneurin C-Terminal Associated Peptides. M. Sc. Thesis. Dept Cell and Systems Biology. University of Toronto.
DeFronzo R A, Jacot E, Jeqirier E, Maeder E, Wahren J, Felber J P. (1981). The effect of insulin on the disposal of intravenous glucose. Results from indirect calorimetry and hepatic and femoral venous catheterization. *Diabetes* 30:1000-1007.
Denver R J. (2009). Structural and functional evolution of vertebrate neuroendocrine stress systems. *Ann NY Acad Sci* 1163:1-16.
Deysl K A, Bowe M A, Leszyks J D, Fallon J R. (1995). The α-Dystroglycan-β-Dystroglycan Complex: Membrane organization and relationship to an agrin receptor. *J Biological Chem* 270(43):25956-25959.

Duelli R & Kuschinsky W. (2001). Brain glucose transporters: relationship to local energy demand. *News Physiol Sci,* 16:71-76.

Ervasti J M, Ohlendieck K, Kahl S D, Gaver M G, Campbell K P. (1990). Deficiency of a glycoprotein component of the dystrophin complex in dystrophic muscle. *Nature* 345:315-319.

Fick L J, Belsham D D. (2010). Nutrient sensing and insulin signaling in neuropeptide-expressing immortalized, hypothalamic neurons: A cellular model of insulin resistance. *Cell Cycle* 9:3186-3193.

Galeffi F, Foster K A, Sadgrove M P, Beaver C J, Turner D A. (2007). Lactate uptake contributes to the NAD(P)H biphase response and tissue oxygen response during synaptic stimulation in area CA1 of rat hippocampal slices. *J Neurochem* 103:2449-2461.

Goldenfield N, Woese C. (2007). Biology's next revolutions. *Nature* 445:369.

Guillam M T, Hummler E, Schaerer E, Yeh J T, Birabanm M J, Beermaan F, Schmidt A, Deriaz N, Thorens B, Wu J Y. (1997). Early diabetes and abnormal postnatal pancreatic islet development in mice Jacking Glut-2. *Nat Genet.* 17:327-30.

Hardie D G, Ross F A, Hawley S A (2012). AMP-activated protein kinase: a target for drugs both ancient and modern. *Chem Biol* 19:1222-1236.

Harmon A W, Paul D S, Patel Y M. (2004). MEK inhibitors impair insulin-stimulated glucose uptake in 3T3-L1 adipocytes. *American J Physiol* 287:758-766.

Hegarty B D, Turner N, Cooney G J, Kraegen E W. (2009). Insulin resistance and fuel homeostasis: the role of AMP-activated protein kinase: *Acta Physiol* 196:129-145.

Hertz L, Peng L, Dienel G A. (2007). Energy metabolism in astrocytes: high rate of oxidative metabolism and spatiotemporal dependence on glycolysis/glycogenolysis. *J Cereb Blood Flow Metab* 27:219-249.

Hu Y, Wilson G S. (1997). A temporary local energy pool coupled to neuronal activity: fluctuations of extracellular lactate levels in rat brain monitored with rapid-response enzyme-based sensor. *J Neurochem* 69:1484-1490.

Hughes B W, Kusner L L, Kaminski H J, (2005). Molecular architecture of the neuromuscular junction. *Muscle & Nerve* 33:445-461.

Ibraghimov-Beskrovnaya O, Ervasti J M, Leveille C J, Slaughter C A, Sernett S W, Campbell K P. (1992) Primary structure of dystrophin-associated glycoproteins linking dystrophin to the extracellular matrix. *Nature* 355(6362):696-702.

Ichijo H, Nishida E, Irie K, ten Dijke P, Saitoh M, Moriguchi T, Takagi M. Matsumoto K, Miyazono K, Gotoh Y. (1997). Induction of apoptosis by ASK1, a mammalian MAPKKK that activates SAPK/JNK and p38 signaling pathways. *Science* 275:90-94.

Jessen N, Goodyear L J. (2005). Contraction signaling to glucose transport in skeletal muscle. *J Appl Physiol* 99:330-337.

Joels M, Karst H, Krugers H J, Lucassen P J. (2007). Chronic stress: implications for neuronal morphology, function and neurogenesis. *Front Neuroendocrinol* 28:72-96.

Kenzelmann D, Chiquet-Ehrismann R, Tucker R P. (2007). Teneurins, a transmembrane protein family involved in cell communication during neuronal development. *Cell Mol Life Sci* 64:1452-1156.

Kreienkamp H J, Soltau M, Richter D, Bockers T. (2002). Interaction of G-protein-coupled receptors with synaptic scaffolding proteins. *Biochem Soc Trans* 30:464-465.

Kruszynska Y T, Ciaraldi T P, Henry R R. Regulation of glucose metabolism in skeletal muscle. In The endocrine pancreas and regulation of metabolism. Cherrington A, Goodman H M. Eds.; Oxford University Press: London. 2001, 2(236)379-607.

Klip A, Ramlal T. (1987). Protein kinase C is not required for insulin stimulation of hexose uptake in muscle cells in culture. *J Biochem* 242:131-136.

Klip A, Schertzer J D, Bilan P J, Thong F, Antouescu C. (2009). Regulation of glucose transporter 4 traffic by energy deprivation from mitochondrial compromise. *Acta Physiol* 196:27-35.

Kyriakis J M, Banerjee P, Nikolakaki E, Dai T, Rubie E A, Ahmad M F, Avruch J, Woodgett J R. (1994). The stress-activated protein kinase subfamily of c-Jun kinases. *Nature* 369:156-160.

Langenhan T, Russ A P. (2010). Latrophillin signalling in tissue polarity and morphogenesis. *Adv Exp Med Biol* 706:37-48.

Langenhan T, Promel S, Mestek L, Esmaelli B, Walter-Evans H, Hennig C, Kohara Y, Avery L, Vakonakis I, Schnabel R, Russ A P. (2009). Latrophillin signalling links anterior-posterior tissue polarity and oriented cell divisions in the *C. elegans* embryo. *Dev Cell* 17:494-504.

Levine A, Bashan-Ahread A Budai-Hadrian O Gartenberg D, Menasherow S, Wides R. (1994). Odd Oz; a novel *Drosophila* pair-rule gene. *Cell* 77:587-598.

Lovejoy D A, Al Chawaf A, Cadinouche M. (2006). Teneurin C-terminal associated peptides: An enigmatic family of neuropeptides with structural similarity to file corticotrophin-releasing factor and calcitonin families of peptides. *Gen Comp Endocrinol* 148:299-305.

Lovejoy D A, Bahnent R J. (1999). Evolution and physiology off the corticotropin-releasing factor (CRF) family of neuropeptides in vertebrates. *Gen Comp Endocrinol* 155:1-22.

Lovejoy D A, Jahan S. (2006). Phylogeny and evolution of the corticotropin releasing factor family of peptides. *Gen Comp Endocrinol* 146:1-8.

Lovejoy D A, Rotzinger S, Barsyte-Lovejoy D. (2009). Evolution of Complementary Peptide Systems: Teneurin C-terminal-associated Peptides and Corticotropin-releasing Factor Superfamilies. *Ann NY Acad Sci* 1163:215-220.

Magnoni S, Ghisoni L, Locatelli M, Caimi M, Colombo A, Valeriani V, Stocchetti N. (2003). Lack of improvement in cerebral metabolism after hyperoxia in severe head injury: a microdialysis study. *J Neurosurg* 98:952-958.

Matsmum K, Ernst, J M, Ohlendieck K, Kahl S D, Campbell K P. (1999). Association of dystrophin-related protein with dystrophin-associated proteins is mdx mouse muscle. *Nature* 360:588-591.

Mayer C M, Belsham D D. (2009). Insulin directly regulates NPY and AgRp gene expression via the MAPK MEK/ERK signal transduction pathway in mHypoE-46 hypothalamic neurons. *Mol Cell Endo* 307(1):99-108.

McEwen B S, Magarinos A M. (1997). Stress effects on morphology and function of the hippocampus. *Ann NY Acad Sci* 821:271-284.

McNay D E, Briancon N, Kokoeva M V, Meratos-Fher E, Flier J S. (2012) Remodeling of the arcuate nucleus energy-balance circuit is inhibited in obese mice. *J Clin Invest.* 122(1):142-52.

Michaluk P, Kolodziej L, Mioduszewska B, Wilczynski G M, Dzwonek J, Jaworski J, Gorecki D C, Ottersen O P, Kaczmarek L. (2007) Beta-dystroglycan as a target far MMP-9, in response to enhanced neuronal activity. *J Biol Chem* 282(22)16036-16041.

Moore S A, Saito F, Chen J, Michele D E, Henry M D, Messing A, Cohn R D, Ross-Barta S E, Westra S, Williamson R A, Hoshi T, Campbell K P. (2002) Deletion of brain dystroglycan recapitulates aspects of congenital muscular dystrophy. *Nature* 418(6896):422-425.

Ng T S J. (2010). The Effect of Teneurin C-terminal Associated Peptide-1 (TCAP-1): Protection Against Hypoxic-stress and Regulation of Brain-derived Neurotrophic Factor (BDNF) in Immortalized Hypothalamic N38 cells. M. Sc. Thesis. Dept. Cell and Systems Biology. University of Toronto.

Ng T, Chand D, Song L, Watson J D, Boutros P C, Barsyte-Lovejoy D, Belsham D D, Lovejoy D A. (25011). Identification of a novel Brain Derived Neurotrophic Factor (BDNF)-inhibitory factor: Regulation of BDNF by Teneurin C-terminal Associated Peptide (TCAP)-1 in immortalized embryonic moose hypothalamic cells *Regul Pept* 174:79-89.

Nobuharu F, Jessen N, Goodyear L J. (2006). AMP-activated protein kinase and the regulation of glucose transport. *Am J Physiol Endocrinol Metab* 291:ES67-E867.

Nock, T G. (2010). Development of an enzyme immunoassay and cellular function assays to probe the function of Teneurin C-Terminal Associated Peptide (TCAP). M.Sc. Thesis. Dept. Cell and Systems Biology. University of Toronto.

Ohno S. (1998). The notion of the Cambrian pananimalia genome and a genomic difference that separated vertebrates from invertebrates. *Prog Mol Subcell Biol* 21:97-117.

Pages G, Lenormand, L'Allemain G, Chambard J C, Meloche S. Ponyssegur J. (1993). Mitogen-activated protein kinases p42-MAPK and p44MAPK are required for fibroblast proliferation. *Proc Natl Acad Sci* 90:8319-8323.

Pellerin L, Bouzier-Sore A, Aubert A, Serres S, Merle M, Costalat R, Magistretti P J. (2007). Activity Dependent Regulation of Energy Metabolism by Astrocytes: An Update. *Glia* 55:1251-1262.

Peng H B, Xie H, Rossi S G, Rotando R L. (1999). Acetylcholinesterase Clustering at the Neuromuscular Junction Involves Perlecan and Dystroglycan. *J Cell Bio* 145(4):911-921.

Qian X. Barsyte-Lovejoy D, Wang L, Chewpoy B, Gautam N, Al Chawaf, A Lovejoy D A. (2004). Cloning and characterization of teneurin C-terminal associated peptide (TCAP)-3 from the hypothalamus of an adult rainbow trout (*Oncorhynchus mykiss*). *Gen Comp Endocrinol* 137 (2):205-216.

Rezniczek G A, Konieczny P, Nikolic B, Reipert S, Schneller D, Abrahamsberg C, Davies K E, Winder S J, Wiche G. (2007). Plectin if scaffolding at the sarcolemma of dystrophic (mdx) muscle fibers through multiple interactions with β-dystroglycan. *J Cell Bio* 176(7):965-977.

Richter E A, Hargreaves M. (2013) Exercise, GLUT4, and skeletal muscle glucose intake. *Physiological Reviews* 92:993-1017.

Rubin B P, Tucker R P, Martin D, Chiquet-Ehrismann R. (1999). Teneurins: a novel family of neuronal cell surface proteins in vertebrates, homologous to the Drosophila pair-rule gene product Ten-m. *Dev Biol* 216:195-209.

Sakamoto K, Holman G D. (2008). Emerging role for ASI60/TBC1D4 and TBC1D1 in the regulation of GLUT4 traffic. *Am J Physiol Endocrinol Metab* 295:E29-E37.

Silva J P, Lelianova V G, Ermolyuk Y S, Vysokov, Hitchen P G, Berninghausen O, Rahman M A, Zangrandi A, Fidalgo S, Tonevitsky A G, Dell A, Volynski K E, Ushkaryov Y A. (2011). *PNAS* 108:12113-12118.

Sohn J W, Elmquist J K, Williams K W. (2013). Neuronal circuits that regulate feeding behaviour and metabotism. *Trends in Neuroscience* 36:504-512.

Sokoloff L. (1999). Energetics of functional activation in neural tissues. *Neurochem Res* 24:321-9.

Stearns S C, Hoekstra R F. (2005). Evolution: An introduction ($2^{nd}$ ed.). Oxford NY: Oxford Univ Press pp. 38-04.

Stobart J L and Anderson C M. (2013) Multifunctional role of astrocytes as gatekeeper of neuronal energy supply. *Frontiers in Cellular Neuroscience* 7:1-21.

Tan L A, Al Chawaf A, Vaccarino F J, Boutros P C, Lovejoy D A. (2011). Teneurin C-terminal associated peptide (TCAP)-1 modulate dendritic morphology in hippocampal neurons and decreases anxiety-like behaviors in rats. *Physiology & Behavior* 104:199-204.

Tan L A, Xu K, Vaccarino F J, Lovejoy D A, Rotzinger S. (2008). Repeated intracerebral teneurin C-terminal associated peptide (TCAP)-1 injections produce enduring changes in behavioral responses to corticotropin-releasing factor (CRF) in rat models of anxiety. *Behavioural Brain Research* 188:395-200.

Tarczyluk M A, Nagel D A, O'Neil J D, Parri H R, Tse E H Y, Coleman M D, Hill E J. (2013) Functional astrocyte-neuron lactate shuttle in a human stem edited neuronal network. *Journal of Cerebral Blood Flow & Metabolism* 33:1386-1393.

Taylor E B, Goodyear L F. (2007). Targeting skeletal muscle AMP-activated protein kinase to treat type 2 diabetes. *Curr Diab Rep* 7:399-401.

Trubiani G, Al Chawaf A, Belsham D, Barsyte-Lovejoy D, Lovejoy D A. (2007) Teneurincarboxy (C)-terminal associated peptide-1 inhibits alkalosis-associated necrotic neuronal death by stimulating superoxide dismutase and catalase activity in immortalized moose hypothalamic cells. *Brain Research* 1176:27-36.

Tsigos C, Chrousus G P. (2002). Hypothalmic-pituitary-adrenal axis, neuroendocrine factors and stress. *J Psychosom Res* 53:865-871.

Tucker R P. (2013). Horizontal gene transfer in choanoflagellates. *J Exp Zoo B Mol Dev Evol* 320:1-9.

Tucker R P, Beckmann J, Leachman N T, Schoter J, Chiquet-Ehrismann R. (2011). Phylogenetic analysis of the teneurins: conserved features and premetazoan ancestry. *Mol Biol Evol* 29:1019-1029.

Tucker R P, Chiquet-Ehrismann R. (2006). Teneurins: a conserved family of transmembrane proteins involved in intercellular signaling during development. *Dev Biol* 290: 237-245.

Tucker R P, Kenzelmaan D, Trzebiatowska A, Chiquet-Ehrismann R. (2007). Teneurins: Transmembrane proteins with fundamental roles in development *Int J Biochem & Cell Bio* 39:292-297.

Turner D A, Adamson D C. (2011). Neuronal-Astrocyte Metabolic Interactions: Understanding the Transition into Abnormal Astrocytoma Metabolism. *J Neuropathol Exp Neurol* 70:167-176.

Uemura E, Greelee H W. (2006). Insulin regulates neuronal glucose uptake by promoting translocation of glucose transporter GLUT3. *Experimental Neurology* 198:48-53.

Ulrich-Lai Y M, Herman J P. (2009). Neural regulation of endocrine and autonomic stress responses. *Nat Rev Neurosci* 10:397-409.

Valentine J W. (1994). Late Precambrian bilaterians: grades and clades. *PNAS* 91:6751-6757.

Vanaucci S J. (1994). Developmental expression of GLUT1 and GLUT3 glucose transporters in the brain. *J Neurochem* 1:240-246.

Verkhrastky A. Toescu E C. (2006). Neuronal-glial networks as substrates for CNS integration. *J Cell Mol Med* 10:826-836.

Wang L, Rotzinger S, Al Chawaf A, Elias C F, Barsyte-Lovejoy D, Qian X, Wang N, de Cristofaro A, Belsham D, Bittencourt J C, Vaccarino F, Lovejoy D A. (2005). Teneurin proteins possess a carboxy terminal sequence with neuromodulatory activity. *Mol Brain Res* 133(2): 253-265.

Weisova P, Conannon C G, Devocelle M, Prehn J, Ward M. (2009). Regulation of glucose transporter 3 surface expression by APM-activated protein kinase mediates tolerance to glutamate excitation in neurons. *J Neurosci;* 29(9): 2997-3008.

Widgren U, Jiang X J, Krook A, Chibalin A V, Bjornholm M, Tally M, Roth R A, Henriksson J, Wallberg-Henriksson H, Zierath J R. (1998). Divergent effects of exercise on metabolic and mitogenic signalling pathways in human skeletal muscle. *FASEB J* 12:1379-1389.

Widgren U, Ryder J W, Zierath J R. (2002). Mitogen activated protein kinase signal transduction in skeletal muscle: effects of exercise and muscle contraction. *Acta Physiol Scand* 172:227-238.

Winder S J. (1996). Structure-function relationships in dystrophin and utrophin. *Biochem Soc Trans* 24:497-501.

Winder S J, Hemmings L. Maciver S K, Bolton S J, Tinsley J M, Davies. (1995). Utrophin ad in binding domain: analysis of actin binding and cellular targeting. *J Cell Sci* 108:63-71.

Woese C R. (2002). On the evolution of cells. *PNAS* 99:8742-8747.

Xu M. (2012). A Novel Pathway for Enhanced Metabolic Capacities Underlies the Neuroprotective Actions of Teneurin C-Terminal Associated Peptide (TCAP)-1. M. Sc Thesis. Dept Cell and Systems Biology, University of Toronto.

Yamazaki T, Komuro I, Kudoh S, Zon Y, Shiojima I, Mizano T, Takano H, Hiroi Y, Ueki K, Tobe K, et al. (1995). Mechanical stress activates protein kinase cascade of phosphoryation in neonatal rat cardiac myocytes. *J Clin Invest* 96:438-446.

Yamazaki T, Tobe K, Hob E. Maemura K, Kaida T, Komuro J, Tamemoto H, Kadowaki T, Nagai R, Yazaki Y. (1993). Mechanical loading activates mitogen-activated protein kinase and S6 peptide kinase in cultured rat cardiac myocytes. *J Biol Chen* 268:120269-12076.

Young T R, Leamey C A. (2009). Teneurins: Important regulators of neural circuitory. *Int. J. Biochem & Cell Bio* 41:990-993.

Zaid H, Talior-Volodarsky I, Antonesen C, Klip A. (2009). GAPDH binds GLUT4 reciprocally to hexokinase-II and regulates glucose transport activity. *Biochem J* 419:475-484.

Zhang D, deSouza R F, Ananantharaman V, Iyer L M, Aravind L. (2012). Polymorphic toxin systems: comprehensive characterization of trafficking modes, mechanism of action, immunity and ecology using comparative genomics. *Biology Direct* 7:18.

Zhao F Q, Keating A F. (2007) Functional properties and genomics of glucose transporters. *Curr Genomics* 8:113-128.

Airley R E, Mobasheri A. (2007). Hypoxic regulation of glucose transport, anaerobic metabolism and angiogenesis in cancer: novel pathways and targets for anticancer therapeutics. *Chemotherapy* 53(4):233-256.

Al Chawaf A, Xu K, Vaccarino F J, Lovejoy D A, Rotzinger S (2007). Corticotropin-releasing factor (CRF)-induced behaviours are modulated by intravenous administration of teneurin C-terminal associated peptide-1 (TCAP-1). *Peptides* 23:1406-1415.

Aronson D, Violan M A, Dufresne S D, Zangen D, Fielding R A, Goodyear. (1997). Exercise stimulates the mitogen-activated protein kinase pathway in human skeletal muscle. *J Clin Invest* 99:1251-1257.

Carey M, Kehlenbrink S, Hawkins M. (2013). Evidence for Central Regulation of Glucose Metabolism. *Journal of Biological Chemistry* 288:34981-34988.

Chand D, Song L, Delanmoy L, Barsyte-Lovejoy D, Ackloo S, Boutros P C, Evans K, Belsham D D, Lovejoy D A. (2012). C-terminal region of teneurin-1 co-localizes with dystroglycan and modulates cytoskeletal organization through an extracellular signal-related kinase-dependent stathmin- and filamin A-mediated mechanism in hippocampal cells. *Neuroscience* 219:255-270.

Harmon A W, Paul D S, Patel Y M. (2004). MEK inhibitors impair insulin stimulated glucose uptake in 3T3-L1 adipocytes. *American J Physio* 287:758-766.

Hughes B W, Kusner L L, Kaminski H J. (2006). Molecular architecture of the neuromuscular junction. *Muscle & Nerve* 33:445-461.

Kolev Y, Uetake H, Takagi Y, Sugihara K. (2008). Lactate dehydrogenase-5 (LDH-5) expression in human gastric cancer, association with hypoxia-inducible factor (HIF-1 alpha) pathway, angiogenic factors production and poor prognosis. *Am Surg Oncol* 15:2336-2344.

Mayer C M, Belsham D D. (2009). Insulin directly regulates NPY and AgRP gene expression via the MAPK MEK/ERK signal transduction pathway in mHypoE-46 hypothalamic neurons. *Mol Cell Endo* 307(1):99-108.

Mihaylova M M, Shaw R J. (2011). The AMPK signalling pathway coordinates cell growth, autophage and metabolism. *Nat Cell Biol.* 13:1016-1023.

Ng T S J. (2010). The Effect of Teneurin C-terminal Associated Peptide-1 (TCAP-1): Protection Against Hypoxic-stress and Regulation of Brain-derived Neurotrophic Factor (BDNF) in Immortalized Hypothalamic N38 cells. M. Sc. Thesis. Dept. Cell and Systems Biology. University of Toronto.

Pelicano H, Martin D S. Xu R H, Huang P. (2006). Glycolysis inhibition for anticancer treatment. *Oncogene* 25:4633-4646.

Sohn J W, Elmquist J K, Williams K W. (2013). Neuronal circuits that regulate feeding behaviour and metabolism. *Trends in Neuroscience* 36:504-512.

Tan L A, Al Chawaf A, Vaccarino H, Boutros P C, Lovejoy D A. (2011). Teneurin C-terminal associated peptide (TCAP)-1 modulates dendritic morphology in hippocampal neurons and decreases anxiety-like behaviors in rats. *Physiology & Behavior* 104:199-204.

Tan L A, Xo K, Vaccarino, F J, Lovejoy D A, Rotzinger S (2009). Teneurin C-terminal associated peptide (TCAP)-1 attenuates corticotropin-releasing factor (CRF)-induced c-Fos expression in the limbic system and modulates anxiety behaviour in male Wistar rats *Behav. Brain Res.* 201:198-206.

Uemura E, Greelee H W. (2006). Insulin regulates neuronal glucose uptake by promoting translocation on of glucose transporter GLUT3. *Experimental Neurology* 198:48-53.

Wick A N, Drury D R, Nakada H I, Wolfe J B. (1957). Localization of the primary metabolic block produced by 2-deoxyglucose. *J Biol Chem* 224:963-969.

Widgren U, Jiang X J, Krook A, Chibalin A V, Bjornholm M, Tally M, Roth R A, Henriksson J, Wallberg-Henriksson H, Zierath J R. (1998). Divergent effects of exercise on metabolic and mitogenic signalling pathways in human skeletal muscle. *FASEB J* 12:1379-1389.

Xu M. (2012). A Novel Pathway for Enhanced Metabolic Capacities Underlies the Neuroprotective Actions of Teneurin C-Terminal Associated Peptide (TCAP)-1. M. Sc Thesis. Dept. Cell and Systems Biology, University of Toronto.

Al Chawaf A, Xu K, Vaccarino F J, Lovejoy D A, Rotzinger S (2007). Corticotropin-releasing factor (CRF)-induced behaviours are modulated by intravenous administration of teneurin C-terminal associated peptide-1 (TCAP-1). *Peptides* 28:1406-1415.

Amaral A L, (2013). Effects of hypoglycaemia on neuronal metabolism in the adult brain-role of alternative substrates to glucose. *J Inherit Metab Dis* 36:621-634.

Aronson D, Violan M A, Dufresne S D, Zangen D, Fielding R A. Goodyear. (1997). Exercise stimulates the mitogen-activated protein kinase pathway in human skeletal muscle. *J Clin Invest* 99:1251-1257.

Barros L F. (2013). Metabolic signalling by lactate in the brain. *Cell Press* 36-396-404.

Bauer M E, Jeckel C M M, Luz C. (2009). The Role of Stress Factors during Aging of the Immune System. Neuroimmunomodulation 1153:139-152.

Beeton C, Garcia A, Chandy K G. (2007). Drawing Blood from Rats through the Saphenous Vein and by Cardiac Puncture. *J Vis Exp.* 7:266.

Belsham D D, Cai F, Cui H, Smukler S R, Salapatek A F, Shkreta L (2004). Generation of a Phenotypic Array of Hypothalamic Neuronal Cell Models to Study Complex Neuroendocrine Disorders. *Endocrinology* 145:393-400.

Berg J M, Tymoczko J L, Stryer L. (2002) Biochemistry. $5^{th}$ edition. W.H. Freeman New York.

Bergstrom J, Hermansen L, Hultman E, Saltin B. (1967). Diet, muscle glycogen and physical performance. *Acta Physiol Scand* 71:140-150.

Biddinger S B & Kahn C R. (2006). From mice to men: Insights info insulin resistance syndromes. *Annu Rev Physiol* 68:123-158.

Boubaker J, Val-Laillet D, Guerin S, Malbert C H. (2012). Brain Processing of Duodenal and Portal Glucose Sensing. *Journal of Neuroendocrinology* 24:1096-1105.

Boucard A A, Maxeiner S, Sudhof T C. (2014). Latrophilins function as heterophilic cell-adhesion molecules by binding to teneurins: regulation by alternative splicing. *J Biol Chem* 289:387-402.

Brunet A, Pouyssegur J. (1997). Mammalian MAP kinase modules: how to transducer specific signals. *Essays Biochem* 32:1-16.

Carey M, Kehlenbrink S, Hawkins M. (2013). Evidence for Central Regulation of Glucose Metabolism. *Journal of Biological Chemistry* 208:34981-34985.

Chand D, Casatti C A, de Lannoy L. Song L, Kollara A, Barsyte-Lovejoy D. Brown T J, Lovejoy D A. (2013). C-terminal processing of the teneurin proteins: Independent actions of a teneurin C-terminal associated peptide in hippocampal cells. *Mol Cell Neurosci* 52:38-50.

Chang F, Steelman L S, Shelton J G, Lee J T, Navolanic P M, Blalock W L, Franklin R, McCubrey J A. (2003). Regulation of cell cycle progression and apoptosis by the Ras/Raf/MEK/ERK pathway. *Int J Oncol* 22:469-480.

Cholet N, Pellerin L, Welker E, Lacombe P, Seylaz J, Magistnetti P J, Bonvento G. (2001) Local injection of antisense oligonucleotides targeted to the glial glutamate transporter GLAST decreases the metabolic response to somatosensory activation. *J. Cereb. Blood Flow Metab.* 21:404-412.

Dienl G A. (2012). Brain lactate metabolism: the discoveries and the controversies. *Journal of Cerebral Blood Flow & Metabolism* 32:1107-1138.

Dommici F P, Argentino D P, Munoz M C, Miquet J G, Sotelo A I, Turyn D. (2005). Influence of the crosstalk between growth hormone and insulin signalling on the modulation of insulin sensitivity. *Growth Horm. IGF Res.* 15:324-336.

Dringen R, Gebhardt R, Hamprecht B. (1993). Glycogen in astrocytes; possible function as lactate supply far neighboring cells. *Brain Res* 623:208-214.

Duelli R & Kuschinsky W. (2001). Brain glucose transporters; relationship to local energy demand. *News Physiol Sci:* 16:71-76.

Fick L J, Belsham D D. (2010). Nutrient sensing and insulin signalling in neuropeptide-expressing immortalized, hypothalamic neurons: A cellular model of insulin resistance. *Cell Cycle* 9:3186-3193.

Force T, Bonventre J V. (1998). Growth factors and mitogen-activated protein kinases. *Hypertension* 31:152-161.

Galloway S, Bodenham A. (2004). Long-term central venous access. *British Journal of Anesthesia* 92:722-734.

German J P, Thaler J P, Wisse B E, Oh-I S, Sanuf D A, Matsen M E, Fischer J D, Taborsky G J, Schwartz M W, Morton G J. (2011). Leptin Activates a Novel CNS Mechanism for Insulin-Independent Normalization of Severe Diabetic Hyperglycemia. *Endocrinology* 152:394-404.

Gjedde A, Marrett S, Vafeee M. (2002) Oxidative and Nonoxidative Metabolism of Excited Neurons and Astrocytes. *Journal of Cerebral Blood Flow & Metabolism* 22:1-14.

Goldstone A P, Prechti C G, Scholtz S, Miras A D, Chhina N, Durighel G, Deliran S S, Beckmann C, Ghatei M A, Ashby D R, Waldman A D, Gaylium B D. Thorner M O, Frost G S, Bloom S R, Bell J D. (2014). Ghrelin mimics fasting to enhance human hedonic, oibitofrontal cortex, and hippocampal responses to food. *Am J Clin Nutr* 99:1319-1330.

Goodyear L J, Chang P Y, Sherwood D J, Dufresne S D, Molter D E. (1996). Effects of exercise and insulin mitogen activated protein kinase signalling pathways in rat skeletal muscle. *Am J Physiol* 271:E403-E408.

Hassel, B. (2001). Pyruvate carboxylation in neurons. *J Neurosci Res* 66:755-762.

Hegarty B D, Turner N, Cooney G J, Kraegen E W. (2009). Insulin resistance and fuel homeostasis: the role of AMP-activated protein kinase. *Acta Physiol* 196:129-145.

Hermansen Land Osnes J B. (1972). Blood and muscle pH after maximal exercise in man *J Appl Physiol* 32:304-308.

Hu Y Wilson O S. (1997). A temporal local energy pool coupled to neuronal activity: fluctuations of extracellular lactate levels in rat brain monitored with rapid-response enzyme-based sensor. *J. Neurochem* 69:1484-1490.

Klip A, Ramlal T. (1987). Protein kinase C is not required ter insulin stimulation of hexose uptake in muscle cells in culture. *J Biochem* 242:131-136.

Kupferschmidt D A, Lovejoy D A, Rotzinger S, Erb S (2010). Teneurin C-terminal associated peptide-1 blocks the effects of corticotrophin-releasing factor on reinstatement of cocaine-induced behavioural sensitization. *Br. J. Pharmacol.* 162:574-583.

Maher F. (1995). Immunocoloralization of GLUT1 and GLUT3 glucose transporters in primary culture neurons and glial. *J Neurosci Res* 42:459-469.

Mosca T J, H W, Dani V S, Favaloro V, Luo L. (2012). Trans-synaptic Teneurin signalling in neuromuscular synapse organization and target choice. *Nature* 484:243.

Parasuraman S, Raveendran R, Kesavan R. (2010). Blood sample collection in small laboratory animals. *J Pharmacol Phamacother.* 1:87-93.

Partridge T A. (2013) The mdx mouse model as a surrogate for Duchenne muscular dystrophy *FEBS journal* 280: 4177-4186.

Pellerin L, Magistretti P J. (1994) Glutamate uptake into astrocytes stimulates aerobic glycolysis, a mechanism coupling neuronal activity to glucose utilization. *Proc. Natl Acad Sci.* 91:10625-10629.

Ren X, Zhou L, Terwilliger R, Newton S S, de Araujo I E. (2009). Sweet taste signaling functions as a hypothalamic glucose sensor. *Front Inregr Neurosci* 3:doi 10.3389/neuro.07.012.2009

Richter E A, Hargreaves M. (2013) Exercise, GLUT4, and skeletal muscle glucose uptake. *Physiological Reviews* 93:993-1017.

Rorabaugh J M, Stratford J M, Zhniser N R. (2014). A Relationship between Reduced Nucleus Accumbens Shell and Enhanced Lateral Hypothalamic Orexin Neuronal Activation in Long-Term Fructose Bingeing Behavior. *PLoS ONE* 9:e95019.

Schwartz M W, Seeley R J, Tschop M H, Woods S C, Morton G J, Myers M G, D'Alessio D. (2013). Cooperation between brain and islet in glucose homeostasis and diabetes. *Nature* 503:59-66.

Shetty P K, Sadgrove M P, Galeffi F, Turner D A. (2012). Pyruvate incubation enhances glycogen stores and sustains neuronal function during subsequent glucose deprivation. *Neurobial Dis* 45:177-187.

Shoobridge E A, Challiss R A, Hayes D J, Radda D A. (1985). Biochemical adaptation m the skeletal muscle of rats depleted of creatine with the substrate analogue beta-guadinopropionic acid. *Biochem J* 232:125-131.

Sohn J W, Elmquist J K, Williams K W. (2013). Neuronal circuits that regulate feeding behaviour and metabolism. *Trends in Neuroscience* 36:504-512.

Sorge R E, Martin I J, Isbester K A, Sotocinal S G, Rosen S, Tuttle A H, Wieskopf J S, Adand E L, Dokova A, Kadoura B, Leger P, Mapplebeck J C S, Mcphail M, Delaney A, Wigerblad G, Schumann A P, Quinn T, Frasnelli J, Sveasson C I, Sternberg W F, Mogil J S. (2014). Olfactory exposure to males, including men, causes stress and related analgesia in rodents. *Nature Methods doi:* 10.1038/meth2935.

Stobart J L, Anderson C M. (2013) Multifunctional role of astrocytes as gatekeepers of neuronal energy supply. *Frontiers in Cellular Neuroscience* 7:1-21.

Tan L A. (2011). The Role of Teneurin C-Terminal Associated Peptide (TCAP)-1 in the Regulation of Stress-Related Behaviours. M. Sc Thesis, Dept. Cell and Systems Biology, University of Toronto.

Tan L A, Xu K, Vaccarino, F J, Lovejoy D A, Rotzinger S (2008). Repeated intracerebralteneurin C-terminal associated peptide (TCAP)-1 injections produce enduring changes in behavioural responses to corticotrophin-releasing factor (CRF) in rat models of anxiety. *Behav. Brain Res.* 188:195-200.

Tan L A, Xu K. Vaccarino, F J, Lovejoy D A, Rotzinger S (2009). Teneurin C-terminal associated peptide (TCAP)-1 attenuates corticotrophin-releasing factor (CRF)-induced c-Fos expression in the limbic system and modulates anxiety behaviour in male Wistar rats *Behav. Brain Res.* 201:198-206.

Taniguchi C M, Emanuelli B, Kahn C R. (2006). Critical nodes in signalling pathways: Insights into insulin action. *Nat Rev. Mol Cell Biol* 7:85-96.

Thrivikraman K V, Huot R L, Plotsky P M. (2002). Jugular vein catheterization for repeated blood sampling in the unrestrained conscious rat. *Brain Research Protocols* 10:84-94.

Trubiani G, Al Chawaf A, Belsham D, Barsyte-Lovejoy D, Lovejoy D A. (2007). Teneurincarboxy (C)-terminal associated peptide-1 inhibits alkalosis-associated necrotic neuronal death by stimulating superoxide dismutase and catalase activity in immortalized mouse hypothalamic cells. *Brain Research* 1176:27-36.

Tsacopoulos M, Magistretti P J. (1996) Metabolic coupling between glia and neurons. *J. Neurosci.* 16:877-885.

Uemura E, Greelee H W. (2006). Insulin regulates neuronal glucose uptake by promoting translocation of glucose transporter GLUT3. *Experimental Neurology* 198:48-53.

Widgren U, Jiang X J, Krook A, Chibalin A V, Bjornholm M, Tally M, Roth R A, Henriksson J, Wallberg-Henriksson H, Zierath J R. (1998). Divergent effects of exercise on metabolic and mitogenic signalling pathways in human skeletal muscle. *FASEB J* 12:1379-1389.

Widgren U, Ryder J W, Zierath J R. (2002). Mitogen activated protein kinase signal transduction in skeletal muscle; effects of exercise and muscle contraction. *Acta Physiol Scand* 172:227-238.

World Health Organization. (2009). Global Risks. Mortality and burden of disease attributable to selected major risks. Geneva. http://www.who.int/mediacentre/factsheets/fe312/en/

Xu J, Messina J L. (2009). Crosstalk between growth hormone and insulin signalling. *Vitamins and Hormones* 80:125-153.

Xu M. (2012). A Novel Pathway for Enhanced Metabolic Capacities Underlies the Neuroprotective Actions of Teneurin C-Terminal Associated Peptide (TCAP)-1. M. Sc Thesis. Dept. Cell and Systems Biology, University of Toronto.

Yaffe D and Saxel O. (1977). Serial passaging and differentiation of myogenic cells isolated from dystrophic mouse muscle. *Nature* 270:725-727.

Yamazaki T, Komuro X, Kudoh S, Zou Y, Shiojima I, Mizuno T, Takano H, Hiroi Y, Ueki K, Tobe K, et al. (1995). Mechanical stress activates protein kinase cascade of phosphorylation in neonatal rat cardiac myocytes. *J Clin Invest* 96:438-446.

Yu S, Tooyama I, Ding W G, Kitasato H, Kimura H. (1995). Immunohistochemical localization of glucose transporters (GLUT1 and GLUT3) in the rat hypothalamus. *Obes Res Suppl* 5:753S-757S.

What is claimed is:

1. A method of increasing energy available to skeletal muscle cells, the method comprising administering to a patient in need thereof an effective amount of an isolated teneurin c-terminal associated peptide (TCAP peptide), or a pharmaceutically acceptable salt thereof, wherein the amino acid sequence of said TCAP peptide consists essentially of:

(i) an amino acid sequence having at least 95% identity to an amino acid sequence selected from the group consisting of SEQ ID NOs: 13, 14, 21, 22, 29, 30, 37, 38, 45, 46, 53, 54, 61, 62, 69, 70, 77, 78, 85, 86, 93, 94, and 101; or (ii) a 38 amino acid sequence from the carboxy terminal end of a peptide having at least 95% identity to an amino acid sequence selected from the group consisting of SEQ ID NOs: 13, 14, 21, 22, 29, 30, 37, 38, 45, 46, 53, 54, 61, 62, 69, 70, 77, 78, 85, 86, 93, 94, and 101; optionally wherein:
(a) the carboxy terminal end of said TCAP peptide is amidated or comprises an amidation signal sequence; or
(b) when the amino terminal amino acid of said TCAP peptide is glutamine, it is in the form of pyroglutamic acid.

2. The method of claim 1, wherein increasing energy available to skeletal muscle cells comprises increasing glucose uptake by skeletal muscle cells under conditions where increased intracellular glucose in skeletal muscle cells is advantageous.

3. The method of claim 1, for increasing energy available to skeletal muscle cells under conditions where increased energy available to skeletal muscle cells is advantageous.

4. The method of claim 3, wherein the conditions where increased energy available to muscle cells is advantageous is a condition in which the skeletal muscle cells exhibit insulin resistance.

5. The method of claim 3, wherein the conditions where increased energy available to muscle cells is advantageous is type 2 diabetes.

6. The method of claim 3, wherein the conditions where increased energy available to muscle cells is advantageous are immediately before, during, or immediately after exercise.

7. The method of claim 3, wherein the conditions where increased energy available to muscle cells is advantageous is selected from the group consisting of: hypoxia, injury, a glycogen storage disorder, and a myopathy.

8. The method of claim 1, wherein the increased energy is available for at least one day.

9. The method of claim 1, wherein the increased energy is available for at least three days.

10. The method of claim 1, wherein the increased energy is available for at least five days.

11. The method of claim 1, wherein the increased energy is available for at least seven days.

12. The method of claim 1 for preventing and/or treating Type-2 diabetes.

13. The method of claim 1, wherein the peptide is administered to a patient with Type 1 or Type 2 diabetes.

14. The method of claim 1, wherein the TCAP peptide is administered or a pharmaceutical composition comprising the peptide is administered.

15. The method of claim 1 wherein the TCAP peptide or a pharmaceutical composition comprising the TCAP peptide is administered and the TCAP peptide consists essentially of:
(i) an amino acid sequence having at least 95% identity to an amino acid sequence consisting of SEQ ID NOs: 38 or 70;
optionally wherein:
(a) the carboxy terminal end of said TCAP peptide is amidated or comprises an amidation signal sequence; or
(b) when the amino terminal amino acid of said TCAP peptide is glutamine, it is in the form of pyroglutamic acid.

16. The method of claim 15, wherein the amino acid sequence of the TCAP peptide consists essentially of an amino acid sequence consisting of SEQ ID NOs: 38 or 70 or an amino acid sequence having 95% identity to same.

17. The method of claim 16, wherein the amino acid sequence of the TCAP peptide consists essentially of an amino acid sequence consisting of SEQ ID NOs: 38 or 70.

18. The method of claim 15, wherein administration is to a patient to whom increased energy available to muscle cells is advantageous and/or to a patient who has a condition in which the skeletal muscle cells exhibit insulin resistance and/or to a patient to whom increased intracellular glucose in skeletal muscle cells is advantageous.

19. The method of claim 18 for the prevention and/or treatment of type 2 diabetes.

20. The method of claim 18, wherein increased energy available to muscle cells is advantageous immediately before, during, or immediately after exercise.

21. The method of claim 18, wherein increased energy available to muscle cells is advantageous in conditions selected from the group consisting of: hypoxia, injury, a glycogen storage disorder, and a myopathy.

* * * * *